(12) United States Patent
Gish et al.

(10) Patent No.: US 10,188,660 B2
(45) Date of Patent: *Jan. 29, 2019

(54) ANTI-HULRRC15 ANTIBODY DRUG CONJUGATES AND METHODS FOR THEIR USE

(71) Applicants: AbbVie Inc., North Chicago, IL (US); AbbVie Biotherapeutics Inc., Redwood City, CA (US)

(72) Inventors: Kurt C. Gish, Piedmont, CA (US); Jonathan A. Hickson, Lake Villa, IL (US); Susan Elizabeth Morgan-Lappe, Riverwoods, IL (US); James W. Purcell, San Francisco, CA (US)

(73) Assignees: AbbVie Inc., North Chicago, IL (US); AbbVie Biotherapeutics Inc., Redwood City, CA (US)

( * ) Notice: Subject to any disclaimer, the term of this patent is extended or adjusted under 35 U.S.C. 154(b) by 25 days.

This patent is subject to a terminal disclaimer.

(21) Appl. No.: 15/363,715

(22) Filed: Nov. 29, 2016

(65) Prior Publication Data

US 2017/0151343 A1 Jun. 1, 2017

Related U.S. Application Data

(60) Provisional application No. 62/417,480, filed on Nov. 4, 2016, provisional application No. 62/261,092, filed on Nov. 30, 2015.

(51) Int. Cl.
| | |
|---|---|
| *A61K 38/07* | (2006.01) |
| *A61K 31/5517* | (2006.01) |
| *C07K 16/30* | (2006.01) |
| *A61K 47/06* | (2006.01) |
| *A61K 39/395* | (2006.01) |
| *C07K 16/28* | (2006.01) |
| *A61K 47/68* | (2017.01) |
| *A61K 39/00* | (2006.01) |

(52) U.S. Cl.
CPC .......... *A61K 31/5517* (2013.01); *A61K 38/07* (2013.01); *A61K 39/3955* (2013.01); *A61K 47/6803* (2017.08); *A61K 47/6849* (2017.08); *A61K 47/6851* (2017.08); *A61K 47/6889* (2017.08); *C07K 16/28* (2013.01); *C07K 16/2818* (2013.01); *C07K 16/30* (2013.01); *A61K 2039/505* (2013.01); *C07K 2317/24* (2013.01); *C07K 2317/73* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,299,216 A | 11/1981 | Bernard et al. |
| 4,444,887 A | 4/1984 | Hoffmann |
| 4,510,245 A | 4/1985 | Cousens |
| 4,634,665 A | 1/1987 | Axel |
| 4,716,111 A | 12/1987 | Osband |
| 4,737,456 A | 4/1988 | Weng |
| 4,816,397 A | 3/1989 | Boss |
| 4,816,457 A | 3/1989 | Baldwin |
| 4,968,615 A | 11/1990 | Koszinowski |
| 5,168,062 A | 12/1992 | Stinski |
| 5,179,017 A | 1/1993 | Axel |
| 5,225,539 A | 7/1993 | Winter |
| 5,413,923 A | 5/1995 | Kucherlapati |
| 5,530,101 A | 6/1996 | Queen |
| 5,545,806 A | 8/1996 | Lonberg |
| 5,565,332 A | 10/1996 | Hoogenboom |
| 5,569,825 A | 10/1996 | Lonberg |
| 5,585,089 A | 12/1996 | Queen |
| 5,625,126 A | 4/1997 | Lonberg |
| 5,633,425 A | 5/1997 | Lonberg |
| 5,658,570 A | 8/1997 | Newman |
| 5,661,016 A | 8/1997 | Lonberg |
| 5,681,722 A | 10/1997 | Newman |
| 5,693,761 A | 12/1997 | Queen |
| 5,693,762 A | 12/1997 | Queen |
| 5,693,780 A | 12/1997 | Newman |
| 5,807,715 A | 9/1998 | Morrison |
| 5,814,318 A | 9/1998 | Lonberg |
| 5,885,793 A | 3/1999 | Griffiths |
| 5,916,771 A | 6/1999 | Hori |
| 5,939,598 A | 8/1999 | Kucherlapati |
| 6,180,370 B1 | 1/2001 | Queen |
| 7,217,797 B2 | 5/2007 | Hinton |
| 7,223,837 B2 | 5/2007 | De Groot |
| 7,399,469 B2 | 7/2008 | Zhang |

(Continued)

FOREIGN PATENT DOCUMENTS

| | | |
|---|---|---|
| EP | 0239400 A2 | 9/1987 |
| EP | 0519596 A1 | 12/1992 |

(Continued)

OTHER PUBLICATIONS

Paul, Fundamental Immunology, 3rd Edition, 1993, pp. 292-295.*

(Continued)

*Primary Examiner* — Hong Sang

(74) *Attorney, Agent, or Firm* — Dechert LLP

(57) ABSTRACT

The present disclosure provides antibodies, antibody binding fragments, and antibody drug conjugates that bind human LRRC15, their methods of making, and their uses to treat patients having cancer.

27 Claims, 58 Drawing Sheets

Figure 4:
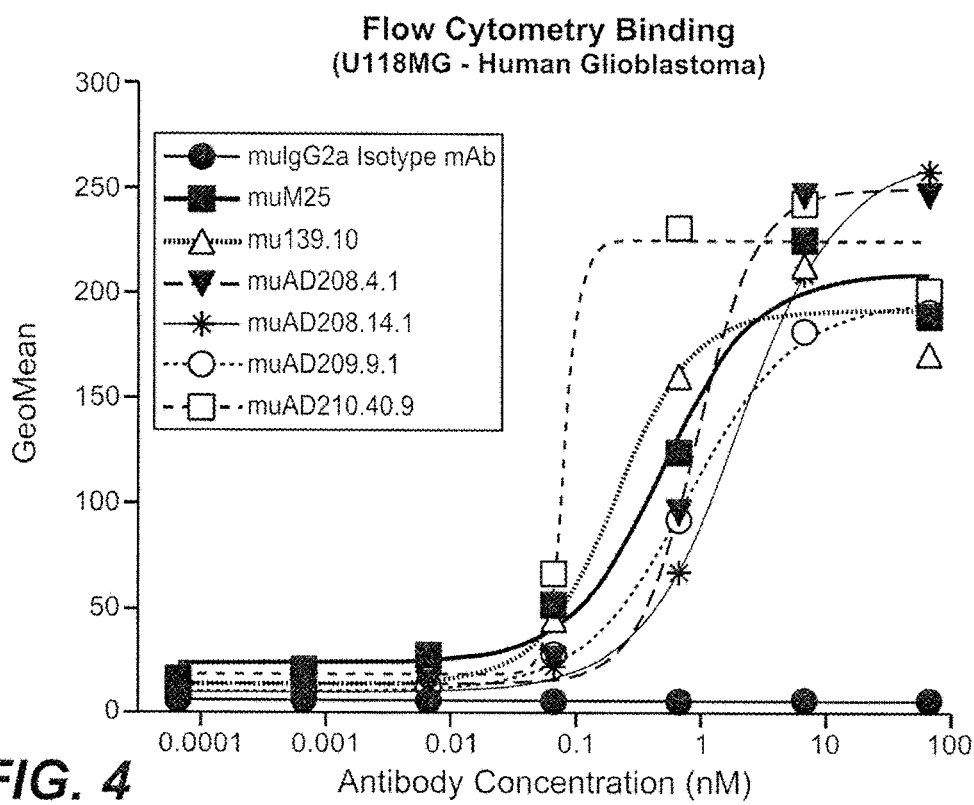

Specification includes a Sequence Listing.

(56) References Cited

U.S. PATENT DOCUMENTS

| | | | |
|---|---|---|---|
| 7,521,541 | B2 | 4/2009 | Eigenbrot |
| 7,855,275 | B2 | 12/2010 | Eigenbrot |
| 7,989,434 | B2 | 8/2011 | Feng |
| 8,455,622 | B2 | 6/2013 | McDonagh |
| 8,535,678 | B2 | 9/2013 | Law |
| 8,568,728 | B2 | 10/2013 | Jeffrey |
| 9,089,615 | B2 | 7/2015 | Stull |
| 9,242,013 | B2 | 1/2016 | Howard |
| 2005/0271615 | A1 | 12/2005 | Shabat |
| 2006/0116422 | A1 | 6/2006 | De Groot |
| 2007/0280931 | A1 | 12/2007 | Chen |
| 2013/0309256 | A1 | 11/2013 | Lyon |

FOREIGN PATENT DOCUMENTS

| | | | |
|---|---|---|---|
| EP | 0592106 A1 | 4/1994 | |
| WO | WO 1989/12624 A2 | 12/1989 | |
| WO | WO 1991/09967 A1 | 7/1991 | |
| WO | WO 1991/10741 A1 | 7/1991 | |
| WO | WO 1992/01047 A1 | 1/1992 | |
| WO | WO 1996/33735 A1 | 10/1996 | |
| WO | WO 1996/34096 A1 | 10/1996 | |
| WO | WO 1997/34631 A1 | 9/1997 | |
| WO | WO 1998/16654 A1 | 4/1998 | |
| WO | WO 1998/24893 A2 | 6/1998 | |
| WO | WO 1998/46645 A2 | 10/1998 | |
| WO | WO 1998/50433 A2 | 11/1998 | |
| WO | WO 2002/060919 A2 | 8/2002 | |
| WO | WO 2004/010957 A2 | 2/2004 | |
| WO | WO 2005/123780 A2 | 12/2005 | |
| WO | WO 2007/089149 A2 | 8/2007 | |
| WO | WO 2009/073445 A2 | 6/2009 | |
| WO | WO 2010/068795 A2 | 6/2010 | |
| WO | WO 2010/138719 A1 | 12/2010 | |
| WO | WO 2011/120053 A1 | 9/2011 | |
| WO | WO 2013/085925 A1 | 6/2013 | |
| WO | WO 2013/096901 A1 | 6/2013 | |
| WO | WO 2014/008375 A1 | 1/2014 | |
| WO | WO 2014/093379 A1 | 6/2014 | |
| WO | WO 2014/093394 A1 | 6/2014 | |
| WO | WO 2014/093640 A1 | 6/2014 | |

OTHER PUBLICATIONS

Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Alley et al., 2008 "Contribution of Linker Stability to the Activities of Anticancer Immunoconjugates," *Bioconjugate Chem* 19(3):759-765.
Axup et al., 2012 "Synthesis of site-specific antibody-drug conjugates using unnatural amino acids," *Proc Natl Acad Sci USA* 109(40):16101-16106.
Bornstein, 2015 "Antibody Drug Conjugates: Preclinical Considerations," *AAPS J* 17(3):525-534.
Boswell et al., 2012 "Differential Effects of Predosing on Tumor and Tissue Uptake of an $^{111}$In-Labeled Anti-TENB2 Antibody-Drug Conjugate," *J Nucl Med* 53(9):1454-1461.
Boswell et al., 2013 "An integrated approach to identify normal tissue expression of targets for antibody-drug conjugates: case study of TENB2," *Br J Pharmacol* 168:415-457.
Burke et al., 2009 "Design, Synthesis, and Biological Evaluation of Antibody—Drug Conjugates Comprised of Potent Camptothecin Analogues," *Bioconjugate Chem* 20(6): 1242-1250.
Camps et al., 1990 "Fibroblast-mediated acceleration of human epithelial tumor growth in vivo," *Proc Natl Acad Sci USA* 87(1):75-79.

Chari, 2008 "Targeted Cancer Therapy: Conferring Specificity to Cytotoxic Drugs," *Acc Chem Res* 47(1):98-107.
Chen et al., 2007 "Armed Antibodies Targeting the Mucin Repeats of the Ovarian Cancer Antigen, MUC16, Are Highly Efficacious in Animal Tumor Models," *Cancer Res* 67(10):4924-4932; 5998 (11 pages).
Cirri et al., 2011 "Cancer associated fibroblasts: the dark side of the coin," *Am J Cancer Res* 1(4):482-497.
Da Fonseca et al., 2016 "Glycosylation in Cancer: Interplay between Multidrug Resistance and Epithelial-to-Mesenchymal Transition?" *Front Oncol* vol. 6, Art. 158, pp. 1-10.
De Wever et al., 2003 "Role of tissue stroma in cancer cell invasion," *J Pathol* 200:429-447.
Diamond et al., 1974 "Interpretation of nonelectrolyte partition coefficients between dimyristoyl lecithin and water," *J Membr Biol* 17(1):121-154.
Dornina et al., 2003 "Development of potent monoclonal antibody auristatin conjugates for cancer therapy," *Nat Biotechnol* 21(7):778-784.
Dornina et al., 2006 "Enhanced Activity of Monomethylauristatin F through Monoclonal Antibody Delivery: Effects of Linker Technology on Efficacy and Toxicity," *Bioconjugate Chem* 17(1): 114-124.
Dornina et al., 2008 "Novel Peptide Linkers for Highly Potent Antibody—Auristatin Conjugate," *Bioconjugate Chem* 19(10):1960-1963.
Droujinine et al., 2013 "To grab the stroma by the horns: From biology to cancer therapy with mesenchymal stem cells," *Oncotarget* 4(5):651-664.
Dubowchik et al., 1998 "Cathepsin B-sensitive dipeptide prodrugs. 1. A model study of structural requirements for efficient release of doxorubicin," *Bioorg Med Chem Lett* 8(23):3341-3346.
Eisenhauer et al., 2009 "New response evaluation criteria in solid tumours: Revised RECIST guideline (version 1.1)," *European Journal of Cancer* 45:228-247.
Elenbaas et al., 2001 "Human breast cancer cells generated by oncogenic transformation of primary mammary epithelial cells," *Genes Dev* 15:50-65.
Francisco et al., 2003 "cAC10-vcMMAE, an anti-CD30-monomethyl auristatin E conjugate with potent and selective anti-tumor activity," *Blood* 102(4):1458-1465.
Gerber et al., 2009 "Antibody drug-cojugates targeting the tumor vasculature," *mAbs* 1(3):247-253.
Goldmacher et al., 2013 "Linker Technology and Impact of Linker Design on ADC Properties," *Antibody-Drug Conjugates and Immunotoxins*, Part of the series *Cancer Drug Discovery and Development* Chapter 7 pp. 117-135.
Griffon-Etienne et al., 1999 "Taxane-induced Apoptosis Decompresses Blood Vessels and Lowers Interstitial Fluid Pressure in Solid Tumors: Clinical Implications," *Cancer Res* 59(15):3776-3782.
Gupta et al., 2009 "Identification of selective inhibitors of cancer stem cells by high-throughput screening," *Cell* 138(4):645-659.
Hamblett et al., 2004 "Effects of Drug Loading on the Antitumor Activity of Monoclonal Antibody Drug Conjugate," *Clin Cancer Res* 20:7063-7070.
Helft et al., 2004 "A Phase I Study of Cantuzumab Mertansine Administered as a Single Intravenous Infusion Once Weekly in Patients with Advanced Solid Tumors," *Clin Cancer Res* 10(13):4363-4368.
Helma et al., 2015 "Nanobodies and recombinant binders in cell biology," *J Cell Biol* 209(5):633-644.
Hollander et al., 2008 "Selection of Reaction Additives Used in the Preparation of Monomeric Antibody—Calicheamicin Conjugates," *Bioconjugate Chem* 19(1):358-361.
Ippolito et al., 2016 "Metabolic shift toward oxidative phosphorylation in docetaxel resistant prostate cancer cells," *Oncotarget* 7(38):61890-61904.
Kalluri, 2016 "The biology and function of fibroblasts in cancer," *Nat Rev Cancer* 16(9):582-598.
Karnoub et al., 2007 "Mesenchymal stem cells within tumour stroma promote breast cancer metastasis," *Nature* 449:557-563.
Kellogg et al., 2011 "Disufide-Linked Antibody-Maytansinoid Conjugates: Optimization of In Vivo Activity by Varying the Steric

(56) References Cited

OTHER PUBLICATIONS

Hindrance at Carbon Atoms Adjacent to the Disfulfide Linkage," *Bioconjugate Chem* 22(4):717-727.
King et al., 2002 "Monoclonal Antibody Conjugates of Doxorubicin Prepared with Branched Peptide Linkers: Inhibition of Aggregation by Methoxytriethyleneglycol Chains," *J Med Chem* 45(19):4336-4343.
Law et al., 2006 "Lymphocyte Activation Antigen CD70 Expressed by Renal Cell Carcinoma Is a Potential Therapeutic Target for Anti-CD70 Antibody-Drug Conjugates," *Cancer Res* 66(4):2328-2337.
Li et al., 2007 "Tumor Microenvironment: The Role of the Tumor Stroma in Cancer," *J Cell Biochem* 101:805-815.
Mack et al., 2014 "The Next Generation of Antibody Drug Conjugates," *Semin Oncol* 41(5):637-652.
Mésange et al., 2014 "Intrinsic bevacizumab resistance is associated with prolonged activation of autocrine VEGF signaling and hypoxia tolerance in colorectal cancer cells and can be overcome by nintedanib, a small molecule angiokinase inhibitor," *Oncotarget* 5(13):4709-4721.
Müller et al., 2014 "Microtubule-Depolymerizing Agents Used in Antibody-Drug Conjugates Induce Antitumor Immunity by Stimulation of Dendritic Cells," *Cancer Immunol Res* 2(8):741-755.
Nishino et al., 2013 "Developing a Common Language for Tumor Response to Immunotherapy: Immune-Related Response Criteria Using Unidimensional Measurements," *Clin Cancer Res* 19(14):3936-3943.
Nishino et al., 2015 "Cancer immunotherapy and immune-related response assessment: The role of radiologists in the new arena of cancer treatment," *Eur J Radiol* 84(7):1259-1268.
Nolting, 2013 Chapter 5 "Linker Technology in Antibody-Drug Conjugates," Antibody-Drug Conjugates, vol. 1045 in *Methods Mol Biol* pp. 71-100.
Okeley et al., 2010 "Intracellular Activation of SGN-35, a Potent Anti-CD30 Antibody-Drug Conjugate," *Clin Cancer Res* 16(3):888-897; 5524.
Olumi et al., 1999 "Carcinoma-associated Fibroblasts Direct Tumor Progression of Initiated Human Prostatic Epithelum," *Cancer Res* 59(19):5002-5011.
Ostermann et al., 2008 "Effective Immunoconjugate Therapy in Cancer Models Targeting a Serine Protease of Tumor Fibroblasts," *Clin Cancer Res* 14(14):4584-4592.
Padlan, 1991 "A possible procedure for reducing the immunogenicity of antibody variable domains while preserving their ligand-binding properties," *Mol Immunol* 28:489-498.
Pak et al., 2012 "Antigen shedding may improve efficiencies for delivery of antibody-based anticancer agents in solid tumors," *Cancer Res* 72(13):3143-3152.
Pak et al., 2014 "Effect of Antigen Shedding on Targeted Delivery of Immunotoxins in Solid Tumors from a Mathematical Model," *PLos ONE* 9(10):e110716-e110716, pp. 1-11.
Palumbo et al., 2011 "A chemically modified antibody mediates complete eradication of tumors by selective disruption of tumour blood vessels," *Br J Cancer* 104:1106-1115.
Pastuskovas et al., 2010 "Effect of Immune Complex Formation on the Distribution of a Novel Antibody to the Ovarian Tumor Antigen CA125." *Drug Metab Dispos* 38(12):2309-2319.
Perez et al., 2014 "Antibody-drug conjugates: current status and future directions," *Drug Discov Today* 19(7):869-881.
Perrino et al., "Curative Properties of Noninternalizing Antibody-Drug Conjugates Based on Maytansinoids," *Cancer Res* 74(9):2569-2578, 3643 correction, 2014.
Riechmann et al., 1988 "Reshaping human antibodies for therapy," *Nature* 332:323-327.
Roguska et al., 1994 "Humanization of murine monoclonal antibodies through variable domain resurfacing," *Proc Natl Acad Sci USA* 91:969-973.
Salnikov et al., 2003 "Lowering of tumor interstitial fluid pressure specifically augments efficacy of chemotherapy," *FASEB J* 17(12):1756-1758.
Sharkey et al., 2008 "Use of antibodies and immunoconjugates for the therapy of more accessible cancers," *Adv Drug Deliv Rev* 60(12):1407-1420 (Author Manuscript, 33 pages).
Singh et al., 2010 "EMT, cancer stem cells and drug resistance: an emerging axis of evil in the war on cancer," *Oncogene* 29:4741-4751.
Storz, 2015 "Antibody-drug conjugates: Intellectual property considerations," *mAbs* 7(6):989-1009.
Studnicka et al., 1994 "Human-engineered monoclonal antibodies retain full specific binding activity by preserving non-CDR complementarity-modulating residues," *Protein Eng Des Sel* 7(6): 805-814.
Sutherland et al., 2013 "SGN-CD33A: a novel CD33-targeting antibody-drug conjugate using a pyrrolobenzodiazepine dimer is active in models of drug-resistant AML," *Blood* 122(8):1455-1463.
Tolcher et al., 2003 "Cantuzumab Mertansine, a Maytansinoid Immunoconjugate Directed to the CanAg Antigen: A Phse I, Pharmacokinetic, and Biologic Correlative Study," *J Clin Oncol* 21(2):211-222.
Toki et al., 2002 "Protease-Mediated Fragmentation of p-Amidobenzyl Ethers: A New Strategy for the Activation of Anticancer Prodrugs," *J Org Chem* 67(6):1866-1872.
Turley et al., 2015 "Immunological hallmarks of stromal cells in the tumour microenviroment," *Nat Rev Immunol* 15(11): 669-682.
Tuxhorn et al., 2003 "Stromal Cells Promote Angiogenesis and Growth of Human Prostate Tumors in a Differential Reactive Stroma (DRS) Xenograft Model," *Cancer Res* 62(11):3298-3307.
Walker et al., 2002 "Synthesis of an immunoconjugate of camptothecin," *Bioorg Med Chem Lett* 12(2):217-219.
Walker et al., 2004 "Monoclonal antibody mediated intracellular targeting of tallysomycin $S_{10b}$," *Bioorg Med Chem Lett* 14(16):4323-4327.
Walter et al., 1986 "Permeability of small nonelectrolytes through lipid bilayer membranes," *J Membr Biol* 90(3):207-217.
Wen et al., 2013 "Targeting cancer cell mitochondria as a therapeutic approach," *Future Med Chem* 5(1):53-67.
Wolchok et al., 2009 "Guidelines for the Evaluation of Immune Therapy Activity in Solid Tumors: Immune-Related Response Criteria," *Clin Cancer Res* 15(23):7412-7420.
Wu et al., 2016 "Epithelial-Mesenchymal Transition to Breast Cancer," *J Clin Med* 5(13):1-18.
Yardley et al., 2015 "EMERGE: A Randomized Phase II Study of the Antibody-Drug Conjugate Glembatumumab Vedotin in Advanced Glycoprotein NMB-Expressing Breast Cancer," *J Clin Oncol* 33(14):1609-1619.
Ye et al., 2015 "Epithelial-Mesenchymal Plasticity: A Central Regulator of Cancer Progression," *Trends Cell Biol* 25(11):675-686.
Zhang et al., 2008 "High Shed Antigen Levels within Tumors: An Additional Barrier to Immunoconjugate Therapy," *Clin Cancer Res* 14(24):7981-7986.

* cited by examiner huLRRC15 isoform 1 (NCBI accession: NP_001128529, REFSEQ: NM_001135057.2)

|     | M | P | L | D | K | A | M | P | L | K | H | Y | L | L | L | L | V | G | C | Q |
|-----|---|---|---|---|---|---|---|---|---|---|---|---|---|---|---|---|---|---|---|---|
| 1   | ATG | CCT | TTG | GAC | AAG | GCT | ATG | CCA | CTG | AAG | CAT | TAT | CTC | CTT | TTG | CTG | GTG | GGC | TGC | CAA |
|     | A | W | G | A | G | L | A | Y | H | G | C | P | T | E | S | C | L | P | W | A |
| 61  | GCC | TGG | GGT | GCA | GGG | TTG | GCC | TAC | CAT | GGC | TGC | CCT | ACC | GAG | AGC | TGT | CTG | CCC | TGG | GCC |
|     | S | Q | V | E | C | T | G | A | R | I | V | A | C | T | N | R | N | L | T | N |
| 121 | TCC | CAG | GTG | GAG | TGC | ACC | GGG | GCA | CGC | ATT | GTG | GCA | TGC | ACT | AAT | CGG | AAC | CTG | ACC | AAC |
|     | A | M | S | S | L | Q | I | L | N | T | H | I | T | E | L | N | E | S | P | L |
| 181 | GCC | ATG | AGC | AGC | CTG | CAG | ATC | CTC | AAT | ACT | CAC | ATC | ACT | GAA | CTC | AAT | GAG | TCC | CCG | CTC |
|     | N | I | S | A | L | I | A | L | R | I | E | K | N | E | L | S | R | I | T | P |
| 241 | AAT | ATC | TCA | GCC | CTC | ATC | GCC | CTG | AGG | ATT | GAG | AAG | AAT | GAA | CTG | TCG | CGC | ATC | ACG | CCT |
|     | G | A | F | R | N | L | G | S | L | R | Y | L | L | L | S | N | N | K | L | Q |
| 301 | GGG | GCC | TTC | CGA | AAC | CTC | GGC | TCG | CTG | CGC | TAT | CTC | CTC | CTC | AGC | AAT | AAC | AAG | CTG | CAG |
|     | V | L | P | P | G | I | F | Q | A | P | A | H | F | P | D | S | L | Q | L | S |
| 361 | GTT | CTG | CCC | CCG | GGC | ATC | TTC | CAG | GCC | CCG | GCA | CAC | TTC | CCT | GAC | AGC | CTC | CTG | TCC | AGT |
|     | N | Q | L | H | L | Q | C | D | C | H | F | P | D | A | F | R | D | W | L | K |
| 421 | AAC | CAG | CTG | CAC | CTG | CAG | TGC | GAC | TGC | CAC | TTC | CCT | GAC | GCC | TTC | AGA | GAC | TGG | CTG | AAG |
|     | L | T | K | N | L | K | N | L | H | I | S | P | V | Q | R | L | Q | C | V | G |
| 481 | CTG | ACG | AAG | AAT | CTG | AAA | AAT | CTG | CAC | ATC | TCA | CCC | GTG | CAG | AGA | CTC | CAG | TGC | GTA | GGA |
|     | P | L | H | L | Q | N | L | R | L | H | D | T | E | L | F | L | T | P | R | V |
| 541 | CCA | CTG | CAC | CTC | CAG | AAT | CTG | CGG | CTG | CAC | GAC | ACC | GAG | CTC | TTT | CTT | ACG | CCC | AGG | GTC |
|     | F | Q | G | L | V | N | L | T | H | L | Y | L | Q | R | C | G | I | T | A | V |
| 601 | TTC | CAG | GGC | CTT | GTC | AAT | CTC | ACG | CAC | CTC | TAT | CTG | CAG | AGA | TGC | GGG | ATC | ACA | GCG | GTC |
|     | P | G | N | A | L | Q | G | L | R | N | L | T | H | L | W | L | A | D | N | N |
| 661 | CCG | GGG | AAT | GCG | CTT | CAG | GGT | CTG | CGG | AAT | CTT | ACG | CAC | CTC | TGG | CTG | GCG | GAT | AAC | AAC |
|     | L | P | E | L | P | A | S | L | F | S | L | P | A | L | Q | E | L | D | L | S |
| 721 | CTC | CCT | GAG | CTT | CCC | GCC | AGC | CTC | TTC | AGC | CTG | CCA | GCA | CTC | CAG | GAG | CTG | GAC | CTG | AGC |
|     | N | N | S | L | T | A | F | H | P | A | S | F | Q | D | L | P | R | L | Q | S |
| 781 | AAC | AAC | TCC | CTG | ACA | GCG | TTC | CAT | CCA | GCG | TCC | TTC | CAG | GAC | CTC | CCT | AGG | CTC | CAG | AGT |
|     | L | S | L | A | G | N | N | L | T | E | L | P | A | H | L | P | P | G | L | S |
| 841 | CTC | TCA | CTG | GCG | GGC | AAC | AAC | CTC | ACT | GAG | CTG | CCC | GCG | CAT | CTG | CCC | CCC | GGG | CTG | TCC |
|     | T | L | E | V | Q | E | N | P | W | N | C | T | C | P | L | T | P | M | M | Y | T |
| 901 | ACT | CTG | GAG | GTG | CAA | GAG | AAC | CCC | TGG | AAT | TGT | ACC | TGT | CCC | CTG | ACC | CCA | ATG | ATG | TAC | ACC |

FIG. 1A

```
                G   A   F   N   G   L   T   E   L   R   E   L   S   L   H   T   N   A   L   Q
1021           GGT GCC TTC AAC GGG CTA ACG GAG CTT CGG GAG CTG TCC CTC CAC ACC AAC GCA CTG CAG
                D   L   D   G   N   V   F   R   M   L   A   N   L   Q   N   I   S   L   Q   N
1081           GAC CTG GAC GGG AAC GTC TTC CGC ATG TTG GCC AAC CTG CAG AAC ATC TCC CTG CAG AAC
                N   R   L   R   Q   L   P   P   G   N   I   F   A   V   N   G   L   M   A   I
1141           AAC CGC CTC AGA CAG CTC CCA CCA GGG AAT ATC TTC GCC GTC AAT GGC CTC ATG GCC ATC
                Q   L   Q   N   N   Q   L   E   L   P   L   G   I   P   D   H   L   G   K
1201           CAG CTG CAG AAC AAC CAG CTG GAG TTG CCC CTC GGG ATC CCC GAT CAC CTG GGG AAA
                L   C   E   L   R   L   Y   D   N   R   W   C   T   D   S   D   I   L   P   L
1261           CTG TGT GAG CTG CGG CTG TAT GAC AAC AGG TGG TGT ACG GAC TCA GAC ATC CTT CCG CTC
                R   N   W   L   L   L   Q   N   P   R   L   G   T   V   D   T   V   P   V   C
1321           CGC AAC TGG CTC CTG CTC CAG AAT CCC AGG TTA GGG ACG GAC ACT GTA CCT GTG TGT TTC
                S   P   A   N   V   R   G   Q   S   L   I   I   N   V   N   Y   A   V   P
1381           AGC CCA GCA AAT GTC CGA GGG CAG TCC CTC ATT ATC AAT GTC AAC TAC GCT GTT CCA
                S   Y   H   V   P   E   T   T   I   P   S   Y   P   E   T   W   P   W   T   P
1441           AGC GTC CAT GTC CCC GAG ACA ACA ATC CCA AGT TAC CCA GAA ACC TGG CCA TGG ACA CCC
                Y   T   D   L   D   L   T   I   Q   V   T   D   D   R   S   V   A   S   C   D
1501           TAT ACT GAC CTG GAT CTG ACT ATC CAG GTC ACT GAT GAC CGC AGC GTT GCC AGC TGT GAC
                A   Q   S   G   L   T   T   I   A   I   C   I   V   G   I   V   L   A   C   S
1561           GCC CAG AGC GGG CTG ACT ACT ATT GCC ATT TGC ATT GTA GGC ATT GTC CTG GCC TGC TCC
                L   A   A   C   C   P   C   V   G   C   C   K   K   R   S   Q   M   T   Q
1621           CTG GCT GCC TGC TGC CCG TGT GTC GGC TGC TGC AAG AAG AGG AGC CAA ATG ACC CAG
                M   K   A   P   N   E   C
1681           ATG AAG GCA CCC AAT GAG TGT                                     (SEQ ID NO:1)
                                                                                (SEQ ID NO:2)
1741 legend:
predicted signal peptide is bold italicized
predicted transmembrane domain is underlined
predicted protease cleavage site is boxed
```

FIG. 1B huLRRC15 isoform 2 (NCBI accession: NP_570843, REFSEQ: NM_130830.4)

```
      M   P   L   K   H   Y   L   L   L   V   G   C   Q   A   W   G   A   G   L
  1   ATG CCA CTG AAG CAT TAT CTC TTG CTG GTG GGC TGC CAA GCC TGG GGT GCA GGG TTG
      A   Y   H   G   C   P   S   E   C   T   C   S   R   A   S   Q   V   E   C
 61   GCC TAC CAT GGC TGC CCT AGC GAG TGT ACC TGC AGG GCC TCC CAG GTG GAG TGC ACC
      G   A   R   I   V   A   V   T   P   L   P   W   N   A   M   S   L   Q   I
121   GGG GCA CGC ATT GTG GCA GTG ACC CCT CTG CCC TGG AAC GCC ATG AGC CTG CAG ATC
      L   N   T   H   I   T   E   L   N   E   S   P   F   L   N   I   S   A   L
181   CTC AAC ACG CAC ATC ACT GAA CTC AAT GAG TCC CCG TTC CTC AAT ATC TCA GCC CTC
      A   L   R   K   I   E   R   Y   L   A   N   N   K   L   T   P   G   R   N
241   GCC CTG AGG AAG ATT GAG TAT CTC GCC AAT AAC AAG CTC ACG CCT GGG CGA AAC CTG
      G   S   L   R   L   D   S   L   E   S   L   L   L   S   N   N   K   L   G
301   GGC TCG CTG CGC CTG GAT AGC CTG GAG TCT CTG CTC CTG AGT AAC AAC AAG CTC GGG
      F   Q   G   P   A   H   F   S   Q   C   Q   N   L   K   E   L   G   L   H
361   TTC CAG GGC CCT GCC CAC TTC TCC CAG TGC CAG AAC CTG AAG GAG CTG GGG CTC CAC
      Q   L   E   Y   L   H   L   Q   L   N   D   L   K   Q   V   G   G   N   L
421   CAG CTG GAA TAC CTG CAC CTG CAG CTG AAC GAC CTG AAG CAG GTA GGA CTC CTC AAT
      L   G   K   N   S   Q   L   T   H   L   D   L   S   R   N   Q   L   L   G
481   CTG GGC AAG AAT AGC CAG CTC ACC CAC CTG GAC CTG TCA CGT AAC CAG CTC CTT CTC
      V   L   R   L   Y   E   L   Y   E   N   R   L   A   L   R   L   L   D   I
541   GGC GTT CTC CGG CTG TAT GAG CTC TAT GAG AAC AGG CTC GCT CTG AGA CTC CTG GAT
      S   N   L   Q   A   L   Q   G   L   G   I   L   R   I   L   S   P   G   L
601   GTC AAC CTG CAG GCG CTG CAG GGG ATC CTG CAC CCT ATT TCC CGC TTC CTG CTG GGC
      F   S   N   L   P   N   L   R   M   P   M   F   N   S   V   N   L   Y   L
661   GTT AAC AGC AAC CTG CCG GAA CTC CAG CCC AAC CTG TTC TCA CCC ATG ATC TAC TTC
      F   K   T   N   T   L   T   N   L   R   L   E   L   L   H   L   Q   L   S
721   TTC CAC AAC AAT ATG CAG CTC AGA CCC ATG ACT CAG AAC CTG AAC CTG CAC CTC CTC
      P   L   K   E   F   S   P   G   F   P   F   L   Q   N   L   L   S   N   L
781   CCA CTG AAG GAG TTC ATG CCG GGG ATC TTC TCT CTT CTT CGG GAG AAC CTC TCC AAT
      L   K   E   L   S   L   T   N   N   L   L   T   T   L   R   S   N   L   W
841   CTG AAG GAG CTC TCT CTA CCC GAC ATC CGC AAC CTG AGC AGC CTT TGG GAG CTT TGG
      Y   D   N   L   I   S   R   N   Q   I   P   S   P   F   N   G   L   Q   L
901   TAT GAC AAC CTC ATT TCT CGC AAT CAG ATC CCG TCC CCG TTC AGC GGC CAG TTG CAG
      V   L   I   L   L   S   L   N   F   I   F   I   S   C   G   L   N   G   L
961   GTC CTG ATT CTT CTA AGC CTC AAT TTC ATC TTC ATC AGC TGC GGT CTC AAC GGG CTA
```

FIG. 1C

```
1021 ACG GAG CTT CGG GAG CTG TCC CTC CAC ACC AAC GCA CTG CAG GAC CTG GAC GGG AAC GTC
      T   E   L   R   E   L   S   L   H   T   N   A   L   Q   D   L   D   G   N   V
1081 TTC CGC ATG TTG GCC AAC CTG CAG CAG AAC ATC TCC CTC ATG CTG CAG AAC CGC CTC AGA CAG CTC
      F   R   M   L   A   N   L   Q   Q   N   I   S   L   M   L   Q   N   R   L   R   Q   L
1141 CCA GGG AAT ATC TTC GCC AAC GTC AAT GGC CTC ATG GCC ATC CAG CAG AAC CTG CAG AAC CAG
      P   G   N   I   F   A   N   V   N   G   L   M   A   I   Q   Q   N   L   Q   N   Q
1201 CTG GAG AAC TTG CCC CTG CAT TTC GAT CAC CTG AAA CTG TGT GAG CTG CTG CGG CTG
      L   E   N   L   P   L   H   F   D   H   L   K   L   C   E   L   L   R   L
1261 TAT GAC AAT CCC TGG AGG TGT GAC TCA GAC ATC CTT CCG CTC CGC AAC TGG AAC CTC CTC
      Y   D   N   P   W   R   C   D   S   D   I   L   P   L   R   N   W   N   L   L
1321 AAC CAG CCT AGG TTA GGG ACG GAC ACT GTA CCT GTG TTT TTC AGC CCA GCC AAT GTC CGA
      N   Q   P   R   L   G   T   D   T   V   P   V   F   F   S   P   A   N   V   R
1381 GGC CAG TCC CTC ATT ATC AAT GTC GCT GTT GCT GAT ACA AGC AGC CAT GTC CCC GAG
      G   Q   S   L   I   I   N   V   A   V   A   D   T   S   S   H   V   P   E
1441 GTG CCT AGT TAC CCA GAA ACA CCA TGG TAC CCA CCC AGT TAC TAC CCT GAC CTG ACA
      V   P   S   Y   P   E   T   P   W   Y   P   P   S   Y   Y   P   D   L   T
1501 TCC GTC TCT TCT ACC GAG CTA ACC AGC CCT GTG GAA GAC TAC ACT CAG AGC GGG ACT ACC
      S   V   S   S   T   E   L   T   S   P   V   E   D   Y   T   Q   S   G   T   T
1561 ATT CAG GTC ACT GAT GAT GAC CGC AGC GTT TGG GGC ATG ACC CAG ACC CAG AGC GGG CTG GCC
      I   Q   V   T   D   D   D   R   S   V   W   G   M   T   Q   T   Q   S   G   V   G
1621 ATT GCC ATT GTA ATT GGG ATT GCC CTG CTG GCT GCC ATG AAG ATG
      I   A   I   V   I   G   I   A   L   L   A   A   M   K   M
1681 TGT TGC TGC AAG AAG AGG AGC CAA CAA CCC AAT GAG
      C   C   C   K   K   R   S   Q   Q   P   N   E
1741 TGT    (SEQ ID NO:3)
      C      (SEQ ID NO:4)

Legend:
predicted signal peptide is bold italicized
predicted transmembrane domain is underlined
predicted protease cleavage site is boxed
```

FIG. 1D

Exemplary Anti-huLRRC15 Antibody V_H Chains

```
                    1          2          3          4          5           6          7          8
           1234567890 1234567890 1234567890 1234567890 12a34567890 1234567890 1234567890 1234567890
huM25      EVQLVQSGAE VKKPGASVKV SCKASGYKFS SYWIEWVKQA PGQGLEWIGE  ILPGSDTTNYN EKFKDRATFT SDTSINTAYM
huAD208.4.1  EVQLVQSGAE VKKPGSSVKV SCKASGFTFT DYYIHWVKQA PGQGLEWIGL VYPYIGGTNYN QKFKGKATLT VDTSTTTAYM
huAD208.12.1 EVQLVQSGAE VKKPGSSVKV SCKASGYTFT NYWMHWVKQA PGQGLEWIGM IHPNSGSTKHN EKFRGKATLT VDESTTTAYM
huAD208.14.1 EVQLVQSGAE VKKPGSSVKV SCKASGFTFT DYYIHWVKQA PGQGLEWIGL VYPYIGGSSYN QQFKGKATLT VDTSTSTAYM
hu139.10   EVQLVESGGG LVQPGGGSLRL SCAVSGFSLT SYGVHWVRQA TGKGLEWLGV IW-AGGSTNYN SALMSRLTIS KENAKSSVYL
muAD210.40.9 QVQLQQSGAE LVRPGTSVKI SCKASGYDFT NYWLGWVKQR PGHGLEWIGD IYPGGGNTYYN EKLKGKATLT ADKSSSTAYI
muAD209.9.1 QIQLVQSGPE LKKPGETVKI SCKASGFAIT NFGMNWVKQA PGKGLKWMGW INLYTGEPTFA DDFKGRFAFS LETSASTAYL 1          1
                                      0                    1
             12abc34567890 1234567890 abcde1234567890 123
huM25        ELSRLRSDDTAVY YCARDRGNYR AWF--GYWGQGTLVT VSS  (SEQ ID NO:16)
huAD208.4.1  EMSSLRSEDTAVY YCARGDNKYD AM---DYWGQGTTVT VSS  (SEQ ID NO:26)
huAD208.12.1 ELSSLRSEDTAVY YCARSDFGNY RWYF-DVWGQGTTVT VSS  (SEQ ID NO:36)
huAD208.14.1 ELSSLRSEDTAVY YCARGDNNYD AM---DYWGQGTTVT VSS  (SEQ ID NO:46)
hu139.10     QMNSLRAGDTAMY YCATHMITED YYGM-DYWGQGTTVT VSS  (SEQ ID NO:56)
muAD210.40.9 HLISLTSEDSSVI FCARWGDKKG NYF--AYWGQGTLVT VSA  (SEQ ID NO:66)
muAD209.9.1  QINNLKNEDTVIY FCARKGETYY RYDGFAYWGQGTLVT VSA  (SEQ ID NO:76)
```

FIG. 2A

Legend:
Complementarity determining regions (CDR's) are underlined

Exemplary Anti-huLRRC15 Antibody V_L Chains

```
              1          2            3                4          5            6          7
           1234567890 1234567890 1234567abcdef890 1234567890 1234567890 1234567890 1234567890
huM25      DIQMTQSPSS LSASVGDRVT ITCRASQ------DIS NYLNWYQQKP GGAVKFLIYY TSRLHSGVPS RFSGSGSGTD
huAD208.4.1  DIVLTQSPDS LAVSLGERAT INCRASQSVST---SSY SYMHWYQQKP GQPPKLLIKY ASSLESGVPD RFSGSGSGTD
huAD208.12.1 EIVLTQSPAT LSLSPGERAT LSCRASQ------SSS NNLHWYQQKP GQAPRVLIKY VSQSISGIPA RFSGSGSGTD
huAD208.14.1 DIVLTQSPDS LAVSLGERAT ISCRASQSVST---STY NYMHWYQQKP GQPPKLLIVKY ASNLESGVPD RFSGSGSGTD
hu139.10    DIVMTQSPDS LAVSLGERAT INCKSSQSLLNSRTRK NYLAWYQQKP GQSPKLLIYW ASTRESGVPD RFSGSGSGTD
muAD210.40.9 QIVLTQSPAI MSASLGERVT MTCTASSS------VYS SYLHWYQQKP GSSPKLWIYS TSNLASGVPG RFSGSGSGTS
muAD209.9.1  DIVMTQAAPS VPVTPGESVS ISCRSSKSLLHS-NGN THLYWFLQRP GQSPQLLIYR MSNLASGVPD RFSGSGSGTA 1
              8          9            0
           1234567890 1234567890 1234567
huM25      YTLTISSLQP EDFATYFCQQ GEALPWTFGG GTKVEIK (SEQ ID NO:17)
huAD208.4.1  FTLTISSLQA EDVAVYYCEQ SWEI-RTFGG GTKVEIK (SEQ ID NO:27)
huAD208.12.1 FTLTISSLEP EDFAVYFCQQ SNSWPFTFGQ GTKLEIK (SEQ ID NO:37)
huAD208.14.1 FTLTISSLQA EDVAVYYCHH TWEI-RTFGG GTKVEIK (SEQ ID NO:47)
hu139.10    FTLTISSLQA EDVAVYYCKQ SYNL-PTFGG GTKVEIK (SEQ ID NO:57)
muAD210.40.9 YSLTISSMEA EDAATYYCHQ YHRS-PTFGG GTKLEIK (SEQ ID NO:67)
muAD209.9.1  FTLRISRVEA EDVGVYYCMQ LLEYPYTFGG GTKLEIE (SEQ ID NO:77)
```

Legend:
Complementarity determining regions (CDR's) are underlined

FIG. 2B

Antibody huM25 Heavy Chain (SEQ ID NO: 18)

EVQLVQSGAE VKKPGASVKV SCKASGYKFS <u>SYWIEWVKQA</u> PGQGLEWIGE <u>ILPGSDTTNY</u> 60
<u>NEKFKDRATF</u> TSDTSINTAY MELSRLRSDD TAVYYCARDR <u>GNYRAWFGYW</u> GQGTLVTVSS 120
*ASTKGPSVFP LAPSSKSTSG GTAALGCLVK DYFPEPVTVS WNSGALTSGV HTFPAVLQSS* 180
*GLYSLSSVVT VPSSSLGTQT YICNVNHKPS NTKVDKKVEP KSCDKTHTCP PCPAPELLGG* 240
*PSVFLFPPKP KDTLMISRTP EVTCVVVDVS HEDPEVKFNW YVDGVEVHNA KTKPREEQYN* 300
*STYRVVSVLT VLHQDWLNGK EYKCKVSNKA LPAPIEKTIS KAKGQPREPQ VYTLPPSREE* 360
*MTKNQVSLTC LVKGFYPSDI AVEWESNGQP ENNYKTTPPV LDSDGSFFLY SKLTVDKSRW* 420
*QQGNVFSCSV MHEALHNHYT QKSLSLSPGK* 450

Legend:
Complementarity determining regions (CDR's) are <u>underlined</u>
Heavy chain $F_c$ gamma (γ) is *italicized*

FIG. 3A

Antibody huM25 Light Chain (SEQ ID NO: 19)

DIQMTQSPSS LSASVGDRVT ITC<u>RASQDIS</u> <u>NYLN</u>WYQQKP GGAVKFLIY<u>Y</u> <u>TSRLHSGVPS</u> 60
RFSGSGSGTD YTLTISSLQP EDFATYFC<u>QQ</u> <u>GEALPWT</u>FGG GTKVEIKRTV *AAPSVFIFPP* 120
*SDEQLKSGTA SVVCLLNNFY PREAKVQWKV DNALQSGNSQ ESVTEQDSKD STYSLSSTLT* 180
*LSKADYEKHK VYACEVTHQG LSSPVTKSFN RGEC*

Legend:
Complementarity determining regions (CDR's) are <u>underlined</u>
Light chain kappa (κ) is *italicized*

FIG. 3B

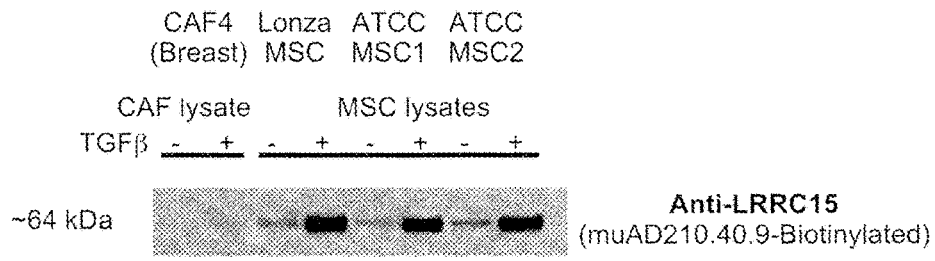
FIG. 9A
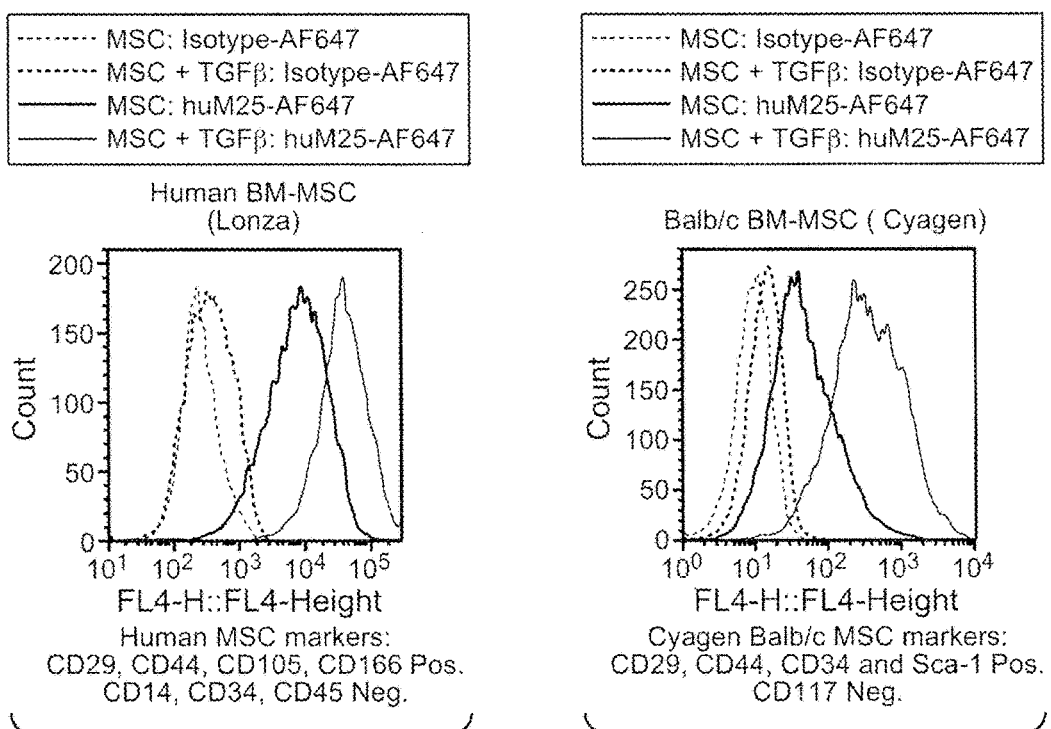
FIG. 9B
FIG. 9C

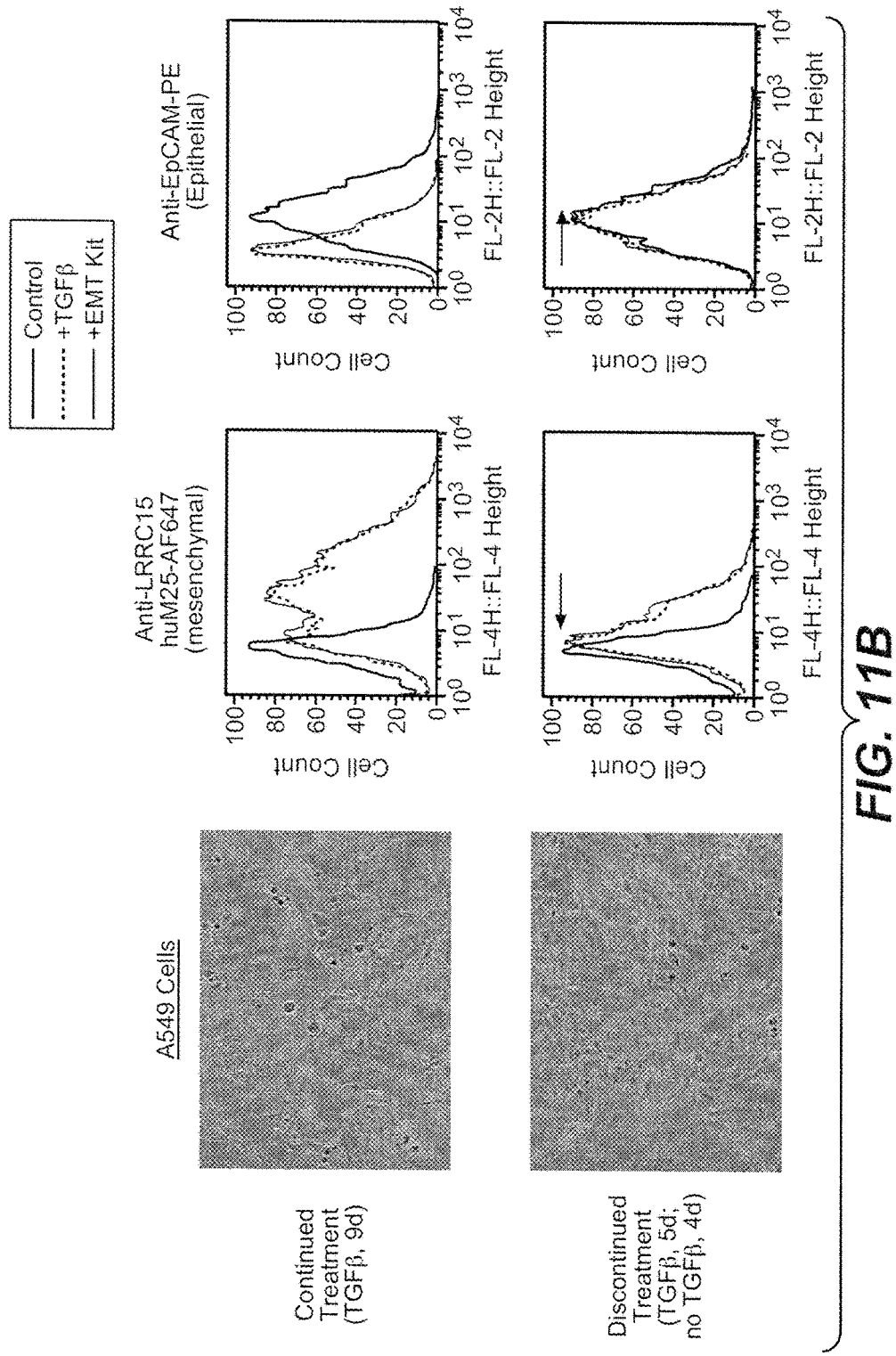

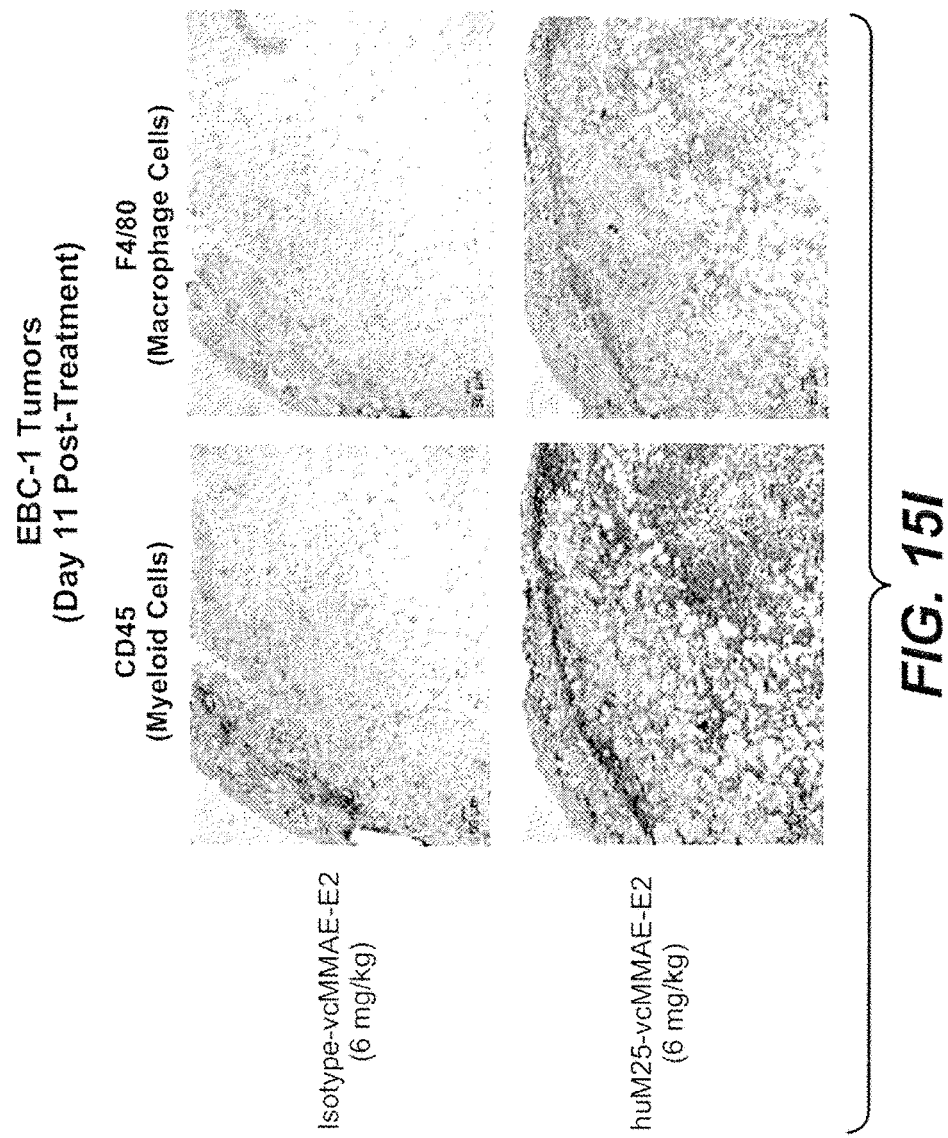

Figure 20A:
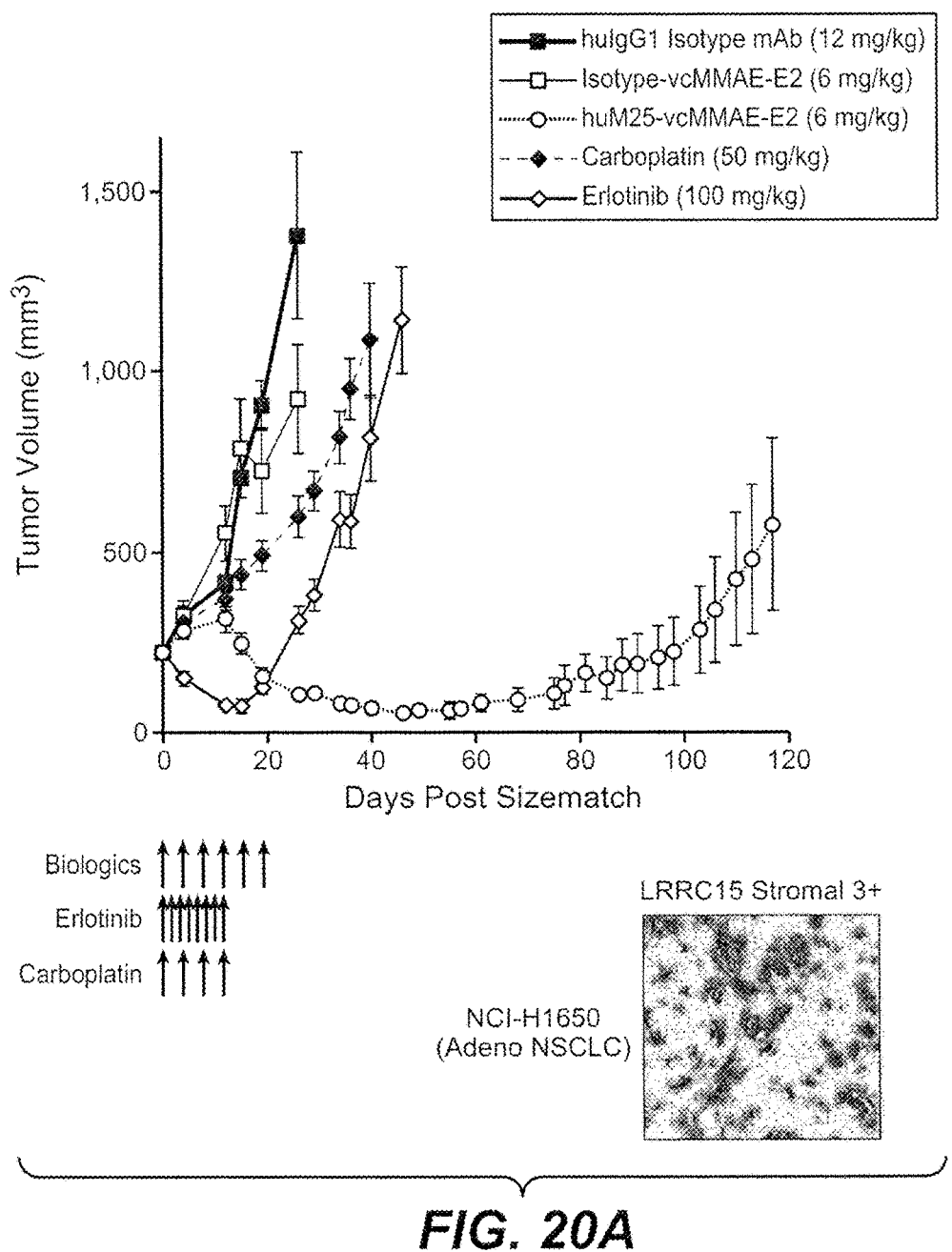

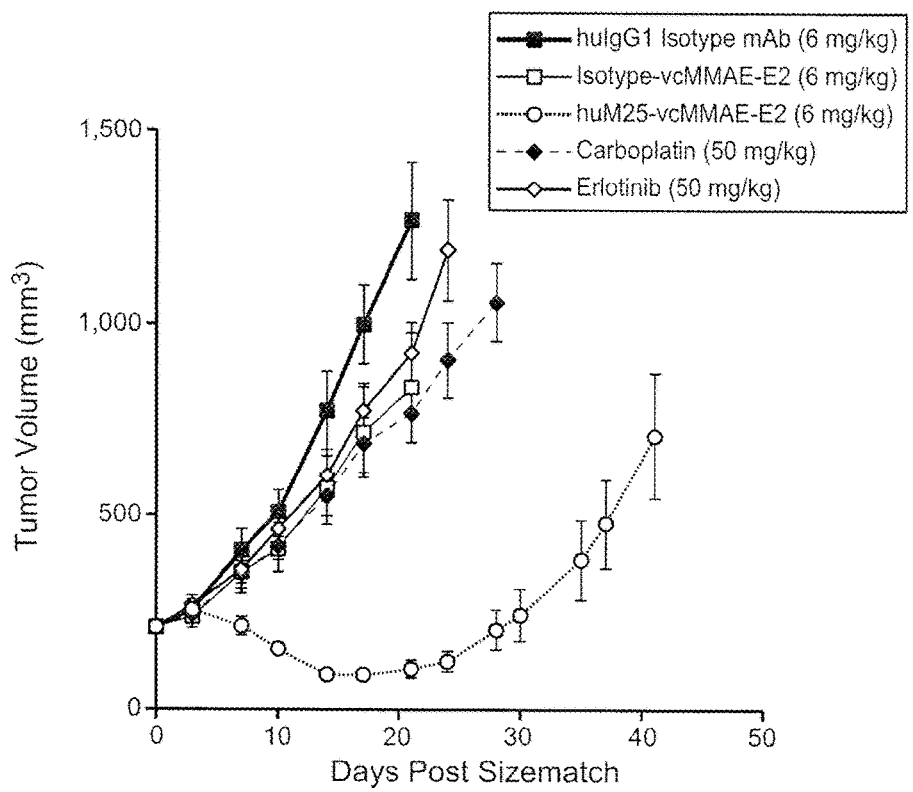
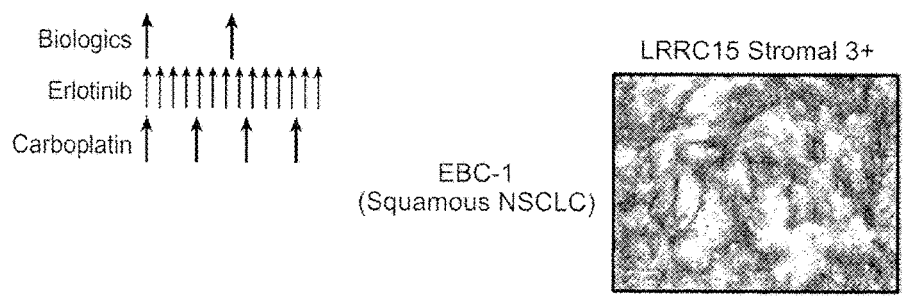
FIG. 20C

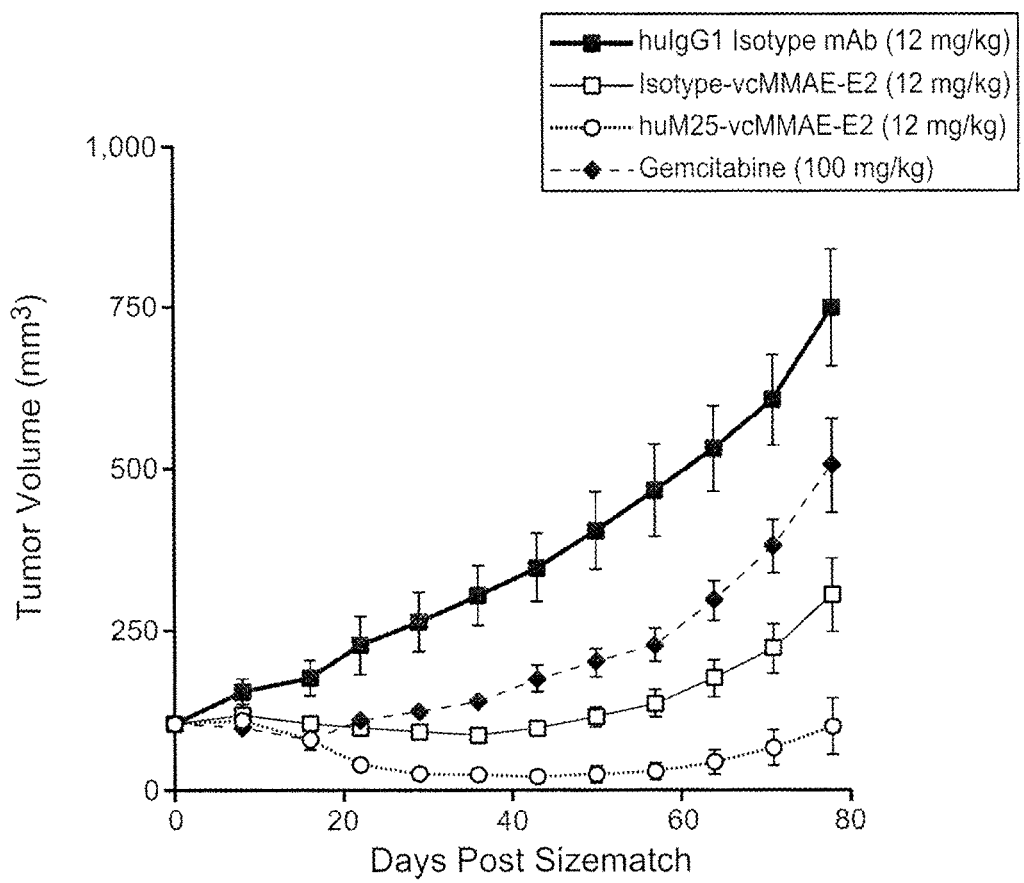
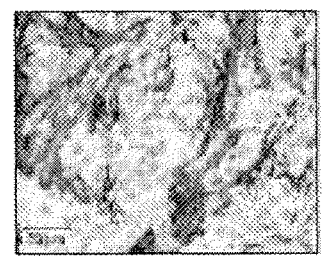
FIG. 20E

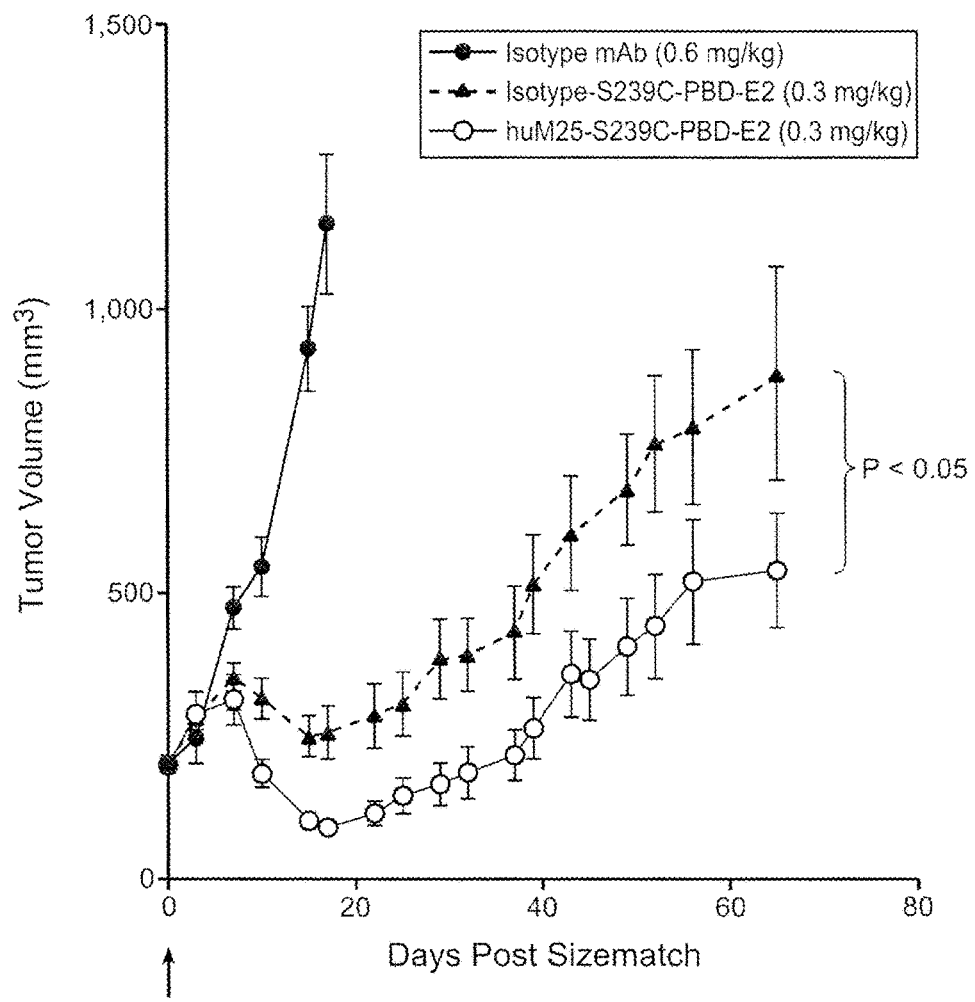
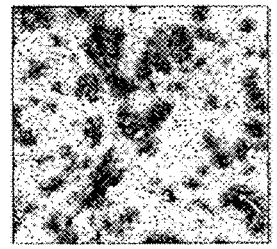
FIG. 24F

ANTI-HULRRC15 ANTIBODY DRUG CONJUGATES AND METHODS FOR THEIR USE

1. CROSS REFERENCE TO RELATED APPLICATIONS

This application claims the benefit under 35 U.S.C. § 119(e) of U.S. provisional application No. 62/261,092, filed Nov. 30, 2015, and U.S. provisional application No. 62/417,480, filed Nov. 4, 2016, the contents of both of which are incorporated herein in their entireties by reference thereto.

2. SEQUENCE LISTING

The instant application contains a Sequence Listing which has been submitted electronically in ASCII format and is hereby incorporated by reference in its entirety. Said ASCII copy, created on Nov. 11, 2016, is named 381493-259US (144357)_SL.txt and is 104,856 bytes in size.

3. FIELD

The present application pertains to, among other things, anti-huLRRC15 antibodies, antibody drug conjugates ("ADCs"), compositions including the ADCs, methods of making the ADCs, and methods of using the ADCs to treat cancers.

4. BACKGROUND

Cancer therapies comprise a wide range of therapeutic approaches, including surgery, radiation, and chemotherapy. While the often complementary approaches allow a broad selection to be available to the medical practitioner to treat the cancer, existing therapeutics suffer from a number of disadvantages, such as a lack of selectivity of targeting cancer cells over normal, healthy cells, and the development of resistance by the cancer to the treatment.

Recent approaches based on targeted therapeutics, which interfere with cellular processes of cancer cells preferentially over normal cells, have led to chemotherapeutic regimens with fewer side effects as compared to non-targeted therapies such as radiation treatment. Nevertheless, cancers treated with targeted therapeutics may still develop resistance. For example, resistance to bevacizumab, a monoclonal antibody therapeutic that targets VEGF-positive cancer cells, has been reported in some colorectal cancers (Mesange et al. Oncotarget 2014; 5(13): 4709-4721).

A mechanism for treatment resistance is believed to be the formation by activated fibroblasts (e.g., cancer associated fibroblasts (CAFs), mesenchymal stem cells (MSCs)) in the tumor microenvironment which prevents cancer drugs from physically reaching the cancer cells (Kalluri R., Nature Reviews Cancer 2016; 16: 582-598). In addition, the fibroblast-mediated stromal barrier is understood to give rise to an immunosuppressive environment that can prevent immune effector cells from penetrating deep into the tumor and targeting cancer cells (Turley, S. J. Nature Reviews Immunology 2015; 15:669-682). Hence, a cancer drug that targets these stromal fibroblast populations within the tumor microenvironment would complement existing therapeutic strategies and may overcome chemoresistance and increase sensitivity to immune mediated therapies.

Another source of treatment resistance is thought to be the plasticity of cancer cells. For example, the plasticity of cancer cells between epithelial and mesenchymal states has been implicated as a mechanism for the generation of cancer stem cells, which can initiate tumors, as well as serve as a starting point for metastasis. See Ye, X.; Weinberg, R. A. Trends in Cell Biology 2015; 25 (11): 675-686. Further, mesenchymal cancer cells have been reported to be resistant to standard cancer therapies, such as docetaxel. See Singh and Settleman. Oncogene 2010; 29(34): 4741-4751; Ippolito, L. et al. Oncotarget 2016; 7 (38): 61890-61904. A cancer therapy that is effective against these resistant cancer cells would complement existing therapeutic approaches.

Thus, cancer therapeutics that spare normal cells and are less prone to developing clinical resistance would provide additional options for treating cancer, such as by augmenting existing standard of care regimens.

5. SUMMARY

Human LRRC15 (leucine-rich repeat-containing protein 15) is a cell surface protein that has been reported to exist in two isoforms: one containing 587 amino acids (SEQ ID NO:1; NP_001128529.2) and another containing 581 amino acids (SEQ ID NO:3; NP_570843.2) that is truncated at its N-terminus as compared to the longer isoform of SEQ ID NO:1. The amino acid sequences of both isoforms are illustrated in FIGS. 1A-1D. For ease of discussion, human LRRC15 is abbreviated herein as "huLRRC15." This abbreviation is intended to refer to either isoform. In instances where a specific isoform is intended, the abbreviations "huLRRC15l" and "huLRRC15s" for the longer isoform of SEQ ID NO:1 and shorter isoform of SEQ ID NO:3, respectively, are used.

Referring to FIGS. 1C-1D (SEQ ID NO:3), huLRRC15 comprises an extracellular domain ("ECD") spanning residues 22 to 538, a transmembrane domain ("TMD") spanning residues 539 to 559, and an intracellular domain ("ICD") spanning residues 560 to 581. The leader sequence of huLRRC15, illustrated in FIGS. 1A-1B (SEQ ID NO:1), is shown in bold text and the transmembrane domain underlined, thereby indicating the ECD, TMD and ICD of their isoforms. Referring again to FIGS. 1C-1D (SEQ ID NO:3), the ECD contains a proteolytic cleavage site approximately between residues $Arg^{527}$ and $Ser^{528}$, the cleavage of which results in shedding of the portion of the ECD spanning approximately residues 24-527 ("shed ECD" or "sECD") from the cell surface and into the blood stream. huLRRC15 is highly expressed in the stromal microenvironment (and specifically on cancer-associated fibroblasts) of several solid tumors (see, e.g., Example 4 and FIG. 7), and exhibits limited expression in normal tissue types (see, e.g., Example 5 and FIG. 8). It is also expressed on certain cancer cells per se (e.g., sarcomas, melanomas and glioblastomas, data not shown). Data presented herein demonstrate, for the first time, that antibody drug conjugates ("ADCs") that specifically target huLRRC15 exhibit potent antitumor effects, both alone and in combination with other targeted and non-targeted antitumor therapies, against solid tumors in which huLRRC15 is expressed in the tumor stromal microenvironment, but not on the cancer cells per se ((referred to herein as "huLRRC15 stromal(+)/cancer(−) tumors")). Data demonstrating in vivo anti-tumor efficacy of anti-huLRRC15 ADCs administered as monotherapy are provided in Example 10 and FIGS. 13A-13C. While not intending to be bound by any theory of operation, it is believed that this potent antitumor effect is mediated, at least in part, via a targeted bystander killing effect (see, e.g., Example 12 and FIGS. 15A-15I and 17B), although direct killing of stromal cells expressing huLRRC15 may also play a role. This potent antitumor activity is surprisingly observed with anti-LRRC15 ADCs that specifically bind the portion of the huLRRC15 ECD domain that is shed from the cell surface, and demonstrates for the first time that such anti-LRRC15 ADCs may be used as therapeutically for the treatment of huLRRC15 stromal(+)/cancer(−) tumors.

Accordingly, in one aspect, the present disclosure provides ADCs that specifically bind huLRRC15 ("anti-huLRRC15 ADCs"). The anti-huLRRC15 ADCs comprise cytotoxic and/or cytostatic agents linked by way of linkers to an antigen binding moiety that specifically binds huLRRC15 at a portion of the ECD that is shed from the cell surface. The antigen binding moiety may be any moiety capable of specifically binding huLRRC15. In some embodiments, the antigen binding moiety is an antibody and/or an antibody antigen binding fragment.

Antibodies and/or binding fragments composing the anti-huLRRC15 ADCs generally comprise a heavy chain comprising a variable region ($V_H$) having three complementarity determining regions ("CDRs") referred to herein (in N→C order) as $V_H$ CDR#1, $V_H$ CDR#2, and $V_H$ CDR#3, and a light chain comprising a variable region ($V_L$) having three complementarity determining regions referred to herein in N→C order) as $V_L$ CDR#1, $V_L$ CDR#2, and $V_L$ CDR#3. The amino acid sequences of exemplary CDRs, as well as the amino acid sequence of the $V_H$ and $V_L$ regions of the heavy and light chains of exemplary anti-huLRRC15 antibodies and/or binding fragments that can be included in antigen binding moieties composing the anti-huLRRC15 ADCs are provided herein. Specific embodiments of anti-huLRRC15 ADCs include, but are not limited to, those that comprise antibodies and/or binding fragments that include these exemplary CDRs and/or $V_H$ and/or $V_L$ sequences, as well as antibodies and/or binding fragments that compete for binding huLRRC15 with such antibodies and/or binding fragments.

Antibodies may be in the form of full-length antibodies, bispecific antibodies, dual variable domain antibodies, multiple chain or single chain antibodies, surrobodies (including surrogate light chain construct), single domain antibodies, camelized antibodies, scFv-Fc antibodies, and the like. They may be of, or derived from, any isotype, including, for example, IgA (e.g., $IgA_1$ or $IgA_2$), IgD, IgE, IgG (e.g., $IgG_1$, $IgG_2$, $IgG_3$ or $IgG_4$), IgM, or IgY. In some embodiments, the anti-huLRRC15 antibody is an IgG (e.g., $IgG_1$, $IgG_2$, $IgG_3$ or $IgG_4$). Antibodies may be of human or non-human origin. Examples of non-human origin include, but are not limited to, mammalian origin (e.g., simians, rodents, goats, and rabbits) or avian origin (e.g., chickens). In specific embodiments, antibodies composing the anti-huLRRC15 ADCs are suitable for administration to humans, such as, for example, humanized antibodies and/or fully human antibodies.

Antibody antigen binding fragments composing the anti-huLRRC15 ADCs may include any fragment of an antibody capable of specifically binding huLRRC15. Specific examples of antibody antigen binding fragments that may be included in the anti-huLRRC15 ADCs include, but are not limited to, Fab, Fab', $(Fab')_2$, Fv and scFv.

Antibodies and/or binding fragments composing the anti-huLRRC15 ADCs may include modifications and/or mutations that alter the properties of the antibodies and/or fragments, such as those that increase half-life, increase or decrease ADCC, etc., as is known in the art.

For therapeutic uses, it may be desirable to utilize anti-huLRRC15 ADCs that bind huLRRC15 with an affinity of at least 100 nM. Accordingly, in some embodiments, the anti-huLRRC15 ADCs comprise an anti-huLRRC15 antibody and/or anti-huLRRC15 binding fragment that binds huLRRC15 with an affinity of at least about 100 nM, or even higher, for example, at least about 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM, or greater. Affinity of anti-huLRRC15 antibodies and/or binding fragments can be determined using techniques well known in the art or described herein, such as for example, ELISA, isothermal titration calorimetry (ITC), surface plasmon resonance, flow cytometry, or fluorescent polarization assay.

The cytotoxic and/or cytostatic agents composing the anti-huLRRC15 ADCs may be any agents known to inhibit the growth and/or replication of, and/or kill cells. Numerous agents having cytotoxic and/or cytostatic properties are known in the literature. Non-limiting examples of classes of cytotoxic and/or cytostatic agents include, by way of example and not limitation, cell cycle modulators, apoptosis regulators, kinase inhibitors, protein synthesis inhibitors, alkylating agents, DNA cross-linking agents, intercalating agents, mitochondria inhibitors, nuclear export inhibitors, topoisomerase I inhibitors, topoisomerase II inhibitors, RNA/DNA antimetabolites and antimitotic agents.

As will be discussed in more detail in the Detailed Description, and while not intending to be bound by any particular theory of operation, data included herein demonstrate that anti-huLRRC15 ADCs exert potent anti-tumor activities mediated, at least in part, by a targeted bystander effect. For example, it is demonstrated herein that an anti-huLRRC15 ADC comprising the microtubule inhibitor monomethyl auristatin E ("MMAE") linked to an anti-huLRRC15 antibody by way of linkers cleavable by lysosomal enzymes potently inhibits and/or kills huLRRC15 stromal(+)/cancer(−) tumors, yet does not significantly inhibit or kill more slowly dividing huLRRC15-expressing stromal fibroblasts (see, e.g., Example 12 and FIGS. 15B-15I and 16). An anti-huLRRC15 ADC comprising the microtubule inhibitor monomethyl auristatin F ("MMAF") linked to an anti-huLRRC15 antibody by way of non-cleavable linkers had potent in vitro activity against cells expressing huLRRC15, but had little efficacy against huLRRC15 stromal(+)/cancer(−) tumors in vivo (see, e.g., Example 12 and FIGS. 17A-17B). Together, these data indicate that anti-huLRRC15 ADCs may be used to potently inhibit huLRRC15 stromal(+)/cancer(−) tumors via two different mechanisms of action, or a combination of both mechanisms: a first mechanism in which the cytotoxic and/or cytostatic agents composing the anti-huLRRC15 ADCs are cytotoxic and/or cytostatic to the huLRRC15-expressing stromal cells per se, thereby disrupting and/or destroying the stromal microenvironment crucial to support and/or growth of the huLRRC15 stromal(+)/cancer(−) tumor; and a second mechanism in which the cytotoxic and/or cytostatic agents composing the anti-huLRRC15 ADCs are not necessarily cytotoxic and/or cytostatic to the huLRRC15-expressing stromal cells, but are cytostatic and/or cytotoxic to the rapidly dividing huLRRC15 cancer(−) cells. Skilled artisans will appreciate that for this latter mechanism of action, the cytotoxic and/or cytostatic agents composing the anti-huLRRC15 ADCs, once cleaved from the anti-huLRRC15 ADCs, should be capable of traversing cell membranes. For the former mechanism of action, the cytotoxic and/or cytostatic agents, once cleaved from the anti-huLRRC15 ADC, need not be capable of traversing cell membranes. Cytotoxic and/or cytostatic agents having hydrophobicities sufficient to traverse cell membranes such that they are useful for inhibiting and/or killing tumors via a targeted bystander effect may be identified using routine methods known to those of skill in the art. Cytotoxic and/or cytostatic agents having hydrophobicities such that they are capable of traversing cell membranes and permeating into cells are referred to herein as "cell-permeating cytotoxic and/or cytostatic agents."

Skilled artisans will also appreciate that the above two mechanisms of action are not mutually exclusive, and that in some embodiments it may be desirable to utilize anti-huLRRC15 ADCs capable of exerting antitumor activity against huLRRC15 stromal(+)/cancer(−) tumors via both mechanisms of action. As a specific example, such an anti-huLRRC15 ADC may include a cell-permeating cytotoxic and/or cytostatic agent that is cytotoxic and/or cytostatic to both huLRRC15-expressing stromal cells and huLRRC15 cancer(−) tumor cells linked to an anti-huLRRC15 antibody by way of a cleavable linker. As another specific embodiment, such an anti-huLRRC15 ADC may include two different cytotoxic and/or cytostatic agents: a first that is cytotoxic and/or cytostatic to the huLRRC15-expressing stromal cells (and optionally, but not necessarily, also cytotoxic and/or cytostatic to the huLRRC15 cancer(−) tumor cells); and a second that is cytotoxic and/or cytostatic to the huLRRC15-expressing stromal cells. The first agent could be, but need not be, a cell-permeating cytotoxic and/or cytostatic agent, and could be, but need not be, linked to the antigen binding moiety of the anti-huLRRC15 ADC by way of a cleavable linker. The second agent is a cell-permeating cytotoxic and/or cytostatic agent and is linked to the antigen binding moiety of the anti-huLRRC15 ADC by way of a cleavable linker.

In a specific embodiment, a cytotoxic and/or cytostatic agent composing an anti-huLRRC15 ADC is a cell-permeating antimitotic agent, such as, for example, an auristatin. Specific examples of cell-permeating auristatins include, but are not limited to, dolastatin-10 and monomethyl auristatin E ("MMAE"). In another specific embodiment, a cytotoxic and/or cytostatic agent composing an anti-huLRRC15 ADC is a cell-permeating DNA cross-linking agent, such as a cell-permeating minor groove-binding DNA cross-linking agent. Specific examples of cell-permeating DNA minor groove-binding agents include, but are not limited to, pyrrolobenzodiazepines ("PBD") and PBD dimers.

The linkers linking the cytotoxic and/or cytostatic agents to the antigen binding moiety of an anti-huLRRC15 ADC may be long, short, flexible, rigid, hydrophilic or hydrophobic in nature, or may comprise segments that have different characteristics, such as segments of flexibility, segments of rigidity, etc. The linker may be chemically stable to extracellular environments, for example, chemically stable in the blood stream, or may include linkages that are not stable and release the cytotoxic and/or cytostatic agents in the extracellular milieu. In some embodiments, the linkers include linkages that are designed to release the cytotoxic and/or cytostatic agents upon internalization of the anti-huLRRC15 ADC within the cell. In some specific embodiments, the linkers includes linkages designed to cleave and/or immolate or otherwise breakdown specifically or non-specifically inside cells. A wide variety of linkers useful for linking drugs to antigen binding moieties such as antibodies in the context of ADCs are known in the art. Any of these linkers, as well as other linkers, may be used to link the cytotoxic and/or cytostatic agents to the antigen binding moiety of the anti-huLRRC15 ADCs described herein.

The number of cytotoxic and/or cytostatic agents linked to the antigen binding moiety of an anti-huLRRC15 ADC can vary (called the "drug-to-antibody ratio," or "DAR"), and will be limited only by the number of available attachments sites on the antigen binding moiety and the number of agents linked to a single linker. Typically, a linker will link a single cytotoxic and/or cytostatic agent to the antigen binding moiety of an anti-huLRRC15 ADC. In embodiments of anti-huLRRC15 ADCs which include more than a single cytotoxic and/or cytostatic agent, each agent may be the same or different. As long as the anti-huLRRC15 ADC does not exhibit unacceptable levels of aggregation under the conditions of use and/or storage, anti-huLRRC15 ADCs with DARs of twenty, or even higher, are contemplated. In some embodiments, the anti-huLRRC15 ADCs described herein may have a DAR in the range of about 1-10, 1-8, 1-6, or 1-4. In certain specific embodiments, the anti-huLRRC15 ADCs may have a DAR of 2, 3 or 4.

In some embodiments, the anti-huLRRC15 ADCs are compounds according to structural formula (I):

or salts thereof, where each "D" represents, independently of the others, a cytotoxic and/or cytostatic agent; each "L" represents, independently of the others, a linker; "Ab" represents an anti-huLRRC15 antigen binding moiety, such as an anti-huLRRC15 antibody or binding fragment; each "XY" represents a linkage formed between a functional group $R^x$ on the linker and a "complementary" functional group $R^y$ on the antigen binding moiety; and n represents the DAR of the anti-huLRRC15 ADC. In a specific exemplary embodiment, the anti-huLRRC15 ADCs are compounds according to structural formula (I) in which each "D" is the same and is either a cell-permeating auristatin (for example, dolastatin-10 or MMAE) or a cell-permeating minor groove-binding DNA cross-linking agent (for example, a PBD or a PBD dimer); each "L" is the same and is a linker cleavable by a lysosomal enzyme; each "XY" is a linkage formed between a maleimide and a sulfydryl group; "Ab" is an antibody comprising six CDRs corresponding to the six CDRs of antibody huM25, huAD208.4.1, huAD208.12.1, huAD208.14.1, hu139.10, muAD210.40.9 or muAD209.9.1, or an antibody that competes for binding huLRRC15 with such an antibody; and n is 2, 3 or 4. In a specific embodiment of this exemplary embodiment or the anti-huLRRC15 ADCs of structural formula (I), "Ab" is a humanized antibody, for example, a humanized antibody comprising $V_H$ and $V_L$ chains corresponding to the $V_H$ and $V_L$ chains of antibody huM25, huAD208.4.1, huAD208.12.1, huAD208.14.1, or hu139.10. In another specific embodiment of this exemplary embodiment or the anti-huLRRC15 ADCs of structural formula (I), Ab is a humanized antibody selected from huM25, huM25-S239C, huAD208.4.1, huAD208.4.1-S239C, huAD208.12.1, huAD208.14.1 and hu139.10.

In another aspect, the present disclosure provides compositions including the anti-huLRRC15 ADCs. The compositions generally comprise one or more anti-huLRRC15 ADCs as described herein, and/or salts thereof, and one or more excipients, carriers or diluents. The compositions may be formulated for pharmaceutical use, or other uses. In one specific embodiment, the composition is formulated for pharmaceutical use and comprises an anti-huLRRC15 ADC according to structural formula (I) or any of the specific exemplary embodiments thereof, and one or more pharmaceutically acceptable excipients, carriers or diluents.

Compositions formulated for pharmaceutical use may be packaged in bulk form suitable for multiple administrations, or may be packaged in the form of unit doses suitable for a single administration. Whether packaged in bulk or in the form of unit doses, the composition may be presented in dry form, such as a lyophilate, or in liquid form. Unit dosage liquid compositions may be conveniently packaged in the form of syringes pre-filled with a quantity of anti-huLRRC15 ADC suitable for a single administration.

Also provided are unconjugated anti-huLRRC15 antibodies and/or binding fragments. Such antibodies may be used in a variety of contexts in vitro and in vivo, including, by way of example and not limitation, as cellular stains for biological assays and as diagnostic agents to monitor treatment of huLRRC15 stromal(+)/cancer(−) tumors, whether the treatment is with anti-huLRRC15 ADCs or other agents, or a combination of agents. The anti-huLRRC15 antibodies and/or binding fragments may be labeled with moieties to aid detection in diagnostic or other assays, or may be unlabeled. Suitable labels include, by way of example and not limitation, isotopic labels, fluorescent labels, chemiluminescent labels, substrates for enzymes or other binding molecules, etc. Exemplary embodiments of anti-huLRRC15 antibodies and/or binding fragments include the various exemplary anti-huLRRC15 antibodies and/or binding fragments described herein in connection with the anti-huLRRC15 antibodies and/or binding fragments described herein in connection with the anti-huLRRC15 ADCs.

Also provided are polynucleotides encoding antigen binding moieties (for example antibodies and/or binding fragments) that compose the anti-huLRRC15 ADCs described herein, host cells transformed or transfected with the polynucleotides, and compositions and methods useful for making the various anti-huLRRC15 ADCs described herein.

As noted above, anti-huLRRC15 ADCs including cell-permeating cytotoxic and/or cytostatic agents exhibit potent antitumor activity against huLRRC15 stromal(+)/cancer(−) tumors that is believed to be mediated, at least in part, by a targeted bystander killing effect, and that this potent antitumor activity is observed with anti-huLRRC15 ADCs that specifically bind the portion of the huLRRC15 ECD that can be shed from the cell surface. This is surprising, as the shed ECD is available as a "sink" or "decoy" for the anti-huLRRC15 ADCs, thereby interfering with their ability to bind and become internalized into huLRRC15-expressing cells. Data provided herein demonstrate, for the first time, that ADCs targeting huLRRC15 may be used therapeutically for the treatment of huLRRC15 stromal(+)/cancer(−) tumors.

Accordingly, in another aspect, the present disclosure provides methods of using anti-huLRRC15 ADCs therapeutically for the treatment of huLRRC15 stromal(+)/cancer(−) tumors. The methods generally involve administering to a human patient having a huLRRC15 stromal(+)/cancer(−) tumor an amount of an anti-huLRRC15 ADC sufficient to provide therapeutic benefit. Human LRRC15 stromal(+)/cancer(−) tumors that can be beneficially treated with anti-huLRRC15 ADCs include, but are not limited to breast cancers, lung cancers (for example, non-small cell lung cancers), head and neck cancers, pancreatic cancers, colorectal cancers, bladder cancers, liver cancers, and ovarian cancers. The cancer may be newly diagnosed and naïve to treatment, or may be relapsed, refractory, or relapsed and refractory, or a metastatic form of a huLRRC15 stromal(+)/cancer(−) tumor.

The anti-huLRRC15 ADCs may be administered as single therapeutic agents (monotherapy) or adjunctive to, or with other anti-cancer treatments and/or therapeutic agents, typically but not necessarily those used to treat the type of huLRRC15 stromal(+)/cancer(−) tumors being treated. Indeed, data presented herein demonstrate that tumors that re-grow post treatment when treated with currently available agents, or that exhibit resistance to other targeted or non-targeted chemotherapies, retain sensitivity to anti-huLRRC15 ADCs (see, e.g., Example 14 and FIGS. 20A-20E). While not wishing to be bound by theory, one possible mechanism of action of the anti-huLRRC15 ADCs of the disclosure may be the killing of cancer cells that exhibit mesenchymal-like properties which lend them resistance to standard therapies. Accordingly, the anti-huLRRC15 ADCs described herein provide significant benefits over current targeted and non-targeted approaches toward the treatment of huLRRC15 stromal(+)/cancer(−) tumors. Adjunctive therapies and/or therapeutic agents typically will be used at their approved dose, route of administration, and frequency of administration, but may be used at lower dosages and/or less frequently. When administered as monotherapy, the anti-huLRRC15 ADC will typically be administered on a schedule that balances patient convenience and therapeutic benefit. It is contemplated that anti-huLRRC15 ADCs administered once a week, once every two weeks, once every three weeks, once every four weeks, once every five weeks, once every six weeks, once every seven weeks or once every eight weeks will provide therapeutic benefit, although more or less frequent administration may be beneficial. When administered adjunctive to or with another therapy and/or agent, the anti-huLRRC15 ADC may be administered before, after or concurrently with the other therapy or agent.

The anti-huLRRC15 ADCs may be administered via a variety of routes or modes of administration, including but not limited to, intravenous infusion and/or injection and subcutaneous injection. The amount administered will depend upon the route of administration, the dosing schedule, the type of cancer being treated, the stage of the cancer being treated, and other parameters such as the age and weight of the patient, as is well known in the art. Specific exemplary dosing schedules expected to provide therapeutic benefit are provided in the Detailed Description. Generally, an amount of anti-huLRRC15 ADC in the range of about 0.01 to 10 mg/kg when administered intravenously on a weekly basis from once weekly to and including once every eight weeks is expected to provide therapeutic benefit.

6. BRIEF DESCRIPTION OF THE FIGURES

FIGS. 1A-1D provide the amino acid sequences of the two reported isoforms of human LRRC15, and the corresponding DNA sequences encoding each. FIGS. 1A-1B show the encoding DNA sequence (SEQ ID NO:2) and amino acid sequence (SEQ ID NO:1) for longer huLRRC15 isoform 1: FIG. 1A corresponds to coding DNA residues 1-1020; FIG. 1B corresponds to coding DNA residues 1021-1761. FIGS. 1C-1D show the encoding DNA sequence (SEQ ID NO:4) and amino acid sequence (SEQ ID NO:3) for shorter huLRRC15 isoform 2: FIG. 1C corresponds to coding DNA residues 1-1020; FIG. 1D corresponds to coding DNA residues 1021-1743. The predicted signal peptide is indicated in bold italics; the predicted protease cleavage site is boxed; and the predicted transmembrane domain is underlined.

FIG. 2A provides the amino acid sequences of the $V_H$ chains of antibodies huM25, huAD208.4.1, huAD208.12.1, huAD208.14.1, hu139.10, muAD210.40.9 and muAD209.9.1. The CDRs are underlined.

FIG. 2B provides the amino acid sequences of the $V_L$ chains of antibodies huM25, huAD208.4.1, huAD208.12.1, huAD208.14.1, hu139.10, muAD210.40.9 and muAD209.9.1. The CDRs are underlined.

FIG. 3A provides the amino acid sequence of the heavy chain of antibody huM25 (SEQ ID NO:18). The CDRs are underlined, and the constant region (Fc gamma) is italicized. Linear amino acid sequence numbering is shown.

FIG. 3B provides the amino acid sequence of the light chain of antibody huM25 (SEQ ID NO:19). The CDRs are underlined, and the constant region (kappa) is italicized. Linear amino acid sequence numbering is shown.

FIG. 4 provides a graph illustrating the ability of various exemplary anti-huLRRC15 antibodies having CDRs that may be included in anti-huLRRC15 ADCs to bind to cells expressing huLRRC15.

Figure 5:
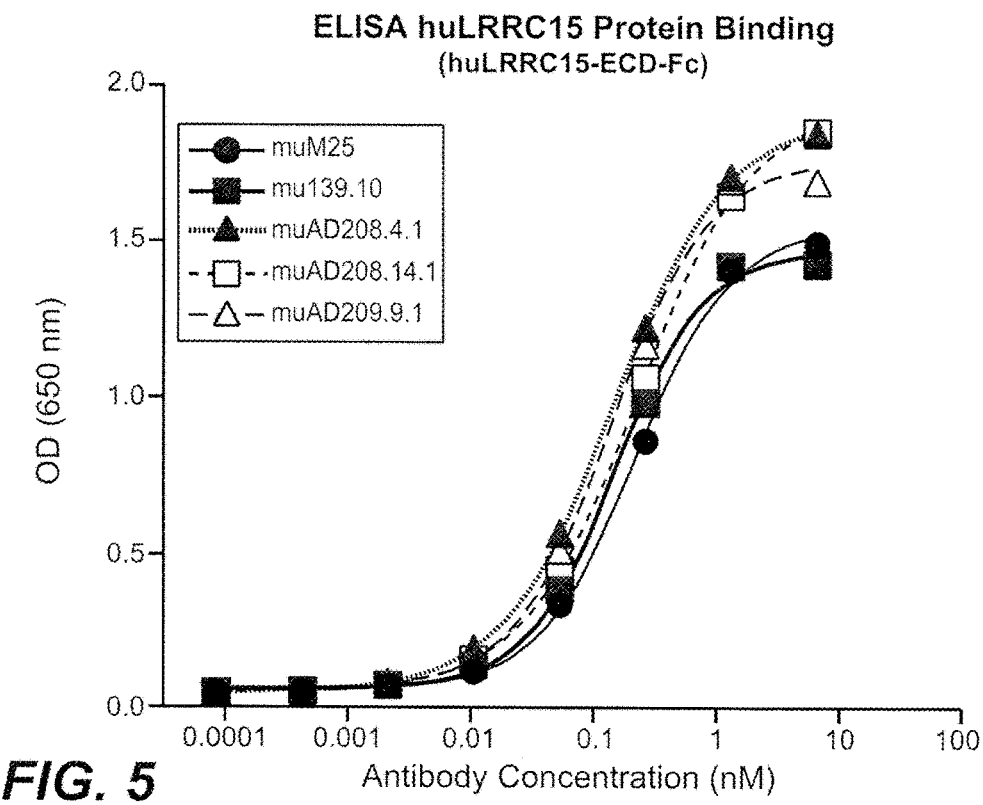

FIG. 5 provides a graph illustrating the ability of various exemplary anti-huLRRC15 antibodies having CDRs that may be included in anti-huLRRC15 to bind the extracellular domain (ECD) of huLRRC15.

Figure 6A:
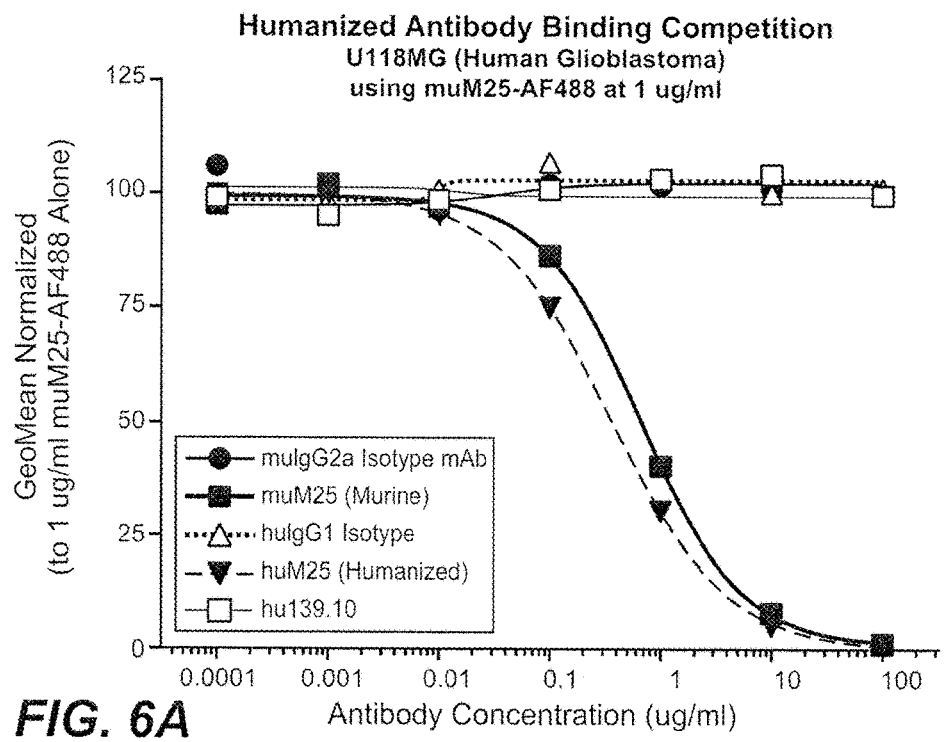
Figure 6B:
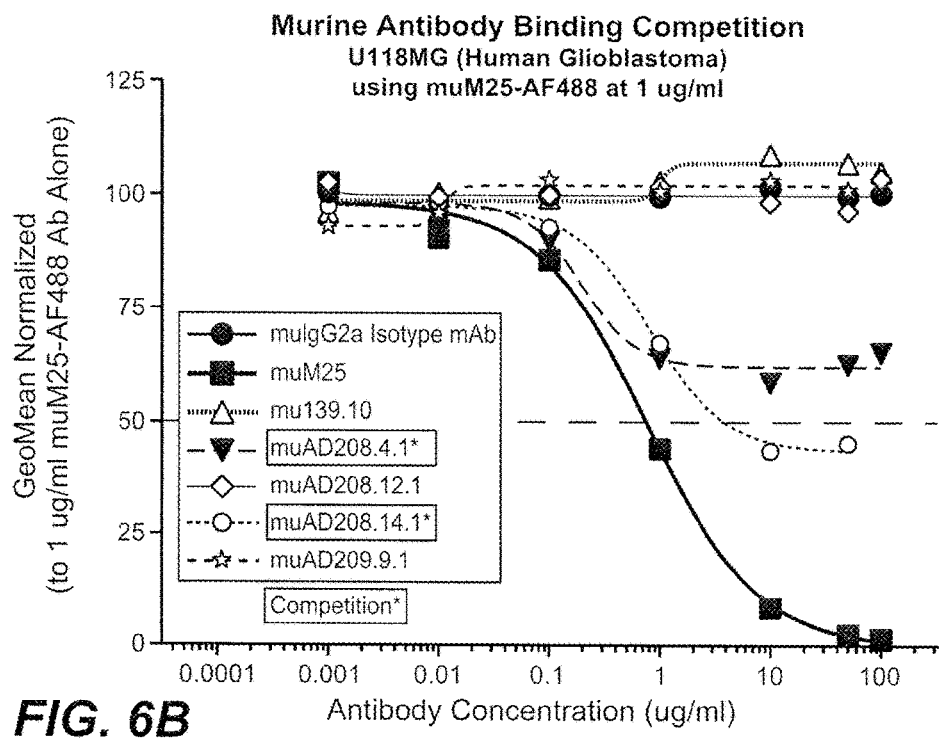

FIGS. 6A and 6B together provide results of antibody competition assays illustrating that exemplary anti-huLRRC15 antibodies having CDRs that may be included in anti-huLRRC15 ADCs bind different epitopes on huLRRC15. FIG. 6A shows binding competition of muM25, huM25, hu139.10 or isotype antibodies against muM25-AF488; FIG. 6B shows binding competition of muM25, muAD208.4.1, muAD208.12.1, muAD208.14.1, muAD209.9.1 or isotype antibodies against muM25-AF488.

Figure 7:
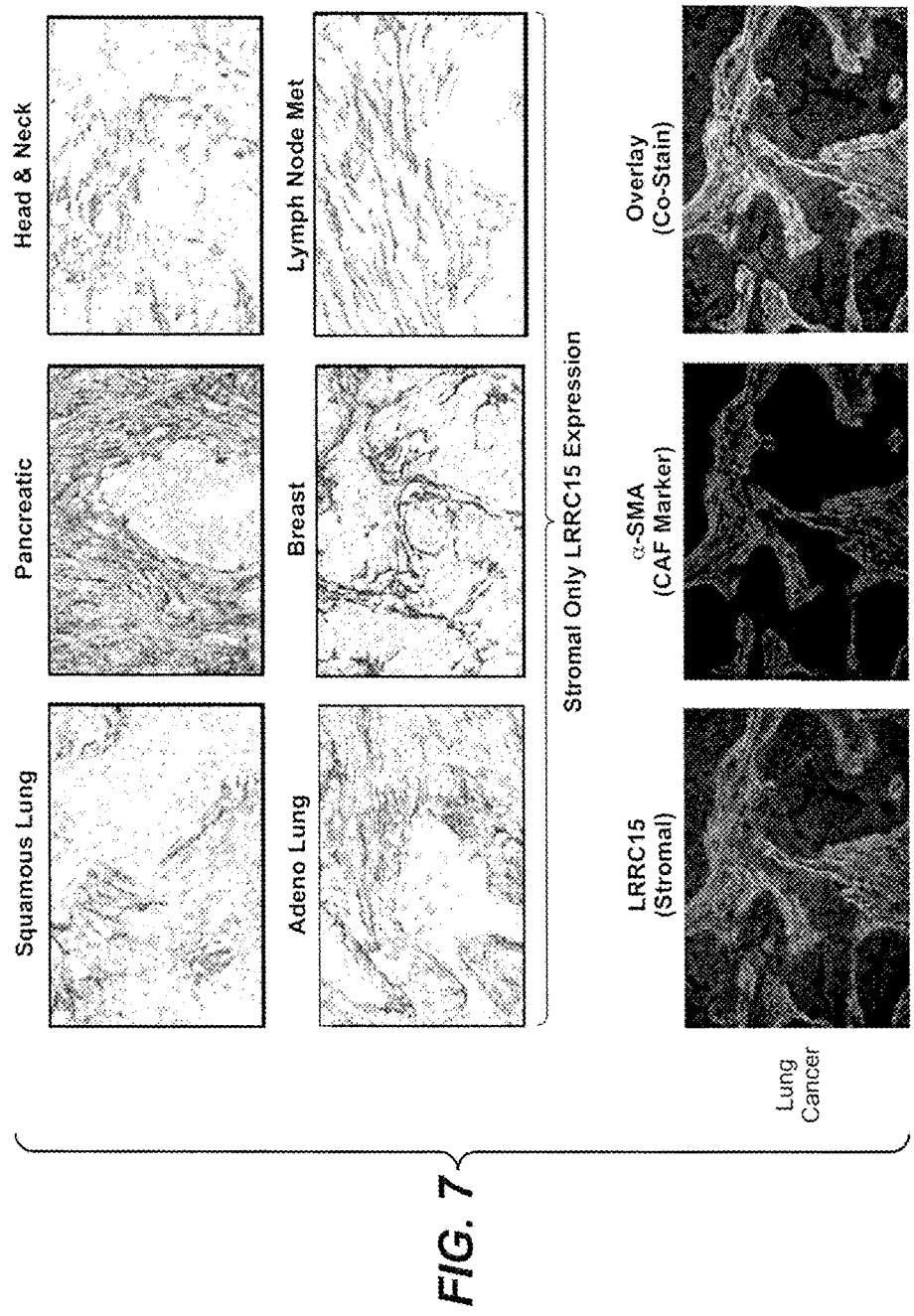

FIG. 7 provides pictures of immunohistochemistry (IHC) and immunofluorescence (IF) stained tissues illustrating that huLRRC15 is highly expressed in the stromal microenvironment of various solid tumors.

Figure 8:
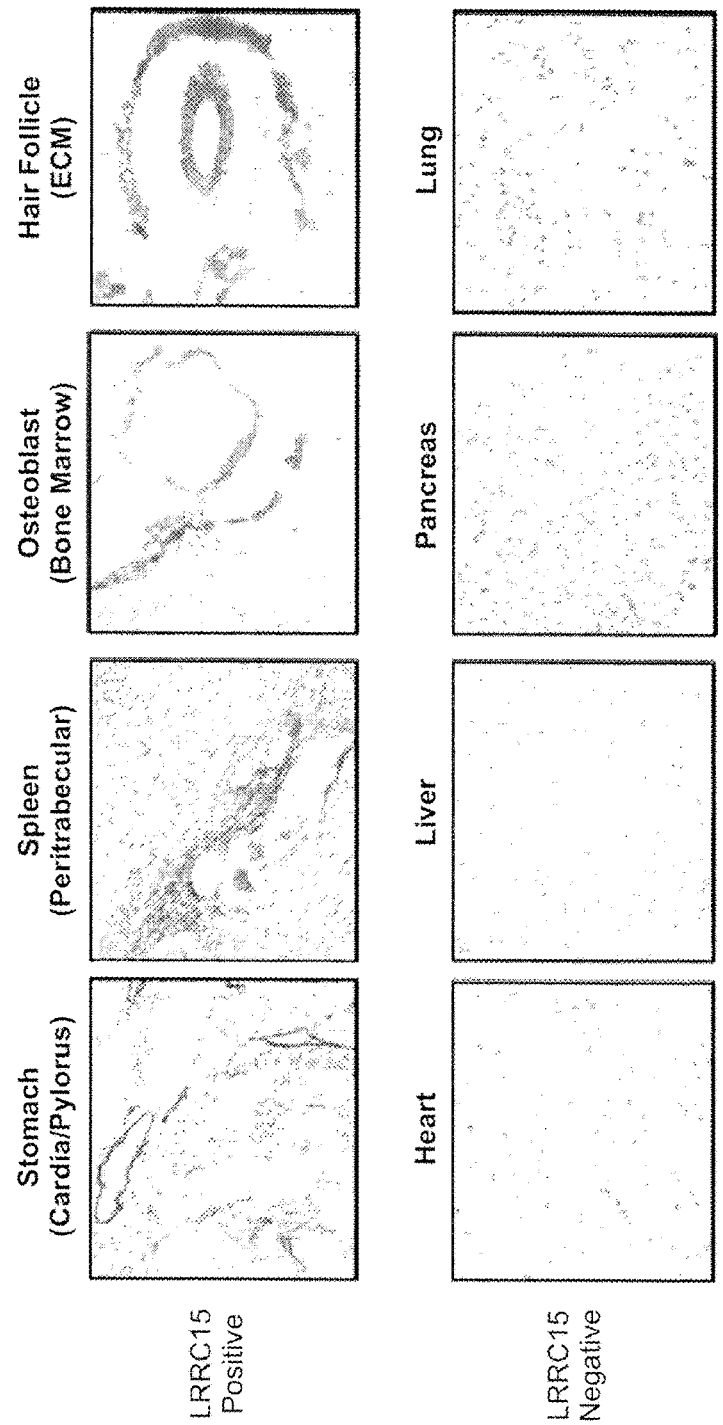

FIG. 8 provides pictures of IHC stained tissues illustrating that huLRRC15 is either not expressed, or only minimally expressed, on various normal tissue types.

FIG. 9A depicts huLRRC15 expression levels as measured by Western blot analysis in a patient-derived breast cancer-associated fibroblast (CAF) lysate, or in commercially available patient-derived mesenchymal stem cell (MSC) lysates from bone marrow, in the absence (−) or presence (+) of 10 ng/mL TGFβ. Anti-huLRRC15 antibody used for detection was muAD210.40.9.

FIGS. 9B-9C depict huLRRC15 expression in commercial mesenchymal stem cell (MSC) lines, with and without 10 ng/mL TGFβ, as measured by flow cytometry: FIG. 9B depicts huLRRC15 expression as compared with isotype in human BM-MSC cells (Lonza); FIG. 9C depicts huLRRC15 expression as compared with isotype in murine Balb/c BM-MSC cells (Cyagen). Anti-huLRRC15 antibody used for detection was AF647-labeled huM25.

Figure 10:
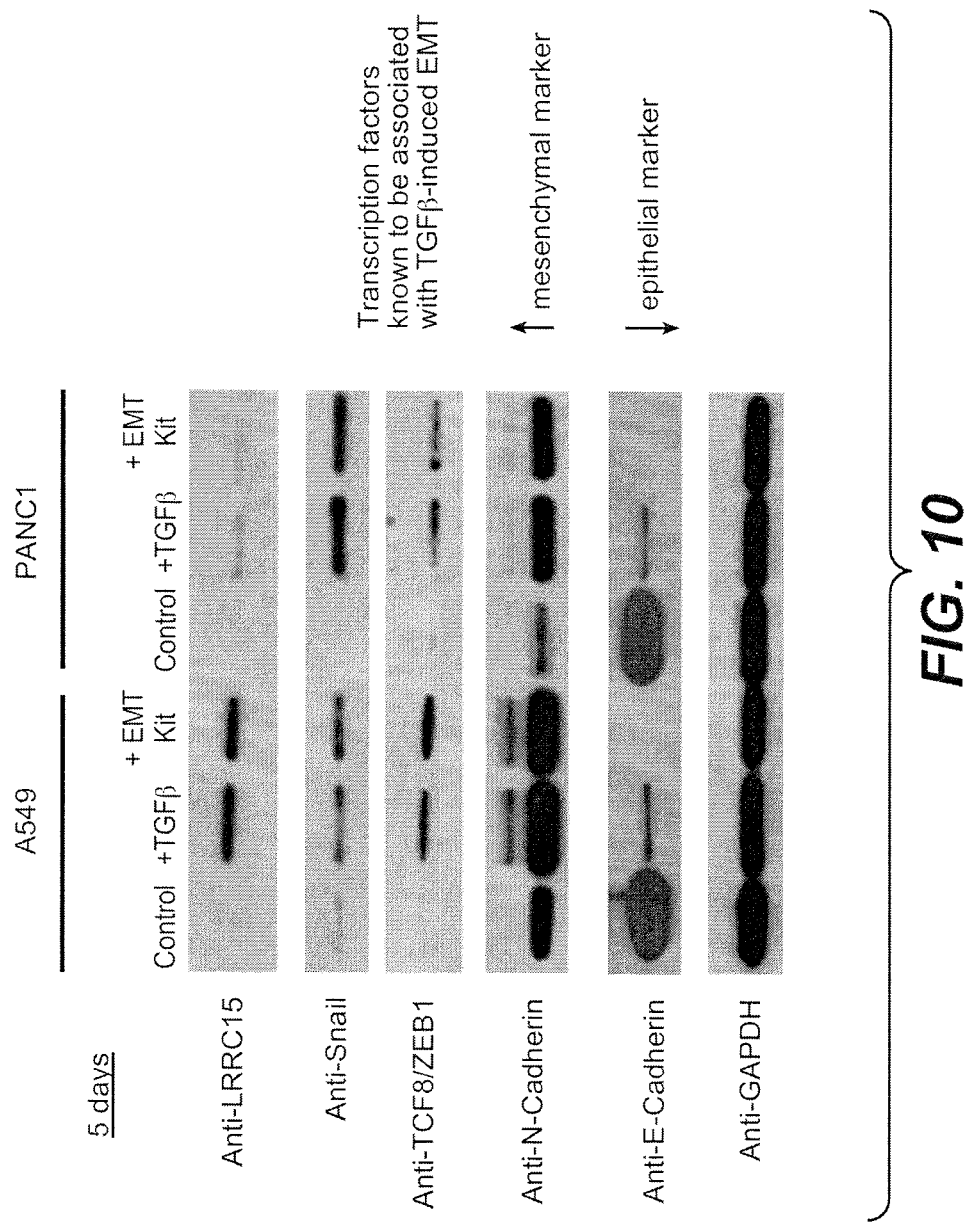

FIG. 10 depicts expression levels of huLRRC15, Snail, TCF8/ZEB1, N-Cadherin, E-Cadherin, and GAPDH as determined by Western blot analysis of A549 lung cancer or PANC1 pancreatic cancer cells with 5 day treatment of 10 ng/mL TGFβ, StemXVivo™ EMT Inducing Media Supplement (R&D Systems, "EMT Kit"), or control. Anti-LRRC15 antibody used for detection was muAD210.40.9; all other antibodies were obtained from the EMT Antibody Panel (Cell Signaling Technology).

Figure 11A:
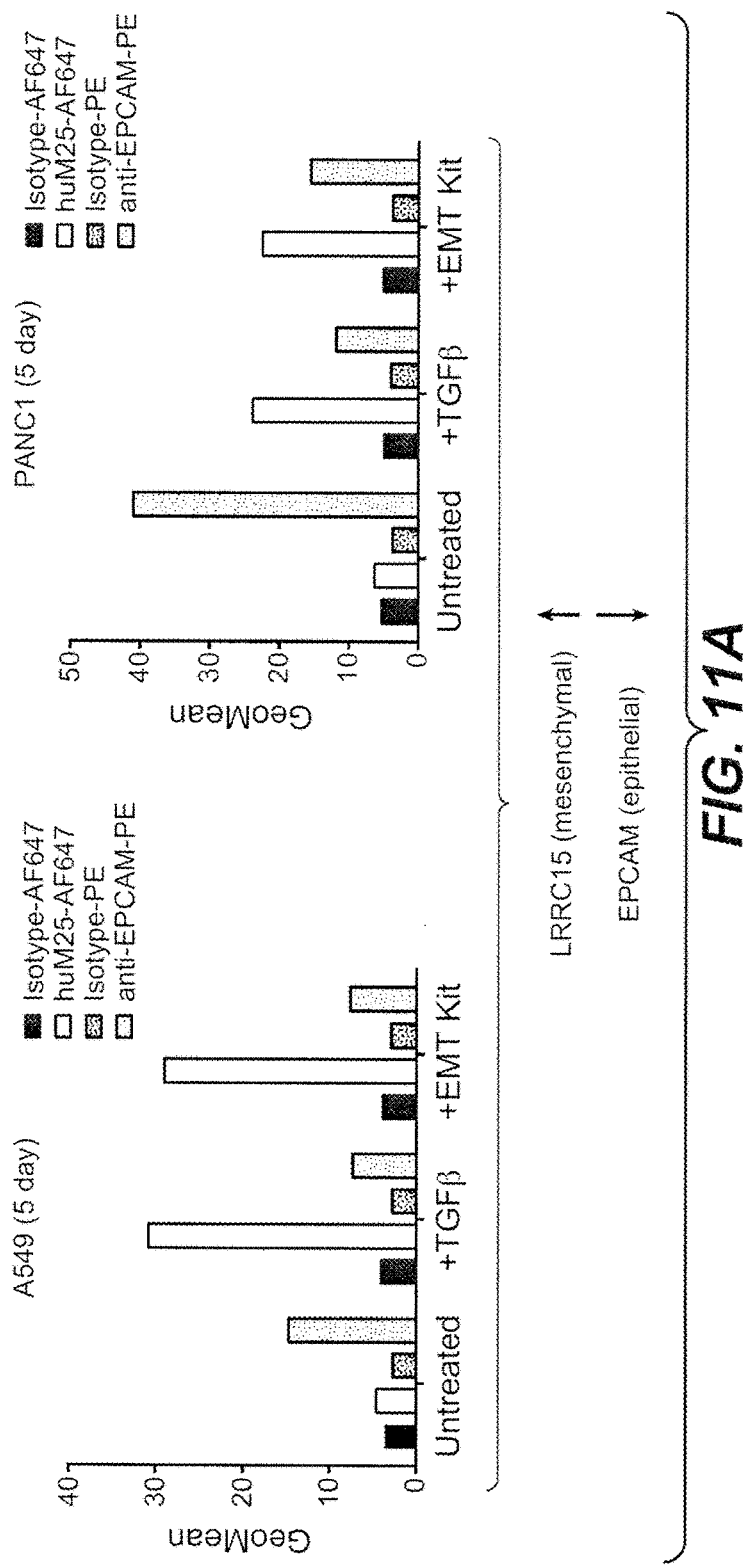

FIG. 11A depicts protein expression as determined by fluorescence in A549 lung cancer or PANC1 pancreatic cancer cells after 5 day treatment of 10 ng/mL TGFβ, StemXVivo™ EMT Inducing Media Supplement (R&D Systems, "EMT Kit"), or control. Fluorescence using AF647-labeled isotype ("Isotype-AF647"), AF647-labeled huM25 ("huM25-AF647"), PE-labeled isotype ("Isotype-PE"), and PE-labeled anti-EpCAM ("anti-EPCAM-PE") antibodies is shown.

FIG. 11B depicts microscopy images of A549 cells after continued treatment of 10 ng/mL TGFβ over 9 days (upper left, "continued treatment"), or treatment with 10 ng/mL TGFβ for 5 days followed by washout and culturing in the absence of TGFβ for an additional 4 days (lower left, "discontinued treatment"). Flow cytometry (middle and right graphs) depicts huLRRC15 (upper and lower middle) and EpCAM (upper and lower right) levels after continued treatment, discontinued treatment, or control. Anti-huLRRC15 antibody huM25-AF647 was used in the analysis.

Figure 11C:
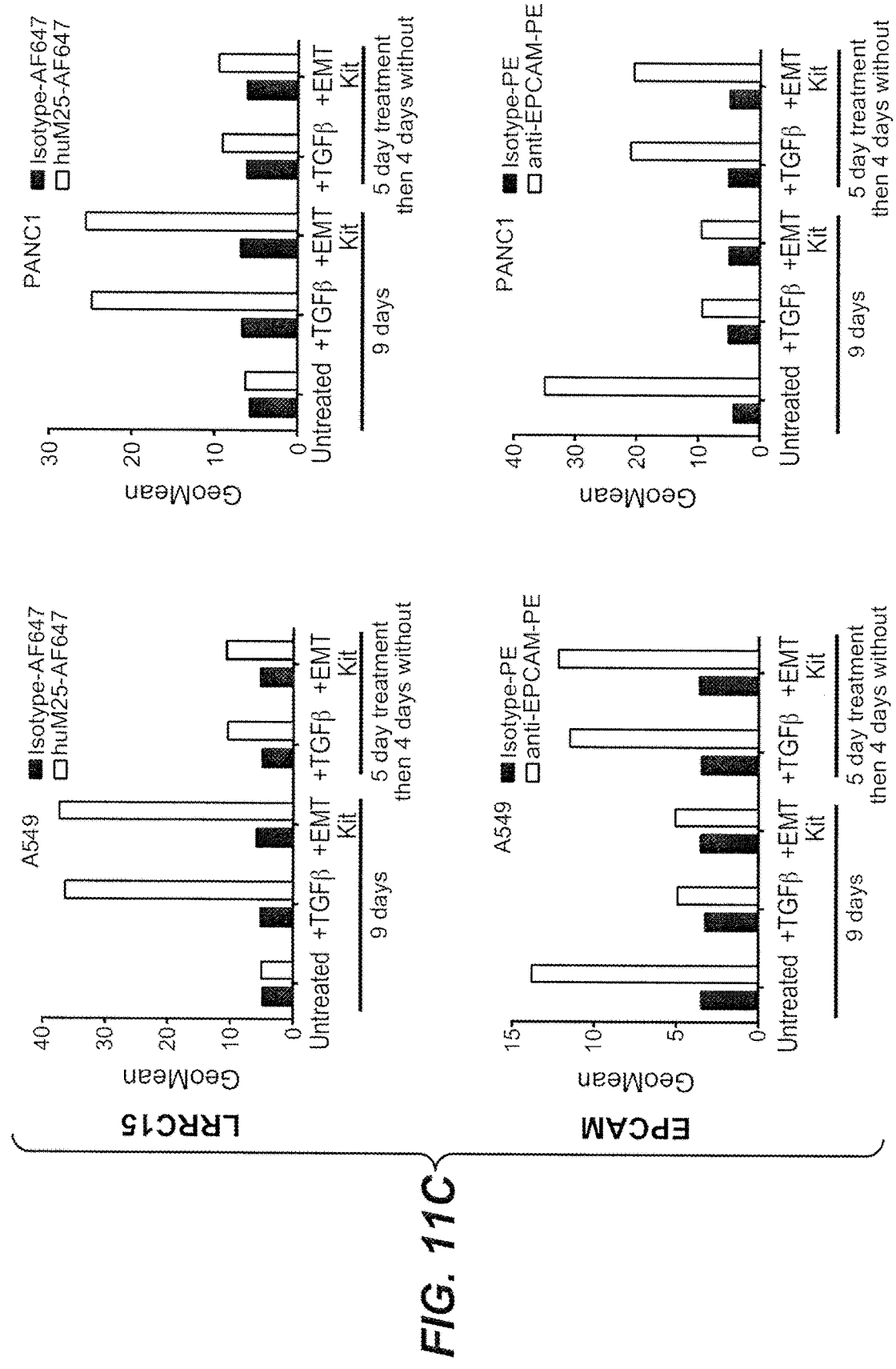

FIG. 11C depicts protein expression as determined by fluorescence in A549 lung cancer (left graphs) or PANC1 pancreatic cancer cells (right graphs) after 9 day continued treatment of 10 ng/mL TGFβ or StemXVivo™ EMT Inducing Media Supplement (R&D Systems, "EMT Kit"), or treatment with TGFβ or EMT Kit for 5 days followed by washout and culturing for an additional 4 days. Top panels depict huLRRC15 levels; bottom panels depict EpCAM levels.

Figure 12:
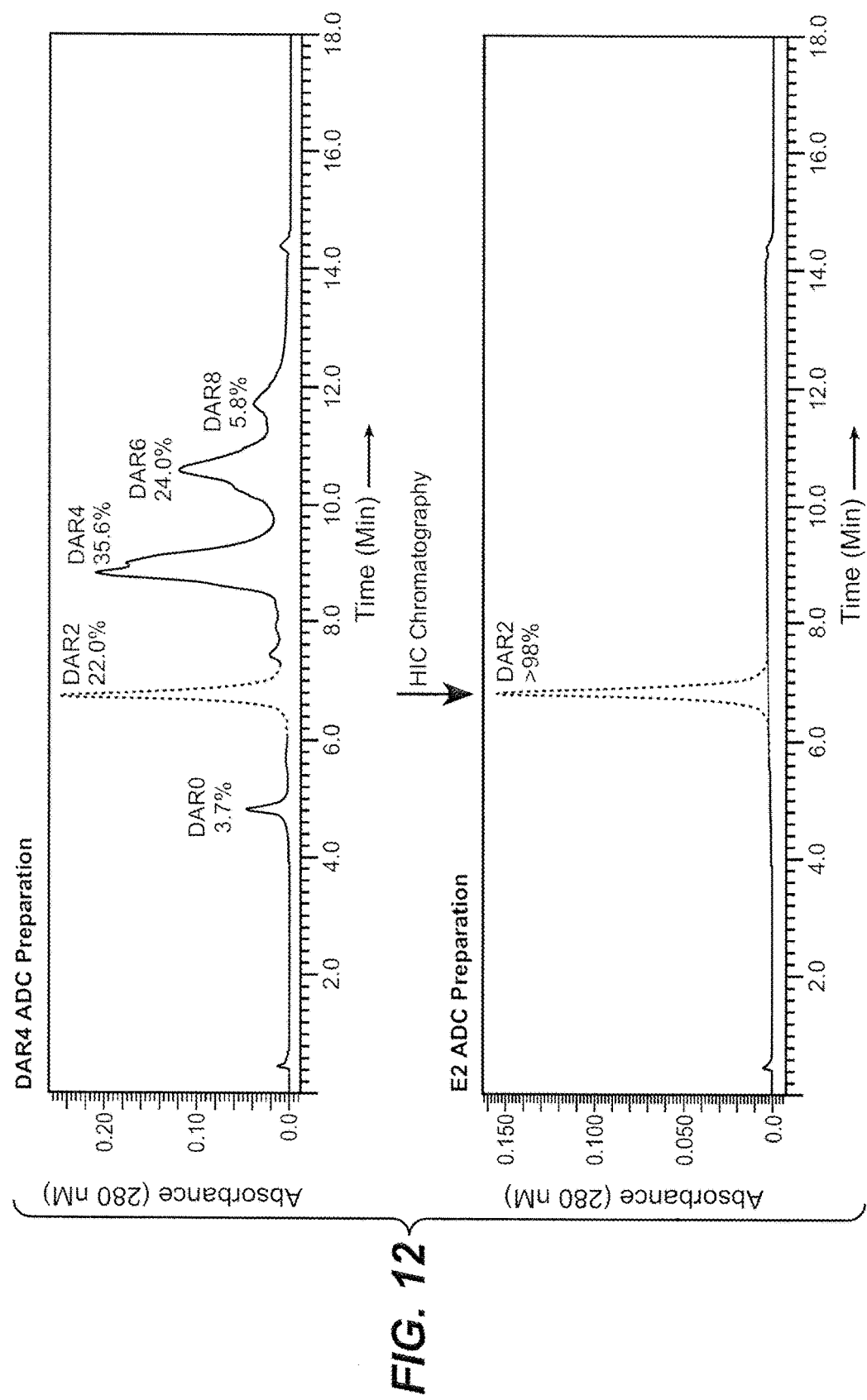

FIG. 12 provides chromatograms of ADC preparations. The top panel illustrates a chromatographic resolution of a conjugation carried out according to Example 8. Several peaks are present, corresponding to antibodies having zero ("DAR0"), two ("DAR2"), four ("DAR4"), six ("DAR6") and eight ("DAR8") linked cytostatic and/or cytotoxic agents. The preparation has an average DAR of 4. This crude average DAR4 preparation was subjected to hydrophobic interaction chromatography to isolate the peak corresponding to DAR2. The chromatogram of the resultant preparation enriched in DAR2 (referred to herein as an "E2" preparation) is shown in the bottom panel. The enriched E2 ADC preparation is approximately 98% pure in ADCs having a DAR of 2.

Figure 13A:
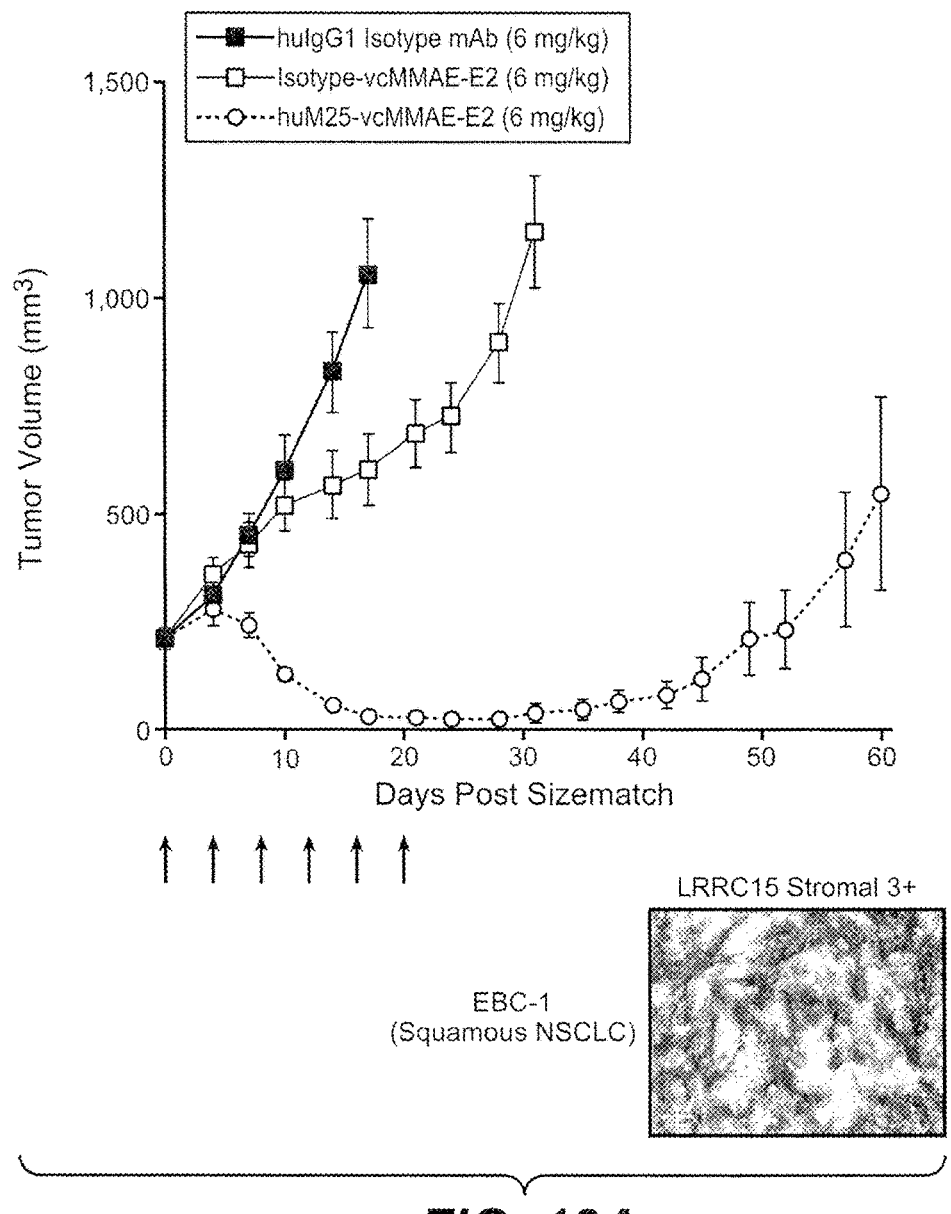
Figure 13B:
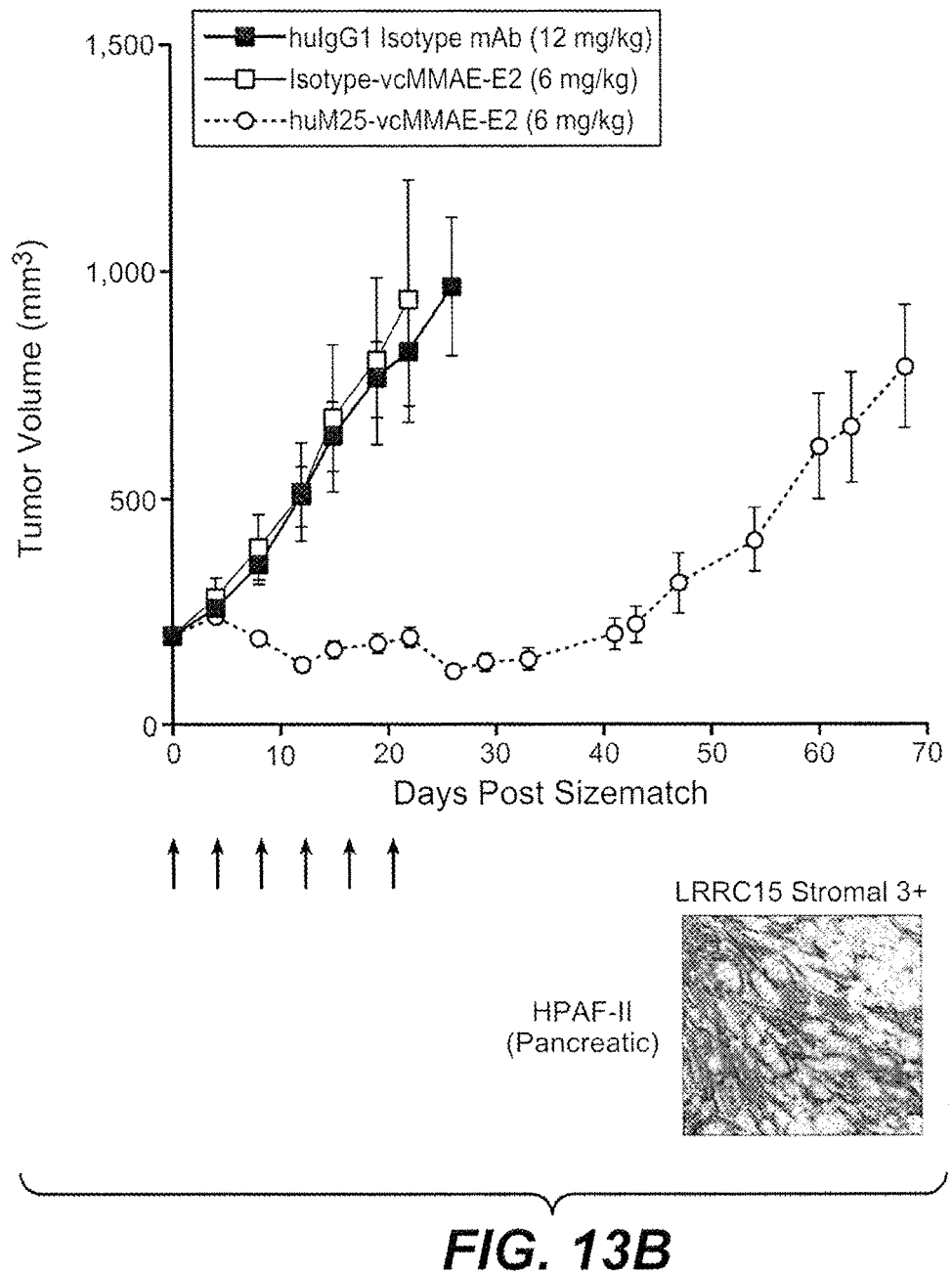
Figure 13C:
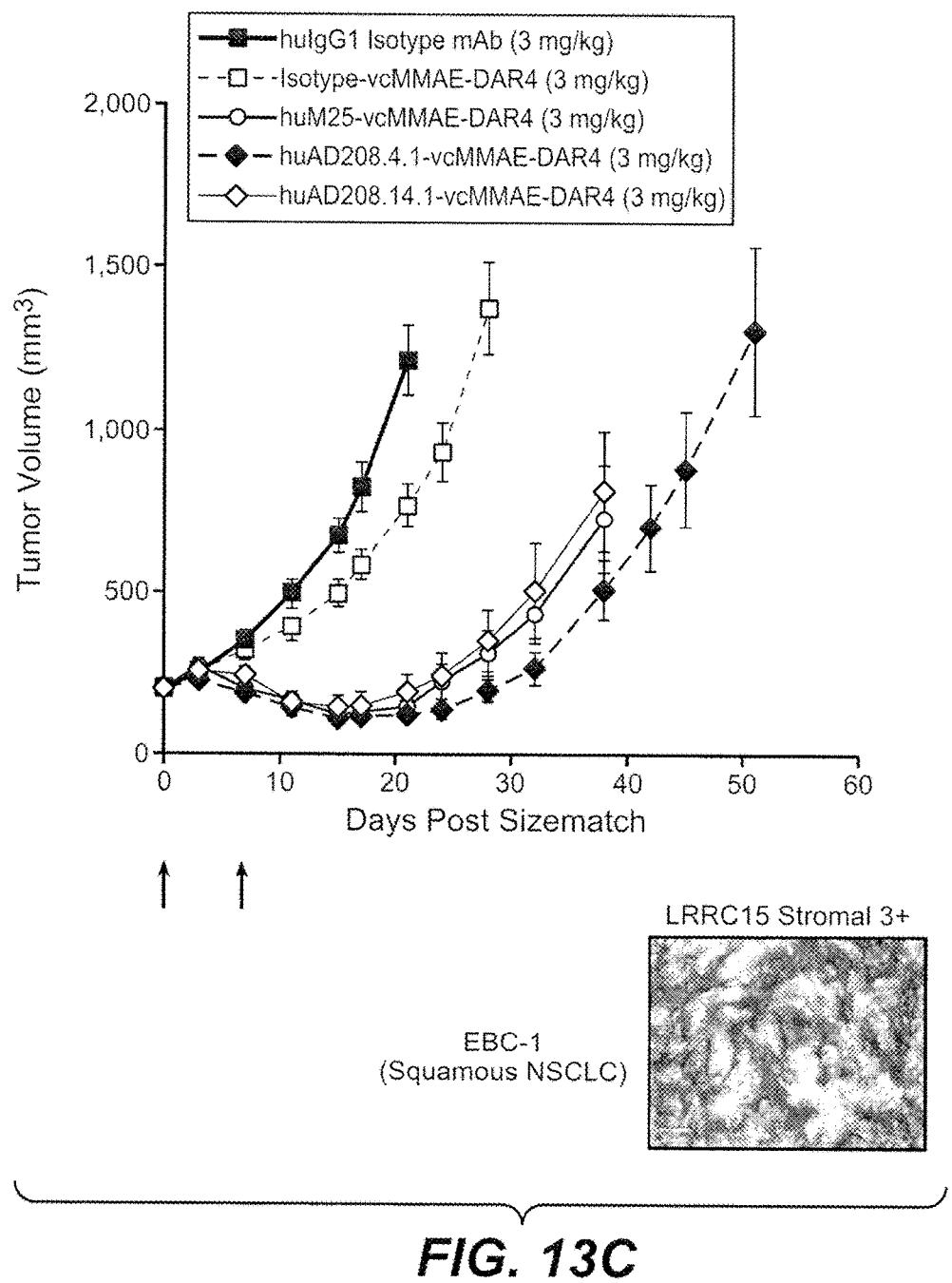

FIGS. 13A-13C provide graphs demonstrating the potent in vivo efficacy of exemplary anti-huLRRC15 ADCs against a variety of stromal(+)/cancer(−) tumors. In the graphs, the arrows indicate dosing days. Also shown are pictures illustrating LRRC15 expression on stromal cells as assessed by IHC in an untreated xenograft tumor of 200-800 mm³ in volume, representative for each xenograft model. FIG. 13A demonstrates in vivo activity of huM25-vcMMAE-E2 in EBC-1 xenografts; FIG. 13B demonstrates in vivo activity of huM25-vcMMAE-E2 in HPAF-II xenografts; and FIG. 13C demonstrates in vivo activity of huM25-vcMMAE-DAR4, huAD208.4.1-vcMMAE-DAR4 and huAD208.14.1-vcMMAE-DAR4 in EBC-1 xenografts.

Figure 13D:
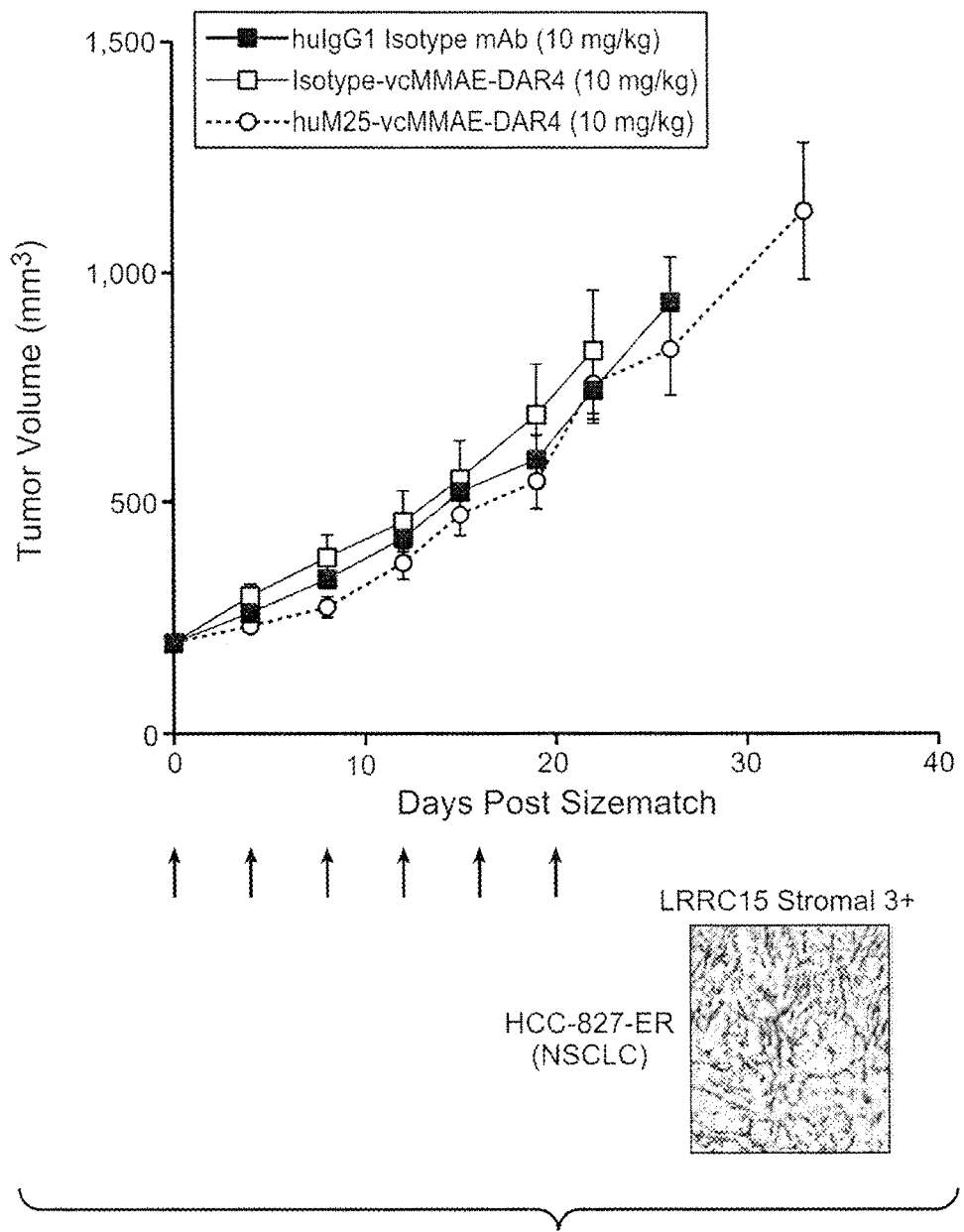

FIG. 13D provides a graph illustrating that huM25-vcMMAE-DAR4 is not active in vivo against xenografts generated with HCC-827-ER despite high huLRRC15 expression in stroma. Arrows indicate dosing days. Also shown is a representative IHC picture illustrating LRRC15 expression on stromal cells for this xenograft model.

Figure 14:
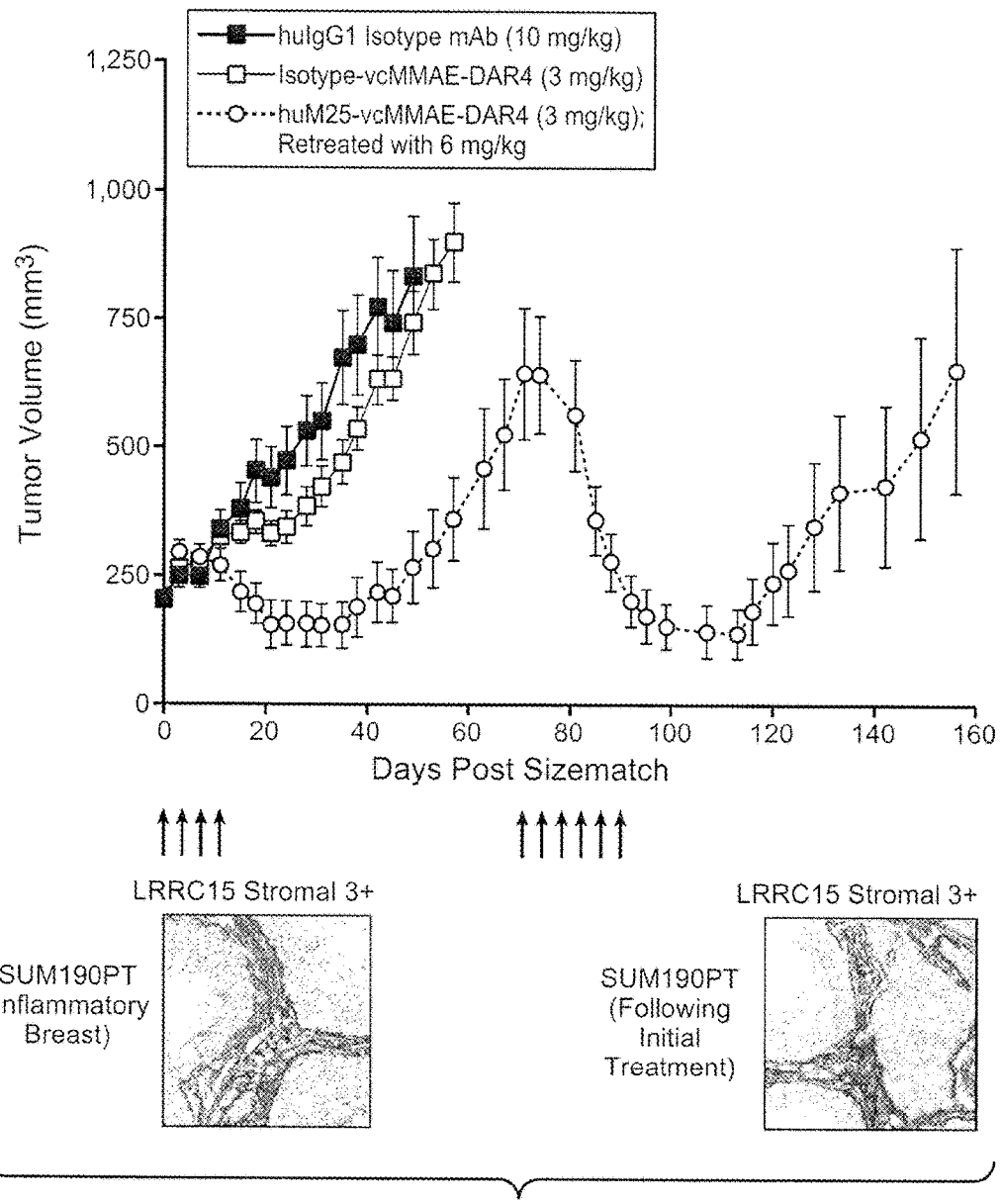

FIG. 14 provides a graph demonstrating that tumors that regrow following treatment with exemplary anti-huLRRC15 ADC huM25-vcMMAE-DAR4 retain expression of huLRRC15, and therefore retain sensitivity to anti-huLRRC15 ADCs. Arrows represent dosing days. Also shown are pictures illustrating LRRC15 expression on stromal cells, as assessed by IHC, in an untreated xenograft tumor immediately prior to treatment (Day 0) or following treatment and regrowth (Day 70).

Figure 15A:
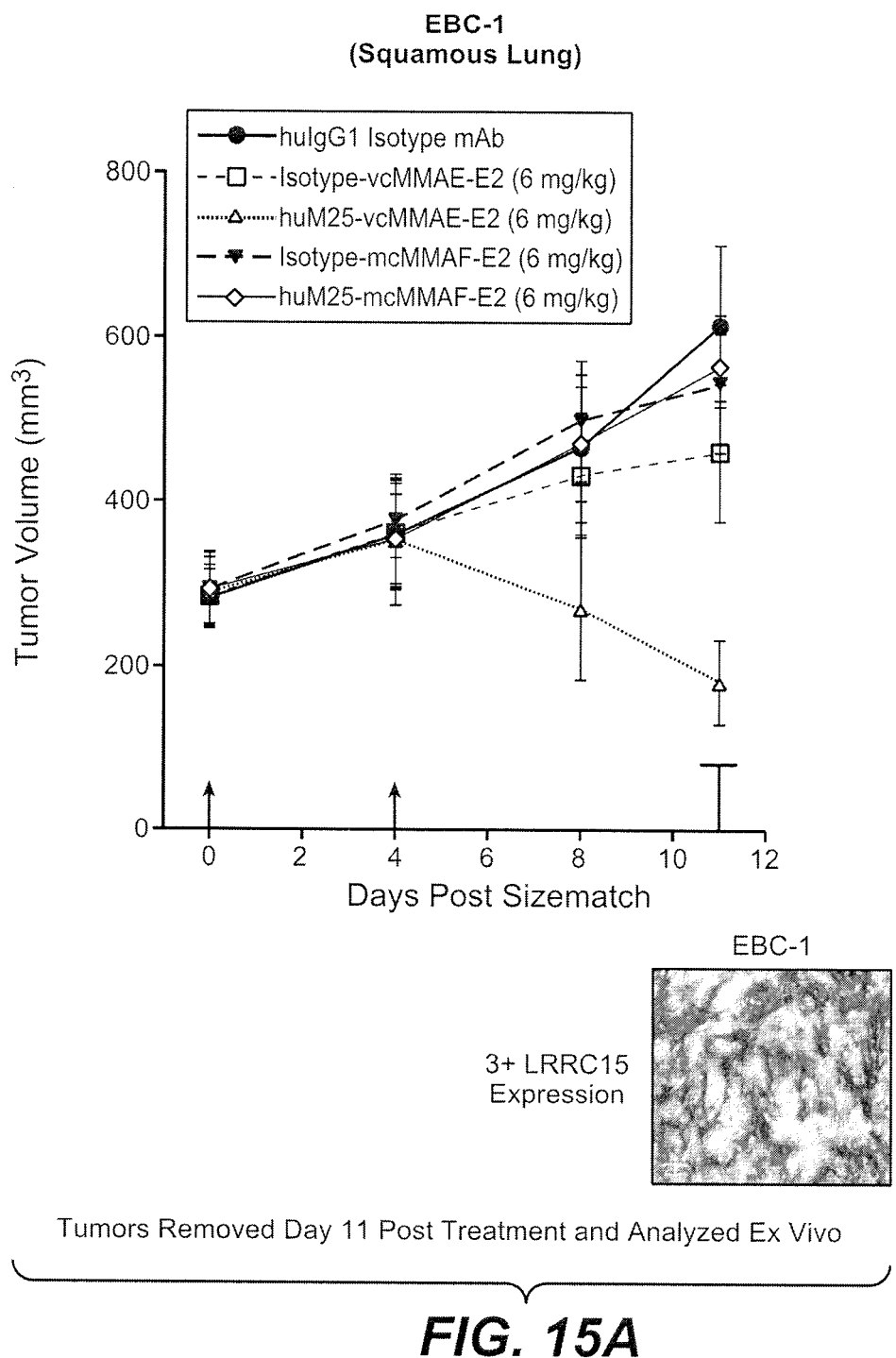
Figure 15B:
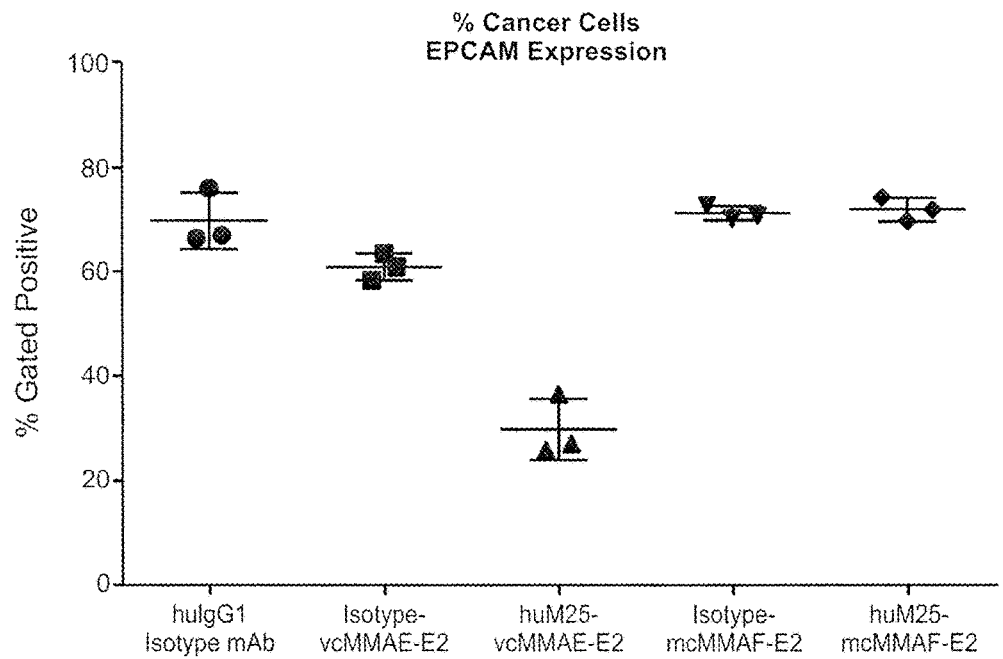
Figure 15C:
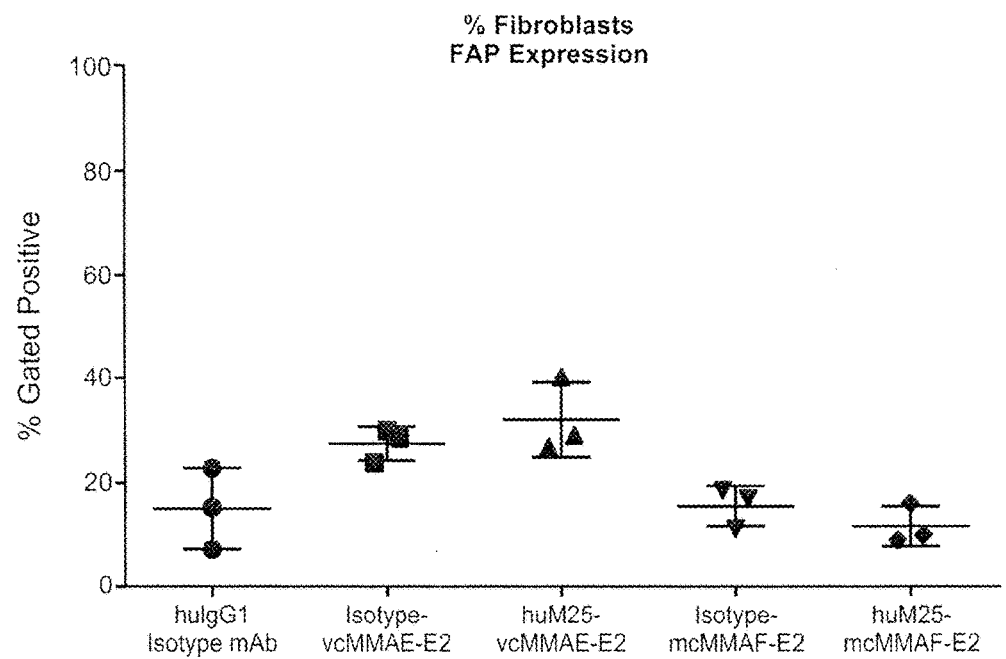
Figure 15D:
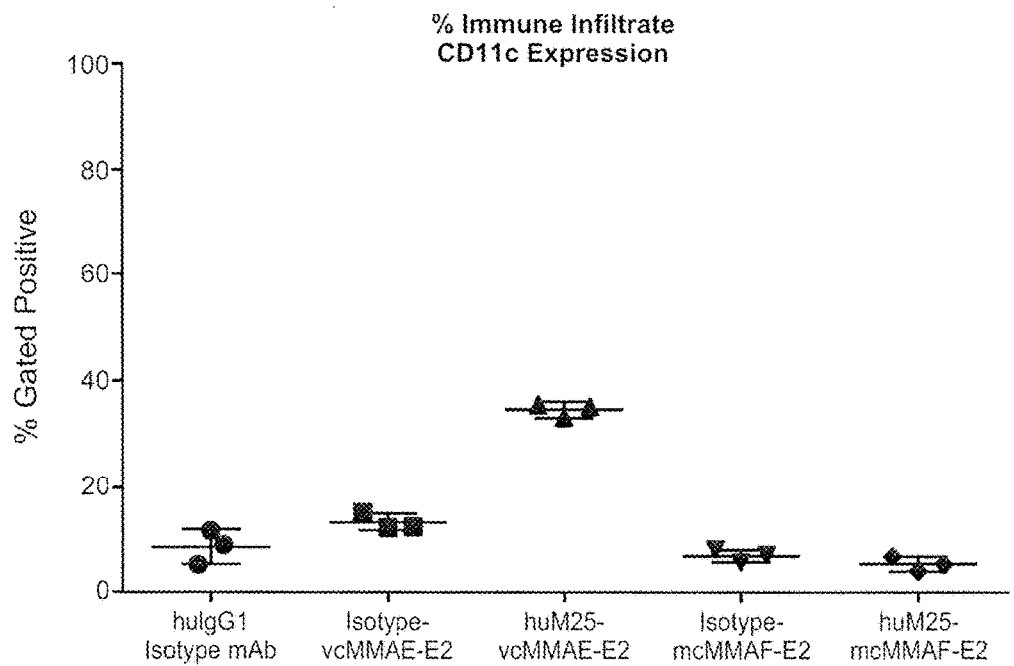
Figure 15E:
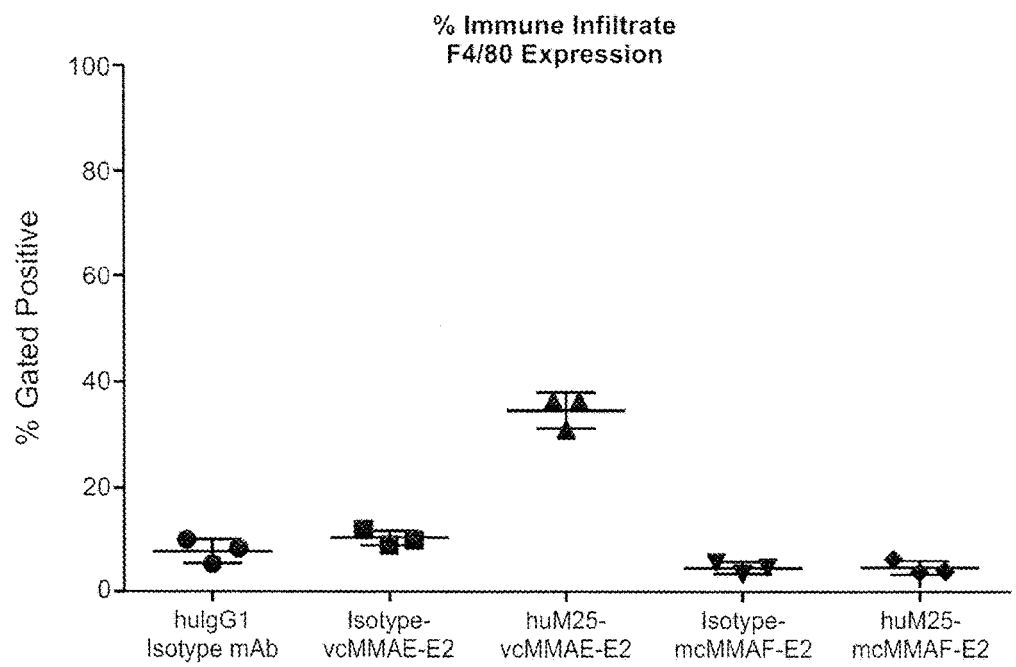
Figure 15F:
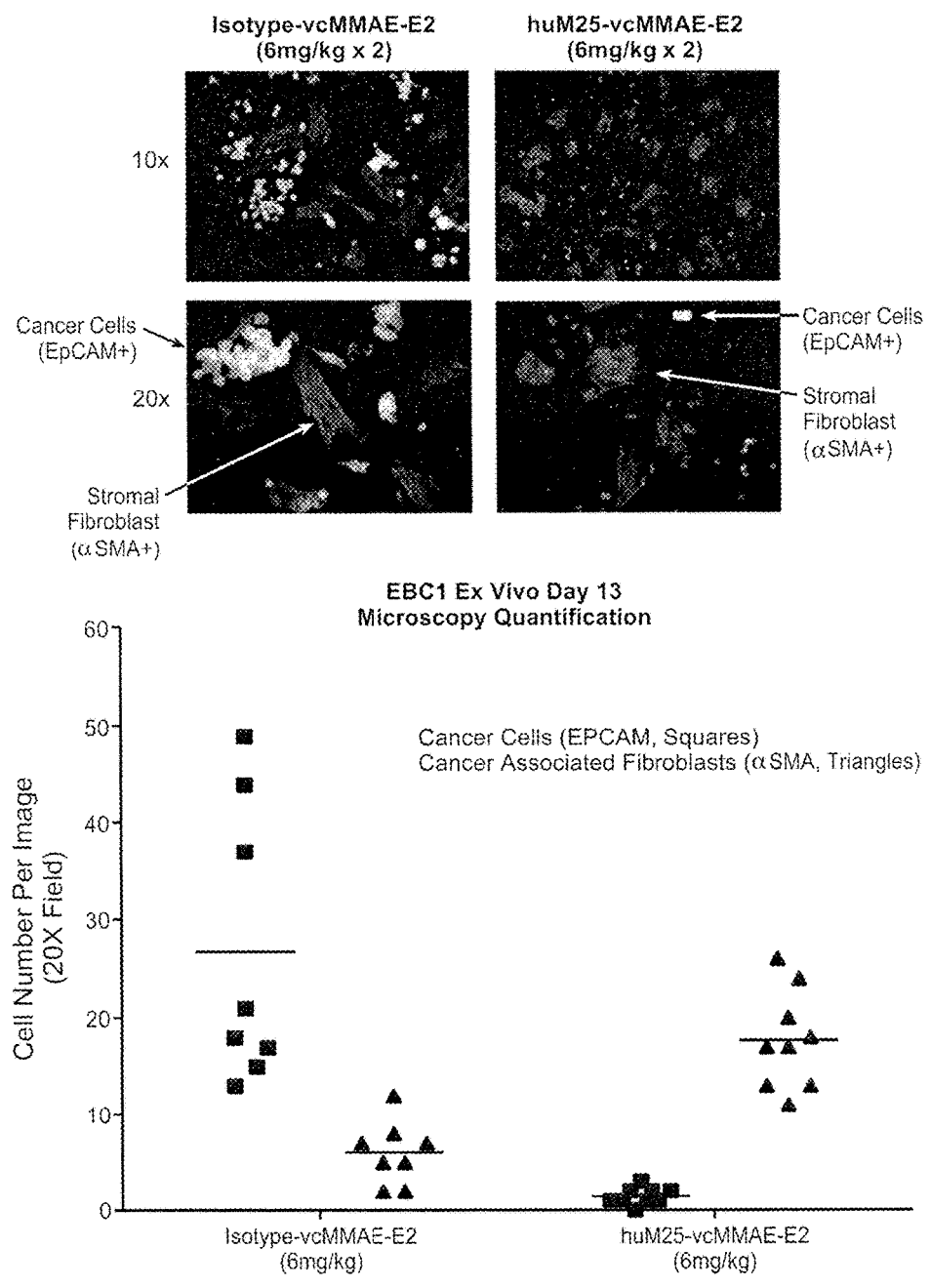
Figure 15G:
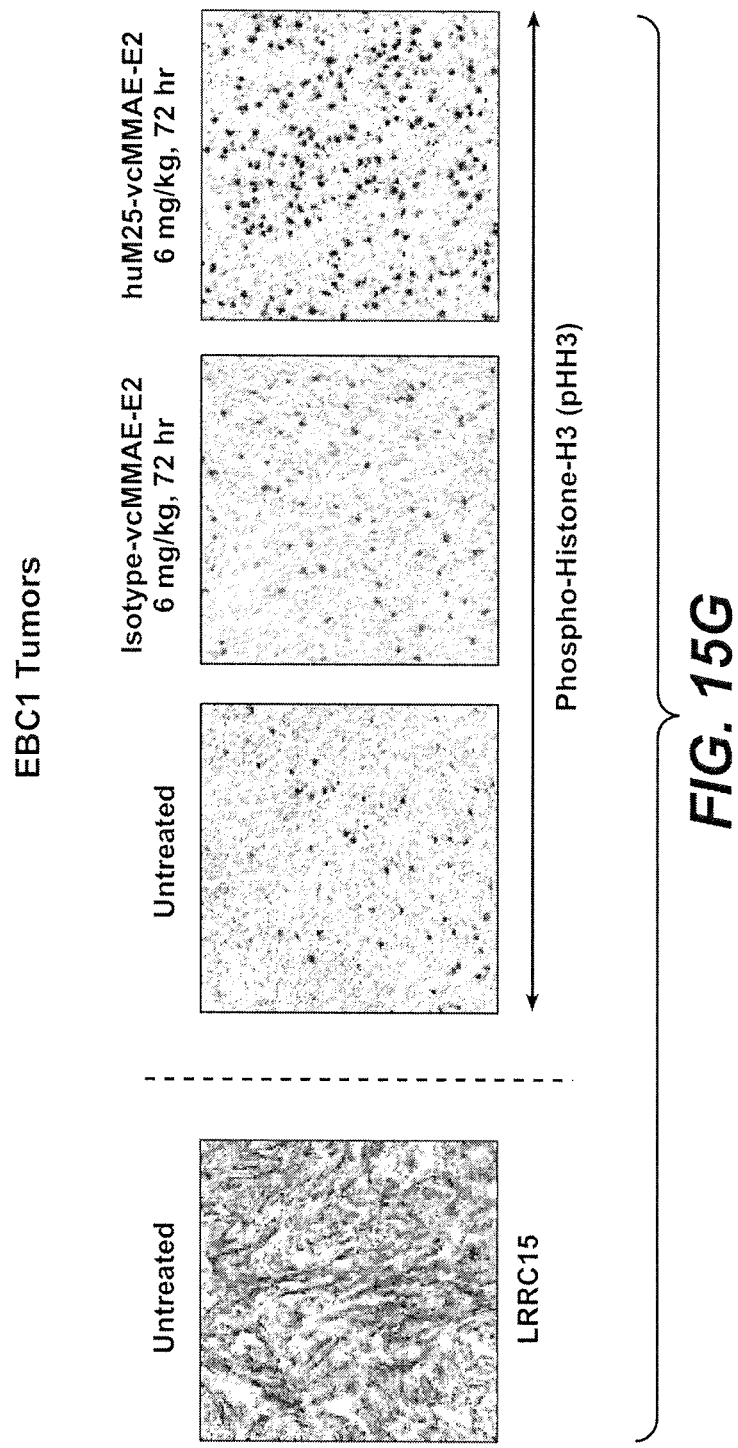
Figure 15H:
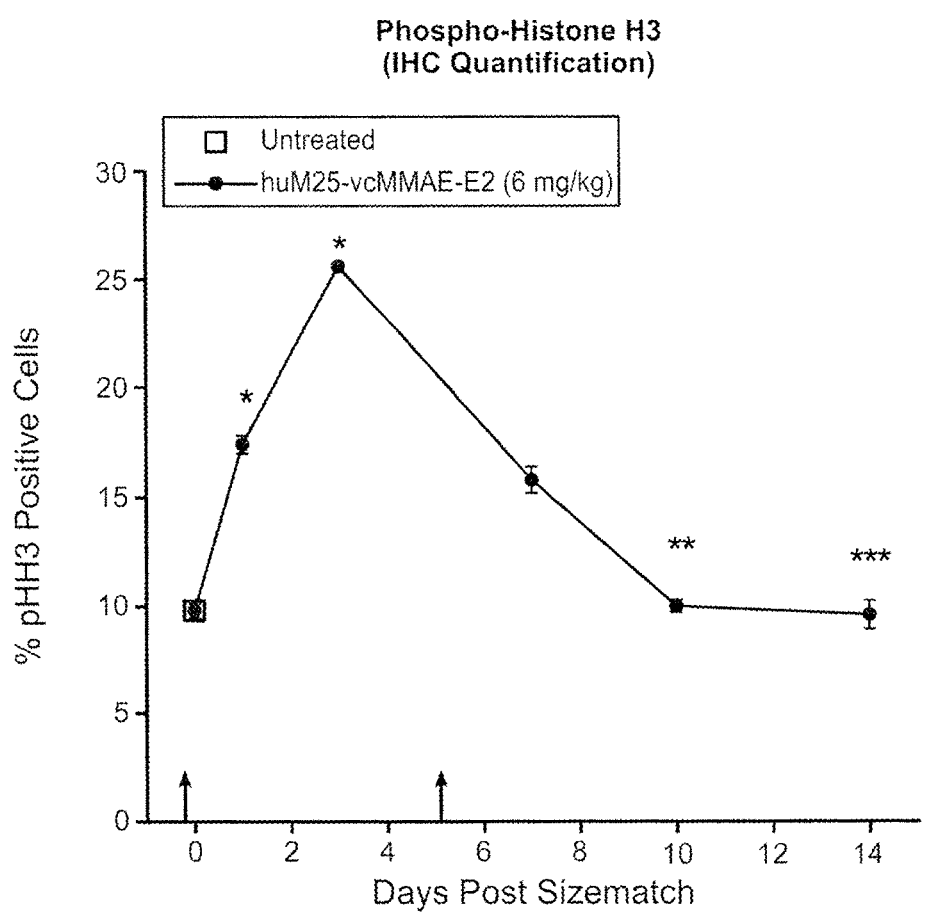

FIGS. 15A-15I provide graphs and pictograms demonstrating that the anti-tumor activity of exemplary anti-huLRRC15 ADC huM25-vcMMAE-E2 against huLRRC15 stromal(+)/cancer(−) tumors is mediated at least in part by a bystander killing effect. Also shown is a representative IHC picture illustrating LRRC15 expression on stromal cells for this xenograft model. FIG. 15A depicts the timing for removal of tumors for ex vivo analysis. FIGS. 15B-15E depict ex vivo flow cytometry data of EBC-1 tumors treated with huM25-vcMMAE-E2 or huM25-mcMMAF-E2: FIG. 15B shows EPCAM expression; FIG. 15C shows FAP expression; FIG. 15D shows CD11c expression; and FIG. 15E shows F4/80 expression. FIG. 15F depicts microscopic analysis of ex vivo EBC-1 tumors treated with huM25-vcMMAE-E2. FIG. 15G depicts immunohistochemical (IHC) staining of EBC-1 tumors showing LRRC15 expression in untreated tumors (left of dashed line), or phospho-histone-H3 (pHH3) staining of untreated tumors or tumors treated with 6 mg/kg of either isotype-vcMMAE-E2 or huM25-vcMMAE-E2 (right of dashed line). FIG. 15H shows quantitated immunohistochemical analysis of percentage phospho-histone-H3 (% pHH3) positive cells vs. days post sizematch in untreated EBC-1 tumors or tumors treated with 6 mg/kg huM25-vcMMAE-E2. FIG. 15I shows expression of CD45 (left) or F4/80 (right) by staining of EBC-1 tumors after 11 days post-treatment with 6 mg/kg of isotype-vcMMAE-E2 (top panels) or huM25-vcMMAE-E2 (bottom panels).

Figure 16:
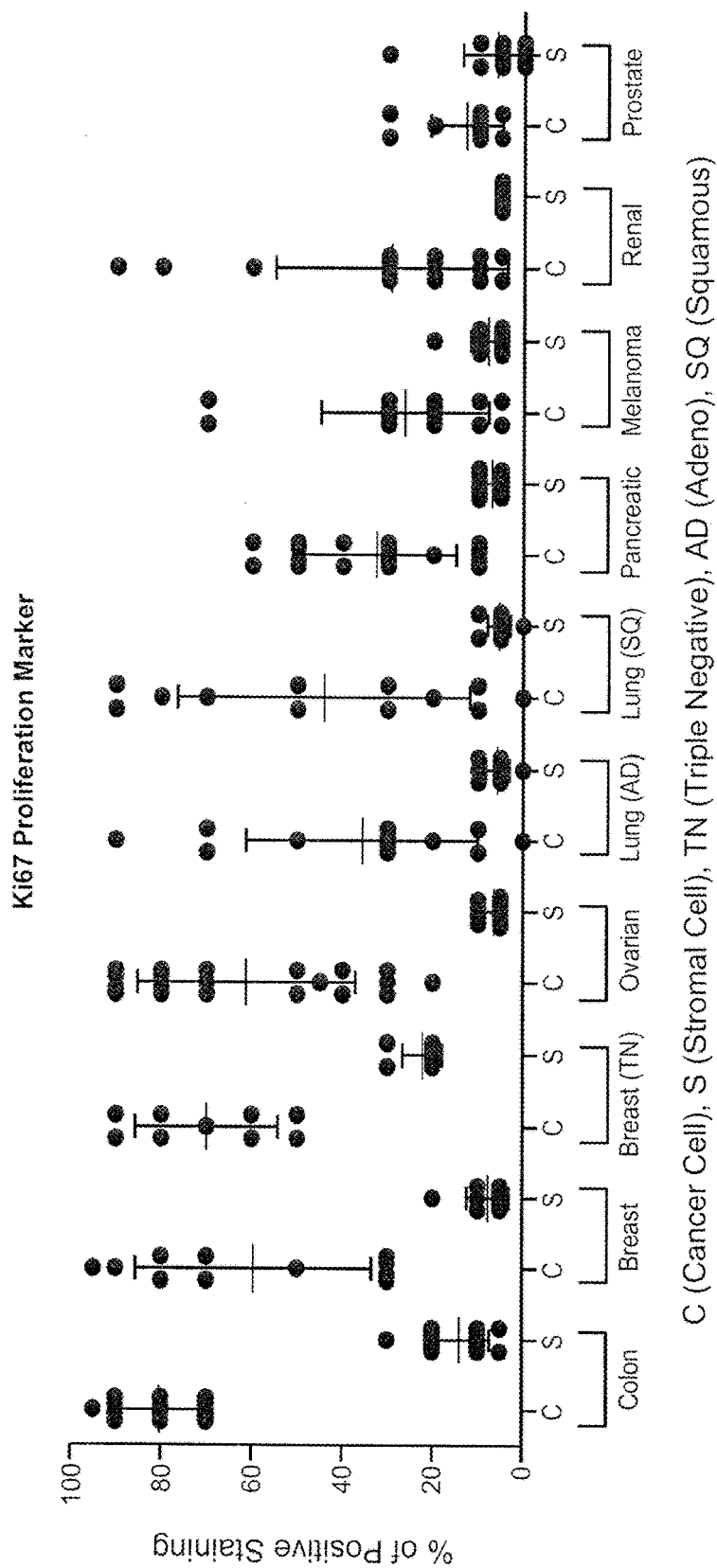

FIG. 16 provides data demonstrating that stromal fibroblasts are less proliferative than cancer cells across a panel of different tumor types, using Ki67 expression as a marker of proliferation.

Figure 17A:
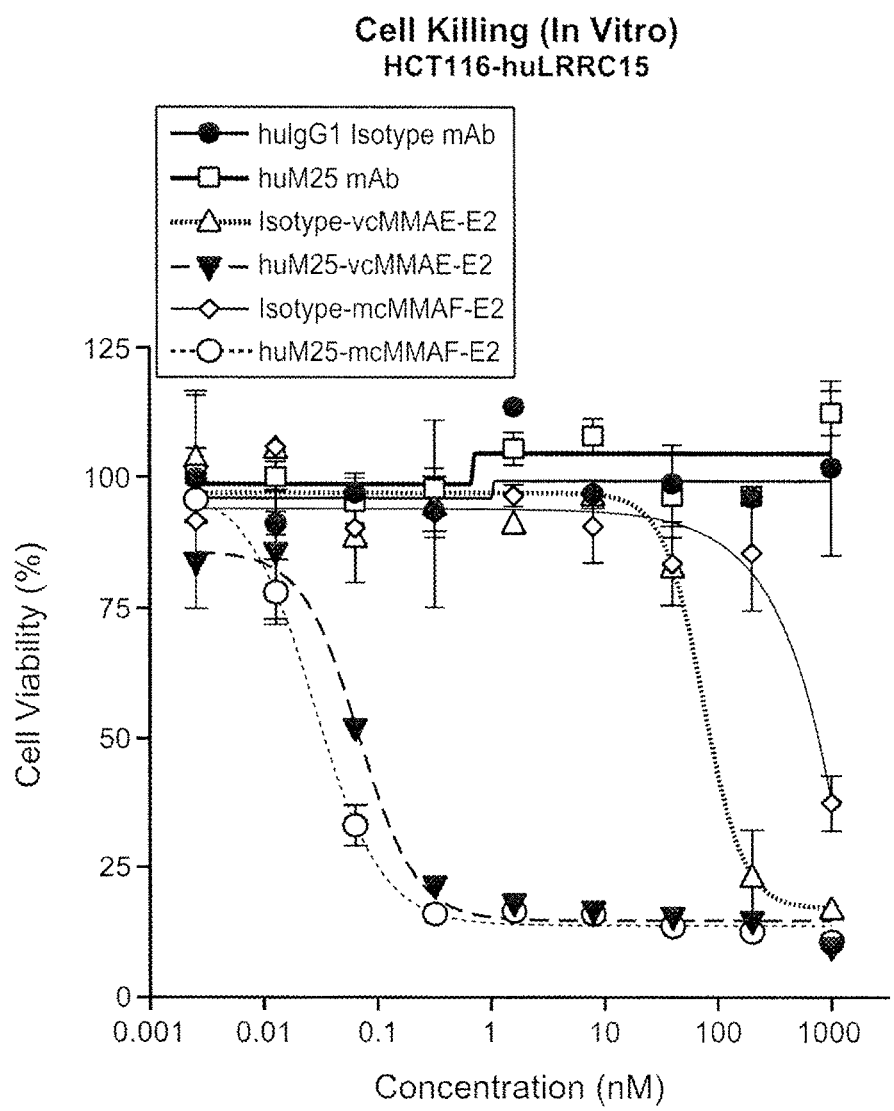
Figure 17B:
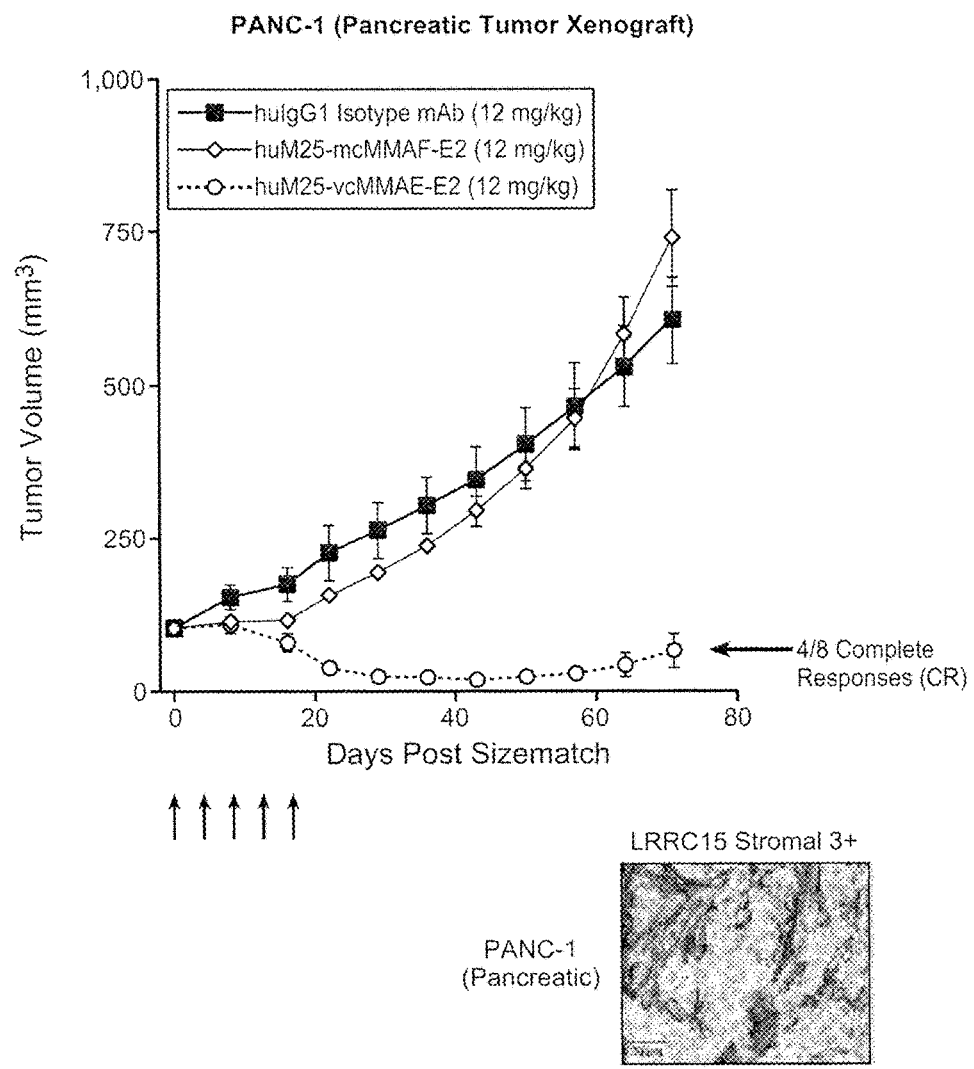

FIGS. 17A and 17B compare the anti-tumor activities of huM25-vcMMAE-E2 and huM25-mcMMAF-E2 in vitro (FIG. 17A) and in vivo (FIG. 17B). In FIG. 17B, arrows represent dosing days. Also shown is a representative IHC picture illustrating LRRC15 expression on stromal cells for this xenograft model.

Figure 18A:
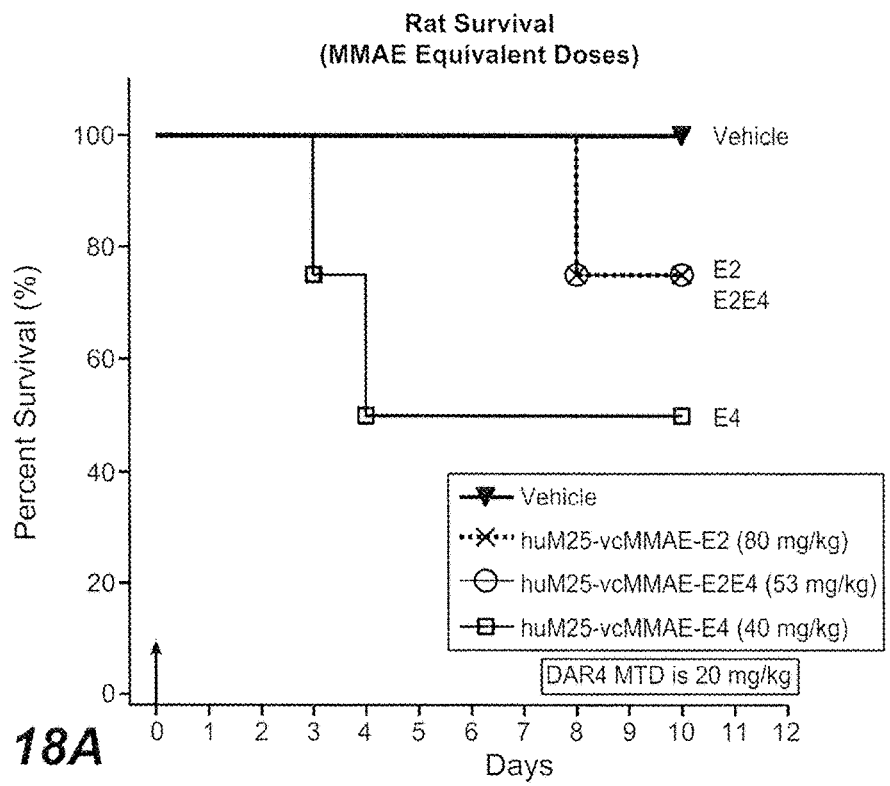
Figure 18B:
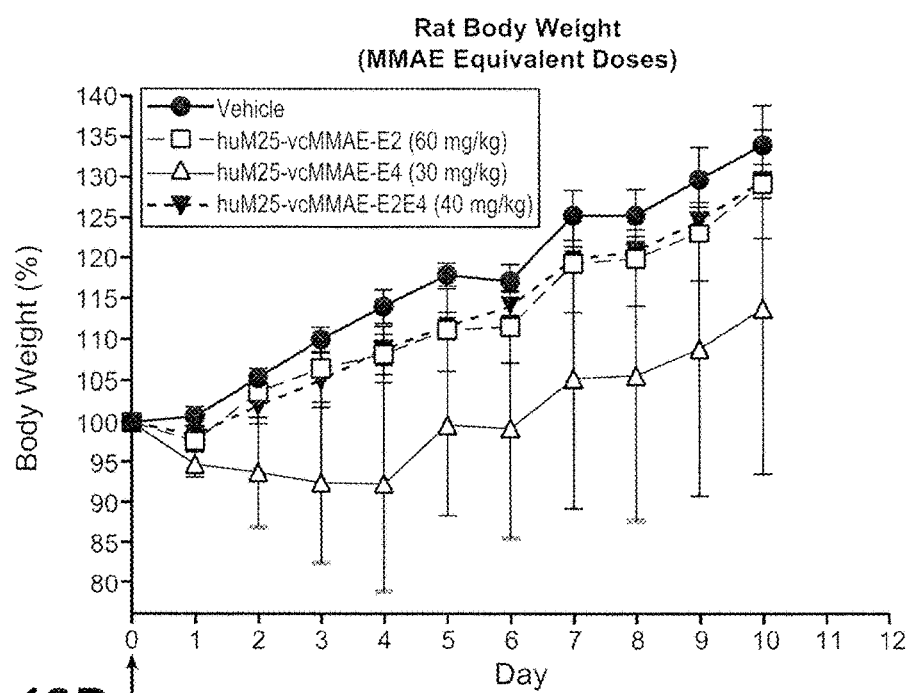

FIGS. 18A and 18B provide data demonstrating that, on an equivalent drug basis, E2 enriched preparations of anti-huLRRC15 ADCs are better tolerated than higher loaded E4 preparations when assessed by survival (FIG. 15A) or weight loss (FIG. 15B). Arrows represent dosing days.

Figure 19:
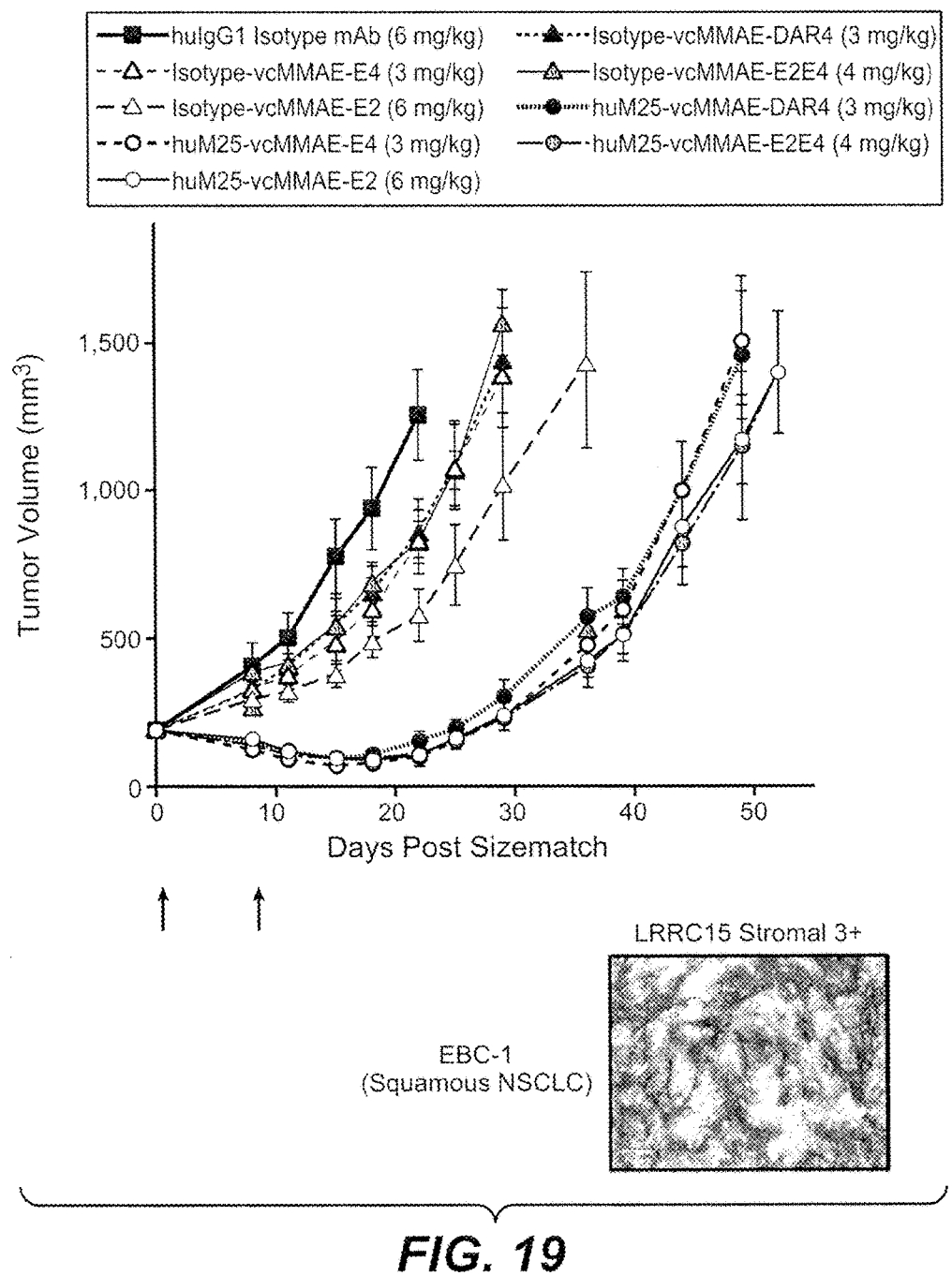

FIG. 19 provides data demonstrating that anti-huLRRC15 ADCs with E2 drug loading have efficacy comparable to anti-huLRRC15 ADCs having higher drug loading, as assessed on an equivalent drug basis. Arrows represent dosing days. Also shown is a representative IHC picture illustrating LRRC15 expression on stromal cells for this xenograft model.

FIGS. 20A-20E provide data demonstrating that anti-huLRRC15 ADCs are superior to current standard of care agents such as carboplatin or erlotinib (FIG. 20A); erlotinib or cetuximab (FIG. 20B); carboplatin or erlotinib (FIG. 20C); doxorubicin (FIG. 20D); and gemcitabine (FIG. 20E) in in vivo models of efficacy. Arrows represent dosing days. Also shown are representative IHC pictures illustrating LRRC15 expression on stromal cells for each of these xenograft models.

Figure 21A:
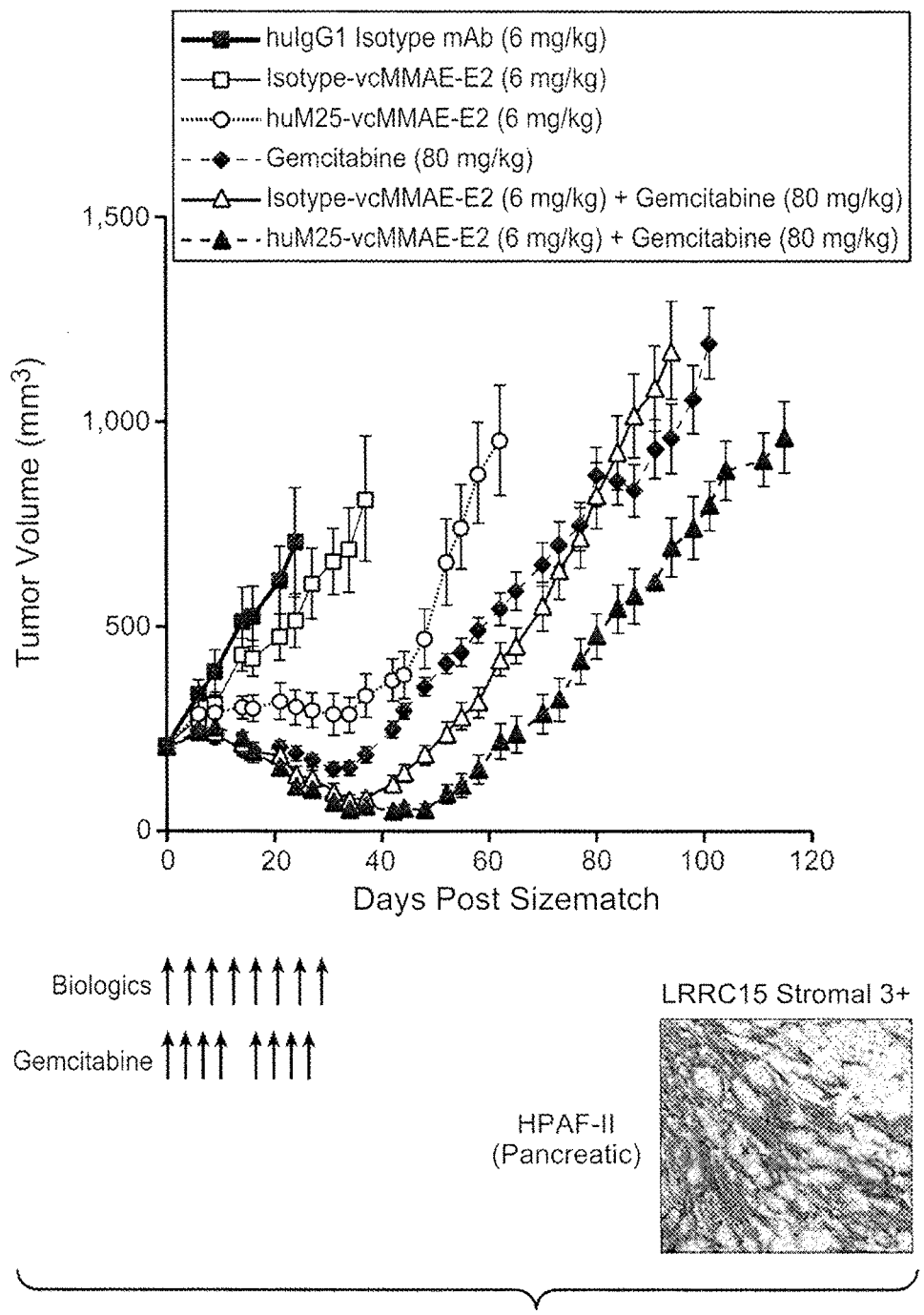
Figure 21B:
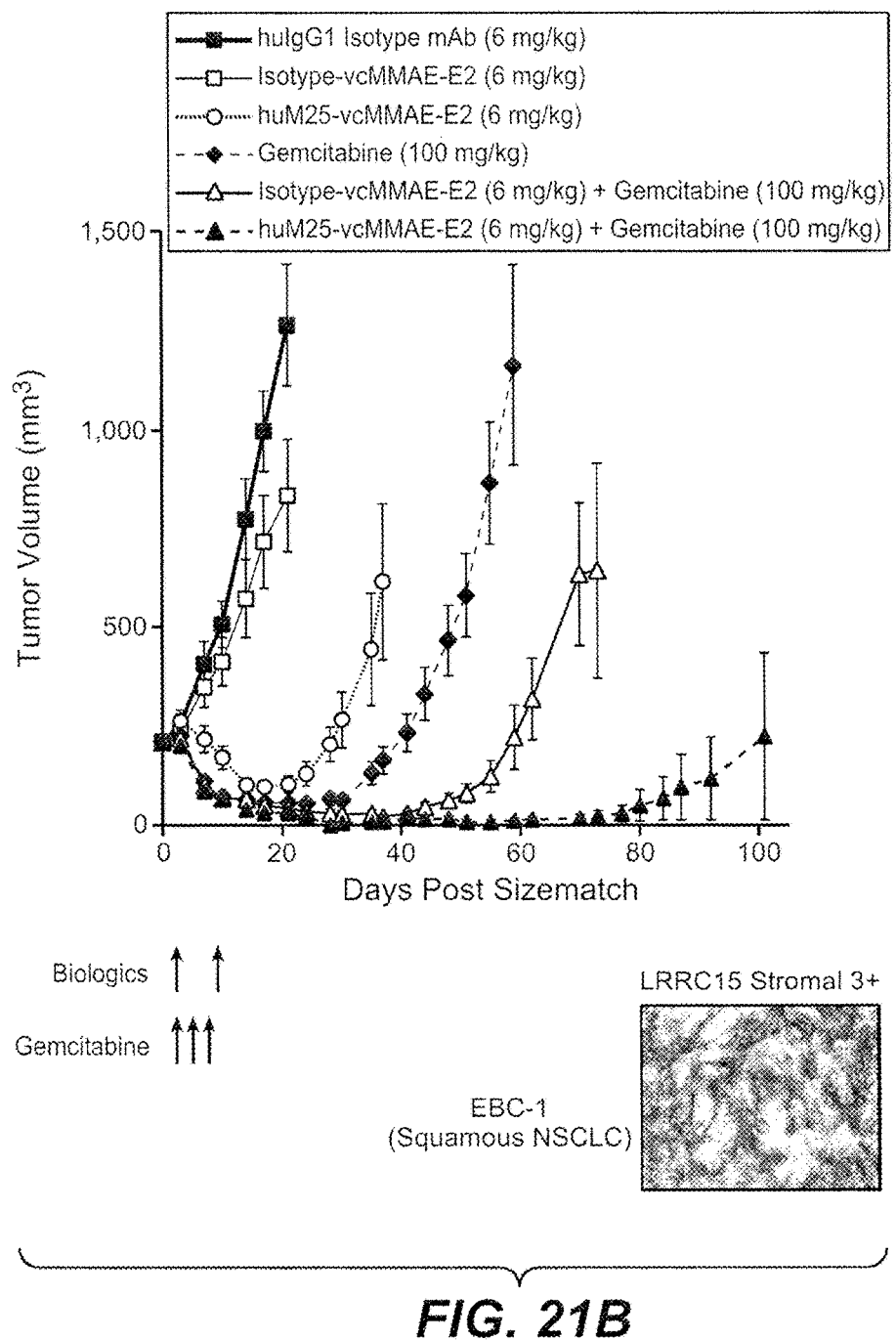
Figure 21C:
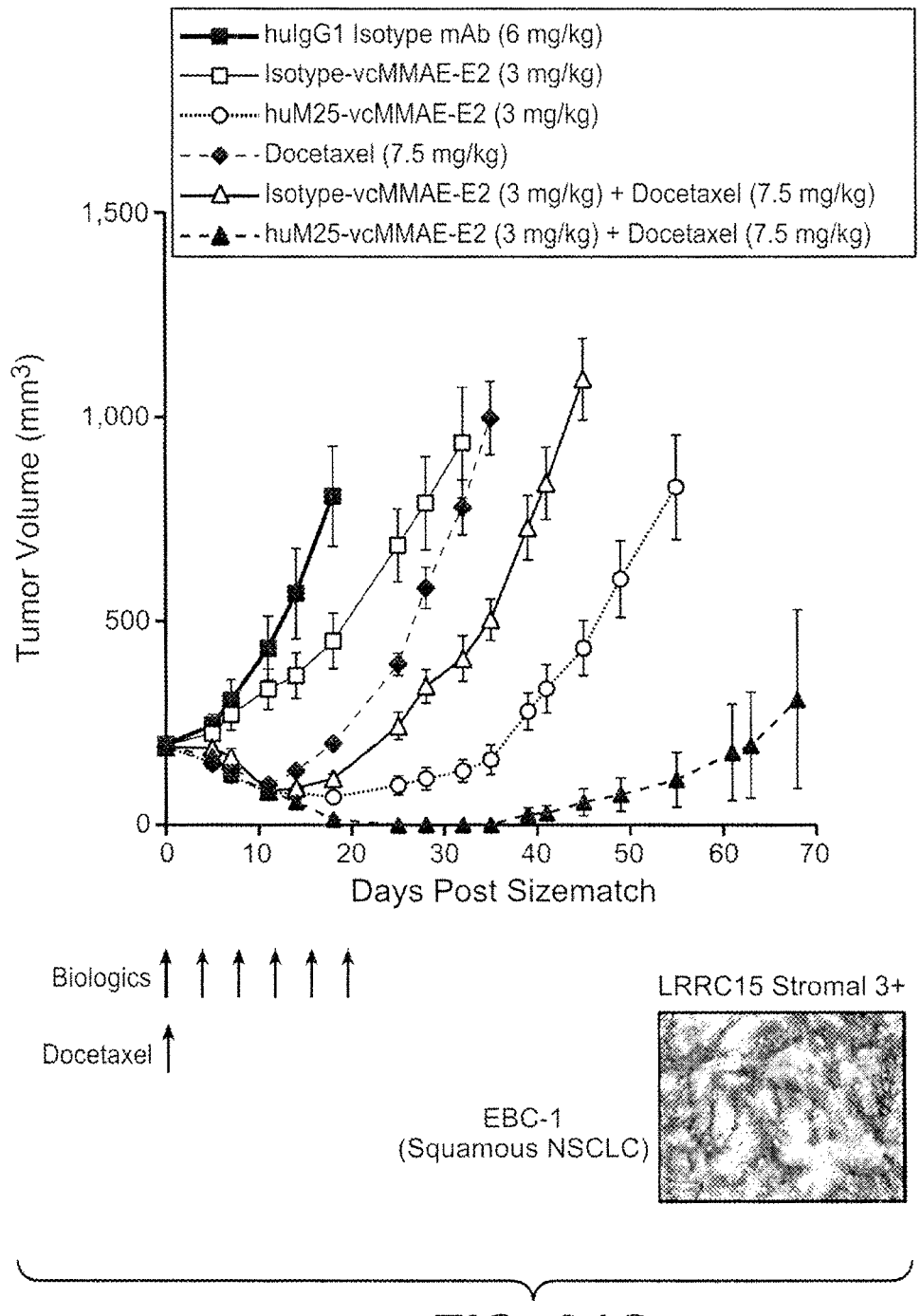
Figure 21D:
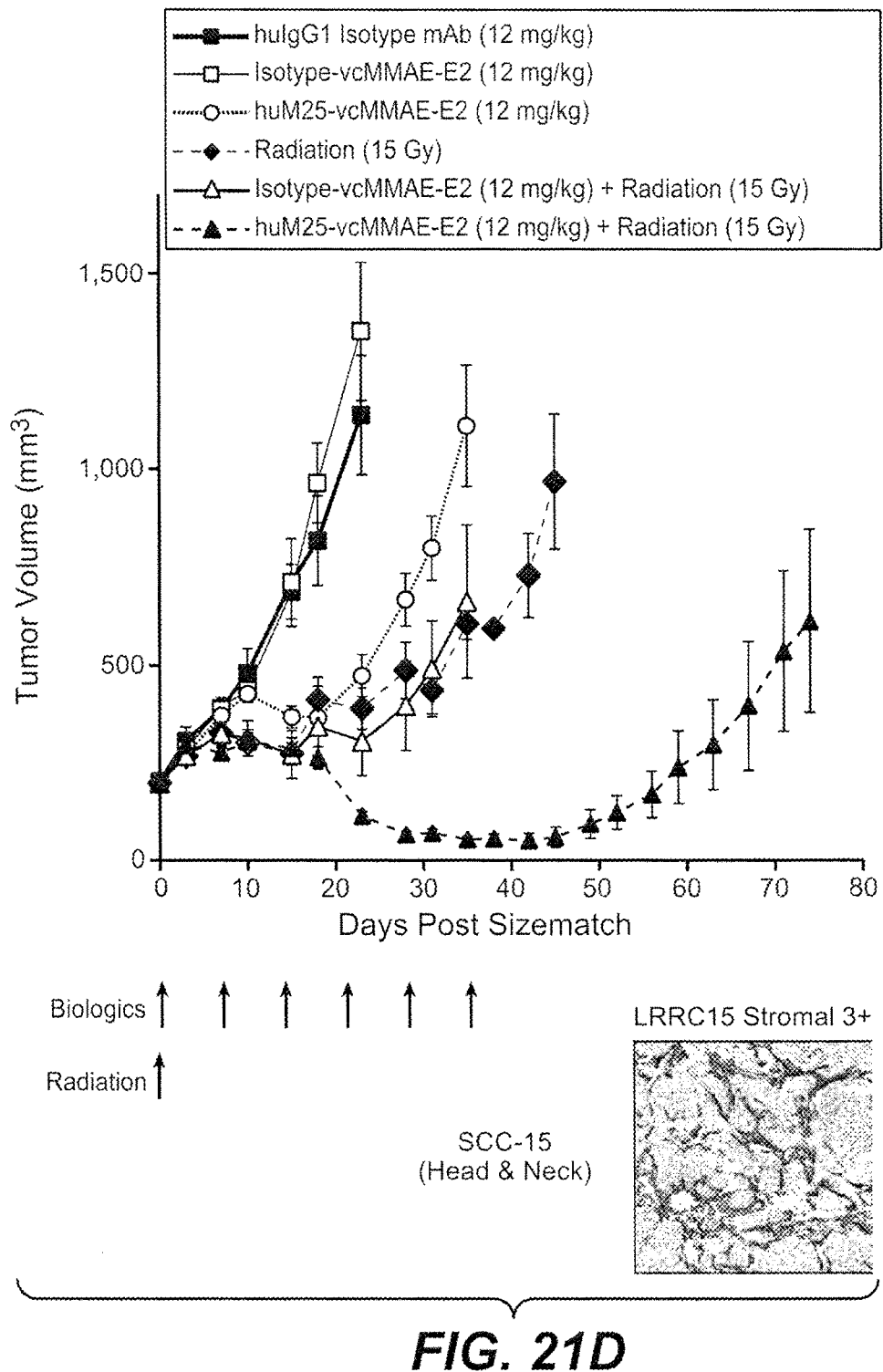
Figure 21E:
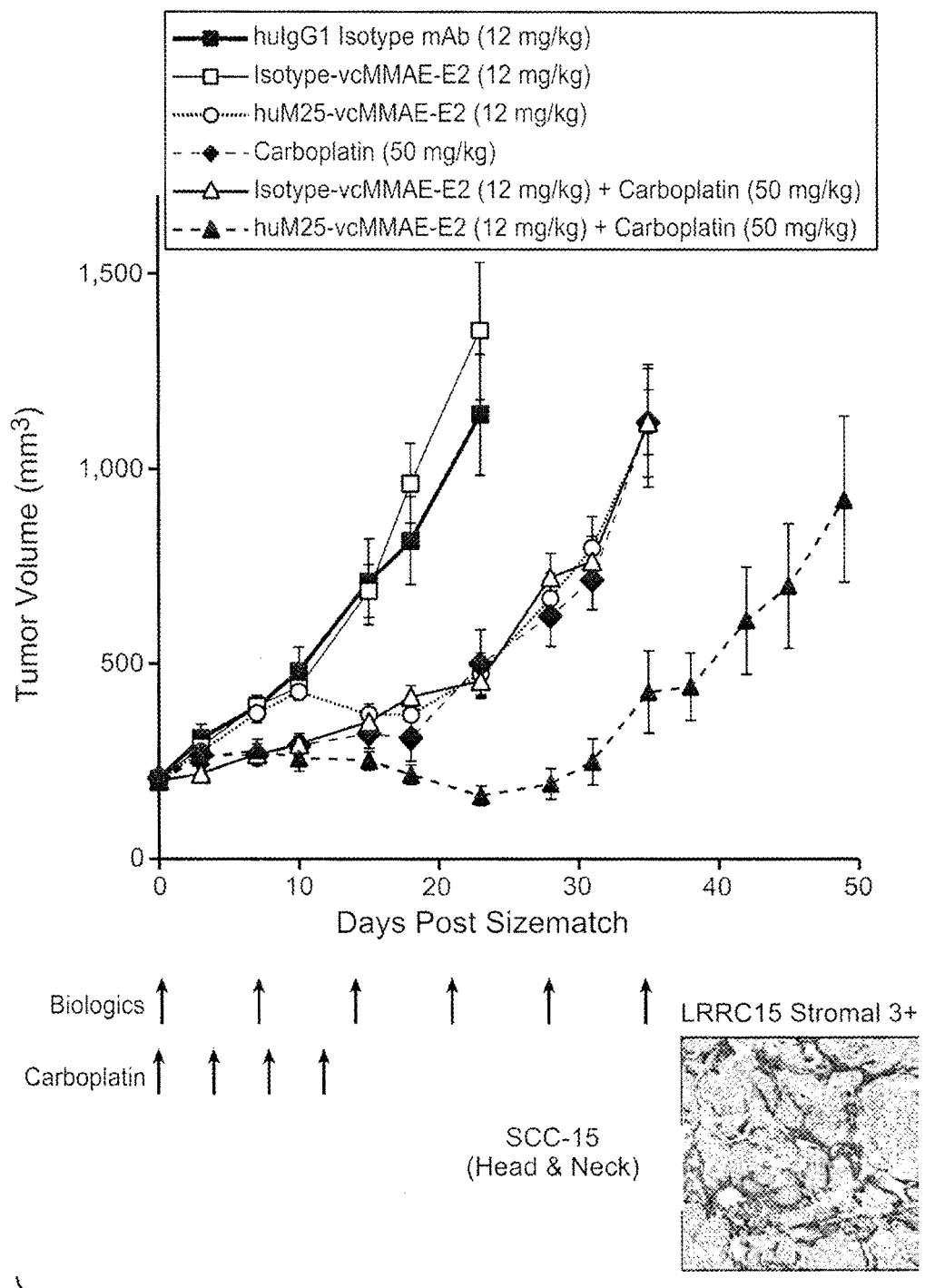

FIGS. 21A-21E provide data demonstrating that anti-huLRRC15 ADCs are effective when administered adjunctive to current standard of care cytotoxic anti-cancer therapies. FIG. 21A depicts the anti-tumor activity of huM25-vcMMAE-E2 with gemcitabine (Gem) in HPAF-II; FIG. 21B depicts the anti-tumor activity of huM25-vcMMAE-E2 with gemcitabine (Gem) in EBC-1; FIG. 21C depicts the anti-tumor activity of huM25-vcMMAE-DAR4 with docetaxel; FIG. 21D depicts the anti-tumor activity of huM25-vcMMAE-E2 with radiation; and FIG. 21E depicts the anti-tumor activity of huM25-vcMMAE-E2 with carboplatin. Arrows represent dosing days. Also shown are representative IHC pictures illustrating LRRC15 expression on stromal cells for each of these xenograft models.

Figure 22A:
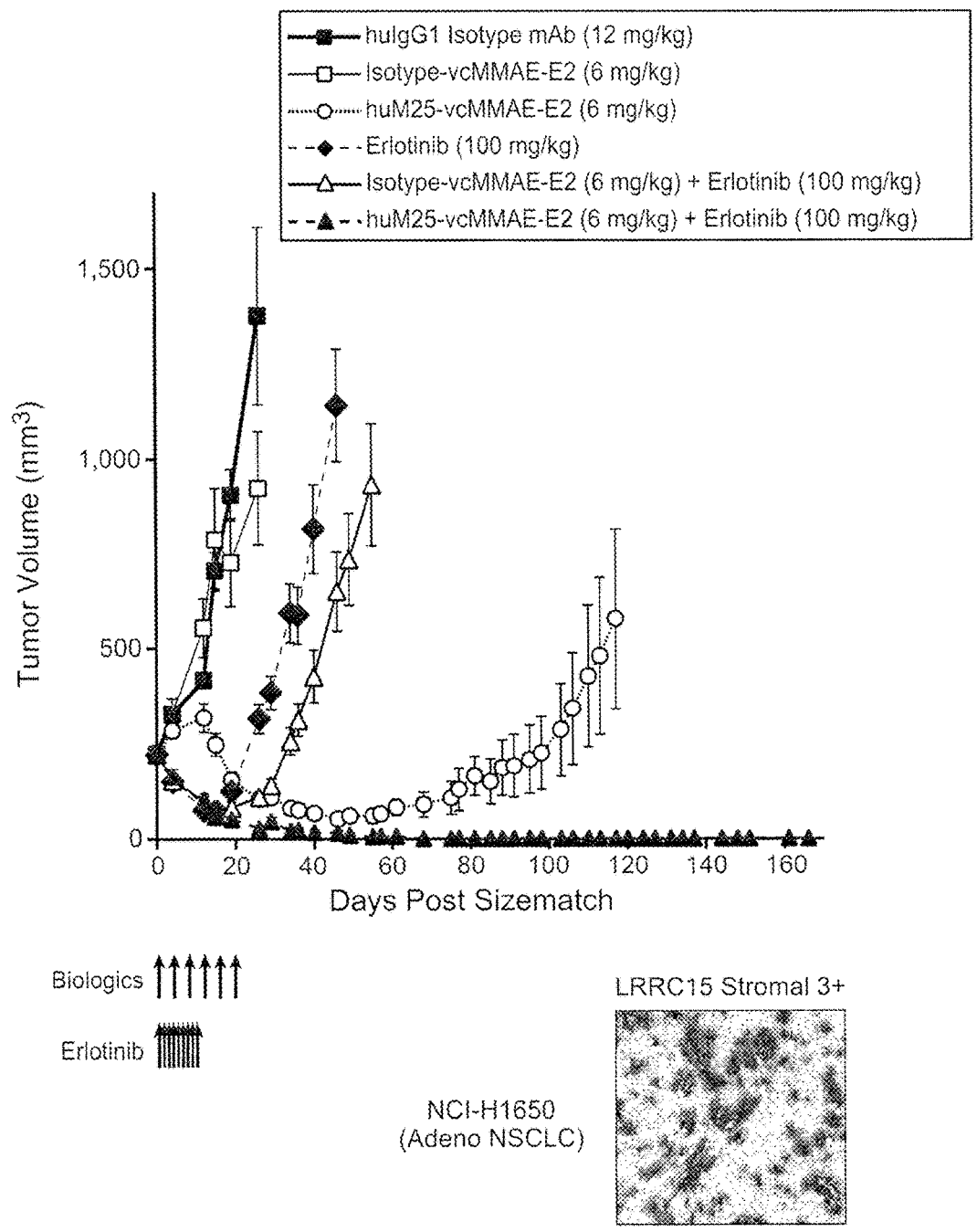
Figure 22B:
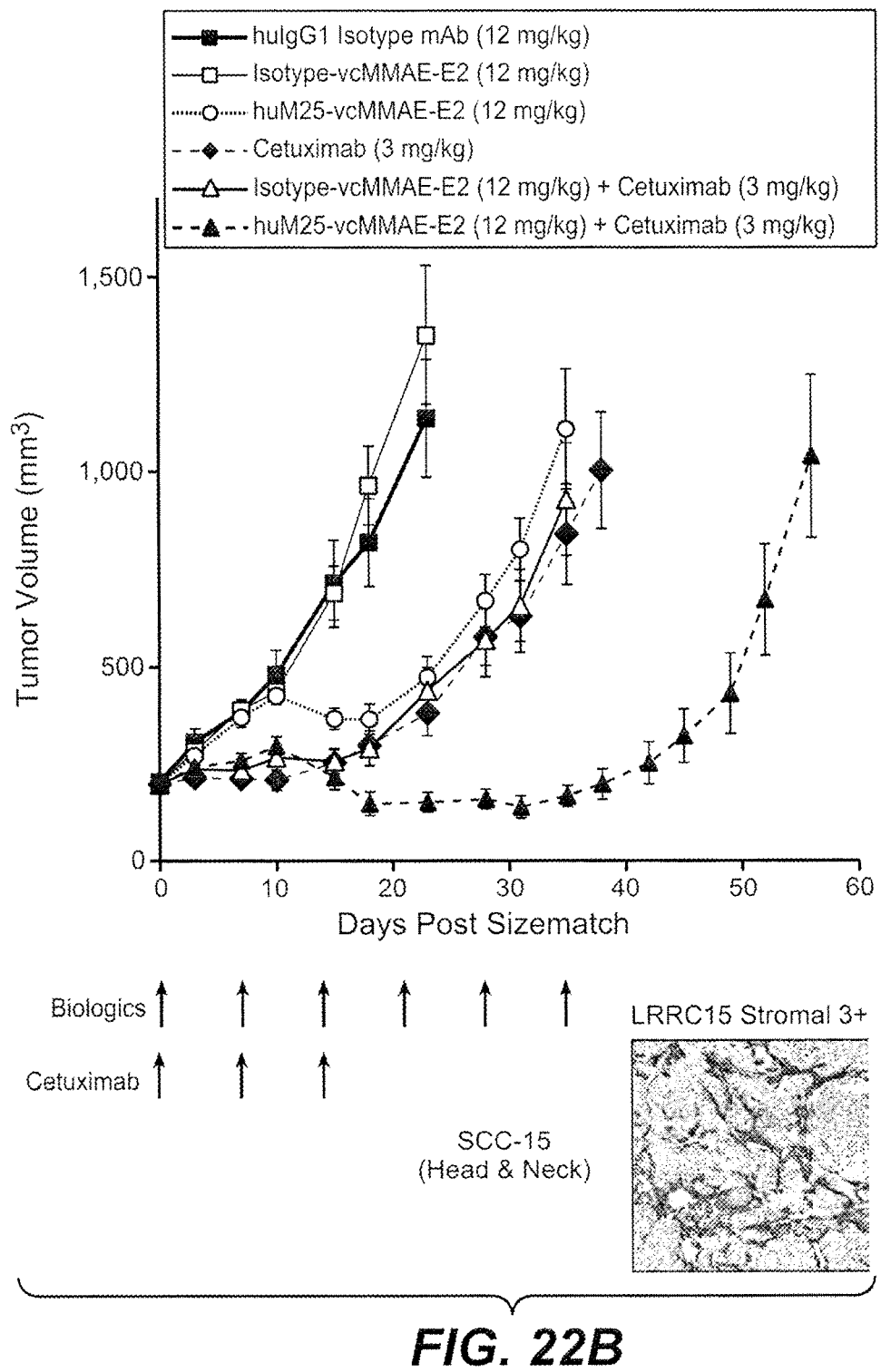
Figure 22C:
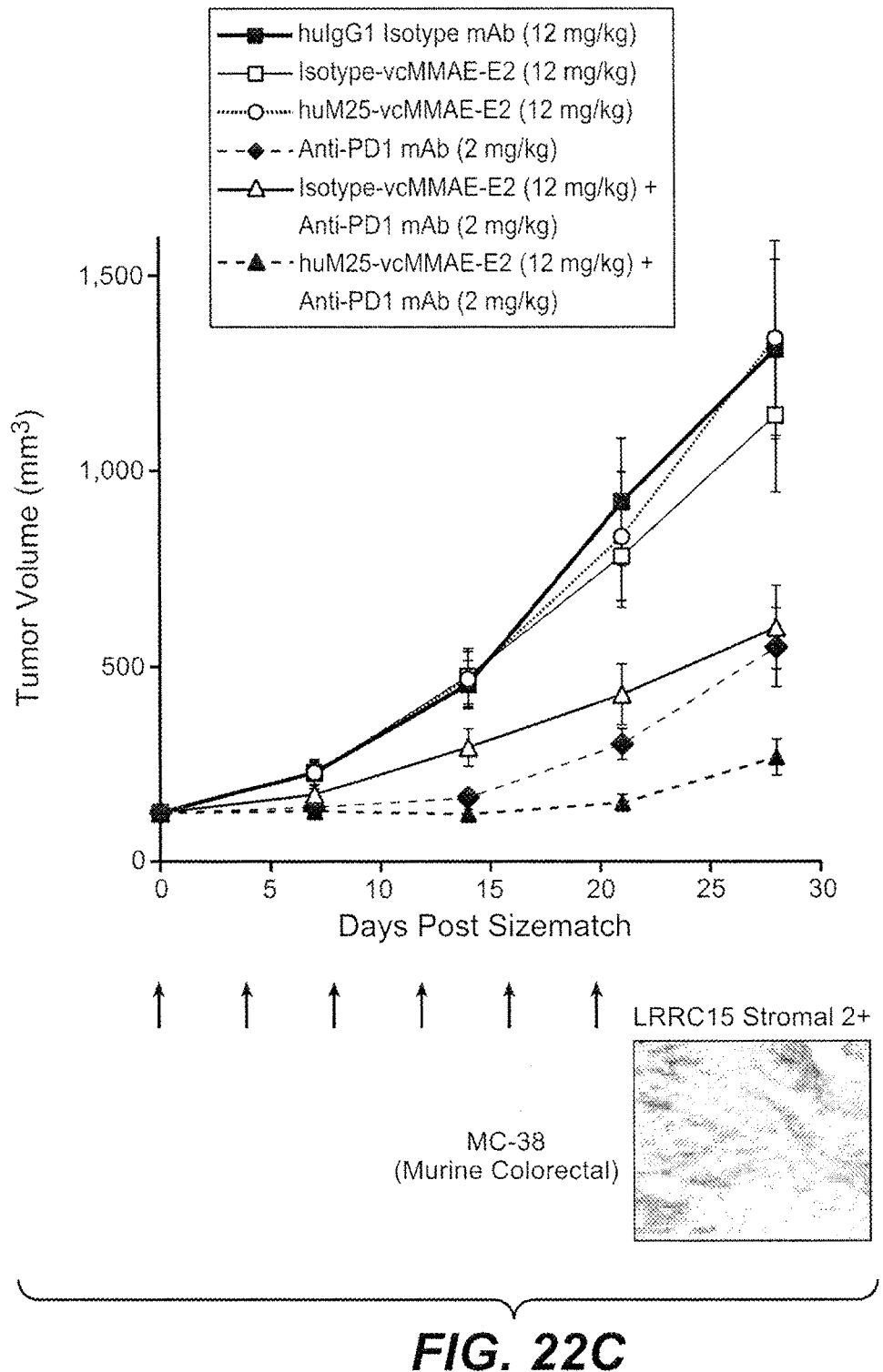

FIGS. 22A-22C provide data demonstrating that anti-huLRRC15 ADCs are effective when administered adjunctive to targeted anti-cancer therapies. FIG. 22A depicts the anti-tumor activity of huM25-vcMMAE-E2 with erlotinib; FIG. 22B depicts the anti-tumor activity of huM25-vcMMAE-E2 with cetuximab; and FIG. 22C depicts the anti-tumor activity of huM25-vcMMAE-E2 with an anti-PD-1 antibody. Arrows represent dosing days. Also shown are representative IHC pictures illustrating LRRC15 expression on stromal cells for each of these xenograft models.

Figure 23A:
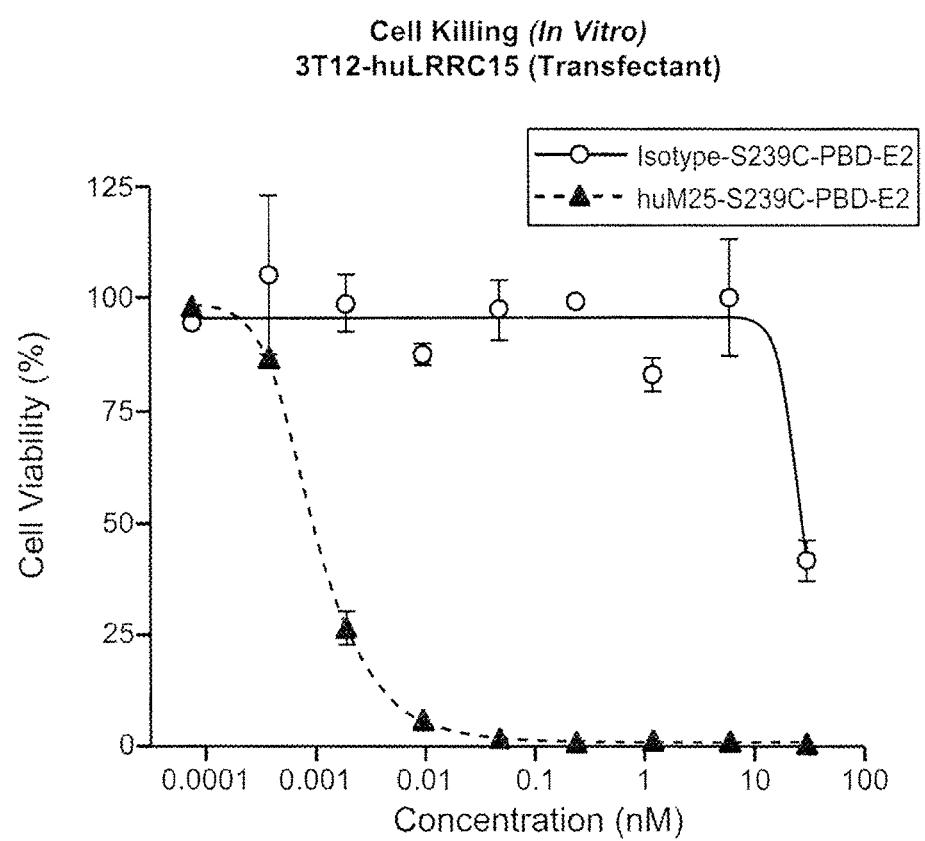
Figure 23B:
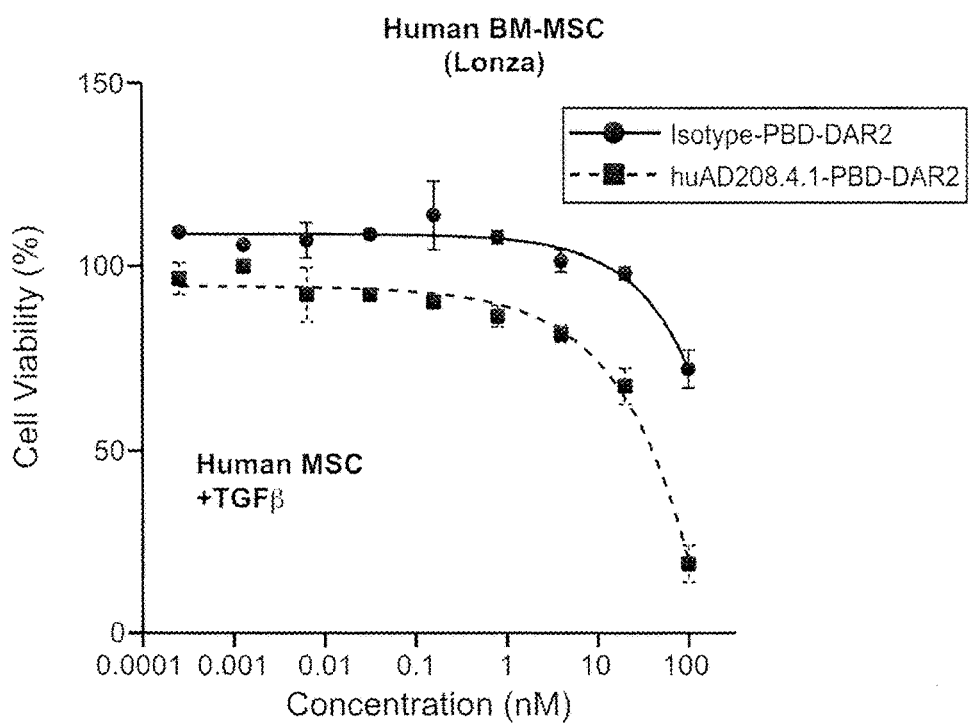
Figure 23C:
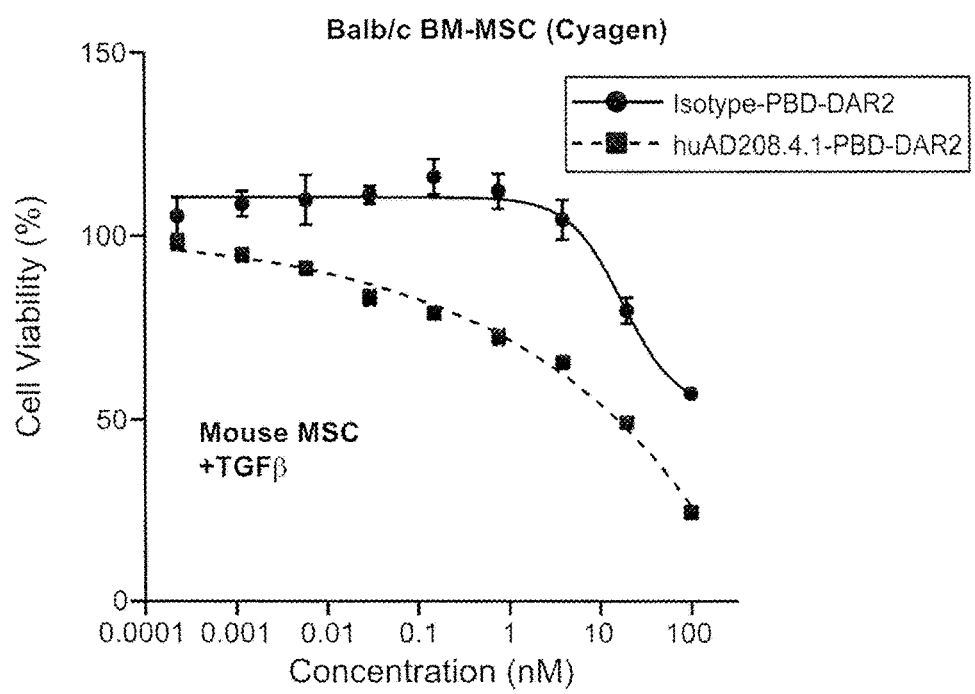
Figure 23D:
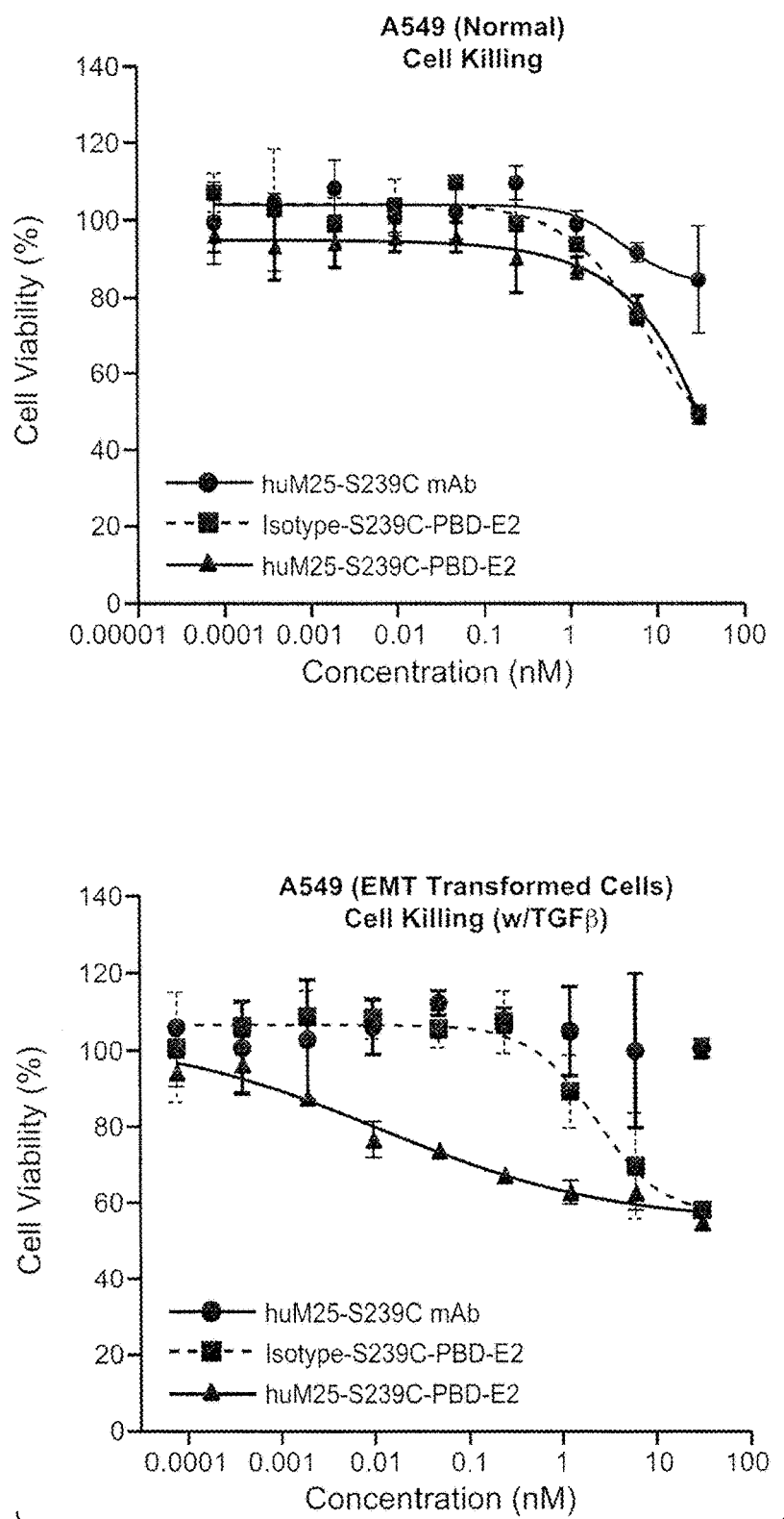

FIGS. 23A-23D show in vitro data for exemplary anti-huLRRC15 ADCs comprising a minor groove binding pyrrolobenzodiazepine (PBD) cytotoxic and/or cytostatic agent. FIG. 23A shows in vitro cell killing in LRRC15 transfected 3T12 cells by isotype-S239C-PBD-E2 (solid line) or huM25-S239C-PBD-E2 (dashed line); FIG. 23B shows in vitro cell killing in human BM-MSC (Lonza) mesenchymal stem cells in the presence of 10 ng/mL TGFβ by isotype-PBD-DAR2 or huAD208.4.1-PBD-DAR2; FIG. 23C shows in vitro cell killing in murine Balb/c BM-MSC (Cyagen) mesenchymal stem cells in the presence of 10 ng/mL TGFβ by isotype-PBD-DAR2 or huAD208.4.1-PBD-DAR2; FIG. 23D shows in vitro cell killing in A549 lung cancer cells (top) or A549 cells that have undergone epithelial to mesenchymal transition (EMT) in the presence of 10 ng/mL TGFβ (bottom) by isotype-S239C-PBD-E2, huM25-S239C-PBD-E2, or huM25-S239C antibody. In the above graphs, the y-axis shows cell viability (%), and the x-axis shows antibody or ADC concentration in nM.

Figure 24A:
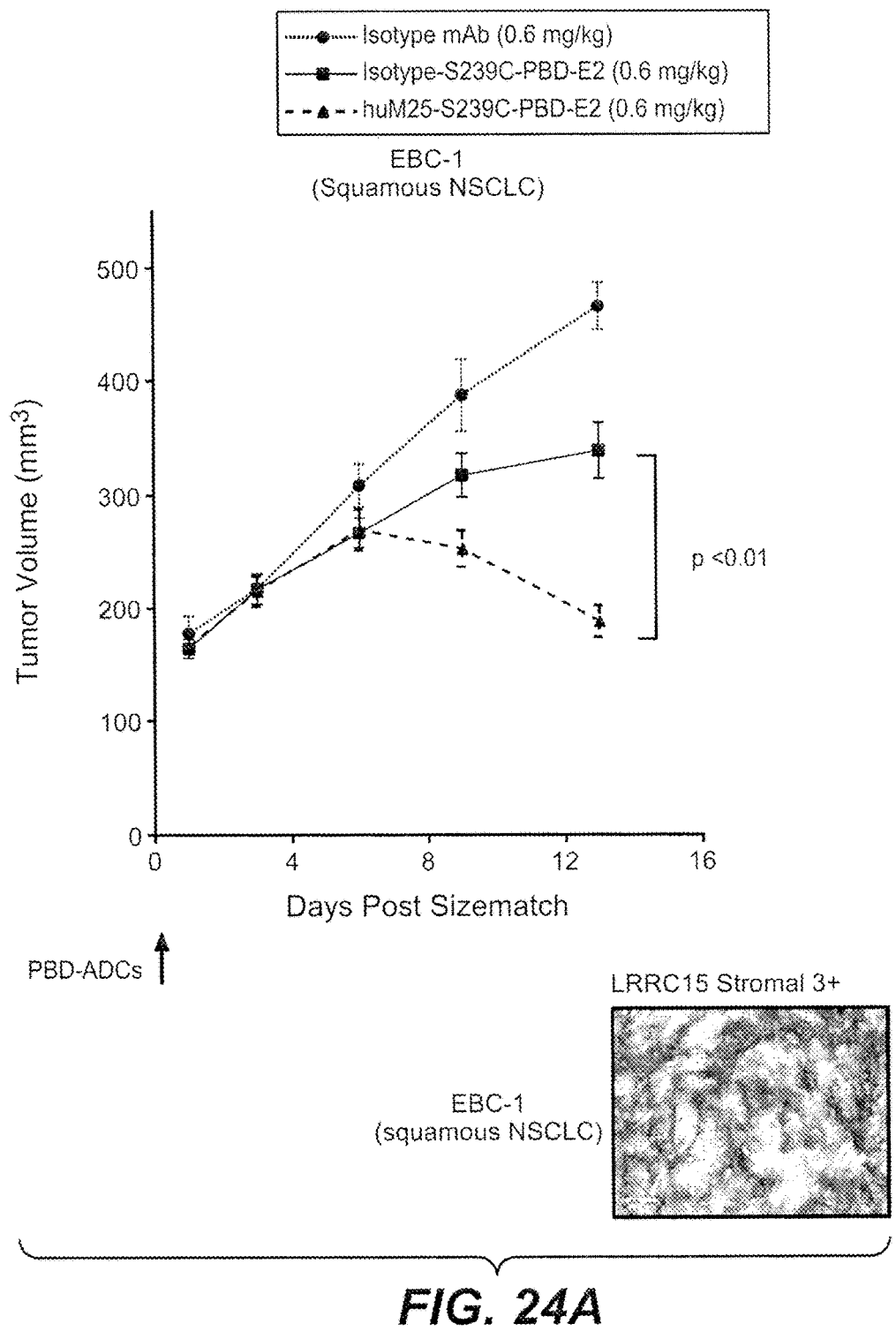
Figure 24B:
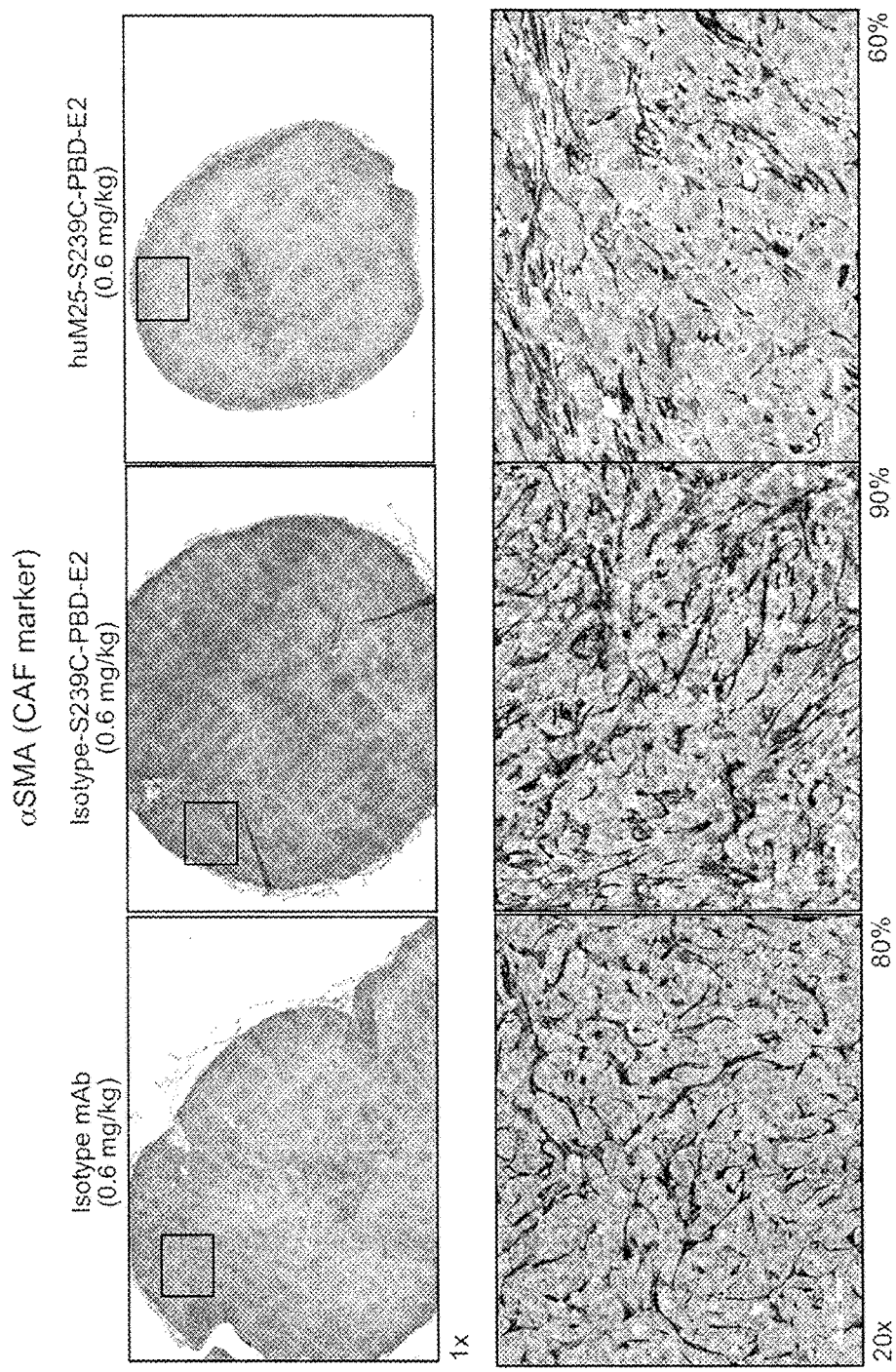
Figure 24C:
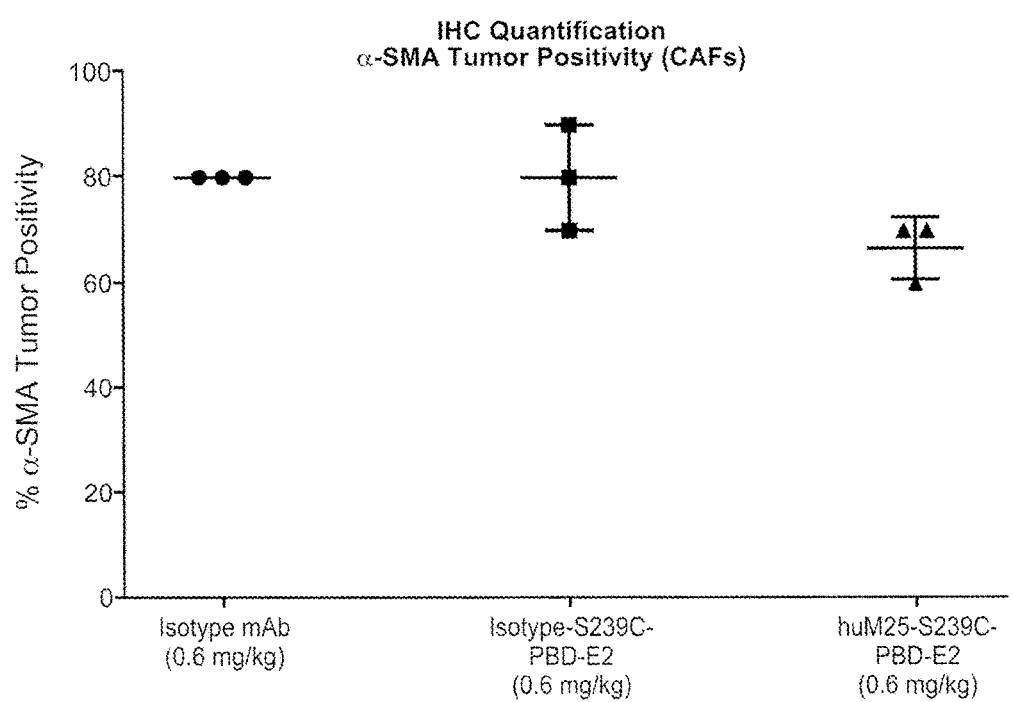
Figure 24D:
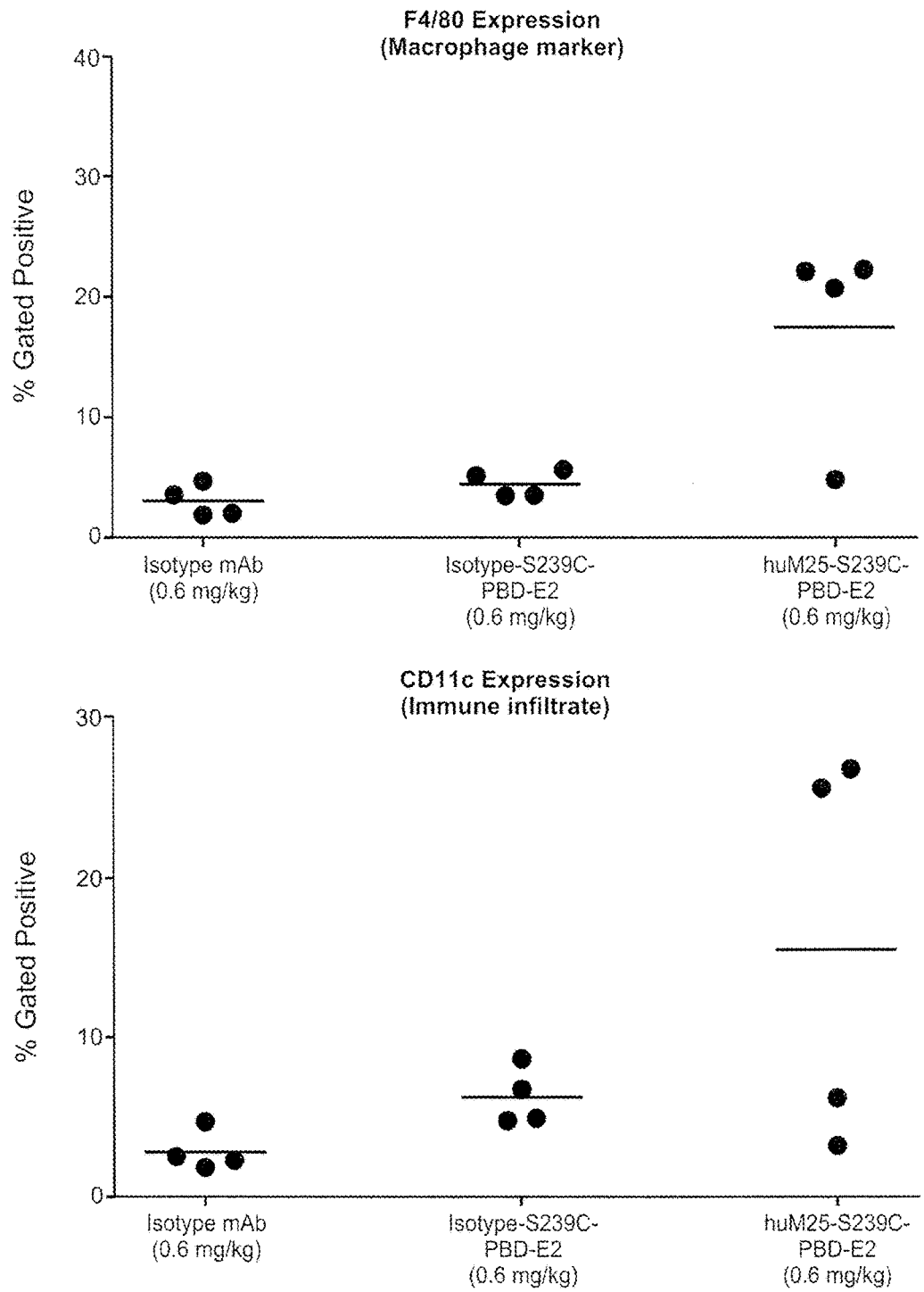
Figure 24E:
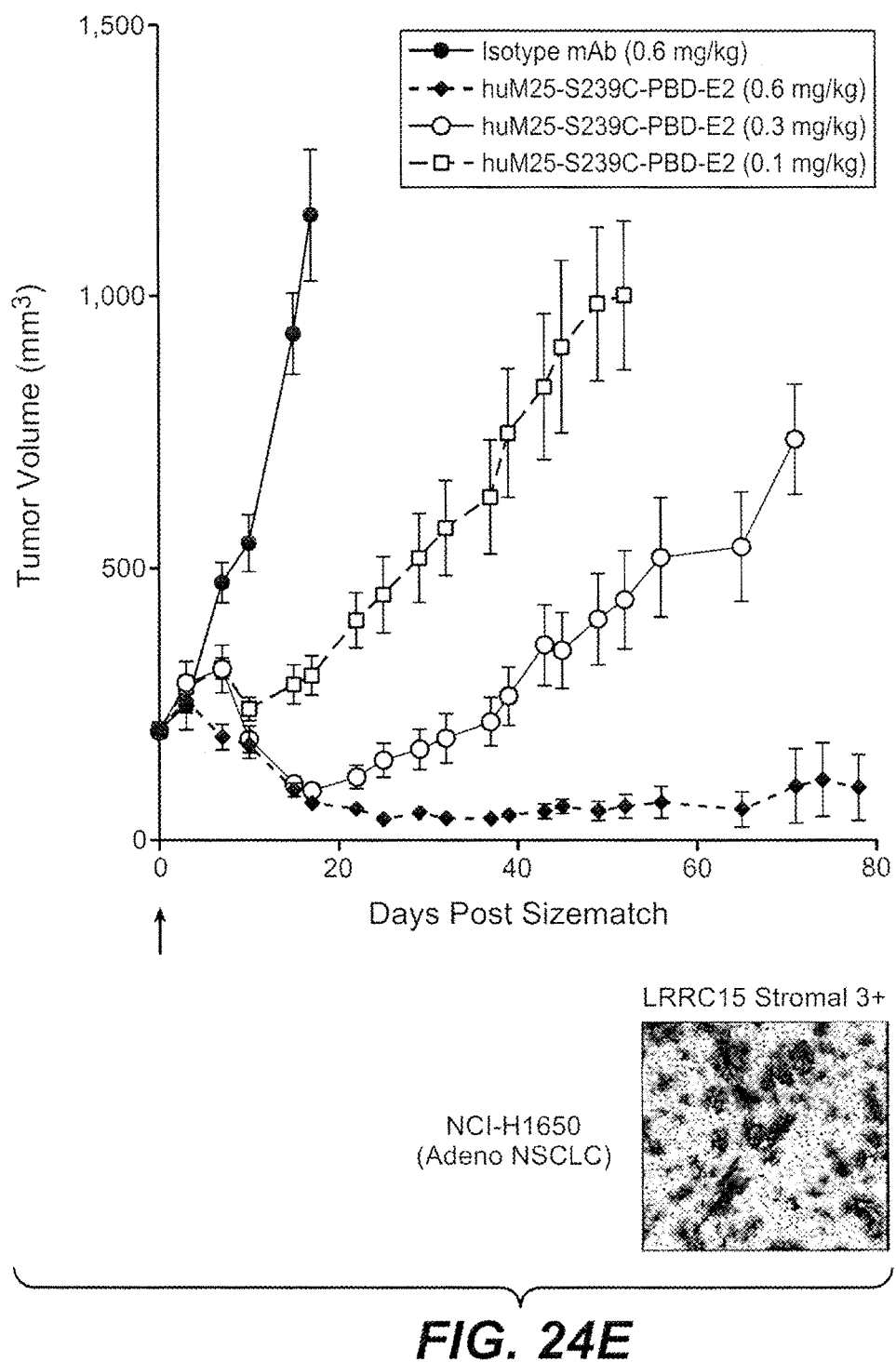
Figure 24G:
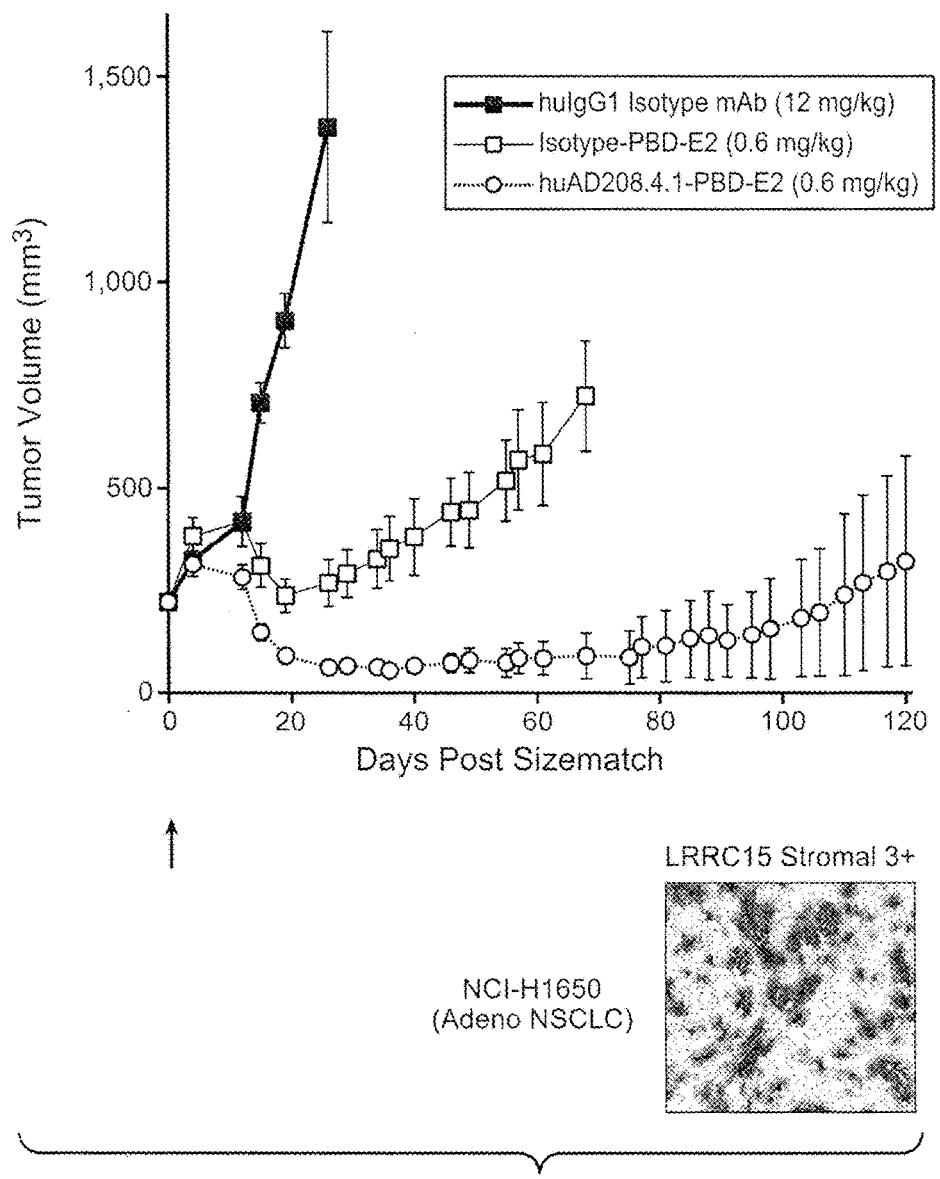
Figure 24H:
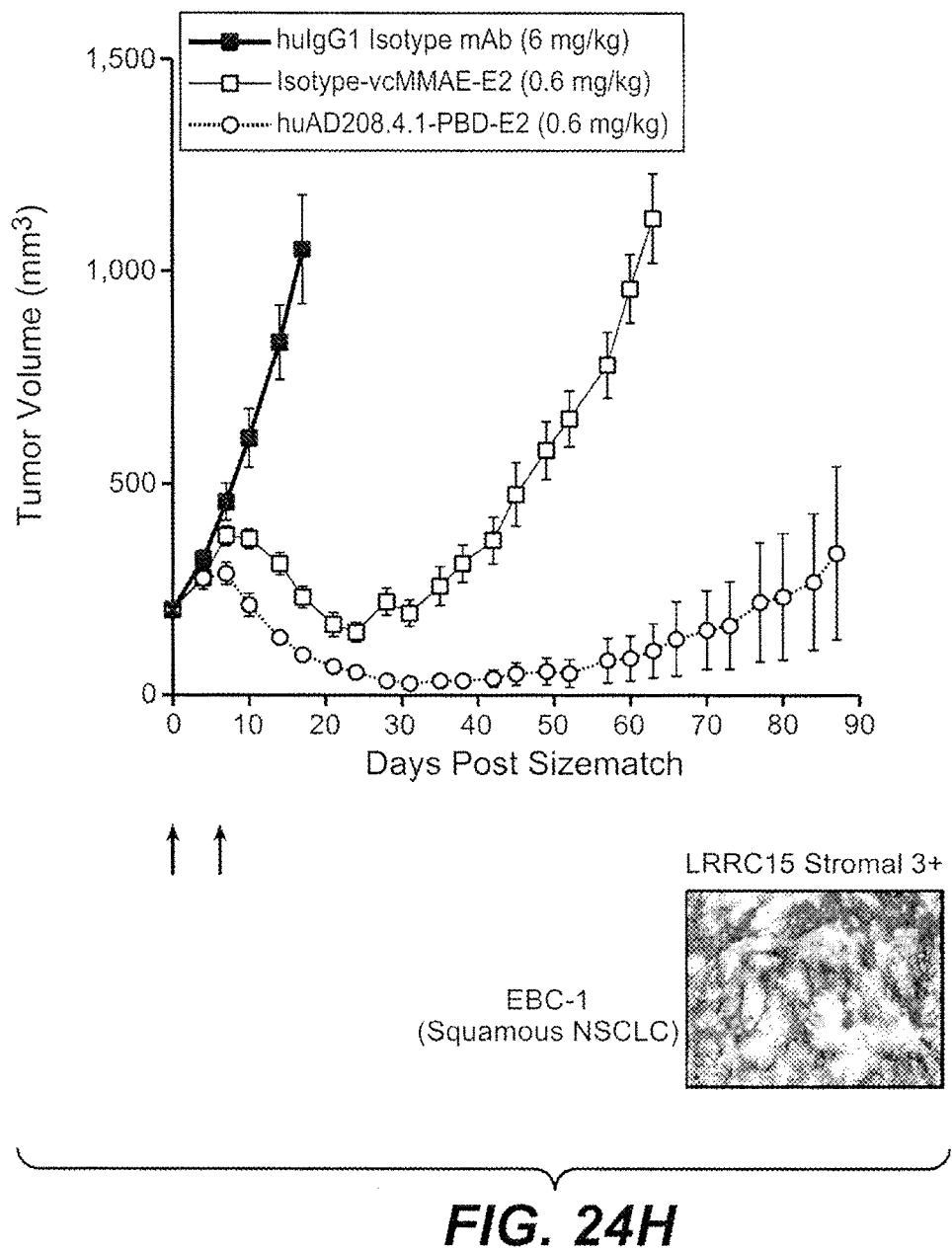

FIGS. 24A-24G provide data demonstrating that anti-huLRRC15 ADCs comprising a minor groove binding pyrrolobenzodiazepine (PBD) cytotoxic and/or cytostatic agent have potential anti-tumor activity against huLRRC15 stromal(+)/cancer(−) tumors in in vivo models: FIG. 24A depicts the effect of a single dose of isotype-S239C-PBD-E2, huM25-S239C-PBD-E2 or isotype antibody at 0.6 mg/kg on in vivo tumor volume (mm$^3$) at 0-14 days post sizematch of EBC-1 tumors. FIG. 24B depicts typical microscopy of tumor samples from experiment of FIG. 24A dosed with isotype antibody (left), isotype-S239C-PBD-E2 (middle), or huM25-S239C-PBD-E2 (right) stained for α-SMA. FIG. 24C depicts quantification of % α-SMA tumor positivity across samples from experiment of FIG. 24A. FIG. 24D depicts F4/80 (left) or CD11c (right) expression in tumor samples from experiment of FIG. 24A, as measured by flow cytometry. FIG. 24E depicts the effect of dosing huM25-S239C-PBD-E2 at 0.6, 0.3, or 0.1 mg/kg, or 0.6 mg/kg isotype antibody, on in vivo tumor volume (mm$^3$) at 0-80 days post sizematch of NCI-H1650 tumors. FIG. 24F depicts the effect of dosing 0.3 mg/kg huM25-S239C-PBD-E2, or 0.3 mg/kg isotype-S239C-PBD-E2, on in vivo tumor volume (mm$^3$) at 0-80 days post sizematch of NCI-H1650 tumors. FIG. 24G shows effects of 0.6 mg/kg isotype-PBD-DAR2 or huAD208.4.1-PBD-DAR2, or 12 mg/kg of huIgG1 isotype antibody, in NCI-H1650 tumors; FIG. 24H shows effects of 0.6 mg/kg isotype-vcMMAE-DAR2 or huAD208.4.1-PBD-DAR2, or 6 mg/kg of huIgG1 isotype antibody, in EBC-1 tumors. Arrows represent dosing days. Also shown are representative IHC pictures illustrating LRRC15 expression on stromal cells for each of these xenograft models.

7. DETAILED DESCRIPTION

The present disclosure concerns antibody drug conjugates that specifically bind human LRRC15, compositions comprising the ADCs, anti-huLRRC15 antibodies and/or binding fragments that can comprise the ADCs, polynucleotides encoding anti-huLRRC15 antibodies and/or binding fragments that comprise the ADCs, host cells capable of producing the antibodies and/or binding fragments, methods and compositions useful for making the antibodies, binding fragments and ADCs, and various methods of using the ADCs.

As will be appreciated by skilled artisans, antibodies and/or binding fragments are "modular" in nature. Throughout the disclosure, various specific embodiments of the various "modules" composing the antibodies and/or binding fragments are described. As specific non-limiting examples, various specific embodiments of $V_H$ CDRs, $V_H$ chains, $V_L$ CDRs and $V_L$ chains are described. It is intended that all of the specific embodiments may be combined with each other as though each specific combination were explicitly described individually.

The ADCs disclosed herein are also "modular" in nature. Throughout the disclosure, various specific embodiments of the various "modules" composing the ADCs are described. As specific non-limiting examples, specific embodiments of antibodies, linkers, and cytotoxic and/or cytostatic agents that may compose the ADCs are described. It is intended that all of the specific embodiments described may be combined with each other as though each specific combination were explicitly described individually.

It will also be appreciated by skilled artisans that the various ADCs described herein may be in the form of salts, and in some specific embodiments, pharmaceutically acceptable salts. The ADCs of the disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counter ion, e.g., a halide such as a bromide, chloride, or fluoride.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, etc. Base addition salts include those derived from inorganic bases, such as ammonium and alkali or alkaline earth metal hydroxides, carbonates, bicarbonates, and the like.

7.1. Abbreviations

The antibodies, binding fragments, ADCs and polynucleotides described herein are, in many embodiments, described by way of their respective polypeptide or polynucleotide sequences. Unless indicated otherwise, polypeptide sequences are provided in N→C orientation; polynucleotide sequences in 5'→3' orientation. For polypeptide sequences, the conventional three or one-letter abbreviations for the genetically encoded amino acids may be used, as noted in TABLE 1, below.

TABLE 1

| Encoded Amino Acid Abbreviations | | |
|---|---|---|
| Amino Acid | Three Letter Abbreviation | One-Letter Abbreviation |
| Alanine | Ala | A |
| Arginine | Arg | R |

TABLE 1-continued

| Encoded Amino Acid Abbreviations | | |
|---|---|---|
| Amino Acid | Three Letter Abbreviation | One-Letter Abbreviation |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Certain sequences are defined by structural formulae specifying amino acid residues belonging to certain classes (e.g., aliphatic, hydrophobic, etc.). The various classes to which the genetically encoded amino acids belong as used herein are noted in TABLE 2, below. Some amino acids may belong to more than one class. Cysteine, which contains a sulfhydryl group, and proline, which is conformationally constrained, are not assigned classes.

TABLE 2

| Encoded Amino Acid Classes | |
|---|---|
| Class | Amino Acids |
| Aliphatic | A, I, L, V |
| Aromatic | F, Y, W |
| Non-Polar | M, A, I, L, V |
| Polar | N, Q, S, T |
| Basic | H, K, R |
| Acidic | D, E |
| Small | A, G |

7.2. Definitions

Unless otherwise defined herein, scientific and technical terms used in connection with the present disclosure shall have the meanings that are commonly understood by those of ordinary skill in the art.

7.3. Anti-huLRRC15 Antibody Drug Conjugates

In one aspect, the disclosure concerns antibody drug conjugates ("ADCs") that specifically bind human LRRC15 isoform 1 (SEQ ID NO:1) or isoform 2 (SEQ ID NO:3). The anti-huLRRC15 ADCs generally comprise an anti-huLRRC15 antigen binding moiety, for example an anti-huLRRC15 antibody or binding fragment, having one or more cytotoxic and/or cytostatic agents linked thereto by way of one or more linkers.

7.3.1. Anti-huLRRC15 Antibodies and Binding Fragments

In specific exemplary embodiments, the antigen binding moiety is an antibody or an antibody antigen binding fragment. Antibodies and/or binding fragments composing the anti-huLRRC15 ADCs specifically bind huLRRC15 at a region of the extracellular domain (residues 22 to 527 of SEQ ID NO:3) that is shed from the cell surface and into the blood stream ("shed ECD" or "sECD") following cleavage at a proteolytic cleavage site between $Arg^{527}$ and $Ser^{528}$ of SEQ ID NO:3.

As used herein, the term "antibody" (Ab) refers to an immunoglobulin molecule that specifically binds to, or is immunologically reactive with, a particular antigen-here, the sECD of huLRRC15. Antibodies comprise complementarity determining regions (CDRs), also known as hypervariable regions, in both the light chain and heavy chain variable domains. The more highly conserved portions of the variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria, while being deemed to be outside a hypervariable region under a different set of criteria. One or more of these positions can also be found in extended hypervariable regions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies. See Kabat et al., Sequences of Proteins of Immunological Interest (National Institute of Health, Bethesda, Md. 1987). As used herein, numbering of immunoglobulin amino acid residues is done according to the immunoglobulin amino acid residue numbering system of Kabat et al. unless otherwise indicated.

Antibodies composing anti-huLRRC15 ADCs may be polyclonal, monoclonal, genetically engineered, and/or otherwise modified in nature, including but not limited to, chimeric antibodies, humanized antibodies, human antibodies, primatized antibodies, single chain antibodies, bispecific antibodies, dual-variable domain antibodies, etc. In various embodiments, the antibodies comprise all or a portion of a constant region of an antibody. In some embodiments, the constant region is an isotype selected from: IgA (e.g., $IgA_1$ or $IgA_2$), IgD, IgE, IgG (e.g., $IgG_1$, $IgG_2$, $IgG_3$ or $IgG_4$), IgM, and IgY. In specific embodiments, antibodies composing an anti-huLRRC15 ADC comprise an $IgG_1$ constant region isotype.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof. In many uses of the present disclosure, including in vivo use of ADCs including anti-huLRRC15 antibodies in humans, chimeric, primatized, humanized, or human antibodies can suitably be used.

The term "chimeric" antibody as used herein refers to an antibody having variable sequences derived from a non-human immunoglobulin, such as a rat or a mouse antibody, and human immunoglobulin constant regions, typically chosen from a human immunoglobulin template. Methods for producing chimeric antibodies are known in the art. See, e.g., Morrison, 1985, Science 229(4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816,397, which are incorporated herein by reference in their entireties.

"Humanized" forms of non-human (e.g., murine) antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and U.S. Pat. No. 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332, all of which are hereby incorporated by reference in their entireties.

"Human antibodies" are antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Medarex (Princeton, N.J.), Astellas Pharma (Deerfield, Ill.), Amgen (Thousand Oaks, Calif.) and Regeneron (Tarrytown, N.Y.) can be engaged to provide human antibodies directed against a selected antigen using technology similar to that described above. Fully human antibodies that recognize a selected epitope can be generated using a technique referred to as "guided selection." In this approach, a selected non-human monoclonal antibody, e.g., a mouse antibody, is used to guide the selection of a completely human antibody recognizing the same epitope (see, Jespers et al., 1988, Biotechnology 12:899-903).

"Primatized antibodies" comprise monkey variable regions and human constant regions. Methods for producing primatized antibodies are known in the art. See, e.g., U.S. Pat. Nos. 5,658,570; 5,681,722; and 5,693,780, which are incorporated herein by reference in their entireties.

Anti-huLRRC15 ADCs may comprise full-length (intact) antibody molecules, as well as antigen binding fragments that are capable of specifically binding huLRRC15. Examples of antibody binding fragments include by way of example and not limitation, Fab, Fab', F(ab')2, Fv fragments, single chain Fv fragments and single domain fragments.

A Fab fragment contains the constant domain of the light chain and the first constant domain ($CH_2$) of the heavy chain. Fab' fragments differ from Fab fragments by the addition of a few residues at the carboxyl terminus of the heavy chain $CH_2$ domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art. Fab and F(ab')$_2$ fragments lack the Fc fragment of intact antibody, clear more rapidly from the circulation of animals, and may have less non-specific tissue binding than an intact antibody (see, e.g., Wahl et al., 1983, J. Nucl. Med. 24:316).

An "Fv" fragment is the minimum fragment of an antibody that contains a complete target recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Often, the six CDRs confer antigen binding specificity upon the antibody. However, in some instances even a single variable domain (or half of an Fv comprising only three CDRs specific for a target) may have the ability to recognize and bind antigen, although at a lower affinity than the entire binding site.

"Single-chain Fv" or "scFv" antibody binding fragments comprise the $V_H$ and $V_L$ domains of an antibody, where these domains are present in a single polypeptide chain. Generally, the Fv polypeptide further comprises a polypeptide linker between the $V_H$ and $V_L$ domains which enables the scFv to form the desired structure for antigen binding.

"Single domain antibodies" are composed of a single $V_H$ or $V_L$ domains which exhibit sufficient affinity to huLRRC15. In a specific embodiment, the single domain antibody is a camelized antibody (See, e.g., Riechmann, 1999, Journal of Immunological Methods 231:25-38).

Antibodies composing the anti-huLRRC15 ADCs may also be bispecific antibodies. Bispecific antibodies are monoclonal, often human or humanized, antibodies that have binding specificities for two different epitopes on the same or different antigens. In the present disclosure, one of the binding specificities can be directed towards huLRRC15, the other can be for any other antigen, e.g., for a cell-surface protein, receptor, receptor subunit, tissue-specific antigen, virally derived protein, virally encoded envelope protein, bacterially derived protein, or bacterial surface protein, etc.

Antibodies composing anti-huLRRC15 ADCs may be derivatized. Derivatized antibodies are typically modified by glycosylation, acetylation, pegylation, phosphorylation, amidation, derivatization by known protecting/blocking groups, proteolytic cleavage, linkage to a cellular ligand or other protein. Any of numerous chemical modifications may be carried out by known techniques, including, but not limited to, specific chemical cleavage, acetylation, formylation, metabolic synthesis of tunicamycin, etc. Additionally, the derivative may contain one or more non-natural amino acids, e.g., using ambrx technology. See, e.g., Wolfson, 2006, Chem. Biol. 13(10):1011-2.

Antibodies or binding fragments composing anti-huLRRC15 ADCs may be antibodies or fragments whose sequences have been modified to alter at least one constant region-mediated biological effector function. For example, in some embodiments, an anti-huLRRC15 antibody may be modified to reduce at least one constant region-mediated biological effector function relative to the unmodified antibody, e.g., reduced binding to the Fc receptor (FcγR). FcγR binding may be reduced by mutating the immunoglobulin constant region segment of the antibody at particular regions necessary for FcγR interactions (See, e.g., Canfield and Morrison, 1991, J. Exp. Med. 173:1483-1491; and Lund et al., 1991, J. Immunol. 147:2657-2662). Reducing FcγR binding may also reduce other effector functions which rely on FcγR interactions, such as opsonization, phagocytosis and antigen-dependent cellular cytotoxicity ("ADCC").

Antibodies or binding fragments composing anti-huLRRC15 ADCs may include modifications that increase or decrease their binding affinities to the neonatal Fc receptor, FcRn, for example, by mutating the immunoglobulin constant region segment at particular regions involved in FcRn interactions (see, e.g., WO 2005/123780). In particular embodiments, an anti-huLRRC15 antibody of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with substitution at positions 250 and 428 being a specific combination. For position 250, the substituting amino acid residue may be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue may be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues may be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. Specific combinations of suitable amino acid substitutions are identified in Table 1 of U.S. Pat. No. 7,217,797, which is incorporated herein by reference. In yet further embodiments, the variant Fc domains have at least one or more modifications that enhance the affinity to FcRn, e.g., a modification of one or more amino acid residues 251-256, 285-290, 308-314, 385-389, and 428-436 (e.g., M428L), or a modification at positions 250 and 428 (e.g., T250Q/M428L). See, e.g., Hinton et al., 2004, J. Biol. Chem. 279 (8): 6213-6216; PCT Publication Nos. WO 97/34631 and WO 02/060919. Such mutations increase binding to FcRn, which protects the antibody from degradation and increases its half-life.

An anti-huLRRC15 antibody and/or binding fragment may have one or more amino acids inserted into one or more of its hypervariable regions, for example as described in Jung & Plückthun, 1997, Protein Engineering 10:9, 959-966; Yazaki et al., 2004, Protein Eng. Des Sel. 17(5):481-9; and U.S. Pat. App. No. 2007/0280931.

Post-translational modifications to the sequences of an antibody included in an anti-huLRRC15 ADC may occur, such as cleavage of one or more (e.g., 1, 2, 3, or more) amino acid residues on the C-terminal end of the antibody heavy chain.

Post-translational modifications of an antibody included in an anti-huLRRC15 ADC may include glycosylation.

Common biantennary complexes can comprise a core structure having two N-acetylglucosamine (GlcNAc), three mannose, and two GlcNAc residues that are β-1,2 linked to α-6 mannose and α-3 mannose to form two antennae. One or more fucose (Fuc), galactose (Gal), high mannose glycans Man-5 or Man-9, bisecting GlcNAc, and sialic acid including N-acetylneuraminic acid (NANA) or N-glycolylneuraminic acid (NGNA) residues may be attached to the core. N-linked glycoforms may include G0 (protein having a core biantennary glycosylation structure), G0F (fucosylated G0), G0F GlcNAc, G1 (protein having a core glycosylation structure with one galactose residue), G1F (fucosylated G1), G2 (protein having a core glycosylation structure with two galactose residues), and/or G2F (fucosylated G2).

Antibodies included in anti-huLRRC15 ADCs may have low levels of, or lack, fucose. Antibodies lacking fucose have been correlated with enhanced ADCC activity, especially at low doses of antibody. See Shields et al., 2002, J. Biol. Chem. 277:26733-26740; Shinkawa et al., 2003, J. Biol. Chem. 278:3466-73. Methods of preparing fucose-less antibodies include growth in rat myeloma YB2/0 cells (ATCC CRL 1662). YB2/0 cells express low levels of FUT8 mRNA, which encodes α-1,6-fucosyltransferase, an enzyme necessary for fucosylation of polypeptides.

Anti-huLRRC15 antibodies and/or binding fragments with high affinity for huLRRC15 may be desirable for therapeutic uses. Accordingly, the present disclosure contemplates ADCs comprising anti-huLRRC15 antibodies and/or binding fragments having a high binding affinity to huLRRC15. In specific embodiments, the antibodies and/or binding fragments bind huLRRC15 with an affinity of at least about 100 nM, but may exhibit higher affinity, for example, at about 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM, or even higher. In some embodiments, the antibodies bind huLRRC15 with an affinity in the range of about 1 pM to about 100 nM, or an affinity ranging between any of the foregoing values, such as but not limited to from about 0.01 to 100, 0.01 to 10, 0.01 to 2, 0.1 to 100, 0.1 to 10, or 0.1 to 2 nM.

Affinity of antibodies and/or binding fragments for huLRRC15 can be determined using techniques well known in the art or described herein, such as for example, but not by way of limitation, ELISA, isothermal titration calorimetry (ITC), surface plasmon resonance, flow cytometry or fluorescent polarization assays.

In some embodiments, an antibody and/or binding fragment composing an anti-huLRRC15 ADC comprises a $V_H$ chain having three CDRs in which $V_H$ CDR#1, $V_H$ CDR#2 and $V_H$ CDR#3 have sequences selected from their respective $V_H$ CDR sequences in the table below:

| CDR | Sequence (N→C) | Identifier |
| --- | --- | --- |
| huM25 $V_H$ CDR#1 | SYWIE | SEQ ID NO: 10 |
| huAD208.4.1 $V_H$ CDR#1 | DYYIH | SEQ ID NO: 20 |
| huAD208.12.1 $V_H$ CDR#1 | NYWMH | SEQ ID NO: 30 |
| huAD208.14.1 $V_H$ CDR#1 | DYYIH | SEQ ID NO: 40 |
| hu139.10 $V_H$ CDR#1 | SYGVH | SEQ ID NO: 50 |
| muAD210.40.9 $V_H$ CDR#1 | NYWLG | SEQ ID NO: 60 |
| muAD209.9.1 $V_H$ CDR#1 | NFGMN | SEQ ID NO: 70 |
| huM25 $V_H$ CDR#2 | EILPGSDTTNYNEKFKD | SEQ ID NO: 11 |
| huAD208.4.1 $V_H$ CDR#2 | LVYPYIGGTNYNQKFKG | SEQ ID NO: 21 |
| huAD208.12.1 $V_H$ CDR#2 | MIHPNSGSTKHNEKFRG | SEQ ID NO: 31 |
| huAD208.14.1 $V_H$ CDR#2 | LVYPYIGGSSYNQQFKG | SEQ ID NO: 41 |
| hu139.10 $V_H$ CDR#2 | VIWAGGSTNYNSALMS | SEQ ID NO: 51 |
| muAD210.40.9 $V_H$ CDR#2 | DIYPGGGNTYYNEKLKG | SEQ ID NO: 61 |
| muAD209.9.1 $V_H$ CDR#2 | WINLYTGEPTFADDFKG | SEQ ID NO: 71 |
| huM25 $V_H$ CDR#3 | DRGNYRAWFGY | SEQ ID NO: 12 |
| huAD208.4.1 $V_H$ CDR#3 | GDNKYDAMDY | SEQ ID NO: 22 |
| huAD208.12.1 $V_H$ CDR#3 | SDFGNYRWYFDV | SEQ ID NO: 32 |
| huAD208.14.1 $V_H$ CDR#3 | GDNNYDAMDY | SEQ ID NO: 42 |
| hu139.10 $V_H$ CDR#3 | HMITEDYYGMDY | SEQ ID NO: 52 |
| muAD210.40.9 $V_H$ CDR#3 | WGDKKGNYFAY | SEQ ID NO: 62 |
| muAD209.9.1 $V_H$ CDR#3 | KGETYYRYDGFAY | SEQ ID NO: 72 |

In some embodiments, an antibody and/or binding fragment composing an anti-huLRRC15 ADC comprises a $V_L$ chain having three CDRs in which $V_L$ CDR#1, $V_L$ CDR#2 and $V_L$ CDR#3 have sequences selected from their respective $V_L$ CDR sequences in the table below:

| CDR | Sequence (N→C) | Identifier |
| --- | --- | --- |
| huM25 $V_L$ CDR#1 | RASQDISNYLN | SEQ ID NO: 13 |
| huAD208.4.1 $V_L$ CDR#1 | RASQSVSTSSYSYMH | SEQ ID NO: 23 |
| huAD208.12.1 $V_L$ CDR#1 | RASQSSSNNLH | SEQ ID NO: 33 |
| huAD208.14.1 $V_L$ CDR#1 | RASQSVSTSTYNYMH | SEQ ID NO: 43 |
| hu139.10 $V_L$ CDR#1 | KSSQSLLNSRTRKNYLA | SEQ ID NO: 53 |
| muAD210.40.9 $V_L$ CDR#1 | TASSSVYSSYLH | SEQ ID NO: 63 |
| muAD209.9.1 $V_L$ CDR#1 | RSSKSLLHSNGNTHLY | SEQ ID NO: 73 |
| huM25 $V_L$ CDR#2 | YTSRLHS | SEQ ID NO: 14 |

| CDR | Sequence (N→C) | Identifier |
|---|---|---|
| huAD208.4.1 V_L CDR#2 | YASSLES | SEQ ID NO: 24 |
| huAD208.12.1 V_L CDR#2 | YVSQSIS | SEQ ID NO: 34 |
| huAD208.14.1 V_L CDR#2 | YASNLES | SEQ ID NO: 44 |
| hu139.10 V_L CDR#2 | WASTRES | SEQ ID NO: 54 |
| muAD210.40.9 V_L CDR#2 | STSNLAS | SEQ ID NO: 64 |
| muAD209.9.1 V_L CDR#2 | RMSNLAS | SEQ ID NO: 74 |
| huM25 V_L CDR#3 | QQGEALPWT | SEQ ID NO: 15 |
| huAD208.4.1 V_L CDR#3 | EQSWEIRT | SEQ ID NO: 25 |
| huAD208.12.1 V_L CDR#3 | QQSNSWPFT | SEQ ID NO: 35 |
| huAD208.14.1 V_L CDR#3 | HHTWEIRT | SEQ ID NO: 45 |
| hu139.10 V_L CDR#3 | KQSYNLPT | SEQ ID NO: 55 |
| muAD210.40.9 V_L CDR#3 | HQYHRSPT | SEQ ID NO: 65 |
| muAD209.9.1 V_L CDR#3 | MQLLEYPYT | SEQ ID NO: 75 |

In some embodiments, an antibody and/or binding fragment composing an anti-huLRRC15 ADC comprises a $V_H$ chain having three CDRs in which $V_H$ CDR#1, $V_H$ CDR#2 and $V_H$ CDR#3 have sequences selected from their respective $V_H$ CDR sequences in the table below, and a $V_L$ chain having three CDRs in which $V_L$ CDR#1, $V_L$ CDR#2 and $V_L$ CDR#3 have sequences selected from their respective $V_L$ CDR sequences in the table below:

| CDR | Sequence (N→C) | Identifier |
|---|---|---|
| huM25 V_H CDR#1 | SYWIE | SEQ ID NO: 10 |
| huAD208.4.1 V_H CDR#1 | DYYIH | SEQ ID NO: 20 |
| huAD208.12.1 V_H CDR#1 | NYWMH | SEQ ID NO: 30 |
| huAD208.14.1 V_H CDR#1 | DYYIH | SEQ ID NO: 40 |
| hu139.10 V_H CDR#1 | SYGVH | SEQ ID NO: 50 |
| muAD210.40.9 V_H CDR#1 | NYWLG | SEQ ID NO: 60 |
| muAD209.9.1 V_H CDR#1 | NFGMN | SEQ ID NO: 70 |
| huM25 V_H CDR#2 | EILPGSDTTNYNEKFKD | SEQ ID NO: 11 |
| huAD208.4.1 V_H CDR#2 | LVYPYIGGTNYNQKFKG | SEQ ID NO: 21 |
| huAD208.12.1 V_H CDR#2 | MIHPNSGSTKHNEKFRG | SEQ ID NO: 31 |
| huAD208.14.1 V_H CDR#2 | LVYPYIGGSSYNQQFKG | SEQ ID NO: 41 |
| hu139.10 V_H CDR#2 | VIWAGGSTNYNSALMS | SEQ ID NO: 51 |
| muAD210.40.9 V_H CDR#2 | DIYPGGGNTYYNEKLKG | SEQ ID NO: 61 |
| muAD209.9.1 V_H CDR#2 | WINLYTGEPTFADDFKG | SEQ ID NO: 71 |
| huM25 V_H CDR#3 | DRGNYRAWFGY | SEQ ID NO: 12 |
| huAD208.4.1 V_H CDR#3 | GDNKYDAMDY | SEQ ID NO: 22 |
| huAD208.12.1 V_H CDR#3 | SDFGNYRWYFDV | SEQ ID NO: 32 |
| huAD208.14.1 V_H CDR#3 | GDNNYDAMDY | SEQ ID NO: 42 |
| hu139.10 V_H CDR#3 | HMITEDYYGMDY | SEQ ID NO: 52 |
| muAD210.40.9 V_H CDR#3 | WGDKKGNYFAY | SEQ ID NO: 62 |
| muAD209.9.1 V_H CDR#3 | KGETYYRYDGFAY | SEQ ID NO: 72 |
| huM25 V_L CDR#1 | RASQDISNYLN | SEQ ID NO: 13 |
| huAD208.4.1 V_L CDR#1 | RASQSVSTSSYSYMH | SEQ ID NO: 23 |
| huAD208.12.1 V_L CDR#1 | RASQSSSNNLH | SEQ ID NO: 33 |
| huAD208.14.1 V_L CDR#1 | RASQSVSTSTYNYMH | SEQ ID NO: 43 |
| hu139.10 V_L CDR#1 | KSSQSLLNSRTRKNYLA | SEQ ID NO: 53 |
| muAD210.40.9 V_L CDR#1 | TASSSVYSSYLH | SEQ ID NO: 63 |
| muAD209.9.1 V_L CDR#1 | RSSKSLLHSNGNTHLY | SEQ ID NO: 73 |
| huM25 V_L CDR#2 | YTSRLHS | SEQ ID NO: 14 |
| huAD208.4.1 V_L CDR#2 | YASSLES | SEQ ID NO: 24 |
| huAD208.12.1 V_L CDR#2 | YVSQSIS | SEQ ID NO: 34 |
| huAD208.14.1 V_L CDR#2 | YASNLES | SEQ ID NO: 44 |
| hu139.10 V_L CDR#2 | WASTRES | SEQ ID NO: 54 |
| muAD210.40.9 V_L CDR#2 | STSNLAS | SEQ ID NO: 64 |
| muAD209.9.1 V_L CDR#2 | RMSNLAS | SEQ ID NO: 74 |
| huM25 V_L CDR#3 | QQGEALPWT | SEQ ID NO: 15 |
| huAD208.4.1 V_L CDR#3 | EQSWEIRT | SEQ ID NO: 25 |
| huAD208.12.1 V_L CDR#3 | QQSNSWPFT | SEQ ID NO: 35 |

-continued

| CDR | Sequence (N→C) | Identifier |
|---|---|---|
| huAD208.14.1 V$_L$ CDR#3 | HHTWEIRT | SEQ ID NO: 45 |
| hu139.10 V$_L$ CDR#3 | KQSYNLPT | SEQ ID NO: 55 |
| muAD210.40.9 V$_L$ CDR#3 | HQYHRSPT | SEQ ID NO: 65 |
| muAD209.9.1 V$_L$ CDR#3 | MQLLEYPYT | SEQ ID NO: 75 |

In some embodiments, an antibody and/or binding fragment composing an anti-huLRRC15 ADC comprises a V$_H$ chain having three CDRs in which:

V$_H$ CDR#1 corresponds in sequence to SEQ ID NO:10, V$_H$ CDR#2 corresponds in sequence to SEQ ID NO:11 and V$_H$ CDR#3 corresponds in sequence to SEQ ID NO:12; or V$_H$ CDR#1 corresponds in sequence to SEQ ID NO:20, V$_H$ CDR#2 corresponds in sequence to SEQ ID NO:21 and V$_H$ CDR#3 corresponds in sequence to SEQ ID NO:22; or V$_H$ CDR#1 corresponds in sequence to SEQ ID NO:30, V$_H$ CDR#2 corresponds in sequence to SEQ ID NO:31 and V$_H$ CDR#3 corresponds in sequence to SEQ ID NO:32; or V$_H$ CDR#1 corresponds in sequence to SEQ ID NO:40, V$_H$ CDR#2 corresponds in sequence to SEQ ID NO:41 and V$_H$ CDR#3 corresponds in sequence to SEQ ID NO:42; or V$_H$ CDR#1 corresponds in sequence to SEQ ID NO:50, V$_H$ CDR#2 corresponds in sequence to SEQ ID NO:51 and V$_H$ CDR#3 corresponds in sequence to SEQ ID NO:52; or V$_H$ CDR#1 corresponds in sequence to SEQ ID NO:60, V$_H$ CDR#2 corresponds in sequence to SEQ ID NO:61 and V$_H$ CDR#3 corresponds in sequence to SEQ ID NO:62; or V$_H$ CDR#1 corresponds in sequence to SEQ ID NO:70, V$_H$ CDR#2 corresponds in sequence to SEQ ID NO:71 and V$_H$ CDR#3 corresponds in sequence to SEQ ID NO:72.

In some embodiments, an antibody and/or binding fragment composing an anti-huLRRC15 ADC comprises a V$_L$ chain having three CDRs in which:

V$_L$ CDR#1 corresponds in sequence to SEQ ID NO:13, V$_L$ CDR#2 corresponds in sequence to SEQ ID NO:14 and V$_L$ CDR#3 corresponds in sequence to SEQ ID NO:15; or V$_L$ CDR#1 corresponds in sequence to SEQ ID NO:23, V$_L$ CDR#2 corresponds in sequence to SEQ ID NO:24 and V$_L$ CDR#3 corresponds in sequence to SEQ ID NO:25; or V$_L$ CDR#1 corresponds in sequence to SEQ ID NO:33, V$_L$ CDR#2 corresponds in sequence to SEQ ID NO:34 and V$_L$ CDR#3 corresponds in sequence to SEQ ID NO:35; or V$_L$ CDR#1 corresponds in sequence to SEQ ID NO:43, V$_L$ CDR#2 corresponds in sequence to SEQ ID NO:44 and V$_L$ CDR#3 corresponds in sequence to SEQ ID NO:45; or V$_L$ CDR#1 corresponds in sequence to SEQ ID NO:53, V$_L$ CDR#2 corresponds in sequence to SEQ ID NO:54 and V$_L$ CDR#3 corresponds in sequence to SEQ ID NO:55; or V$_L$ CDR#1 corresponds in sequence to SEQ ID NO:63, V$_L$ CDR#2 corresponds in sequence to SEQ ID NO:64 and V$_L$ CDR#3 corresponds in sequence to SEQ ID NO:65; or V$_L$ CDR#1 corresponds in sequence to SEQ ID NO:73, V$_L$ CDR#2 corresponds in sequence to SEQ ID NO:74 and V$_L$ CDR#3 corresponds in sequence to SEQ ID NO:75.

In some embodiments, an antibody and/or binding fragment composing an anti-huLRRC15 ADC comprises:

a V$_H$ chain having three CDRs in which V$_H$ CDR#1 corresponds in sequence to SEQ ID NO:10, V$_H$ CDR#2 corresponds in sequence to SEQ ID NO:11 and V$_H$ CDR#3 corresponds in sequence to SEQ ID NO:12 and a V$_L$ chain having three CDRs in which V$_L$ CDR#1 corresponds in sequence to SEQ ID NO:13, V$_L$ CDR#2 corresponds in sequence to SEQ ID NO:14 and V$_L$ CDR#3 corresponds in sequence to SEQ ID NO:15; or a V$_H$ chain having three CDRs in which V$_H$ CDR#1 corresponds in sequence to SEQ ID NO:20, V$_H$ CDR#2 corresponds in sequence to SEQ ID NO:21 and V$_H$ CDR#3 corresponds in sequence to SEQ ID NO:22 and a V$_L$ chain having three CDRs in which V$_L$ CDR#1 corresponds in sequence to SEQ ID NO:23, V$_L$ CDR#2 corresponds in sequence to SEQ ID NO:24 and V$_L$ CDR#3 corresponds in sequence to SEQ ID NO:25; or a V$_H$ chain having three CDRs in which V$_H$ CDR#1 corresponds in sequence to SEQ ID NO:30, V$_H$ CDR#2 corresponds in sequence to SEQ ID NO:31 and V$_H$ CDR#3 corresponds in sequence to SEQ ID NO:32 and a V$_L$ chain having three CDRs in which V$_L$ CDR#1 corresponds in sequence to SEQ ID NO:33, V$_L$ CDR#2 corresponds in sequence to SEQ ID NO:34 and V$_L$ CDR#3 corresponds in sequence to SEQ ID NO:35; or a V$_H$ chain having three CDRs in which V$_H$ CDR#1 corresponds in sequence to SEQ ID NO:40, V$_H$ CDR#2 corresponds in sequence to SEQ ID NO:41 and V$_H$ CDR#3 corresponds in sequence to SEQ ID NO:42 and a V$_L$ chain having three CDRs in which V$_L$ CDR#1 corresponds in sequence to SEQ ID NO:43, V$_L$ CDR#2 corresponds in sequence to SEQ ID NO:44 and V$_L$ CDR#3 corresponds in sequence to SEQ ID NO:45; or a V$_H$ chain having three CDRs in which V$_H$ CDR#1 corresponds in sequence to SEQ ID NO:50, V$_H$ CDR#2 corresponds in sequence to SEQ ID NO:51 and V$_H$ CDR#3 corresponds in sequence to SEQ ID NO:52 and a V$_L$ chain having three CDRs in which V$_L$ CDR#1 corresponds in sequence to SEQ ID NO:53, V$_L$ CDR#2 corresponds in sequence to SEQ ID NO:54 and V$_L$ CDR#3 corresponds in sequence to SEQ ID NO:55; or a V$_H$ chain having three CDRs in which V$_H$ CDR#1 corresponds in sequence to SEQ ID NO:60, V$_H$ CDR#2 corresponds in sequence to SEQ ID NO:61 and V$_H$ CDR#3 corresponds in sequence to SEQ ID NO:62 and a V$_L$ chain having three CDRs in which V$_L$ CDR#1 corresponds in sequence to SEQ ID NO:63, V$_L$ CDR#2 corresponds in sequence to SEQ ID NO:64 and V$_L$ CDR#3 corresponds in sequence to SEQ ID NO:65; or a V$_H$ chain having three CDRs in which V$_H$ CDR#1 corresponds in sequence to SEQ ID NO:70, V$_H$ CDR#2 corresponds in sequence to SEQ ID NO:71 and V$_H$ CDR#3 corresponds in sequence to SEQ ID NO:72 and a V$_L$ chain having three CDRs in which V$_L$ CDR#1 corresponds in sequence to SEQ ID NO:73, V$_L$ CDR#2 corresponds in sequence to SEQ ID NO:74 and V$_L$ CDR#3 corresponds in sequence to SEQ ID NO:75.

In some embodiments, an antibody and/or binding fragment composing an anti-huLRRC15 ADC comprises a V$_H$ chain having a sequence corresponding to a sequence selected from one of the sequences in the table below:

| Chain | Sequence (N→C) | Identifier |
|---|---|---|
| huM25 $V_H$ | EVQLVQSGAEVKKPGASVKVSCKASGYKFSSYWIEWVKQAPGQGLEWIGEILPGSDTTNYNEKFKDRATFTSDTSINTAYMELSRLRSDDTAVYYCARDRGNYRAWFGYWGQGTLVTVSS | SEQ ID NO: 16 |
| huAD208.4.1 $V_H$ | EVQLVQSGAEVKKPGSSVKVSCKASGFTFTDYYIHWVKQAPGQGLEWIGLVYPYIGGTNYNQKFKGKATLTVDTSTTTAYMEMSSLRSEDTAVYYCARGDNKYDAMDYWGQGTTVTVSS | SEQ ID NO: 26 |
| huAD208.12.1 $V_H$ | EVQLVQSGAEVKKPGSSVKVSCKASGYTFTNYWMHWVKQAPGQGLEWIGMIHPNSGSTKHNEKFRGKATLTVDESTTTAYMELSSLRSEDTAVYYCARSDFGNYRWYFDVWGQGTTVTVSS | SEQ ID NO: 36 |
| huAD208.14.1 $V_H$ | EVQLVQSGAEVKKPGSSVKVSCKASGFTFTDYYIHWVKQAPGQGLEWIGLVYPIGGSSYNQQFKGKATLTVDTSTSTAYMELSSLRSEDTAVYYCARGDNNYDAMDYWGQGTTVTVSS | SEQ ID NO: 46 |
| hu139.10 $V_H$ | EVQLVESGGGLVQPGGSLRLSCAVSGFSLTSYGVHWVRQATGKGLEWLGVIWAGGSTNYNSALMSRLTISKENAKSSVYLQMNSLRAGDTAMYYCATHMITEDYYGMDYWGQGTTVTVSS | SEQ ID NO: 56 |
| muAD210.40.9 $V_H$ | QVQLQQSGAELVRPGTSVKISCKASGYDFTNYWLGWVKQRPGHGLEWIGDIYPGGGNTYYNEKLKGKATLTADKSSSTAYIHLISLTSEDSSVYFCARWGDKKGNYFAYWGQGTLVTVSA | SEQ ID NO: 66 |
| muAD209.9.1 $V_H$ | QIQLVQSGPELKKPGETVKISCKASGFAITNFGMNWVKQAPGKGLKWMGWINLYTGEPTFADDPKGRFAFSLETSASTAYLQINNLKNEDTVIYFCARKGETYYRYDGFAYWGQGTLVTVSA | SEQ ID NO: 76 |

In some embodiments, an antibody and/or binding fragment composing an anti-huLRRC15 ADC comprises a $V_L$ chain having a sequence corresponding to a sequence selected from one of the sequences in the table below:

| Chain | Sequence (N→C) | Identifier |
|---|---|---|
| huM25 $V_L$ | DIQMTQSPSSLSASVGDRVTITCRASQDISNYLNWYQQKPGGAVKFLIYYTSRLHSGVPSRFSGSGSGTDYTLTISSLQPEDFATYFCQQGEALPWTFGGGTKVEIK | SEQ ID NO: 17 |
| huAD208.4.1 $V_L$ | DIVLTQSPDSLAVSLGERATINCRASQSVSTSSYSYMHWYQQKPGQPPKLLIKYASSLESGVPDRFSGSGSGTDFTLTISSLQAEDVAVYYCEQSWEIRTFGGGTKVEIK | SEQ ID NO: 27 |
| huAD208.12.1 $V_L$ | EIVLTQSPATLSLSPGERATLSCRASQSSSNNLHWYQQKPGQAPRVLIKYVSQSISGIPARFSGSGSGTDFTLTISSLEPEDFAVYFCQQSNSWPFTFGQGTKLEIK | SEQ ID NO: 37 |
| huAD208.14.1 $V_L$ | DIVLTQSPDSLAVSLGERATISCRASQSVSTSTYNYMHWYQQKPGQPPKLLVKYASNLESGVPDRFSGSGSGTDFTLTISSLQAEDVAVYYCHHTWEIRTFGGGTKVEIK | SEQ ID NO: 47 |
| hu139.10 $V_L$ | DIVMTQSPDSLAVSLGERATINCKSSQSLLNSRTRKNYLAWYQQKPGQSPKLLIYWASTRESGVPDRFSGSGSGTDFTLTISSLQAEDVAVYYCKQSYNLPTFGGGTKVEIK | SEQ ID NO: 57 |
| muAD210.40.9 $V_L$ | QIVLTQSPAIMSASLGERVTMTCTASSSVYSSYLHWYQQKPGSSPKLWIYSTSNLASGVPGRFSGSGSGTSYSLTISSMEAEDAATYYCHQYHRSPTFGGGTKLEIK | SEQ ID NO: 67 |
| muAD209.9.1 $V_L$ | DIVMTQAAPSVPVTPGESVSISCRSSKSLLHSNGNTHLYWFLQRPGQSPQLLIYRMSNLASGVPDRFSGSGSGTAFTLRISRVEAEDVGVYYCMQLLEYPYTFGGGTKLEIE | SEQ ID NO: 77 |

In some embodiments, an antibody and/or binding fragment composing an anti-huLRRC15 ADC comprises:

a $V_H$ chain having a sequence corresponding to SEQ ID NO:16 and a $V_L$ chain corresponding in sequence to SEQ ID NO:17; or a $V_H$ chain having a sequence corresponding to SEQ ID NO:26 and a $V_L$ chain corresponding in sequence to SEQ ID NO:27; or a $V_H$ chain having a sequence corresponding to SEQ ID NO:36 and a $V_L$ chain corresponding in sequence to SEQ ID NO:37; or a $V_H$ chain having a sequence corresponding to SEQ ID NO:46 and a $V_L$ chain corresponding in sequence to SEQ ID NO:47; or a $V_H$ chain having a sequence corresponding to SEQ ID NO:56 and a $V_L$ chain corresponding in sequence to SEQ ID NO:57; or a $V_H$ chain having a sequence corresponding to SEQ ID NO:66 and a $V_L$ chain corresponding in sequence to SEQ ID NO:67; or a V$_H$ chain having a sequence corresponding to SEQ ID NO:76 and a V$_L$ chain corresponding in sequence to SEQ ID NO:77.

The anti-huLRRC15 ADCs have myriad uses, and in particular are useful therapeutically for the treatment of huLRRC15 stromal(+)/cancer(−) tumors in humans. Accordingly, in some embodiments, an anti-huLRRC15 antibody and/or binding fragment composing an anti-huLRRC15 ADC is suitable for administration to humans. In a specific embodiment, the anti-huLRRC15 antibody is humanized. In some embodiments, the humanized anti-huLRRC15 antibody and/or binding fragment composing an anti-huLRRC15 ADC is an antibody and/or binding fragment comprising a V$_H$ chain corresponding in sequence to SEQ ID NO:16, SEQ ID NO:26, SEQ ID NO:36, SEQ ID NO:46 or SEQ ID NO:56 and a V$_L$ chain corresponding in sequence to SEQ ID NO:17, SEQ ID NO:27, SEQ ID NO:37, SEQ ID NO:47 or SEQ ID NO:57. In some embodiments, the humanized anti-huLRRC15 antibody and/or binding fragment is a full length antibody selected from huM25, huM25-S239C, huAD208.4.1, huAD208.4.1-S239C, huAD208.12.1, huAD208.14.1 and hu139.10.

In some embodiments, an anti-huLRRC15 antibody and/or binding fragment composing an anti-huLRRC15 ADC is an IgG$_1$.

In some embodiments, an anti-huLRRC15 antibody composing an anti-huLRRC15 ADC comprises a heavy chain having a constant region corresponding in sequence to residues 121-450 of SEQ ID NO:18 by linear amino acid sequence numbering.

In some embodiments, an anti-huLRRC15 antibody composing an anti-huLRRC15 ADC comprises a light chain having a constant region corresponding in sequence to residues 108-214 of SEQ ID NO:19 by linear amino acid sequence numbering.

In some embodiments, an anti-huLRRC15 antibody composing an anti-huLRRC15 ADC comprises a heavy chain having a constant region corresponding in sequence to residues 121-450 of SEQ ID NO:18 and a light chain having a constant region corresponding in sequence to residues 108-214 of SEQ ID NO:19 by linear amino acid sequence numbering.

In some embodiments, anti-huLRRC15 antibodies and/or binding fragments composing an anti-huLRRC15 ADC compete for binding huLRRC15 on cells expressing huLRRC15, or the sECD of huLRRC15, in in vitro assays with a reference antibody. The reference antibody may be any antibody that specifically binds huLRRC15 within a region of the sECD. In one specific embodiment, the reference antibody is huM25, huM25-S239C, huAD208.4.1, huAD208.4.1-S239C, huAD208.12.1, huAD208.14.1, hu139.10, muAD210.40.9 or muAD209.9.1.

In some embodiments, an anti-huLRRC15 antibody composing an anti-huLRRC15 ADC has a heavy chain amino acid sequence (N→C) according to:

```
                                    (SEQ ID NO: 100)
EVQLVQSGAEVKKPGASVKVSCKASGYKFSSYWIEWVKQAPGQGLEWIGE

ILPGSDTTNYNEKFKDRATFTSDTSINTAYMELSRLRSDDTAVYYCARDR

GNYRAWFGYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVIVHKPSNTKVDKKVEPKSCDKTHTCPPCPAPELLGGPCVFLFPPK
```

-continued
```
PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K,
``` and a light chain amino acid sequence (N→C) according to SEQ ID NO: 19, wherein the underlined amino acids represent the CDRs and the italicized amino acids represent the constant regions.

In some embodiments, an anti-huLRRC15 antibody composing an anti-huLRRC15 ADC has a heavy chain amino acid sequence (N→C) according to:

```
                                    (SEQ ID NO: 102)
EVQLVQSGAEVKKPGASVKVSCKASGYKFSSYWIEWVKQAPGQGLEWIGE

ILPGSDTTNYNEKFKDRATFTSDTSINTAYMELSRLRSDDTAVYYCARDR

GNYRAWFGYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVIVHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSL

SPG,
``` and a light chain amino acid sequence (N→C) according to SEQ ID NO: 19, wherein the underlined amino acids represent the CDRs and the italicized amino acids represent the constant regions.

In some embodiments, an anti-huLRRC15 antibody composing an anti-huLRRC15 ADC has a heavy chain amino acid sequence (N→C) according to:

```
                                    (SEQ ID NO: 103)
EVQLVQSGAEVKKPGASVKVSCKASGYKFSSYWIEWVKQAPGQGLEWIGE

ILPGSDTTNYNEKFKDRATFTSDTSINTAYMELSRLRSDDTAVYYCARDR

GNYRAWFGYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPCVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG,
``` and a light chain amino acid sequence (N→C) according to SEQ ID NO: 19, wherein the underlined amino acids represent the CDRs and the italicized amino acids represent the constant regions.

In some embodiments, an anti-huLRRC15 antibody composing an anti-huLRRC15 ADC has a heavy chain amino acid sequence (N→C) according to SEQ ID NO: 18 or 102; and a light chain amino acid sequence (N→C) according to:

(SEQ ID NO: 110)
DIQMTQSPSSLSASVGDRVTITC<u>RASQDISNYLN</u>WYQQKPGGAVKFLIY<u>Y</u>
<u>TSRLHS</u>GVPSRFSGSGSGTDYTLTISSLQPEDFATYFC<u>QQGEALPWT</u>FGG
G*TKVEIKRTVAAPSVFIFPPSDEQLKSGTASVVCLLNNFYPREAKVQWKV*
*DNALQSGNSQESVTEQDSKDSTYSLSSTLTLSKADYEKHKVYACEVTHQG*
*LSSPVTKSFNRGEA,* wherein the underlined amino acids represent the CDRs and the italicized amino acids represent the constant regions.

In some embodiments, an anti-huLRRC15 antibody composing an anti-huLRRC15 ADC has a heavy chain amino acid sequence (N→C) according to:

(SEQ ID NO: 28)
EVQLVQSGAEVKKPGSSVKVSCKASGFTFT<u>DYYIH</u>WVKQAPGQGLEWIG<u>L</u>
<u>VYPYIGGTNYNQKF</u>KGKATLTVDTSTTTAYMEMSSLRSEDTAVYYCAR<u>GD</u>
<u>NKYDAMDY</u>WGQGTTVTVSS*ASTKGPSVFPLAPSSKSTSGGTAALGCLVKD*
*YFPEPVTVSWNSGALTSGVHTFPAVLQSSGLYSLSSVVTVPSSSLGTQTY*
*ICNVNHKPSNTKVDKKVEPKSCDKTHTCPPCPAPELLGGPSVFLFPPKPK*
*DTLMISRTPEVTCVVVDVSHEDPEVKFNWYVDGVEVHNAKTKPREEQYNS*
*TYRVVSVLTVLHQDWLNGKEYKCKVSNKALPAPIEKTISKAKGQPREPQV*
*YTLPPSREEMTKNQVSLTCLVKGFYPSDIAVEWESNGQPENNYKTTPPVL*
*DSDGSFFLYSKLTVDKSRWQQGNVFSCSVMHEALHNHYTQKSLSLSPGK;* and a light chain amino acid sequence (N→C) according to:

(SEQ ID NO: 29)
DIVLTQSPDSLAVSLGERATINC<u>RASQSVSTSSYSYMH</u>WYQQKPGQPPKL
LIK<u>YASSLES</u>GVPDRFSGSGSGTDFTLTISSLQAEDVAVYYC<u>EQSWEIRT</u>
FGGGTKVEIKR*TVAAPSVFIFPPSDEQLKSGTASVVCLLNNFYPREAKVQ*
*WKVDNALQSGNSQESVTEQDSKDSTYSLSSTLTLSKADYEKHKVYACEVT*
*HQGLSSPVTKSFNRGEC,* wherein the underlined amino acids represent the CDRs and the italicized amino acids represent the constant regions.

In some embodiments, an anti-huLRRC15 antibody composing an anti-huLRRC15 ADC has a heavy chain amino acid sequence (N→C) according to:

(SEQ ID NO: 101)
EVQLVQSGAEVKKPGSSVKVSCKASGFTFT<u>DYYIH</u>WVKQAPGQGLEWIG<u>L</u>
<u>VYPYIGGTNYNQKF</u>KGKATLTVDTSTTTAYMEMSSLRSEDTAVYYCAR<u>GD</u>
<u>NKYDAMDY</u>WGQGTTVTVSS*ASTKGPSVFPLAPSSKSTSGGTAALGCLVKD*
*YFPEPVTVSWNSGALTSGVHTFPAVLQSSGLYSLSSVVTVPSSSLGTQTY*
*ICNVNHKPSNTKVDKKVEPKSCDKTHTCPPCPAPELLGGPCVFLFPPKPK*
*DTLMISRTPEVTCVVVDVSHEDPEVKFNWYVDGVEVHNAKTKPREEQYNS*
*TYRVVSVLTVLHQDWLNGKEYKCKVSNKALPAPIEKTISKAKGQPREPQV*
*YTLPPSREEMTKNQVSLTCLVKGFYPSDIAVEWESNGQPENNYKTTPPVL*
*DSDGSFFLYSKLTVDKSRWQQGNVFSCSVMHEALHNHYTQKSLSLSPGK;* and a light chain amino acid sequence (N→C) according to SEQ ID NO: 29, wherein the underlined amino acids represent the CDRs and the italicized amino acids represent the constant regions.

In some embodiments, an anti-huLRRC15 antibody composing an anti-huLRRC15 ADC has a heavy chain amino acid sequence (N→C) according to:

(SEQ ID NO: 104)
EVQLVQSGAEVKKPGSSVKVSCKASGFTFT<u>DYYIH</u>WVKQAPGQGLEWIG<u>L</u>
<u>VYPYIGGTNYNQKF</u>KGKATLTVDTSTTTAYMEMSSLRSEDTAVYYCAR<u>GD</u>
<u>NKYDAMDY</u>WGQGTTVTVSS*ASTKGPSVFPLAPSSKSTSGGTAALGCLVKD*
*YFPEPVTVSWNSGALTSGVHTFPAVLQSSGLYSLSSVVTVPSSSLGTQTY*
*ICNVNHKPSNTKVDKKVEPKSCDKTHTCPPCPAPELLGGPSVFLFPPKPK*
*DTLMISRTPEVTCVVVDVSHEDPEVKFNWYVDGVEVHNAKTKPREEQYNS*
*TYRVVSVLTVLHQDWLNGKEYKCKVSNKALPAPIEKTISKAKGQPREPQV*
*YTLPPSREEMTKNQVSLTCLVKGFYPSDIAVEWESNGQPENNYKTTPPVL*
*DSDGSFFLYSKLTVDKSRWQQGNVFSCSVMHEALHNHYTQKSLSLSPG;* and a light chain amino acid sequence (N→C) according to SEQ ID NO: 29, wherein the underlined amino acids represent the CDRs and the italicized amino acids represent the constant regions.

In some embodiments, an anti-huLRRC15 antibody composing an anti-huLRRC15 ADC has a heavy chain amino acid sequence (N→C) according to:

(SEQ ID NO: 105)
EVQLVQSGAEVKKPGSSVKVSCKASGFTFT<u>DYYIH</u>WVKQAPGQGLEWIG<u>L</u>
<u>VYPYIGGTNYNQKF</u>KGKATLTVDTSTTTAYMEMSSLRSEDTAVYYCAR<u>GD</u>
<u>NKYDAMDY</u>WGQGTTVTVSS*ASTKGPSVFPLAPSSKSTSGGTAALGCLVKD*
*YFPEPVTVSWNSGALTSGVHTFPAVLQSSGLYSLSSVVTVPSSSLGTQTY*
*ICNVNHKPSNTKVDKKVEPKSCDKTHTCPPCPAPELLGGPCVFLFPPKPK*
*DTLMISRTPEVTCVVVDVSHEDPEVKFNWYVDGVEVHNAKTKPREEQYNS*
*TYRVVSVLTVLHQDWLNGKEYKCKVSNKALPAPIEKTISKAKGQPREPQV*
*YTLPPSREEMTKNQVSLTCLVKGFYPSDIAVEWESNGQPENNYKTTPPVL*
*DSDGSFFLYSKLTVDKSRWQQGNVFSCSVMHEALHNHYTQKSLSLSPG;* and a light chain amino acid sequence (N→C) according to SEQ ID NO: 29, wherein the underlined amino acids represent the CDRs and the italicized amino acids represent the constant regions.

In some embodiments, an anti-huLRRC15 antibody composing an anti-huLRRC15 ADC has a heavy chain amino acid sequence (N→C) according to SEQ ID NO: 28 or 104; and a light chain amino acid sequence (N→C) according to:

(SEQ ID NO: 111)
DIVLTQSPDSLAVSLGERATINC<u>RASQSVSTSSYSYMH</u>WYQQKPGQPPKL
LIK<u>YASSLES</u>GVPDRFSGSGSGTDFTLTISSLQAEDVAVYYC<u>EQSWEIRT</u>
FGGGTKVEIKR*TVAAPSVFIFPPSDEQLKSGTASVVCLLNNFYPREAKVQ*
*WKVDNALQSGNSQESVTEQDSKDSTYSLSSTLTLSKADYEKHKVYACEVT*
*HQGLSSPVTKSFNRGEA,* wherein the underlined amino acids represent the CDRs and the italicized amino acids represent the constant regions.

Assays for competition include, but are not limited to, a radioactive material labeled immunoassay (RIA), an enzyme-linked immunosorbent assay (ELISA), a sandwich ELISA, flow cytometry assays and surface plasmon resonance assays.

In one exemplary embodiment of conducting an antibody competition assay between a reference antibody and a test antibody (irrespective of species or isotype), one may first label the reference with a detectable label, such as a fluorophore, biotin or an enzymatic (or even radioactive label) to enable subsequent detection. In this case, cells expressing huLRRC15, or the sECD of huLRRC15, are incubated with unlabeled test antibody, labeled reference antibody is added, and the intensity of the bound label is measured. If the test antibody competes with the labeled reference antibody by binding to the same, proximal or overlapping epitope, the intensity of the detection signal will be decreased relative to a control reaction carried out without test antibody.

In a specific embodiment of this assay, the concentration of labeled reference antibody that yields 80% of maximal binding ("$conc_{80\%}$") under the assay conditions (e.g., a specified density of cells or a specified concentration of sECD) is first determined, and a competition assay is carried out with 10× $conc_{80\%}$ of unlabeled test antibody and $conc_{80\%}$ of labeled reference antibody.

In another exemplary embodiment of conducting a flow cytometry competition assay, cells expressing huLRRC15 are incubated with a titration series of antibodies comprising increasing rations of unlabeled test antibody versus fluorescently labeled anti-huLRRC15 reference antibody. The labeled reference anti-huLRRC15 antibody is used at a fixed concentration X (for example, X=1 µg/ml) and the unlabeled test antibody is used in a range of concentrations (for example, from 10'X to 100X). Cells or sECD is incubated with both unlabeled test antibody and labeled reference antibody concurrently. Flow cytometry data is normalized relative to fluorescently labeled reference antibody alone, where the fluorescence intensity of a sample carried out without unlabeled test antibody is assigned 100% binding. If a test antibody competes for binding huLRRC15 with the labeled reference antibody, an assay carried out with equal concentration of each (for example, 1 µg/mL of unlabeled test antibody and 1 µg/mL of labeled reference antibody) will yield an approx. 50% reduction in fluorescence intensity as compared to the 100% control, indicating approx. 50% binding.

The inhibition can be expressed as an inhibition constant, or $K_i$, which is calculated according to the following formula:

$$K_i = IC_{50}/(1+[\text{reference Ab concentration}]/K_d),$$

where $IC_{50}$ is the concentration of test antibody that yields a 50% reduction in binding of the reference antibody and $K_d$ is the dissociation constant of the reference antibody, a measure of its affinity for huLRRC15. Antibodies that compete with reference anti-huLRRC15 antibodies can have a $K_i$ from 10 pM to 10 nM under assay conditions described herein.

In various embodiments, a test antibody is considered to compete with a reference antibody if it decreases binding of the reference antibody to cells expressing huLRRC15 or the sECD by at least about 20% or more, for example, by at least about 20%, 30%, 40%, 50%, 60%, 70%, 80%, 90%, 95% or even more, or by a percentage ranging between any of the foregoing values, at a reference antibody concentration that is 80% of maximal binding under the specific assay conditions used, and a test antibody concentration that is 10-fold higher than the reference antibody concentration.

In various embodiments of a flow cytometry competition assay, a test antibody is considered to compete with a reference antibody if it decreases binding of the reference antibody to cells expressing huLRRC15 by at least about 20% or more, for example, by at least about 20%, 30%, 40%, 50%, 60%, 70%, 80%, 90%, 95% or even more, or by a percentage ranging between any of the foregoing values, at a concentration of test antibody that is 10× greater than that of the reference antibody.

A specific assay and assay conditions useful for assessing whether an antibody competes for binding huLRRC15 with a reference antibody as described herein is provided in Example 3.

The anti-huLRRC15 antibodies described herein may be used in the non-ADC context for a variety of purposes, such as to assist purification of huLRRC15 and/or huLRRC15 sECD, in vitro, in vivo and ex vivo diagnostics, cell and/or tissue stains, etc. As a specific example, the antibodies have use in immunoassays for qualitatively and/or quantitatively measuring levels of huLRRC15 in biological samples. See, e.g., Harlow et al., Antibodies: A Laboratory Manual, Second Edition (Cold Spring Harbor Laboratory Press, 1988).

For such uses, detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody (or fragment thereof) or indirectly, through an intermediate (such as, for example, a linker known in the art) using techniques known in the art. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, acetylcholinesterase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$ or $^{99m}Tc$.

Detection of expression of huLRRC15 generally involves contacting a biological sample (cells, tissue, or body fluid of an individual) with one or more anti-huLRRC15 antibodies described herein (optionally conjugated to detectable moiety), and detecting whether or not the sample is positive for huLRRC15 expression, or whether the sample has altered (e.g., reduced or increased) expression as compared to a control sample.

7.3.2. Polynucleotides Encoding Anti-huLRRC15 Antibodies, Expression Systems and Methods of Making the Antibodies Anti-huLRRC15 antibodies can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N.Y., 1989), Current Protocols in Molecular Biology (Ausubel, F. M. et al., eds., Greene Publishing Associates, 1989) and in U.S. Pat. No. 4,816,397.

To generate nucleic acids encoding such anti-huLRRC15 antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR). Germline DNA sequences for human heavy and light chain variable region genes are known in the art (See, e.g., the "VBASE" human germline sequence database; see also Kabat et al., 1991, Sequences of Proteins of Immunological Interest, Fifth Edition, U.S. Department of Health and Human Services, NIH Publication No. 91-3242; Tomlinson et al., 1992, J. Mol. Biol. 22T:116-198; and Cox et al., 1994, Eur. J. Immunol. 24:827-836; the contents of each of which are incorporated herein by reference).

Once DNA fragments encoding anti-huLRRC15 antibody-related $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($CH_1$, $CH_2$, $CH_3$ and, optionally, $CH_4$). The sequences of human heavy chain constant region genes are known in the art (See, e.g., Kabat et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but in certain embodiments is an $IgG_1$ or $IgG_4$ constant region. For a Fab fragment heavy chain gene, the $V_H$-encoding DNA can be operatively linked to another DNA molecule encoding only the heavy chain $CH_1$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (See, e.g., Kabat et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but in certain embodiments is a kappa constant region. To create a scFv gene, the $V_H$- and $V_L$-encoding DNA fragments are operatively linked to another fragment encoding a flexible linker, e.g., encoding the amino acid sequence $(Gly_4\sim Ser)_3$ (SEQ ID NO:82), such that the $V_H$ and $V_L$ sequences can be expressed as a contiguous single-chain protein, with the $V_L$ and $V_H$ regions joined by the flexible linker (See, e.g., Bird et al., 1988, Science 242:423-426; Huston et al., 1988, Proc. Natl. Acad. Sci. USA 85:5879-5883; McCafferty et al., 1990, Nature 348:552-554).

To express the anti-huLRRC15 antibodies, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-huLRRC15 antibody-related light or heavy chain sequences, the expression vector can already carry antibody constant region sequences. For example, one approach to converting the anti-hPG monoclonal antibody-related $V_H$ and $V_L$ sequences to full-length antibody genes is to insert them into expression vectors already encoding heavy chain constant and light chain constant regions, respectively, such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185, Academic Press, San Diego, Calif., 1990. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al., and U.S. Pat. No. 4,968,615 by Schaffner et al.

Recombinant expression vectors of the disclosure can carry sequences in addition to the antibody chain genes and regulatory sequences, such as sequences that regulate replication of the vector in host cells (e.g., origins of replication) and selectable marker genes. Selectable marker genes facilitate selection of host cells into which the vector has been introduced (See, e.g., U.S. Pat. Nos. 4,399,216, 4,634,665 and 5,179,017, all by Axel et al.). For example, typically a selectable marker gene confers resistance to drugs, such as G418, hygromycin or methotrexate, on a host cell into which the vector has been introduced. Suitable selectable marker genes include the dihydrofolate reductase (DHFR) gene (for use in DHFR⁻ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE—dextran transfection and the like.

It is possible to express anti-huLRRC15 antibodies composing anti-huLRRC15 ADCs in either prokaryotic or eukaryotic host cells. In certain embodiments, expression of antibodies is performed in eukaryotic cells, e.g., mammalian host cells, of optimal secretion of a properly folded and immunologically active antibody. Exemplary mammalian host cells for expressing the recombinant antibodies of the disclosure include Chinese Hamster Ovary (CHO cells) (including DHFR⁻ CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-huLRRC15 antibody.

Recombinant DNA technology can also be used to remove some or all of the DNA encoding either or both of the light and heavy chains that is not necessary for binding to huLRRC15. The molecules expressed from such truncated DNA molecules are also encompassed by the antibodies of the disclosure.

For recombinant expression of an anti-huLRRC15 antibody, the host cell can be co-transfected with two expression vectors, the first vector encoding a heavy chain derived polypeptide and the second vector encoding a light chain derived polypeptide. The two vectors can contain identical selectable markers, or they can each contain a separate selectable marker. Alternatively, a single vector can be used which encodes both heavy and light chain polypeptides.

Once a nucleic acid encoding one or more portions of an anti-huLRRC15 antibody is obtained, further alterations or mutations can be introduced into the coding sequence, for example to generate nucleic acids encoding antibodies with different CDR sequences, antibodies with reduced affinity to the Fc receptor, or antibodies of different subclasses.

Antibodies and/or binding fragments composing anti-huLRRC15 ADCs can also be produced by chemical synthesis (e.g., by the methods described in Solid Phase Peptide Synthesis, $2^{nd}$ ed., 1984 The Pierce Chemical Co., Rockford, Ill.). Variant antibodies can also be generated using a cell-free platform, See, e.g., Chu et al., Biochemia No. 2, 2001 (Roche Molecular Biologicals) and Murray et al., 2013, Current Opinion in Chemical Biology, 17:420-426.

Once an anti-huLRRC15 antibody and/or binding fragment has been produced by recombinant expression, it can be purified by any method known in the art for purification of an immunoglobulin molecule, for example, by chromatography (e.g., ion exchange, affinity, and sizing column chromatography), centrifugation, differential solubility, or by any other standard technique for the purification of proteins. Further, the anti-huLRRC15 antibodies and/or binding fragments can be fused to heterologous polypeptide sequences described herein or otherwise known in the art to facilitate purification.

Once isolated, the anti-huLRRC15 antibody and/or binding fragment can, if desired, be further purified, e.g., by high performance liquid chromatography. (see, e.g., Fisher, Laboratory Techniques In Biochemistry And Molecular Biology, Work and Burdon, eds., Elsevier, 1980), or by gel filtration chromatography on a Superdex™ 75 column (Pharmacia Biotech AB, Uppsala, Sweden).

7.4. Specific Anti-huLRRC15 Antibody Drug Conjugates

As mentioned, anti-huLRRC15 ADCs generally comprise an anti-huLRRC15 antigen binding moiety, such as an anti-huLRRC15 antibody and/or binding fragment, having one or more cytotoxic and/or cytostatic agents, which may be the same or different, linked thereto by way of one or more linkers, which may also be the same or different. In specific embodiments, the anti-huLRRC15 ADCs are compounds according to structural formula (I):

$$[D\text{-}L\text{-}XY]_n\text{-}Ab \qquad (I)$$

or salts thereof, where each "D" represents, independently of the others, a cytotoxic and/or cytostatic agent ("drug"); each "L" represents, independently of the others, a linker; "Ab" represents an anti-huLRRC15 antigen binding moiety, such as an anti-huLRRC15 antibody or binding fragment; each "XY" represents a linkage formed between a functional group $R^x$ on the linker and a "complementary" functional group W on the antigen binding moiety; and n represents the number of drugs linked to Ab, or the drug-to-antibody ratio (DAR), of the ADC.

Specific embodiments of various antibodies or binding fragments (Ab) that may compose ADCs according to structural formula (I) include the various embodiments of anti-huLRRC15 antibodies and/or binding fragments described above.

In some specific embodiments of the ADCs or salts of structural formula (I), each D is the same and/or each L is the same.

Specific embodiments of cytotoxic and/or cytostatic agents (D) and linkers (L) that may compose the anti-huLRRC15 ADCs, as well as the number of cytotoxic and/or cytostatic agents linked to the anti-huLRRC15 ADCs, are described in more detail below.

7.4.1. Cytotoxic and/or Cytostatic Agents

The cytotoxic and/or cytostatic agents may be any agents known to inhibit the growth and/or replication of and/or kill cells, and in particular cancer and/or tumor cells. Numerous agents having cytotoxic and/or cytostatic properties are known in the literature. Non-limiting examples of classes of cytotoxic and/or cytostatic agents include, by way of example and not limitation, radionuclides, alkylating agents, DNA cross-linking agents, DNA intercalating agents (e.g., groove binding agents such as minor groove binders), cell cycle modulators, apoptosis regulators, kinase inhibitors, protein synthesis inhibitors, mitochondria inhibitors, nuclear export inhibitors, topoisomerase I inhibitors, topoisomerase II inhibitors, RNA/DNA antimetabolites and antimitotic agents.

Specific non-limiting examples of agents within certain of these various classes are provided below.

Alkylating Agents:

asaley (L-Leucine, N—[N-acetyl-4-[bis-(2-chloroethyl) amino]-DL-phenylalanyl]-, ethylester); AZQ (1,4-cyclohexadiene-1,4-dicarbamic acid, 2, 5-bis(1-aziridinyl)-3,6-dioxo-, diethyl ester); BCNU (N,N'-Bis(2-chloroethyl)-N-nitrosourea); busulfan (1,4-butanediol dimethanesulfonate); (carboxyphthalato)platinum; CBDCA (cis-(1,1-cyclobutanedicarboxylato)diammineplatinum(II))); CCNU (N-(2-chloroethyl)-N'-cyclohexyl-N-nitrosourea); CHIP (iproplatin; NSC 256927); chlorambucil; chlorozotocin (2-[[[(2-chloroethyl) nitrosoamino]carbonyl]amino]-2-deoxy-D-glucopyranose); cis-platinum (cisplatin); clomesone; cyanomorpholinodoxorubicin; cyclodisone; dianhydrogalactitol (5,6-diepoxydulcitol); fluorodopan ((5-[(2-chloroethyl)-(2-fluoroethyl)amino]-6-methyl-uracil); hepsulfam; hycanthone; indolinobenzodiazepine dimer DGN462; melphalan; methyl CCNU ((1-(2-chloroethyl)-3-(trans-4-methylcyclohexane)-1-nitrosourea); mitomycin C; mitozolamide; nitrogen mustard ((bis(2-chloroethyl) methylamine hydrochloride); PCNU ((1-(2-chloroethyl)-3-(2,6-dioxo-3-piperidyl)-1-nitrosourea)); piperazine alkylator ((1-(2-chloroethyl)-4-(3-chloropropyl)-piperazine dihydrochloride)); piperazinedione; pipobroman (N,N'-bis(3-bromopropionyl) piperazine); porfiromycin (N-methylmitomycin C); spirohydantoin mustard; teroxirone (triglycidylisocyanurate); tetraplatin; thio-tepa (N,N',N''-tri-1,2-ethanediylthio phosphoramide); triethylenemelamine; uracil nitrogen mustard (desmethyldopan); Yoshi-864 ((bis(3-mesyloxy propyl)amine hydrochloride).

DNA Alkylating-Like Agents:

Cisplatin; Carboplatin; Nedaplatin; Oxaliplatin; Satraplatin; Triplatin tetranitrate; Procarbazine; altretamine; dacarbazine; mitozolomide; temozolomide.

Alkylating Antineoplastic Agents:

Carboquone; Carmustine; Chlornaphazine; Chlorozotocin; Duocarmycin; Evofosfamide; Fotemustine; Glufosfamide; Lomustine; Mannosulfan; Nimustine; Phenanthriplatin; Pipobroman; Ranimustine; Semustine; Streptozotocin; ThioTEPA; Treosulfan; Triaziquone; Triethylenemelamine; Triplatin tetranitrate.

DNA Replication and Repair Inhibitors:

Altretamine; Bleomycin; Dacarbazine; Dactinomycin; Mitobronitol; Mitomycin; Pingyangmycin; Plicamycin; Procarbazine; Temozolomide; ABT-888 (veliparib); olaparib; KU-59436; AZD-2281; AG-014699; BSI-201; BGP-15; INO-1001; ONO-2231.

Cell Cycle Modulators:

Paclitaxel; Nab-Paclitaxel; Docetaxel; Vincristine; Vinblastine; ABT-348; AZD-1152; MLN-8054; VX-680; Aurora A-specific kinase inhibitors; Aurora B-specific kinase inhibitors and pan-Aurora kinase inhibitors; AZD-5438; BMI-1040; BMS-032; BMS-387; CVT-2584; flavopyridol; GPC-286199; MCS-5A; PD0332991; PHA-690509; seliciclib (CYC-202, R-roscovitine); ZK-304709; AZD4877, ARRY-520: GSK923295A.

Apoptosis Regulators:

AT-101 ((−)gossypol); G3139 or oblimersen (Bcl-2-targeting antisense oligonucleotide); IPI-194; IPI-565; N-(4-(4-((4'-chloro(1,1'-biphenyl)-2-yl)methyl)piperazin-1-yl-benzoyl)-4-(((1R)-3-(dimethylamino)-1-((phenylsulfanyl) methyl)propyl)amino)-3-nitrobenzenesulfonamide); N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide); GX-070 (Obatoclax®; 1H-Indole, 2-(2-((3,5-dimethyl-1H-pyrrol-2-yl)methylene)-3-methoxy-2H-pyrrol-5-yl)-)); HGS1029; GDC-0145; GDC-0152; LCL-161; LBW-242; venetoclax; agents that target TRAIL or death receptors (e.g., DR4 and DR5) such as ETR2-ST01, GDC0145, HGS-1029, LBY-135, PRO-1762; drugs that target caspases, caspase-regulators, BCL-2 family members, death domain proteins, TNF family members, Toll family members, and/or NF-kappa-B proteins.

Angiogenesis Inhibitors:

ABT-869; AEE-788; axitinib (AG-13736); AZD-2171; CP-547,632; IM-862; pegaptamib; sorafenib; BAY43-9006; pazopanib (GW-786034); vatalanib (PTK-787, ZK-222584); sunitinib; SU-11248; VEGF trap; vandetanib; ABT-165; ZD-6474; DLL4 inhibitors.

Proteasome Inhibitors:

Bortezomib; Carfilzomib; Epoxomicin; Ixazomib; Salinosporamide A.

Kinase Inhibitors:

Afatinib; Axitinib; Bosutinib; Crizotinib; Dasatinib; Erlotinib; Fostamatinib; Gefitinib; Ibrutinib; Imatinib; Lapatinib; Lenvatinib; Mubritinib; Nilotinib; Pazopanib; Pegaptanib; Sorafenib; Sunitinib; SU6656; Vandetanib; Vemurafenib; CEP-701 (lesaurtinib); XL019; INCB018424 (ruxolitinib); ARRY-142886 (selemetinib); ARRY-438162 (binimetinib); PD-325901; PD-98059; AP-23573; CCI-779; everolimus; RAD-001; rapamycin; temsirolimus; ATP-competitive TORC1/TORC2 inhibitors including PI-103, PP242, PP30, Torin 1; LY294002; XL-147; CAL-120; ONC-21; AEZS-127; ETP-45658; PX-866; GDC-0941; BGT226; BEZ235; XL765.

Protein Synthesis Inhibitors:

Streptomycin; Dihydrostreptomycin; Neomycin; Framycetin; Paromomycin; Ribostamycin; Kanamycin; Amikacin; Arbekacin; Bekanamycin; Dibekacin; Tobramycin; Spectinomycin; Hygromycin B; Paromomycin; Gentamicin; Netilmicin; Sisomicin; Isepamicin; Verdamicin; Astromicin; Tetracycline; Doxycycline; Chlortetracycline; Clomocycline; Demeclocycline; Lymecycline; Meclocycline; Metacycline; Minocycline; Oxytetracycline; Penimepicycline; Rolitetracycline; Tetracycline; Glycylcyclines; Tigecycline; Oxazolidinone; Eperezolid; Linezolid; Posizolid; Radezolid; Ranbezolid; Sutezolid; Tedizolid; Peptidyl transferase inhibitors; Chloramphenicol; Azidamfenicol; Thiamphenicol; Florfenicol; Pleuromutilins; Retapamulin; Tiamulin; Valnemulin; Azithromycin; Clarithromycin; Dirithromycin; Erythromycin; Flurithromycin; Josamycin; Midecamycin; Miocamycin; Oleandomycin; Rokitamycin; Roxithromycin; Spiramycin; Troleandomycin; Tylosin; Ketolides; Telithromycin; Cethromycin; Solithromycin; Clindamycin; Lincomycin; Pirlimycin; Streptogramins; Pristinamycin; Quinupristin/dalfopristin; Virginiamycin.

Histone Deacetylase Inhibitors:

Vorinostat; Romidepsin; Chidamide; Panobinostat; Valproic acid; Belinostat; Mocetinostat; Abexinostat; Entinostat; SB939 (pracinostat); Resminostat; Givinostat; Quisinostat; thioureidobutyronitrile (Kevetrin™); CUDC-10; CHR-2845 (tefinostat); CHR-3996; 4SC-202; CG200745; ACY-1215 (rocilinostat); ME-344; sulforaphane.

Topoisomerase I Inhibitors:

camptothecin; various camptothecin derivatives and analogs (for example, NSC 100880, NSC 603071, NSC 107124, NSC 643833, NSC 629971, NSC 295500, NSC 249910, NSC 606985, NSC 74028, NSC 176323, NSC 295501, NSC 606172, NSC 606173, NSC 610458, NSC 618939, NSC 610457, NSC 610459, NSC 606499, NSC 610456, NSC 364830, and NSC 606497); morpholinisoxorubicin; SN-38.

Topoisomerase II Inihibitors:

doxorubicin; amonafide (benzisoquinolinedione); m-AMSA (4'-(9-acridinylamino)-3'-methoxymethanesulfonanilide); anthrapyrazole derivative ((NSC 355644); etoposide (VP-16); pyrazoloacridine ((pyrazolo[3,4,5-kl]acridine-2(6H)-propanamine, 9-methoxy-N, N-dimethyl-5-nitro-, monomethanesulfonate); bisantrene hydrochloride; daunorubicin; deoxydoxorubicin; mitoxantrone; menogaril; N,N-dibenzyl daunomycin; oxanthrazole; rubidazone; teniposide.

DNA Intercalating Agents:

anthramycin; chicamycin A; tomaymycin; DC-81; sibiromycin; pyrrolobenzodiazepine derivative; SGD-1882 ((S)-2-(4-aminophenyl)-7-methoxy-8-(3 S)-7-methoxy-2-(4-methoxyphenyl)-5-oxo-5,11a-dihydro-1H-benzo[e]pyrrolo[1,2-a][1,4]diazepin-8-yl)oxy)propoxy)-1H-benzo[e]pyrrolo[1,2-a][1,4]diazepin-5(11aH)-one); SG2000 (SJG-136; (11aS,11a'S)-8,8'-(propane-1,3-diylbis(oxy))bis(7-methoxy-2-methylene-2,3-dihydro-1H-benzo[e]pyrrolo[1,2-a][1,4]diazepin-5(11aH)-one)).

RNA/DNA Antimetabolites:

L-alanosine; 5-azacytidine; 5-fluorouracil; acivicin; aminopterin derivative N-[2-chloro-5[[(2, 4-diamino-5-methyl-6-quinazolinyl)methyl]amino]benzoyl]L-aspartic acid (NSC 132483); aminopterin derivative N-[4-[[(2, 4-diamino-5-ethyl-6-quinazolinyl)methyl]amino]benzoyl]L-aspartic acid; aminopterin derivative N-[2-chloro-4-[[(2, 4-diamino-6-pteridinyl)methyl]amino]benzoyl]L-aspartic acid monohydrate; antifolate PT523 ((N$^\alpha$-(4-amino-4-deoxypteroyl)-N$^\gamma$-hemiphthaloyl-L-ornithine)); Baker's soluble antifol (NSC 139105); dichlorallyl lawsone ((2-(3, 3-dichloroallyl)-3-hydroxy-1,4-naphthoquinone); brequinar; ftorafur ((pro-drug; 5-fluoro-1-(tetrahydro-2-furyl)-uracil); 5,6-dihydro-5-azacytidine; methotrexate; methotrexate derivative (N-[[4-[[(2, 4-diamino-6-pteridinyl)methyl]methylamino]-1-naphthalenyl]carbonyl]L-glutamic acid); PALA ((N-(phosphonoacetyl)-L-aspartate); pyrazofurin; trimetrexate.

DNA Antimetabolites:

3-HP; 2'-deoxy-5-fluorouridine; 5-HP; α-TGDR (α-2'-deoxy-6-thioguanosine); aphidicolin glycinate; ara C (cytosine arabinoside); 5-aza-2'-deoxycytidine; β-TGDR (β-2'-deoxy-6-thioguanosine); cyclocytidine; guanazole; hydroxyurea; inosine glycodialdehyde; macbecin II; pyrazoloimidazole; thioguanine; thiopurine.

Mitochondria Inhibitors:

pancratistatin; phenpanstatin; rhodamine-123; edelfosine; d-alpha-tocopherol succinate; compound 11β; aspirin; ellipticine; berberine; cerulenin; GX015-070 (Obatoclax®; 1H-Indole, 2-(2-((3,5-dimethyl-1H-pyrrol-2-yl)methylene)-3-methoxy-2H-pyrrol-5-yl)-); celastrol (tripterine); metformin; Brilliant green; ME-344.

Antimitotic Agents:

allocolchicine; auristatins, such as MMAE (monomethyl auristatin E) and MMAF (monomethyl auristatin F); halichondrin B; cemadotin; colchicine; cholchicine derivative (N-benzoyl-deacetyl benzamide); dolastatin-10; dolastatin-15; maytansine; maytansinoids, such as DM1 ($N_2$'-deacetyl-$N_2$'-(3-mercapto-1-oxopropyl)-maytansine); rhozoxin; paclitaxel; paclitaxel derivative ((2'-N-[3-(dimethylamino)propyl]glutaramate paclitaxel); docetaxel; thiocolchicine; trityl cysteine; vinblastine sulfate; vincristine sulfate.

Nuclear Export Inhibitors:

callystatin A; delactonmycin; KPT-185 (propan-2-yl (Z)-3-[3-[3-methoxy-5-(trifluoromethyl)phenyl]-1,2,4-triazol-1-yl]prop-2-enoate); kazusamycin A; leptolstatin; leptofuranin A; leptomycin B; ratjadone; Verdinexor ((Z)-3-[3-[3,5-bis(trifluoromethyl)phenyl]-1,2,4-triazol-1-yl]-N-pyridin-2-ylprop-2-enehydrazide).

hormonal therapies: anastrozole; exemestane; arzoxifene; bicalutamide; cetrorelix; degarelix; deslorelin; trilostane; dexamethasone; flutamide; raloxifene; fadrozole; toremifene; fulvestrant; letrozole; formestane; glucocorticoids; doxercalciferol; sevelamer carbonate; lasofoxifene; leuprolide acetate; megesterol; mifepristone; nilutamide; tamoxifen citrate; abarelix; prednisone; finasteride; rilostane; buserelin; luteinizing hormone releasing hormone (LHRH); Histrelin; trilostane or modrastane; fosrelin; goserelin.

Any of these agents that include, or that may be modified to include, a site of attachment to an antibody and/or binding fragment may be included in an anti-huLRRC15 ADC.

Data presented herein demonstrate that anti-huLRRC15 ADCs exert potent anti-tumor activity against huLRRC15 stromal(+)/cancer(−) tumors that is mediated, at least in part, by a targeted bystander killing effect. For example, as demonstrated in FIG. 14A, cells expressing huLRRC15 are sensitive in vitro to anti-huLRRC15 ADCs containing either monomethyl auristatin E ("MMAE") or monomethyl auristatin F ("MMAF") as the drug. However, in vivo, huLRRC15 stromal(+)/cancer (−) PANC-1 xenografts are sensitive to the MMAE anti-huLRRC15 ADC, whereas the MMAF anti-huLRRC15 ADC does not shrink tumors, as demonstrated in FIG. 17B. This is also observed with huLRRC15 stromal(+)/cancer (−) EBC-1 xenografts, as demonstrated in FIG. 15A. MMAE released from the ADCs internalized in huLRRC15-expressing stromal cells is cell permeable, allowing targeted bystander killing of cancer cells adjacent to the stromal cells. MMAF is not cell permeable, is retained within the huLRRC15-expressing stromal cells, and does not migrate to kill neighboring cancer cells. The huLRRC15-expressing stromal cells divide at a much slower rate than cancer cells in vivo and are therefore intrinsically less sensitive than rapidly dividing cancer cells to anti-mitotic agents such as MMAE and MMAF (as shown in FIG. 16). Together, these data demonstrate that anti-huLRRC15 ADCs containing cell-permeating cytostatic and/or cytotoxic agents exert anti-tumor activity against huLRRC15 stromal(+)/cancer (−) tumors via targeted bystander killing and are useful therapeutically for the treatment of huLRRC15 stromal(+)/cancer (−) tumors.

Accordingly, in some embodiments, the cytotoxic and/or cytostatic agents included in an anti-huLRRC15 ADC will, upon cleavage of the ADC, be able to traverse cell membranes ("cell permeable cytostatic and/or cytotoxic agents"). Specific cytotoxic and/or cytostatic agents of interest, and/or cleavage products of ADCs including such agents, may be tested for the ability to traverse cell membranes using routine methods known to those of skill in the art. Permeability (P) of molecules across a membrane can be expressed as $P=KD/\Delta x$ where K is the partition coefficient, D is the diffusion coefficient, and $\Delta x$ is the thickness of the cell membrane. The diffusion coefficient (D) is a measure of the rate of entry into the cytoplasm depending on the molecular weight or size of a molecule. K is a measure of the solubility of the substance in lipids. A low value of K describes a molecule like water that is not soluble in lipid. Graphically, it is expected that permeability (P) as a function of the partition coefficient (K) will increase linearly when D and $\Delta x$ are constants. (Walter & Gutknecht, 1986, "Permeability of small nonelectrolytes through lipid bilayer membranes," Journal of Membrane Biology 90:207-217; Diamond & Katz, 1974, "Interpretation of nonelectrolyte partition coefficients between dimyristoyl lecithin and water," Journal of Membrane Biology 17:121-154).

In a specific embodiment, the cytotoxic and/or cytostatic agent is a cell-permeable antimitotic agent.

In another specific embodiment, the cytotoxic and/or cytostatic agent is a cell-permeable auristatin, such as, for example, dolastatin-10 or MMAE.

In another specific embodiment, the cytotoxic and/or cytostatic agent is a cell-permeable minor groove-binding DNA cross-linking agent, such as, for example, a pyrrolobenzodiazepine ("PBD") dimer.

7.4.2. Linkers

In the anti-huLRRC15 ADCs described herein, the cytotoxic and/or cytostatic agents are linked to the antigen binding moiety by way of linkers. The linkers may be short, long, hydrophobic, hydrophilic, flexible or rigid, or may be composed of segments that each independently have one or more of the above-mentioned properties such that the linker may include segments having different properties. The linkers may be polyvalent such that they covalently link more than one agent to a single site on the antibody, or monovalent such that covalently they link a single agent to a single site on the antibody.

As will be appreciated by skilled artisans, the linkers link the cytotoxic and/or cytostatic agents to the antigen binding moiety by forming a covalent linkage to the cytotoxic and/or cytostatic agent at one location and a covalent linkage to the antigen binding moiety at another. The covalent linkages are formed by reaction between functional groups on the linker and functional groups on the agents and the antigen binding moiety. As used herein, the expression "linker" is intended to include (i) unconjugated forms of the linker that include a functional group capable of covalently linking the linker to a cytotoxic and/or cytostatic agent and a functional group capable of covalently linking the linker to the antigen binding moiety such as an antibody; (ii) partially conjugated forms of the linker that includes a functional group capable of covalently linking the linker to an antigen binding moiety such as an antibody and that is covalently linked to a cytotoxic and/or cytostatic agent, or vice versa; and (iii) fully conjugated forms of the linker that is covalently linked to both a cytotoxic and/or cytostatic agent and an antigen binding moiety such as an antibody. In some specific embodiments of linkers and ADCs described herein, as well as synthons used to conjugate linker-agents to antibodies, moieties comprising the functional groups on the linker and covalent linkages formed between the linker and antibody are specifically illustrated as $R^x$ and XY, respectively.

The linkers are preferably, but need not be, chemically stable to conditions outside the cell, and may be designed to cleave, immolate and/or otherwise specifically degrade inside the cell. Alternatively, linkers that are not designed to specifically cleave or degrade inside the cell may be used. Particular linkers may also be processed extracellularly in the tumor microenvironment by enzymes present at high levels in tumor stroma. Choice of stable versus unstable linker may depend upon the toxicity of the cytotoxic and/or cytostatic agent. A wide variety of linkers useful for linking drugs to antibodies in the context of ADCs are known in the art. Any of these linkers, as well as other linkers, may be used to link the cytotoxic and/or cytostatic agents to the antibody of the ADCs described herein.

Exemplary polyvalent linkers that may be used to link many cytotoxic and/or cytostatic agents to a single antibody molecule are described, for example, in WO 2009/073445; WO 2010/068795; WO 2010/138719; WO 2011/120053; WO 2011/171020; WO 2013/096901; WO 2014/008375; WO 2014/093379; WO 2014/093394; WO 2014/093640, the contents of which are incorporated herein by reference in their entireties. For example, the Fleximer linker technology developed by Mersana et al. has the potential to enable high-DAR ADCs with good physicochemical properties. As shown below, the Mersana technology is based on incorporating drug molecules into a solubilizing poly-acetal backbone via a sequence of ester bonds. The methodology renders highly-loaded ADCs (DAR up to 20) while maintaining good physicochemical properties.

Additional examples of dendritic type linkers can be found in US 2006/116422; US 2005/271615; de Groot et al (2003) Angew. Chem. Int. Ed. 42:4490-4494; Amir et al (2003) Angew. Chem. Int. Ed. 42:4494-4499; Shamis et al (2004) J. Am. Chem. Soc. 126:1726-1731; Sun et al (2002) Bioorganic & Medicinal Chemistry Letters 12:2213-2215; Sun et al (2003) Bioorganic & Medicinal Chemistry 11:1761-1768; King et al (2002) Tetrahedron Letters 43:1987-1990, each of which is incorporated herein by reference.

Exemplary monovalent linkers that may be used are described, for example, in Nolting, 2013, Antibody-Drug Conjugates, Methods in Molecular Biology 1045:71-100; Kitson et al., 2013, CROs/CMOs—Chemica Oggi—Chemistry Today 31(4):30-38; Ducry et al., 2010, Bioconjugate Chem. 21:5-13; Zhao et al., 2011, J. Med. Chem. 54:3606-3623; U.S. Pat. No. 7,223,837; U.S. Pat. No. 8,568,728; U.S. Pat. No. 8,535,678; and WO2004010957, each of which is incorporated herein by reference.

By way of example and not limitation, some cleavable and noncleavable linkers that may be included in the anti-huLRRC15 ADCs described herein are described below.

7.4.2.1. Cleavable Linkers

In certain embodiments, the linker selected is cleavable in vivo. Cleavable linkers may include chemically or enzymatically unstable or degradable linkages. Cleavable linkers generally rely on processes inside the cell to liberate the drug, such as reduction in the cytoplasm, exposure to acidic conditions in the lysosome, or cleavage by specific proteases or other enzymes within the cell. Cleavable linkers generally incorporate one or more chemical bonds that are either chemically or enzymatically cleavable while the remainder of the linker is noncleavable. In certain embodiments, a linker comprises a chemically labile group such as hydrazone and/or disulfide groups. Linkers comprising chemically labile groups exploit differential properties between the plasma and some cytoplasmic compartments. The intracellular conditions to facilitate drug release for hydrazone containing linkers are the acidic environment of endosomes and lysosomes, while the disulfide containing linkers are reduced in the cytosol, which contains high thiol concentrations, e.g., glutathione. In certain embodiments, the plasma stability of a linker comprising a chemically labile group may be increased by introducing steric hindrance using substituents near the chemically labile group.

Acid-labile groups, such as hydrazone, remain intact during systemic circulation in the blood's neutral pH environment (pH 7.3-7.5) and undergo hydrolysis and release the drug once the ADC is internalized into mildly acidic endosomal (pH 5.0-6.5) and lysosomal (pH 4.5-5.0) compartments of the cell. This pH dependent release mechanism has been associated with nonspecific release of the drug. To increase the stability of the hydrazone group of the linker, the linker may be varied by chemical modification, e.g., substitution, allowing tuning to achieve more efficient release in the lysosome with a minimized loss in circulation.

Hydrazone-containing linkers may contain additional cleavage sites, such as additional acid-labile cleavage sites and/or enzymatically labile cleavage sites. ADCs including exemplary hydrazone-containing linkers include the following structures:

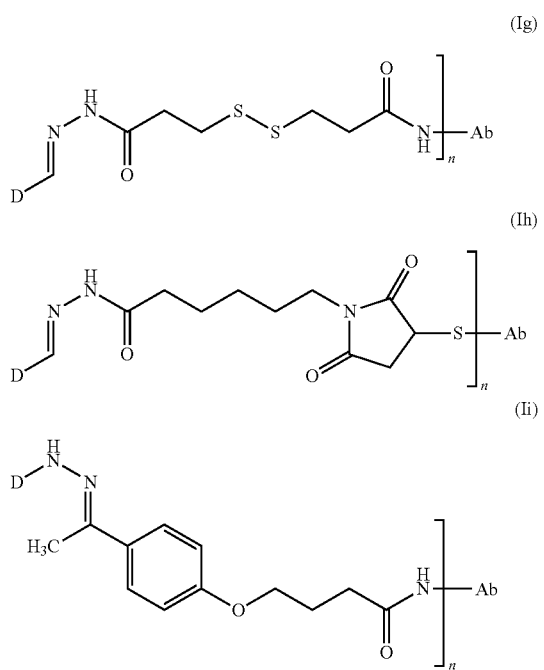

wherein D and Ab represent the cytotoxic and/or cytostatic agent (drug) and antibody, respectively, and n represents the number of drug-linkers linked to the antibody. In certain linkers such as linker (Ig), the linker comprises two cleavable groups—a disulfide and a hydrazone moiety. For such linkers, effective release of the unmodified free drug requires acidic pH or disulfide reduction and acidic pH. Linkers such as (Ih) and (Ii) have been shown to be effective with a single hydrazone cleavage site.

Other acid-labile groups that may be included in linkers include cis-aconityl-containing linkers. cis-Aconityl chemistry uses a carboxylic acid juxtaposed to an amide bond to accelerate amide hydrolysis under acidic conditions.

Cleavable linkers may also include a disulfide group. Disulfides are thermodynamically stable at physiological pH and are designed to release the drug upon internalization inside cells, wherein the cytosol provides a significantly more reducing environment compared to the extracellular environment. Scission of disulfide bonds generally requires the presence of a cytoplasmic thiol cofactor, such as (reduced) glutathione (GSH), such that disulfide-containing linkers are reasonably stable in circulation, selectively releasing the drug in the cytosol. The intracellular enzyme protein disulfide isomerase, or similar enzymes capable of cleaving disulfide bonds, may also contribute to the preferential cleavage of disulfide bonds inside cells. GSH is reported to be present in cells in the concentration range of 0.5-10 mM compared with a significantly lower concentration of GSH or cysteine, the most abundant low-molecular weight thiol, in circulation at approximately 5 μM. Tumor cells, where irregular blood flow leads to a hypoxic state, result in enhanced activity of reductive enzymes and therefore even higher glutathione concentrations. In certain embodiments, the in vivo stability of a disulfide-containing linker may be enhanced by chemical modification of the linker, e.g., use of steric hinderance adjacent to the disulfide bond.

ADCs including exemplary disulfide-containing linkers include the following structures:

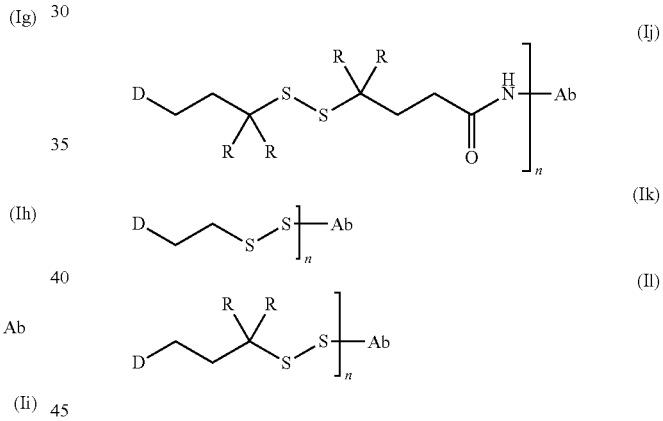

wherein D and Ab represent the drug and antibody, respectively, n represents the number of drug-linkers linked to the antibody, and R is independently selected at each occurrence from hydrogen or alkyl, for example. In certain embodiments, increasing steric hinderance adjacent to the disulfide bond increases the stability of the linker. Structures such as (Ij) and (Il) show increased in vivo stability when one or more R groups is selected from a lower alkyl such as methyl.

Another type of cleavable linker that may be used is a linker that is specifically cleaved by an enzyme. Such linkers are typically peptide-based or include peptidic regions that act as substrates for enzymes. Peptide based linkers tend to be more stable in plasma and extracellular milieu than chemically labile linkers. Peptide bonds generally have good serum stability, as lysosomal proteolytic enzymes have very low activity in blood due to endogenous inhibitors and the unfavorably high pH value of blood compared to lysosomes. Release of a drug from an antibody occurs specifically due to the action of lysosomal proteases, e.g., cathepsin and plasmin. These proteases may be present at elevated levels in certain tumor cells.

In exemplary embodiments, the cleavable peptide is selected from tetrapeptides such as Gly-Phe-Leu-Gly (SEQ ID NO:80), Ala-Leu-Ala-Leu (SEQ ID NO:81) or dipeptides such as Val-Cit, Val-Ala, Met-(D)Lys, Asn-(D)Lys, Val-(D) Asp, Phe-Lys, Ile-Val, Asp-Val, His-Val, NorVal-(D)Asp, Ala-(D)Asp, Met-Lys, Asn-Lys, Ile-Pro, Me3Lys-Pro, PhenylGly-(D)Lys, Met-(D)Lys, Asn-(D)Lys, Pro-(D)Lys, Met-(D)Lys, Asn-(D)Lys, Met-(D)Lys, Asn-(D)Lys. In certain embodiments, dipeptides are preferred over longer polypeptides due to hydrophobicity of the longer peptides.

A variety of dipeptide-based cleavable linkers useful for linking drugs such as doxorubicin, mitomycin, campotothecin, tallysomycin and auristatin/auristatin family members to antibodies have been described (see, Dubowchik et al., 1998, *J Org. Chem.* 67:1866-1872; Dubowchik et al., 1998, *Bioorg. Med. Chem. Lett.* 8(21):3341-3346; Walker et al., 2002, *Bioorg. Med. Chem. Lett.* 12:217-219; Walker et al., 2004, *Bioorg. Med. Chem. Lett.* 14:4323-4327; and Francisco et al., 2003, *Blood* 102:1458-1465, Dornina et al., 2008, Bioconjugate Chemistry 19:1960-1963, of each of which is incorporated herein by reference). All of these dipeptide linkers, or modified versions of these dipeptide linkers, may be used in the ADCs described herein. Other dipeptide linkers that may be used include those found in ADCs such as Seattle Genetics' Brentuximab Vendotin SGN-35 (Adcetris™), Seattle Genetics SGN-75 (anti-CD-70, Val-Cit-MMAF), Celldex Therapeutics glembatumumab (CDX-011) (anti-GPNMB, Val-Cit-MMAE), and Cytogen PSMA-ADC (PSMA-ADC-1301) (anti-PSMA, Val-Cit-MMAE).

Enzymatically cleavable linkers may include a self-immolative spacer to spatially separate the drug from the site of enzymatic cleavage. The direct attachment of a drug to a peptide linker can result in proteolytic release of an amino acid adduct of the drug, thereby impairing its activity. The use of a self-immolative spacer allows for the elimination of the fully active, chemically unmodified drug upon amide bond hydrolysis.

One self-immolative spacer is the bifunctional para-aminobenzyl alcohol group, which is linked to the peptide through the amino group, forming an amide bond, while amine containing drugs may be attached through carbamate functionalities to the benzylic hydroxyl group of the linker (PABC). The resulting prodrugs are activated upon protease-mediated cleavage, leading to a 1,6-elimination reaction releasing the unmodified drug, carbon dioxide, and remnants of the linker group. The following scheme depicts the fragmentation of p-amidobenzyl ether and release of the drug:

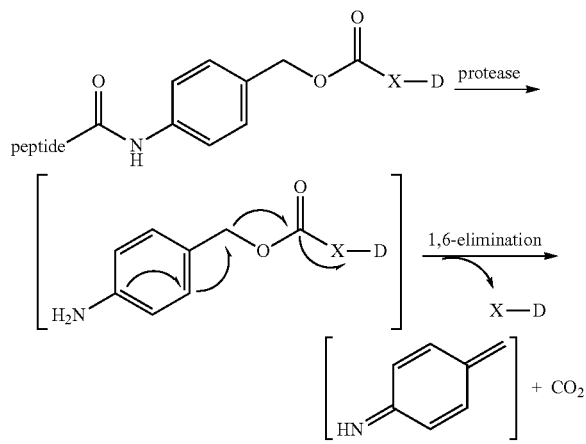

wherein X-D represents the unmodified drug.

Heterocyclic variants of this self-immolative group have also been described. See for example, U.S. Pat. No. 7,989,434, incorporated herein by reference.

In some embodiments, the enzymatically cleavable linker is a ß-glucuronic acid-based linker. Facile release of the drug may be realized through cleavage of the ß-glucuronide glycosidic bond by the lysosomal enzyme ß-glucuronidase. This enzyme is present abundantly within lysosomes and is overexpressed in some tumor types, while the enzyme activity outside cells is low. ß-Glucuronic acid-based linkers may be used to circumvent the tendency of an ADC to undergo aggregation due to the hydrophilic nature of ß-glucuronides. In some embodiments, ß-glucuronic acid-based linkers are preferred as linkers for ADCs linked to hydrophobic drugs. The following scheme depicts the release of the drug from and ADC containing a ß-glucuronic acid-based linker:

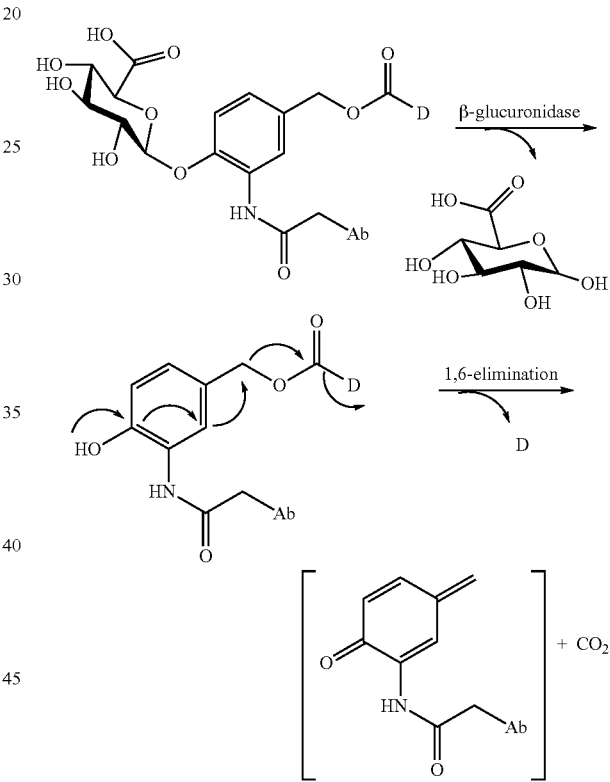

A variety of cleavable ß-glucuronic acid-based linkers useful for linking drugs such as auristatins, camptothecin and doxorubicin analogues, CBI minor-groove binders, and psymberin to antibodies have been described (see, see Nolting, Chapter 5 "Linker Technology in Antibody-Drug Conjugates," In: *Antibody-Drug Conjugates: Methods in Molecular Biology*, vol. 1045, pp. 71-100, Laurent Ducry (Ed.), Springer Science & Business Medica, LLC, 2013; Jeffrey et al., 2006, *Bioconjug. Chem.* 17:831-840; Jeffrey et al., 2007, *Bioorg. Med. Chem. Lett.* 17:2278-2280; and Jiang et al., 2005, *J Am. Chem. Soc.* 127:11254-11255, each of which is incorporated herein by reference). All of these ß-glucuronic acid-based linkers may be used in the anti-huLRRC15 ADCs described herein.

Additionally, cytotoxic and/or cytostatic agents containing a phenol group can be covalently bonded to a linker through the phenolic oxygen. One such linker, described in WO 2007/089149, relies on a methodology in which a diamino-ethane "SpaceLink" is used in conjunction with traditional "PABO"-based self-immolative groups to deliver phenols. The cleavage of the linker is depicted schematically below, where D represents a cytotoxic and/or cytostatic agent having a phenolic hydroxyl group.

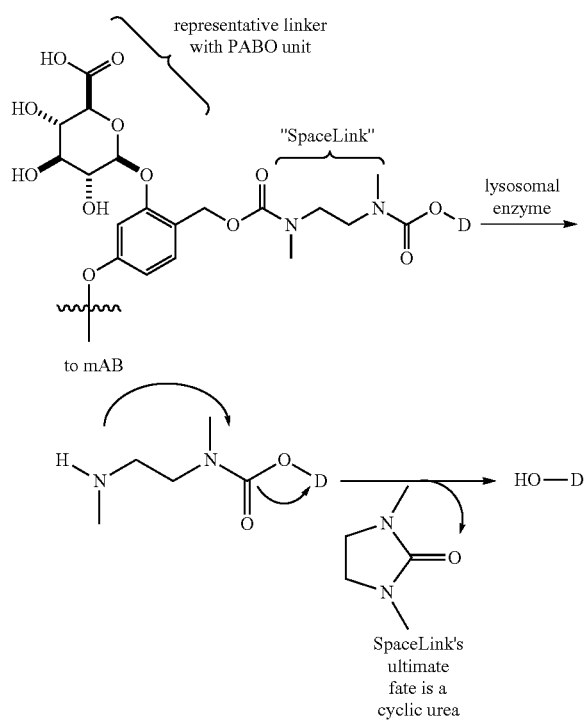

Cleavable linkers may include noncleavable portions or segments, and/or cleavable segments or portions may be included in an otherwise non-cleavable linker to render it cleavable. By way of example only, polyethylene glycol (PEG) and related polymers may include cleavable groups in the polymer backbone. For example, a polyethylene glycol or polymer linker may include one or more cleavable groups such as a disulfide, a hydrazone or a dipeptide.

Other degradable linkages that may be employed in linkers include, but are not limited to, ester linkages formed by the reaction of PEG carboxylic acids or activated PEG carboxylic acids with alcohol groups on a biologically active agent, wherein such ester groups generally hydrolyze under physiological conditions to release the biologically active agent. Hydrolytically degradable linkages include, but are not limited to, carbonate linkages; imine linkages resulting from reaction of an amine and an aldehyde; phosphate ester linkages formed by reacting an alcohol with a phosphate group; acetal linkages that are the reaction product of an aldehyde and an alcohol; orthoester linkages that are the reaction product of a formate and an alcohol; and oligo-nucleotide linkages formed by a phosphoramidite group, including but not limited to, at the end of a polymer, and a 5'-hydroxyl group of an oligonucleotide.

In certain embodiments, the linker comprises an enzymatically cleavable peptide moiety, for example, a linker comprising structural formula (IVa), (IVb), (IVc), or (IVd):

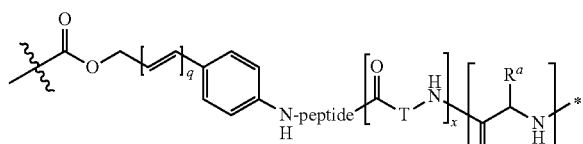

(IVa)

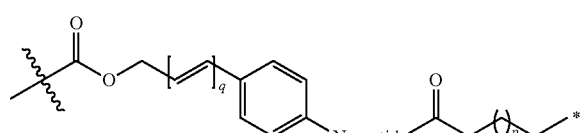

(IVb)

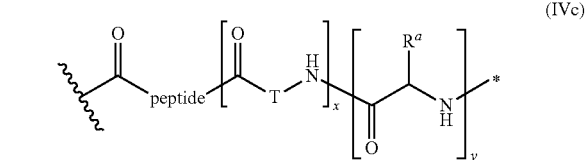

(IVc)

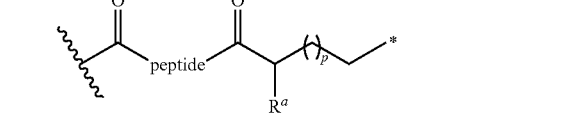

(IVd)

or a salt thereof, wherein:

peptide represents a peptide (illustrated C→N and not showing the carboxy and amino "termini") cleavable by a lysosomal enzyme;

T represents a polymer comprising one or more ethylene glycol units or an alkylene chain, or combinations thereof;

$R^a$ is selected from hydrogen, alkyl, sulfonate and methyl sulfonate;

p is an integer ranging from 0 to 5;

q is 0 or 1;

x is 0 or 1;

y is 0 or 1;

✦ represents the point of attachment of the linker to a cytotoxic and/or cytostatic agent; and

* represents the point of attachment to the remainder of the linker.

In certain embodiments, the peptide is selected from a tripeptide or a dipeptide. In particular embodiments, the dipeptide is selected from: Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; Val-Ala; Phe-Lys; Val-Lys; Ala-Lys; Phe-Cit; Leu-Cit; Ile-Cit; Phe-Arg; and Trp-Cit.

Specific exemplary embodiments of linkers according to structural formula (IVa) that may be included in the ADCs described herein include the linkers illustrated below (as illustrated, the linkers include a group suitable for covalently linking the linker to an antibody):

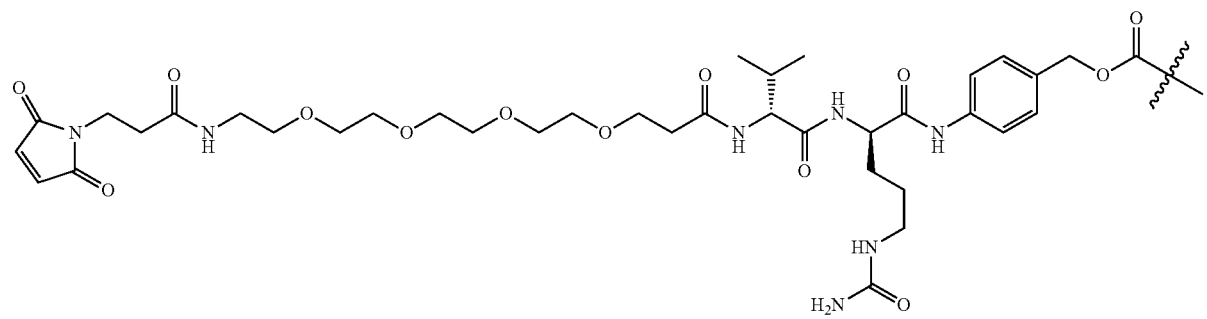
(IVa.1)
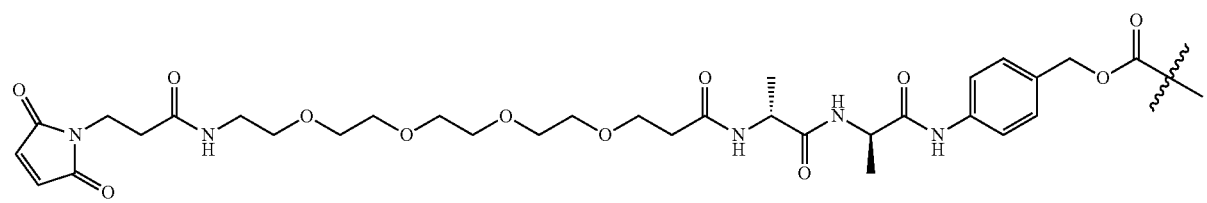
(IVa.2)
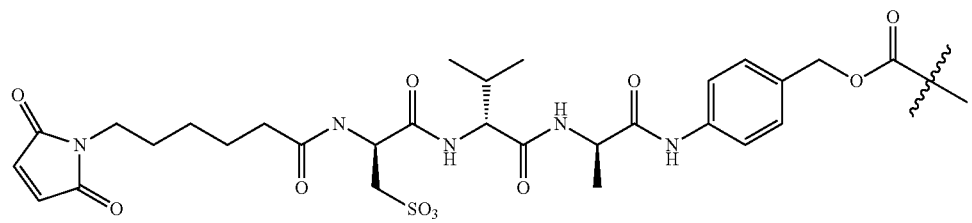
(IVa.3)
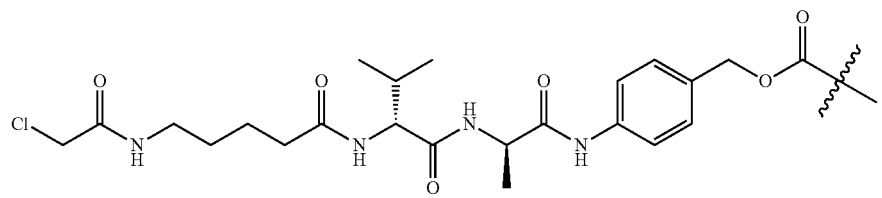
(IVa.4)
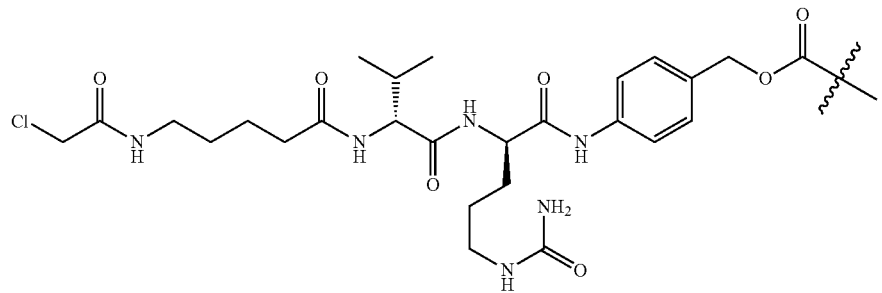
(IVa.5)

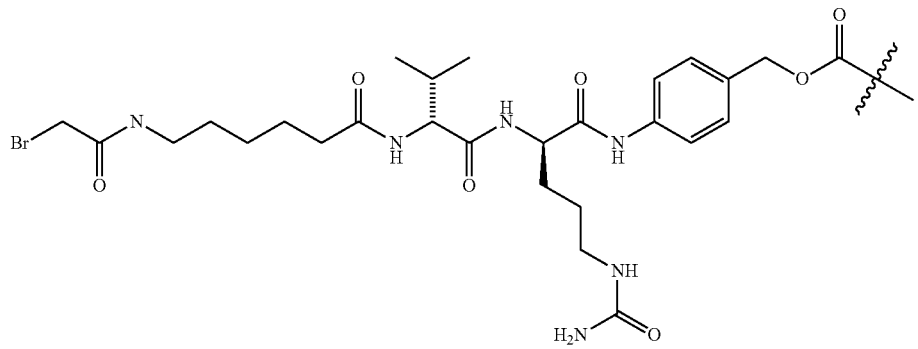
(IVa.6)
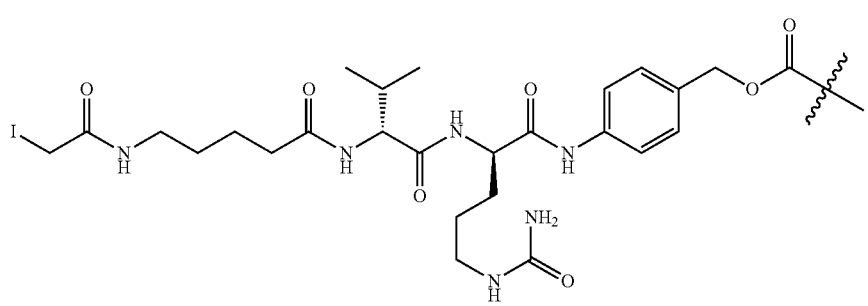
(IVa.7)
Specific exemplary embodiments of linkers according to structural formula (IVb) that may be included in the ADCs described herein include the linkers illustrated below (as illustrated, the linkers include a group suitable for covalently linking the linker to an antibody):
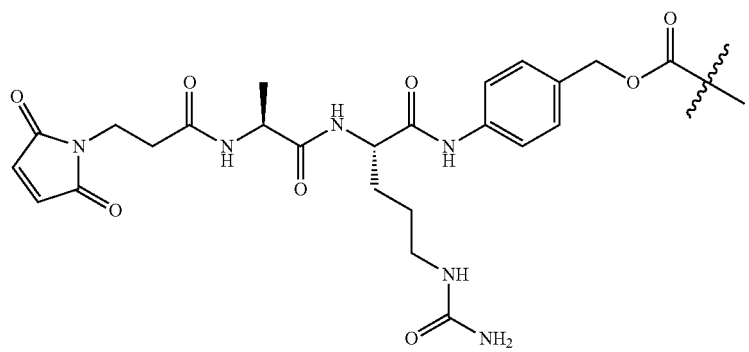
(IVb.1)
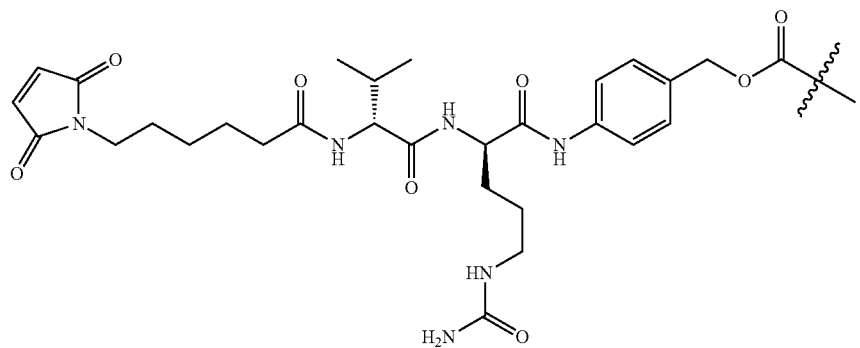
(IVb.2)

(IVb.3)
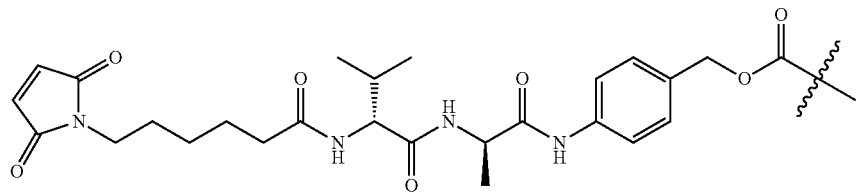
(IVb.4)
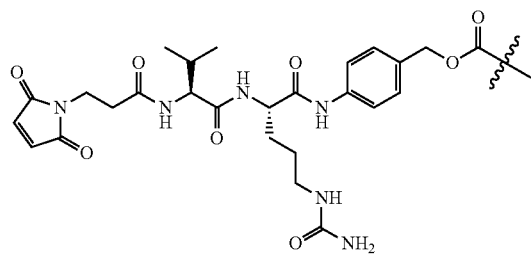
(IVb.5)
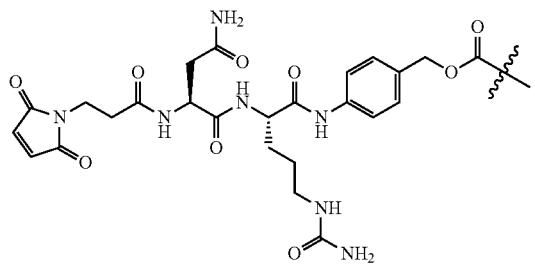
(IVb.6)
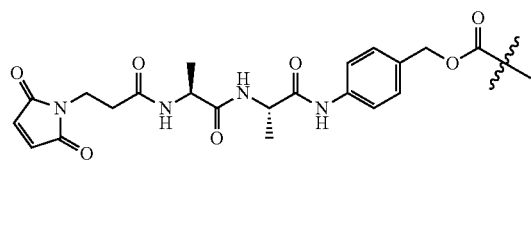
(IVb.7)
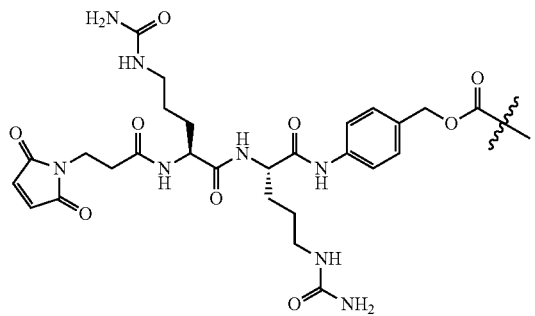
(IVb.8)
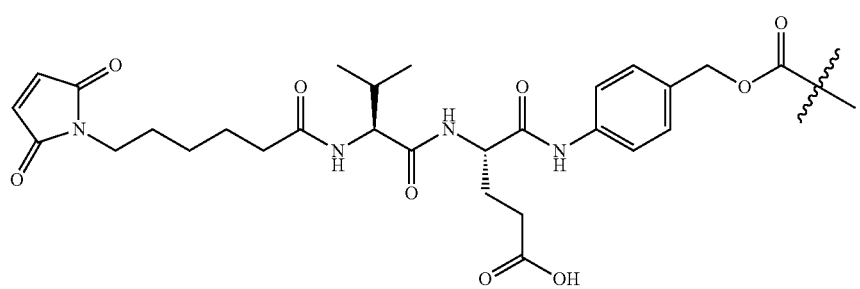
(IVb.9)
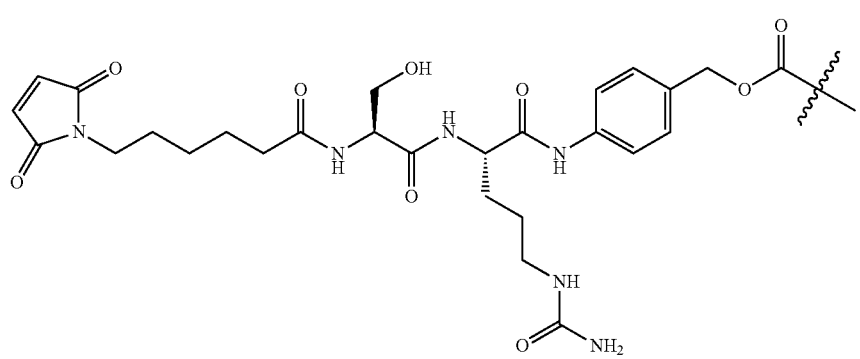

(IVb.10)
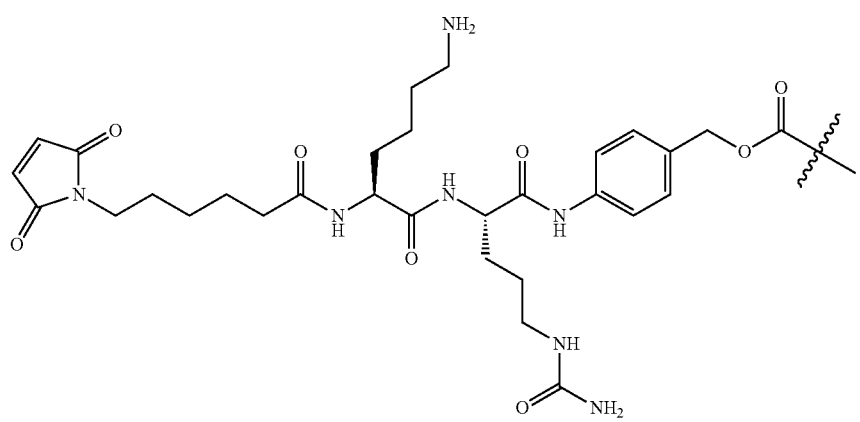
(IVb.11) (IVb.12)
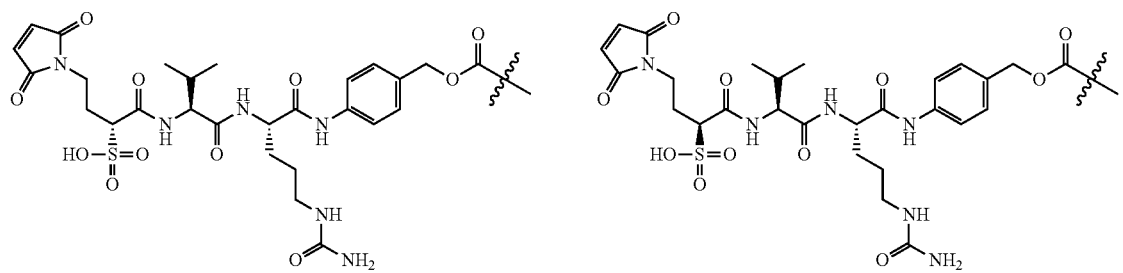
(IVb.13)
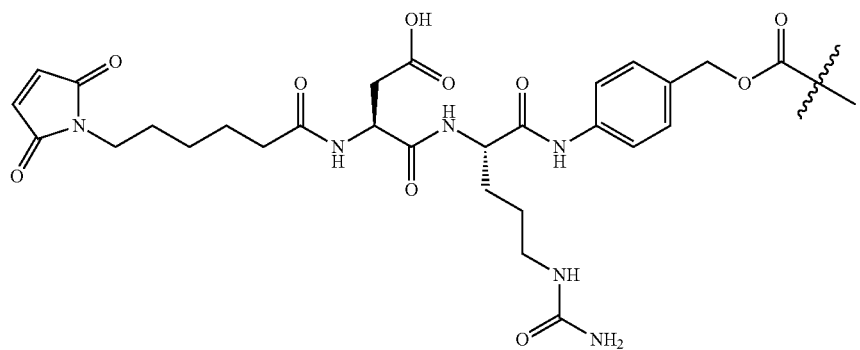
(IVb.14)
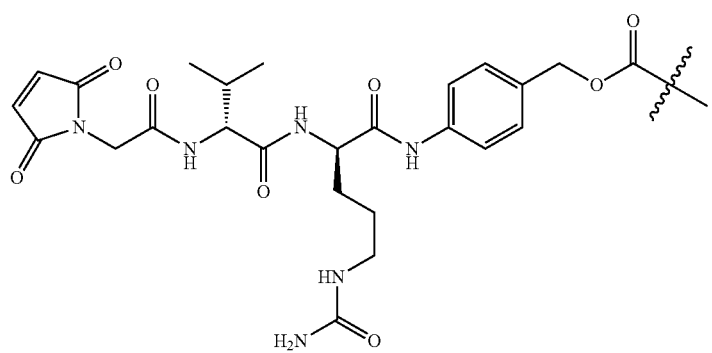

-continued
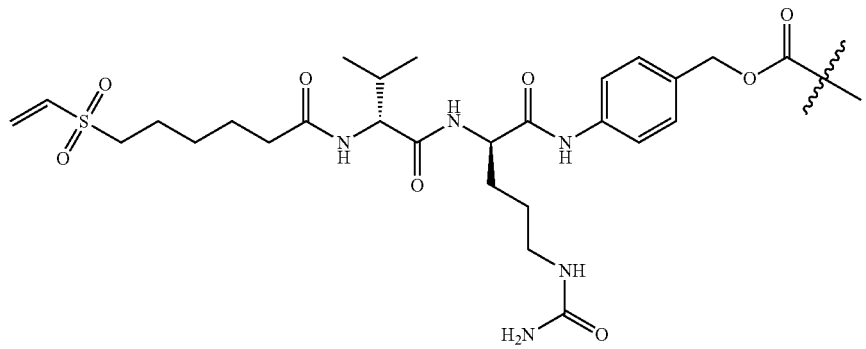
(IVb.15)
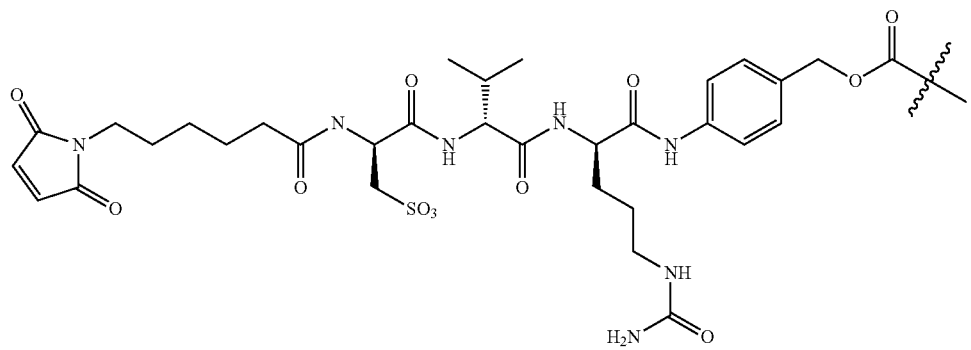
(IVb.16)
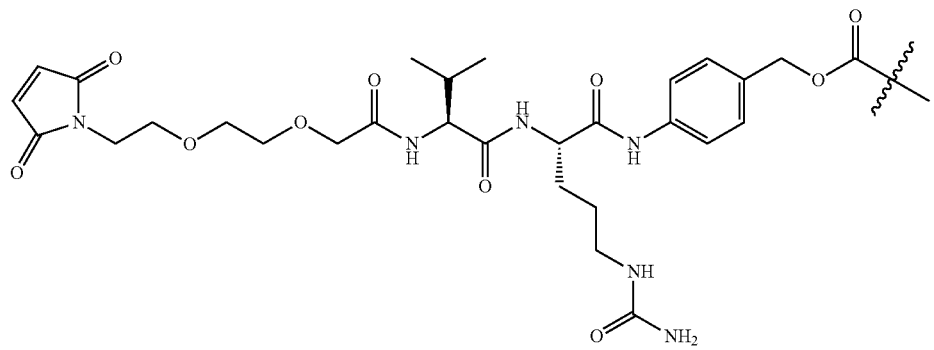
(IVb.17)
Specific exemplary embodiments of linkers according to structural formula (IVc) that may be included in the ADCs described herein include the linkers illustrated below (as illustrated, the linkers include a group suitable for covalently linking the linker to an antibody):
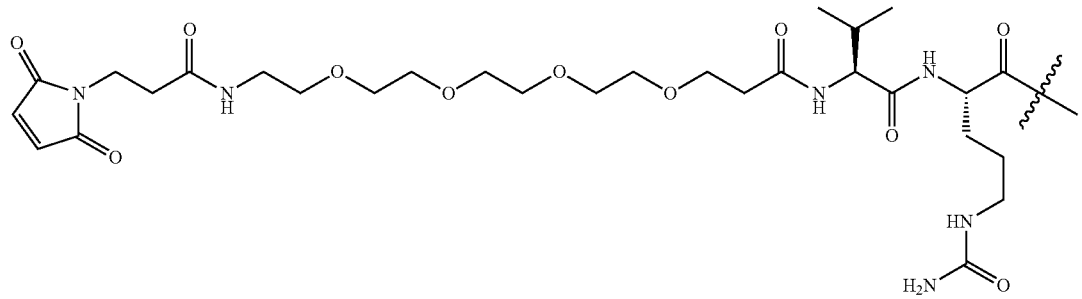
(IVc.1)

(IVc.2)
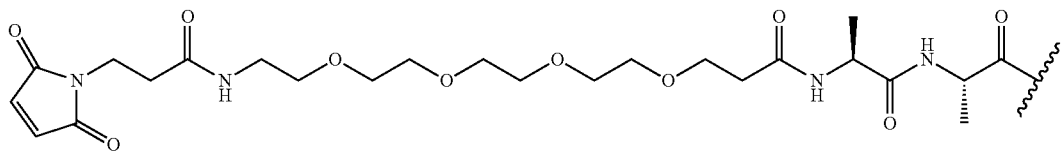
(IVc.3)
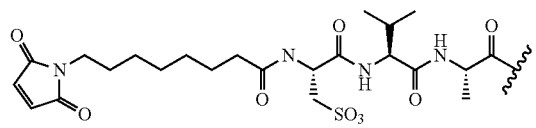
(IVc.4)
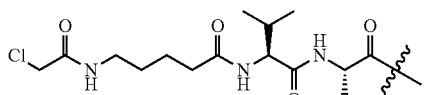
(IVc.5)
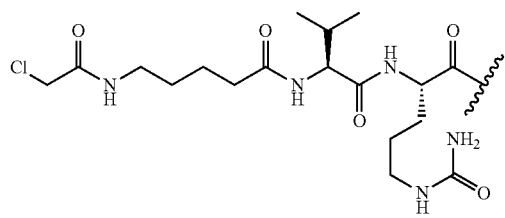
(IVc.6)
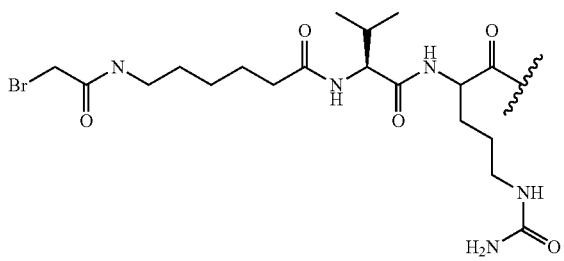
(IVc.7)
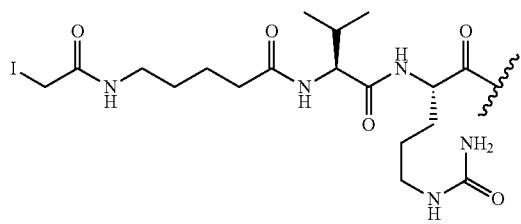
Specific exemplary embodiments of linkers according to structural formula (IVd) that may be included in the ADCs described herein include the linkers illustrated below (as illustrated, the linkers include a group suitable for covalently linking the linker to an antibody):
(IVd.1)
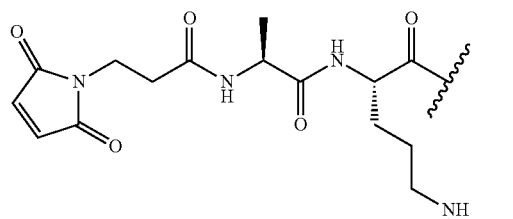
-continued
(IVd.2)
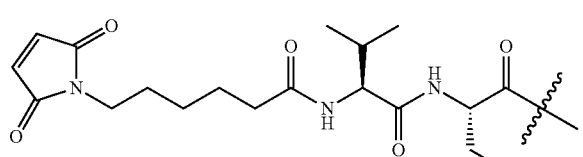
(IVd.3)
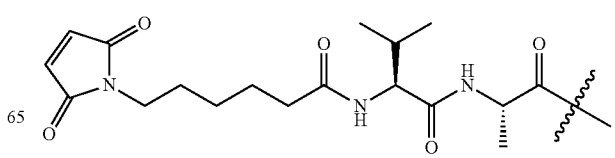

(IVd.4)
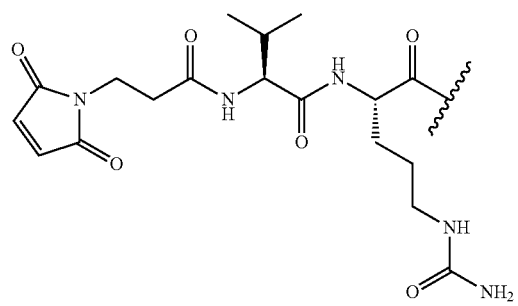
(IVd.5)
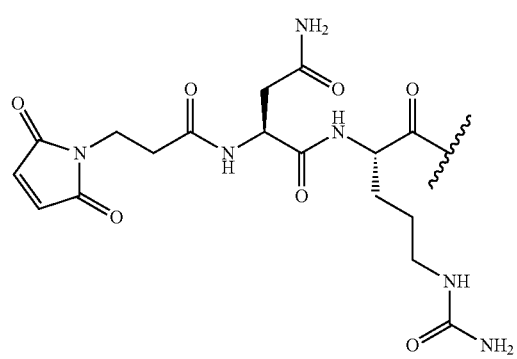
(IVd.6)
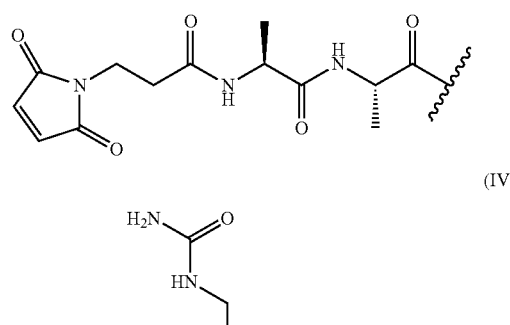
(IVd.7)
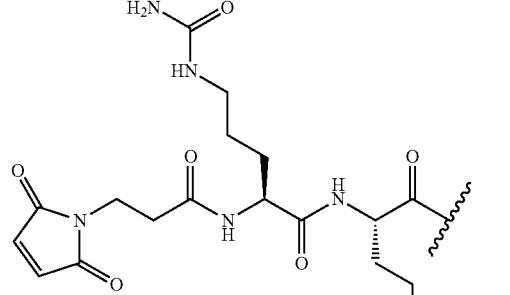
(IVd.8)
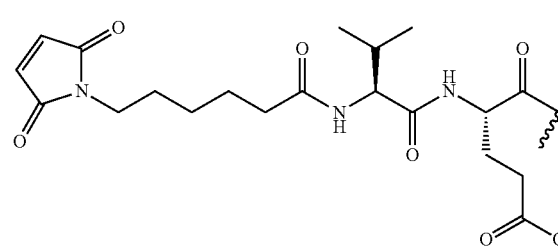
(IVd.9)
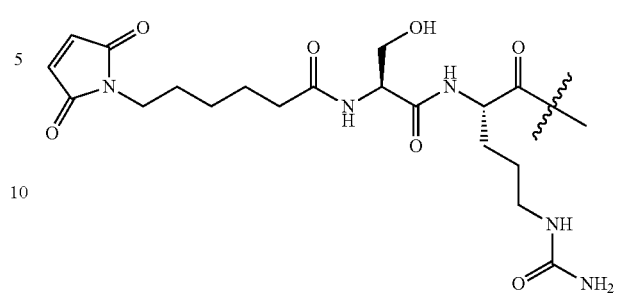
(IVd.10)
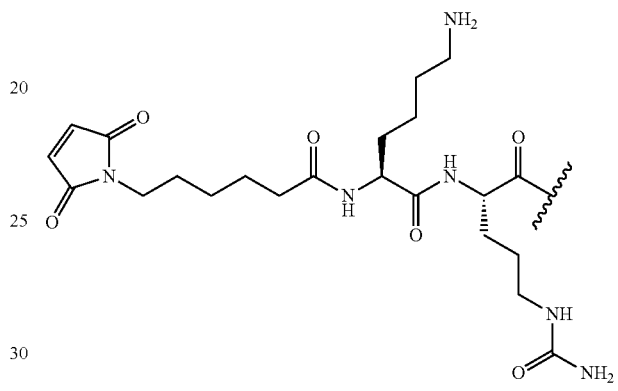
(IVd.11)
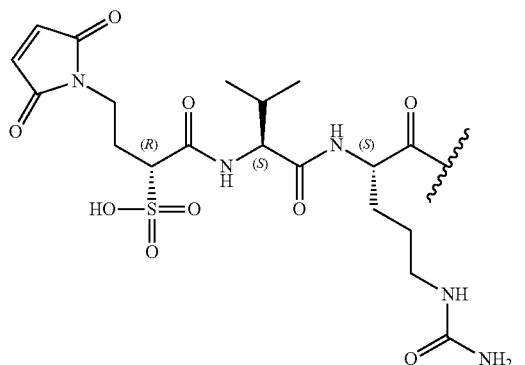
(IVd.12)
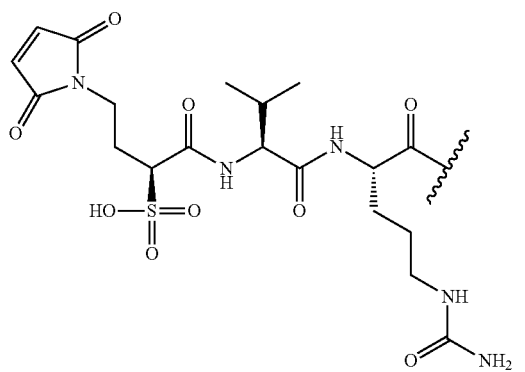

-continued

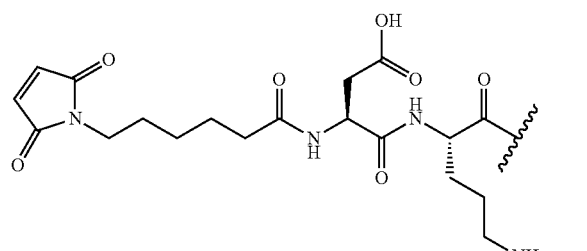
(IVd.13)

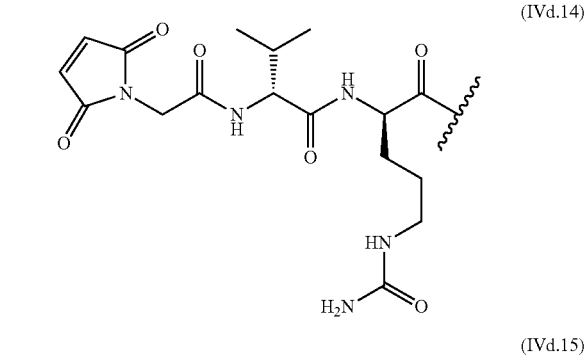
(IVd.14)

(IVd.15)

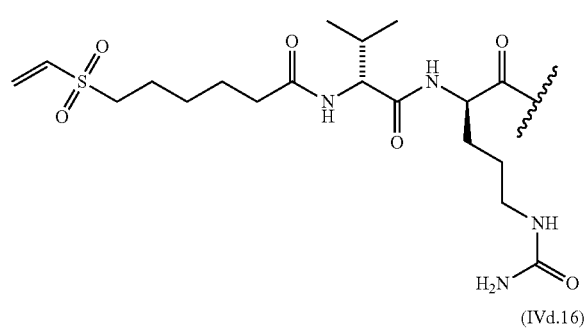
(IVd.16)

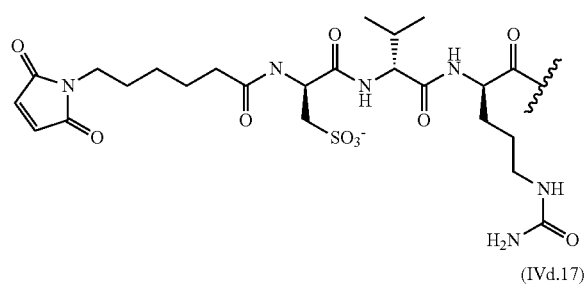
(IVd.17)

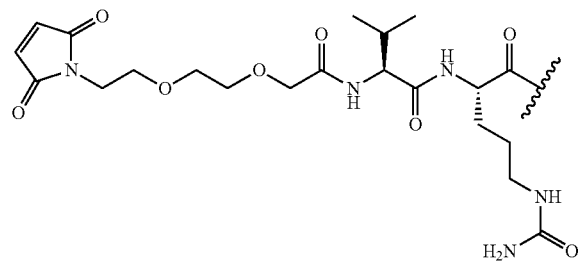

In certain embodiments, the linker comprising structural formula (IVa), (IVb), (IVc), or (IVd) further comprises a carbonate moiety cleavable by exposure to an acidic medium. In particular embodiments, the linker is attached through an oxygen to a cytotoxic and/or cytostatic agent.

7.4.2.2. Non-Cleavable Linkers

Although cleavable linkers may provide certain advantages, the linkers composing the ADC described herein need not be cleavable. For non-cleavable linkers, the release of drug does not depend on the differential properties between the plasma and some cytoplasmic compartments. The release of the drug is postulated to occur after internalization of the ADC via antigen-mediated endocytosis and delivery to lysosomal compartment, where the antibody is degraded to the level of amino acids through intracellular proteolytic degradation. This process releases a drug derivative, which is formed by the drug, the linker, and the amino acid residue to which the linker was covalently attached. The amino acid drug metabolites from conjugates with non-cleavable linkers are more hydrophilic and generally less membrane permeable, which leads to less bystander effects and less nonspecific toxicities compared to conjugates with a cleavable linker. In general, ADCs with noncleavable linkers have greater stability in circulation than ADCs with cleavable linkers. Non-cleavable linkers may be alkylene chains, or may be polymeric in nature, such as, for example, those based upon polyalkylene glycol polymers, amide polymers, or may include segments of alkylene chains, polyalkylene glycols and/or amide polymers.

A variety of non-cleavable linkers used to link drugs to antibodies have been described. See, Jeffrey et al., 2006, *Bioconjug. Chem.* 17; 831-840; Jeffrey et al., 2007, *Bioorg. Med. Chem. Lett.* 17:2278-2280; and Jiang et al., 2005, *J. Am. Chem. Soc.* 127:11254-11255, each of which is incorporated herein by reference. All of these linkers may be included in the ADCs described herein.

In certain embodiments, the linker is non-cleavable in vivo, for example a linker according to structural formula (VIa), (VIb), (VIc) or (VId) (as illustrated, the linkers include a group suitable for covalently linking the linker to an antibody:

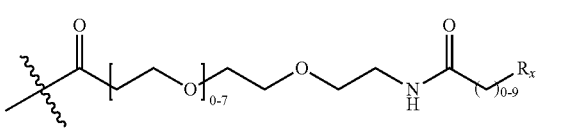
(VIa)

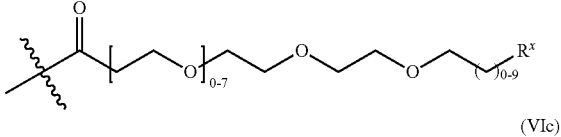
(VIb)

(VIc)

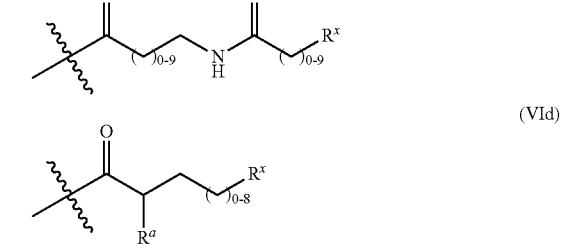
(VId)

or salts thereof, wherein:

R$^a$ is selected from hydrogen, alkyl, sulfonate and methyl sulfonate;

R$^x$ is a moiety including a functional group capable of covalently linking the linker to an antibody; and ✓ represents the point of attachment of the linker to a cytotoxic and/or cytostatic agent.

Specific exemplary embodiments of linkers according to structural formula (VIa)-(VId) that may be included in the ADCs described herein include the linkers illustrated below (as illustrated, the linkers include a group suitable for covalently linking the linker to an antibody, and "✓" represents the point of attachment to a cytotoxic and/or cytostatic agent):

can be electrophilic in nature and include: maleimide groups, activiated disulfides, active esters such as NHS esters and HOBt esters, haloformates, acid halides, alkyl and benzyl halides such as haloacetamides. As discussed below, there are also emerging technologies related to "self-stabilizing" maleimides and "bridging disulfides" that can be used in accordance with the disclosure. The specific group used will depend, in part, on the site of attachment to the antibody.

One example of a "self-stabilizing" maleimide group that hydrolyzes spontaneously under antibody conjugation conditions to give an ADC species with improved stability is

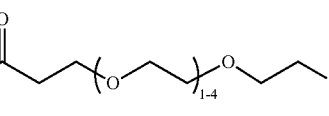

(VIa.1)

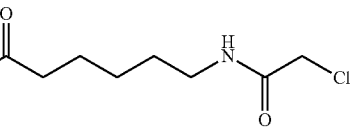

(VIc.1)

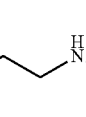

(VIc.2)

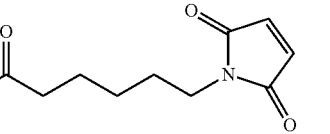

(VId.1)

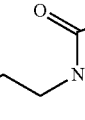

(VId.2)

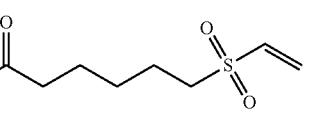

(VId.3)

7.4.2.3. Groups Used to Attach Linkers to Antibodies

A variety of groups may be used to attach linker-drug synthons to antibodies to yield ADCs. Attachment groups depicted in the schematic below. See US20130309256 A1; also Lyon et al., Nature Biotech published online, doi: 10.1038/nbt.2968).

Normal system:
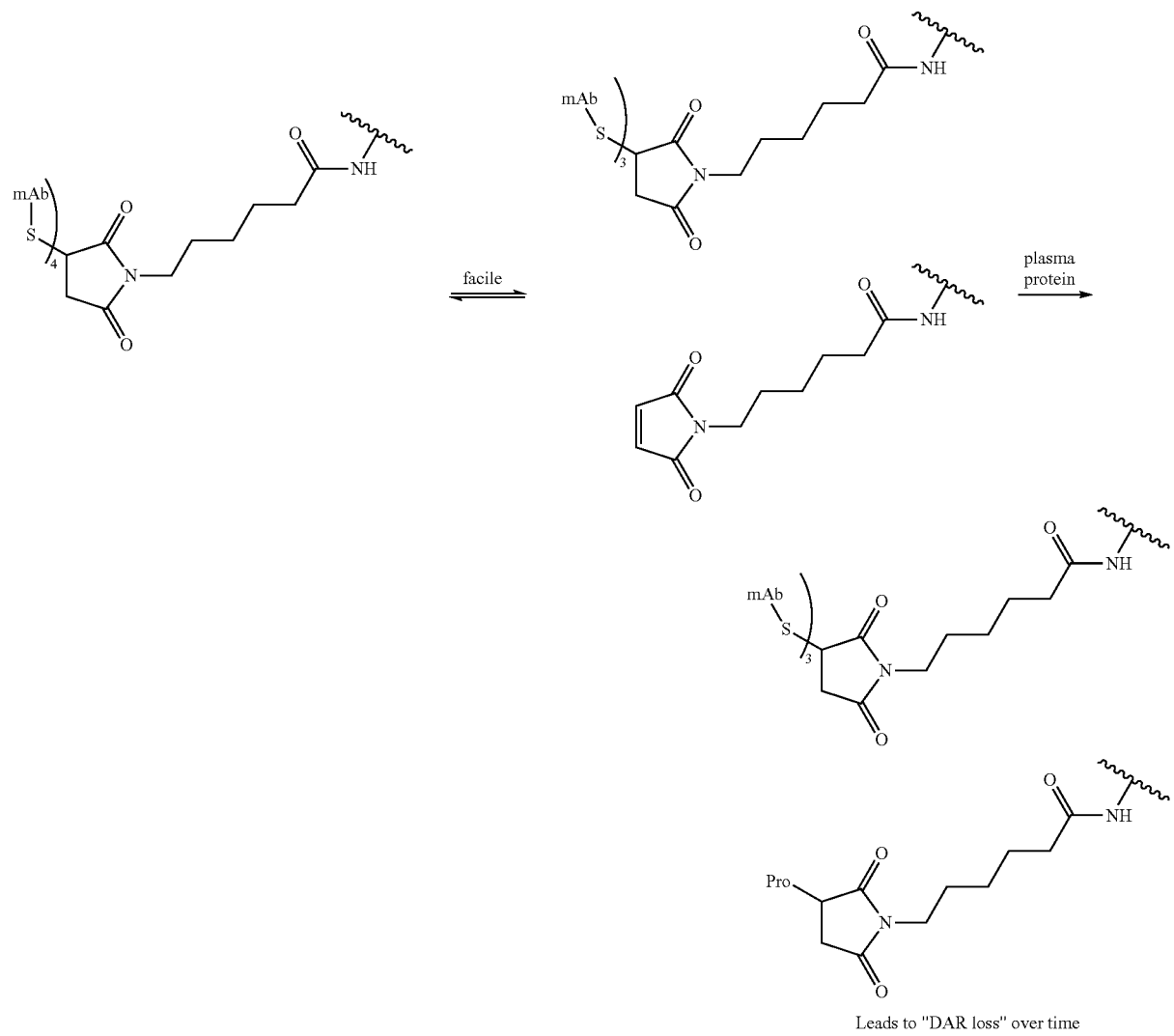
Leads to "DAR loss" over time
SGN MalDPR (maleimido dipropylamino) system:
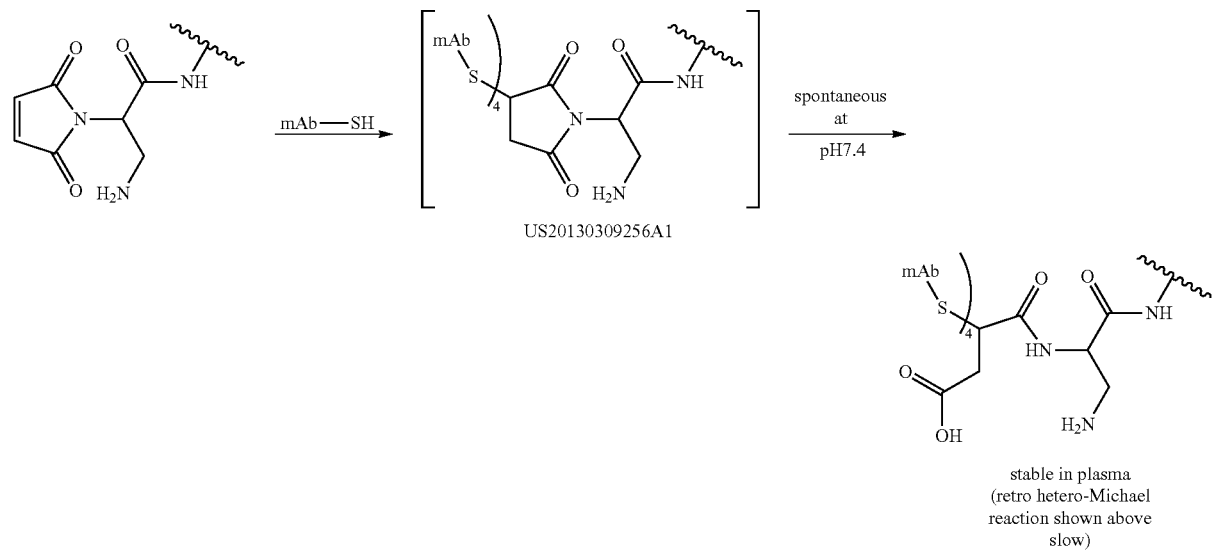
stable in plasma
(retro hetero-Michael
reaction shown above
slow)

Polytherics has disclosed a method for bridging a pair of sulfhydryl groups derived from reduction of a native hinge disulfide bond. See, Badescu et al., 2014, Bioconjugate Chem. 25:1124-1136. The reaction is depicted in the schematic below. An advantage of this methodology is the ability to synthesize homogeneous DAR4 ADCs by full reduction of IgGs (to give 4 pairs of sulfhydryls) followed by reaction with 4 equivalents of the alkylating agent. ADCs containing "bridged disulfides" are also claimed to have increased stability.

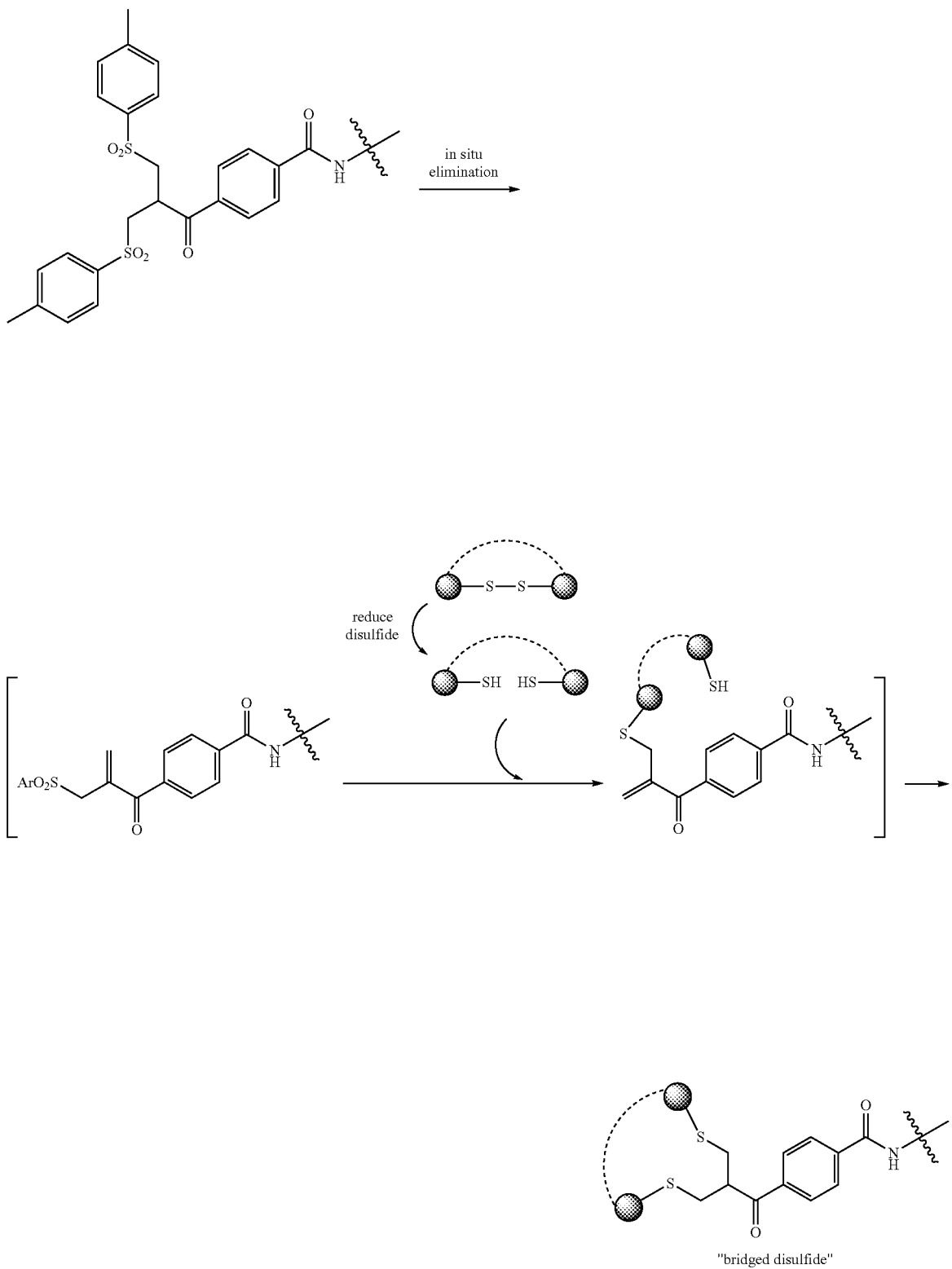

Similarly, as depicted below, a maleimide derivative (1, below) that is capable of bridging a pair of sulfhydryl groups has been developed. See WO2013/085925.

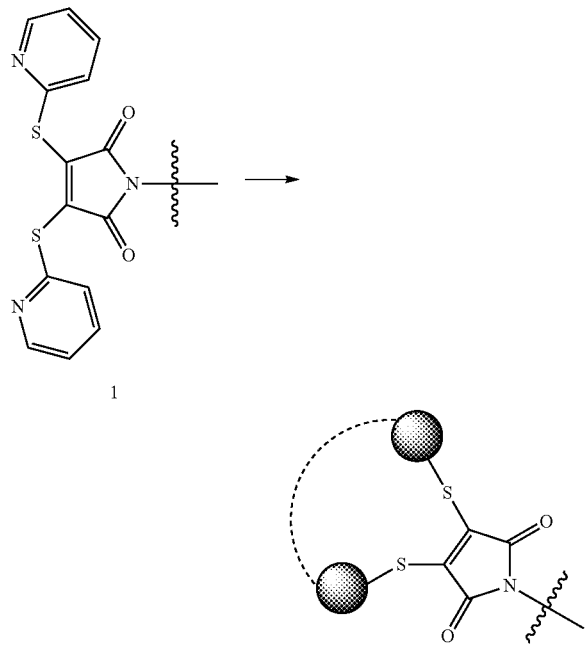

1

7.4.2.4. Linker Selection Considerations

As is known by skilled artisans, the linker selected for a particular ADC may be influenced by a variety of factors, including but not limited to, the site of attachment to the antibody (e.g., Lys, Cys or other amino acid residues), structural constraints of the drug pharmacophore and the lipophilicity of the drug. The specific linker selected for an ADC should seek to balance these different factors for the specific antibody/drug combination. For a review of the factors that are influenced by choice of linkers in ADCs, see Nolting, Chapter 5 "Linker Technology in Antibody-Drug Conjugates," In: Antibody-Drug Conjugates: Methods in Molecular Biology, vol. 1045, pp. 71-100, Laurent Ducry (Ed.), Springer Science & Business Medica, LLC, 2013.

For example, as discussed above, anti-huLRRC15 ADCs have been observed to induce bystander killing of cancer cells present in the vicinity of huLRRC15-expressing stromal cells for huLRRC15 stromal(+)/cancer (−) tumors. The mechanism of bystander cell killing by ADCs has indicated that metabolic products formed during intracellular processing of the ADCs may play a role. Cell-permeable cytotoxic and/or cytostatic metabolites generated by metabolism of the ADCs in huLRRC15-expressing cells appear to play a role in bystander cell killing, while non-cell-permeable metabolites, which are incapable of traversing the cell membrane and diffusing into the medium cannot effect bystander killing. In certain embodiments, the linker is selected to effect, enhance or increase the bystander killing effect of the anti-huLRRC15 ADCs.

The properties of the linker may also impact aggregation of the ADC under conditions of use and/or storage. Typically, ADCs reported in the literature contain no more than 3-4 drug molecules per antigen-binding moiety, for example, per antibody molecule (see, e.g., Chari, 2008, Acc Chem Res 41:98-107). Attempts to obtain higher drug-to-antibody ratios ("DAR") often failed, particularly if both the drug and the linker were hydrophobic, due to aggregation of the ADC (King et al., 2002, J Med Chem 45:4336-4343; Hollander et al., 2008, Bioconjugate Chem 19:358-361; Burke et al., 2009 Bioconjugate Chem 20:1242-1250). In many instances, DARs higher than 3-4 could be beneficial as a means of increasing potency. In instances where the cytotoxic and/or cytostatic agent is hydrophobic in nature, it may be desirable to select linkers that are relatively hydrophilic as a means of reducing ADC aggregation, especially in instances where DARS greater than 3-4 are desired. Thus, in certain embodiments, the linker incorporates chemical moieties that reduce aggregation of the ADCs during storage and/or use. A linker may incorporate polar or hydrophilic groups such as charged groups or groups that become charged under physiological pH to reduce the aggregation of the ADCs. For example, a linker may incorporate charged groups such as salts or groups that deprotonate, e.g., carboxylates, or protonate, e.g., amines, at physiological pH.

Exemplary polyvalent linkers that have been reported to yield DARs as high as 20 that may be used to link numerous cytotoxic and/or cytostatic agents to an antibody are described in WO 2009/073445; WO 2010/068795; WO 2010/138719; WO 2011/120053; WO 2011/171020; WO 2013/096901; WO 2014/008375; WO 2014/093379; WO 2014/093394; WO 2014/093640, the contents of which are incorporated herein by reference in their entireties.

In particular embodiments, the aggregation of the ADCs during storage or use is less than about 10% as determined by size-exclusion chromatography (SEC). In particular embodiments, the aggregation of the ADCs during storage or use is less than 10%, such as less than about 5%, less than about 4%, less than about 3%, less than about 2%, less than about 1%, less than about 0.5%, less than about 0.1%, or even lower, as determined by size-exclusion chromatography (SEC). In particular embodiments, the aggregation of the ADCs during storage or use is in a range of any two of the foregoing values, such as but not limited to from about 0.1% to 10%, 0.1% to 5%, 0.5% to 10%, 0.5% to 5%, or 1% to 10%.

7.4.3. Embodiments of Anti-huLRRC15 Antibody Drug Conjugates

As described above, embodiments of an anti-huLRRC15 ADC include compounds having a structure according to formula (I): [D-L-XY-]$_n$-Ab (I), or a salt thereof, wherein D is the cytotoxic and/or cytostatic agent; L is the linker; Ab is the antibody; XY represents a covalent linkage linking linker L to antibody Ab; and n is an integer ranging from 2 to 8.

In some embodiments, XY is a linkage formed with an amino group on antibody Ab, such as an amide or a thiourea, or a linkage formed with a sulfydryl group on antibody Ab, such as a thioether. In certain such embodiments, XY is a thioether.

In some embodiments, L comprises Val-Cit or Val-Ala.

In some embodiments, the compound according to structural formula (I) has a structure of formula (IIa):

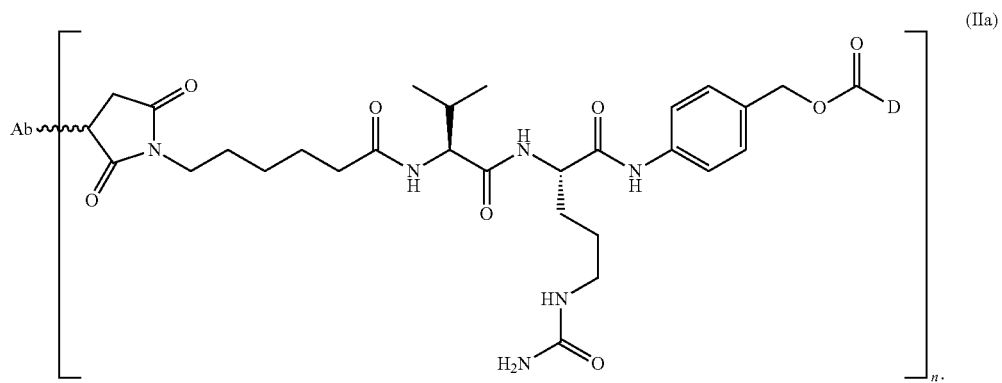

In some embodiments, the compound according to structural formula (I) has a structure of formula (IIb):

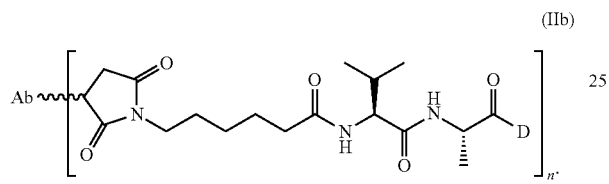

In some embodiments of the compound of formula (I), (IIa), or (IIb), D is an antimitotic agent or a DNA-intercalating agent. In some such embodiments, D is an antimitotic agent which is a cell-permeable antimitotic agent. In certain such embodiments, the cell-permeable antimitotic agent is MMAE. In other such embodiments, D is a DNA-intercalating agent which is a pyrrolobenzodiazepine (PBD) dimer.

In some embodiments, the compound according to structural formula (I) has a structure of formula (IIIa):

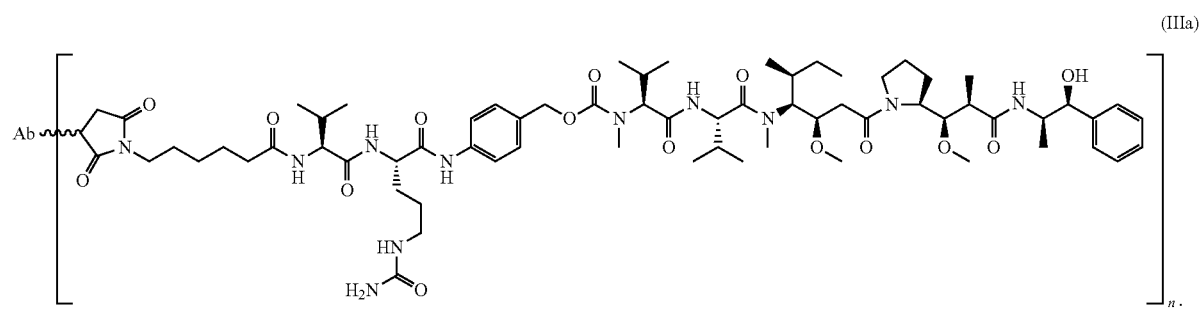

In some embodiments, the compound according to structural formula (I) has a structure of formula (IIIb):

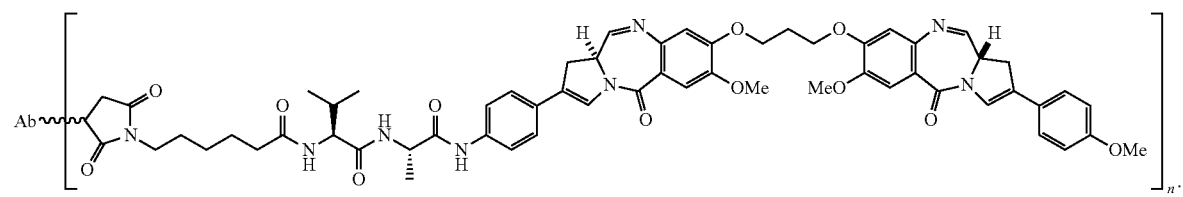

In some embodiments of the compound of formula (I), (IIa), (IIb), (IIIa), or (IIIb), Ab is an antibody comprising three $V_H$ CDRs corresponding in sequence, respectively, to SEQ ID NO:10, SEQ ID NO:11 and SEQ ID NO:12 and three $V_L$ CDRs corresponding in sequence, respectively, to SEQ ID NO:13, SEQ ID NO:14 and SEQ ID NO:15. In some such embodiments, Ab is an antibody with a $V_H$ having an amino acid sequence of SEQ ID NO:16, and a $V_L$ having an amino acid sequence of SEQ ID NO:17. In other embodiments, Ab is an antibody comprising three $V_H$ CDRs corresponding in sequence, respectively, to SEQ ID NO:20, SEQ ID NO:21 and SEQ ID NO:22 and three $V_L$ CDRs corresponding in sequence, respectively, to SEQ ID NO:23, SEQ ID NO:24 and SEQ ID NO:25. In some such embodiments, Ab is an antibody with a $V_H$ having an amino acid sequence of SEQ ID NO:26, and a $V_L$ having an amino acid sequence of SEQ ID NO:27. In some embodiments, Ab is a human $IgG_1$. In some such embodiments, Ab is an antibody with a heavy chain having an amino acid sequence of SEQ ID NO:18 or 102, and a light chain having an amino acid sequence of SEQ ID NO:19. In other such embodiments, Ab is an antibody with a heavy chain having an amino acid sequence of SEQ ID NO:100 or 103, and a light chain having an amino acid sequence of SEQ ID NO:19. In other such embodiments, Ab is an antibody with a heavy chain having an amino acid sequence of SEQ ID NO:28 or 101, and a light chain having an amino acid sequence of SEQ ID NO:29. In other such embodiments, Ab is an antibody with a heavy chain having an amino acid sequence of SEQ ID NO:104 or 105, and a light chain having an amino acid sequence of SEQ ID NO:29. In some embodiments, Ab is an antibody selected from huM25, huM25-S239C, huAD208.4.1, and huAD208.4.1-S239C. In certain such embodiments, Ab is huM25. In other such embodiments, Ab is huM25-S239C. In yet other such embodiments, Ab is huAD208.4.1. In yet other such embodiments, Ab is huAD208.4.1-S239C.

In some embodiments of the compound of formula (I), (IIa), (IIb), (IIIa), or (IIIb), n is 2, 3, or 4. In certain such embodiments, n is 2 or 4.

7.5. Methods of Making Anti-huLRRC15 Antibody Drug Conjugates

The ADCs described herein may be synthesized using chemistries that are well-known. The chemistries selected will depend upon, among other things, the identity of the cytotoxic and/or cytostatic agent(s), the linker and the groups used to attach linker to the antibody. Generally, ADCs according to formula (I) may be prepared according to the following scheme:

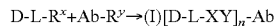

D-L-R$^x$+Ab-R$^y$→(I)[D-L-XY]$_n$-Ab where D, L, Ab, XY and n are as previously defined, and R$^x$ and R$^y$ represent complementary groups capable of forming covalent linkages with one another, as discussed above.

The identities of groups R$^x$ and R$^y$ will depend upon the chemistry used to link synthon D-L-R$^x$ to the antibody. Generally, the chemistry used should not alter the integrity of the antibody, for example its ability to bind its target. Preferably, the binding properties of the conjugated antibody will closely resemble those of the unconjugated antibody. A variety of chemistries and techniques for conjugating molecules to biological molecules such as antibodies are known in the art and in particular to antibodies, are well-known. See, e.g., Amon et al., "Monoclonal Antibodies For Immunotargeting Of Drugs In Cancer Therapy," in: *Monoclonal Antibodies And Cancer Therapy*, Reisfeld et al. Eds., Alan R. Liss, Inc., 1985; Hellstrom et al., "Antibodies For Drug Delivery," in: *Controlled Drug Delivery*, Robinson et al. Eds., Marcel Dekker, Inc., 2nd Ed. 1987; Thorpe, "Antibody Carriers Of Cytotoxic Agents In Cancer Therapy: A Review," in: *Monoclonal Antibodies '84: Biological And Clinical Applications*, Pinchera et al., Eds., 1985; "Analysis, Results, and Future Prospective of the Therapeutic Use of Radiolabeled Antibody In Cancer Therapy," in: *Monoclonal Antibodies For Cancer Detection And Therapy*, Baldwin et al., Eds., Academic Press, 1985; Thorpe et al., 1982, *Immunol. Rev.* 62:119-58; PCT publication WO 89/12624. Any of these chemistries may be used to link the synthons to an antibody.

A number of functional groups R$^x$ and chemistries useful for linking synthons to accessible lysine residues are known, and include by way of example and not limitation NHS-esters and isothiocyanates.

A number of functional groups R$^x$ and chemistries useful for linking synthons to accessible free sulfhydryl groups of cysteine residues are known, and include by way of example and not limitation haloacetyls and maleimides.

However, conjugation chemistries are not limited to available side chain groups. Side chains such as amines may be converted to other useful groups, such as hydroxyls, by linking an appropriate small molecule to the amine. This strategy can be used to increase the number of available linking sites on the antibody by conjugating multifunctional small molecules to side chains of accessible amino acid residues of the antibody. Functional groups R$^x$ suitable for covalently linking the synthons to these "converted" functional groups are then included in the synthons.

An antibody may also be engineered to include amino acid residues for conjugation. An approach for engineering antibodies to include non-genetically encoded amino acid residues useful for conjugating drugs in the context of ADCs is described by Axup et al., 2012, *Proc Natl Acad Sci USA*. 109(40):16101-16106, as are chemistries and functional groups useful for linking synthons to the non-encoded amino acids.

Typically, the synthons are linked to the side chains of amino acid residues of the antibody, including, for example, the primary amino group of accessible lysine residues or the sulfhydryl group of accessible cysteine residues. Free sulfhydryl groups may be obtained by reducing interchain disulfide bonds.

For linkages where R$^y$ is a sulfhydryl group (for example, when R$^x$ is a maleimide), the antibody is generally first fully or partially reduced to disrupt interchain disulfide bridges between cysteine residues. Specific cysteine residues and interchain disulfide bridges that may be reduced for attachment of drug-linker synthons including a group suitable for conjugation to a sulfhydryl group for exemplary antibodies huM25, huAD208.4.1, huAD208.12.1, huAD208.14.1, hu139.10, muAD208.9.1, muAD210.40.9, include by way of example and not limitation, residues C233, C239, and C242 (Kabat numbering system; corresponding to residues C220, C226, and C229 Eu numbering) on the human $IgG_1$ heavy chain, and residue C214 (Kabat numbering system) on the human Ig kappa light chain.

Cysteine residues for synthon attachment that do not participate in disulfide bridges may be engineered into an antibody by mutation of one or more codons. Reducing these unpaired cysteines yields a sulfhydryl group suitable for conjugation. Preferred positions for incorporating engineered cysteines include, by way of example and not limitation, positions S112C, S113C, A114C, S115C, A176C, S180C, S239C, S252C, V286C, V292C, S357C, A359C, S398C, S428C (Kabat numbering) on the human IgG₁ heavy chain and positions V110C, S114C, S121C, S127C, S168C, V205C (Kabat numbering) on the human Ig kappa light chain (see, e.g., U.S. Pat. No. 7,521,541, U.S. Pat. No. 7,855,275 and U.S. Pat. No. 8,455,622).

Mutation of a cysteine residue known to participate in an existing disulfide bridge may also be engineered such that the resulting unpaired cysteine partner is available to form a sulfide linker to a drug. Examples of engineered cysteine mutations include, but are not limited to, light chain constant C214 mutations, for example C214A.

As will be appreciated by skilled artisans, the number of cytotoxic and/or cytostatic agents linked to an antibody molecule may vary, such that an ADC preparation may be heterogeneous in nature, where some antibodies in the preparation contain one linked agent, some two, some three, etc. (and some none). The degree of heterogeneity will depend upon, among other things, the chemistries used for linking the cytotoxic and/or cytostatic agents. For example, where the antibodies are reduced to yield sulfhydryl groups for attachment, heterogenous mixtures of antibodies having zero, 2, 4, 6 or 8 linked agents per molecule are often produced. Furthermore, by limiting the molar ratio of attachment compound, antibodies having zero, 1, 2, 3, 4, 5, 6, 7 or 8 linked agents per molecule are often produced. Thus, it will be understood that depending upon context, stated drug antibody ratios (DARs) may be averages for a collection of antibodies. For example, "DAR4" refers to an ADC preparation that has not been subjected to purification to isolate specific DAR peaks and comprises a heterogeneous mixture of ADC molecules having different numbers of cytostatic and/or cytotoxic agents attached per antibody (e.g., 0, 2, 4, 6, 8 agents per antibody), but has an average drug-to-antibody ratio of 4. Similarly, "DAR8" refers to a heterogeneous ADC preparation in which the average drug-to-antibody ratio is 8.

Heterogeneous ADC preparations may be processed, for example, by hydrophobic interaction chromatography ("HIC") to yield preparations enriched in an ADC having a specified DAR of interest (or a mixture of two or more specified DARS). Such enriched preparations are designed herein as "EX," where "E" indicates the ADC preparation has been processed and is enriched in an ADC having a specific DAR and "X" represents the number of cytostatic and/or cytotoxic agents linked per ADC molecule. Preparations enriched in a mixture of ADCs having two specific DARs are designated "EX/EY," three specific DARs "EX/EY/EZ" etc., where "E" indicates the ADC preparation has been processed to enrich the specified DARs and "X," "Y" and "Z" represent the DARs enriched. As specific examples, "E2" refers to an ADC preparation that has been enriched to contain primarily ADCs having two cytostatic and/or cytotoxic agents linked per ADC molecule. "E4" refers to an ADC preparation that has been enriched to contain primarily ADCs having four cytostatic and/or cytotoxic agents linked per ADC molecule. "E2/E4" refers to an ADC preparation that has been enriched to contain primarily two ADC populations, one having two cytostatic and/or cytotoxic agents linked per ADC molecule and another having four cytostatic and/or cytotoxic agents linked per ADC molecule.

An enriched "E" preparation can also refer to an ADC that has been prepared from an antibody that has been engineered, e.g., by insertion or deletion of a cysteine residue, to form a linkage to a drug at a specific site. For example, an antibody with a S239C mutation in each heavy chain can primarily have a drug attached via a linker at that site, and, hence, can afford an E2 ADC preparation having mostly DAR2 without additional processing, such as chromatographic processing.

As used herein, enriched "E" preparations will generally be at least about 80% pure in the stated DAR ADCs, although higher levels of purity, such as purities of at least about 85%, 90%, 95%, 98%, 99% or even higher, may be obtainable and desirable. In some embodiments, the enriched "E" preparations have a range of purity within any two of the foregoing values, such as but not limited to from about 80-99%, 80-98%, 85-95%, 90-98%, 95-98%, or 80-90%. For example, an "EX" preparation will generally be at least about 80% pure in ADCs having X cytostatic and/or cytotoxic agents linked per ADC molecule. For "higher order" enriched preparations, such as, for example, "EX/EY" preparations, the sum total of ADCs having X and Y cytostatic and/or cytotoxic agents linked per ADC molecule will generally comprise at least about 80% of the total ADCs in the preparation. Similarly, in an enriched "EX/EY/EZ" preparation, the sum total of ADCs having X, Y and Z cytostatic and/or cytotoxic agents linked per ADC molecule will comprise at least about 80% of the total ADCs in the preparation.

Purity may be assessed by a variety of methods, as is known in the art. As a specific example, an ADC preparation may be analyzed via HPLC or other chromatography and the purity assessed by analyzing areas under the curves of the resultant peaks. Specific chromatography methods that may be employed to assess purity of ADC preparations are provided in Example 8.

FIG. 12 is illustrative. The top panel shows a chromatogram of a crude preparation of an ADC prepared according to Example 8. The preparation contains antibodies having no cytostatic and/or cytotoxic agents attached (DAR0), two agents attached (DAR2), four agents (DAR4), six agents attached (DAR6) and eight agents attached (DAR8). This crude preparation has an average DAR of 4. HIC chromatography yields an E2 preparation in which approximately 95% of the ADCs in the preparation have two cytostatic and/or cytotoxic agents linked per ADC molecule (stated another way, approximately 95% of the ADCs are DAR2).

Specific methods for obtaining heterogenous mixtures of ADCs comprising humanized antibody huM25 having an average DAR of 4, as well as highly purified preparations containing 2 and 4 linked agents are provided in the Examples section. These specific methods may be modified using routine skill to obtain heterogeneous and/or homogeneous ADCs comprising other anti-huLRRC15 antibodies, linkers and/or cytotoxic and/or cytostatic agents.

7.6. Compositions

The ADCs described herein may be in the form of compositions comprising the ADC and one or more carriers, excipients and/or diluents. The compositions may be formulated for specific uses, such as for veterinary uses or pharmaceutical uses in humans. The form of the composition (e.g., dry powder, liquid formulation, etc.) and the excipients, diluents and/or carriers used will depend upon the intended uses of the antibody and/or ADC and, for therapeutic uses, the mode of administration.

For therapeutic uses, the compositions may be supplied as part of a sterile, pharmaceutical composition that includes a pharmaceutically acceptable carrier. This composition can be in any suitable form (depending upon the desired method of administering it to a patient). The pharmaceutical composition can be administered to a patient by a variety of routes such as orally, transdermally, subcutaneously, intranasally, intravenously, intramuscularly, intratumorally, intrathecally, topically or locally. The most suitable route for administration in any given case will depend on the particular antibody and/or ADC, the subject, and the nature and severity of the disease and the physical condition of the subject. Typically, the pharmaceutical composition will be administered intravenously or subcutaneously.

Pharmaceutical compositions can be conveniently presented in unit dosage forms containing a predetermined amount of an antibody and/or ADC described herein per dose. The quantity of antibody and/or ADC included in a unit dose will depend on the disease being treated, as well as other factors as are well known in the art. Such unit dosages may be in the form of a lyophilized dry powder containing an amount of antibody and/or ADC suitable for a single administration, or in the form of a liquid. Dry powder unit dosage forms may be packaged in a kit with a syringe, a suitable quantity of diluent and/or other components useful for administration. Unit dosages in liquid form may be conveniently supplied in the form of a syringe pre-filled with a quantity of antibody and/or ADC suitable for a single administration.

The pharmaceutical compositions may also be supplied in bulk form containing quantities of ADC suitable for multiple administrations.

Pharmaceutical compositions may be prepared for storage as lyophilized formulations or aqueous solutions by mixing an antibody and/or ADC having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives should be nontoxic to the recipients at the dosages and concentrations employed.

Buffering agents help to maintain the pH in the range which approximates physiological conditions. They may be present at a wide variety of concentrations, but will typically be present in concentrations ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium gluconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives may be added to retard microbial growth, and can be added in amounts ranging from about 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinositol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thiosulfate; low molecular weight polypeptides (e.g., peptides of 10 residues or fewer); proteins such as human serum albumin, bovine serum albumin, gelatin or immunoglobulins; hydrophilic polymers, such as polyvinylpyrrolidone monosaccharides, such as xylose, mannose, fructose, glucose; disaccharides such as lactose, maltose, sucrose and trehalose; and trisaccharides such as raffinose; and polysaccharides such as dextran. Stabilizers may be present in amounts ranging from 0.5 to 10 weight % per weight of ADC.

Non-ionic surfactants or detergents (also known as "wetting agents") may be added to help solubilize the glycoprotein as well as to protect the glycoprotein against agitation-induced aggregation, which also permits the formulation to be exposed to shear surface stressed without causing denaturation of the protein. Suitable non-ionic surfactants include polysorbates (20, 80, etc.), poloxamers (184, 188 etc.), and pluronic polyols. Non-ionic surfactants may be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

A specific exemplary embodiment of an aqueous composition suitable for administration via intravenous infusion comprises 20 mg/mL anti-huLRRC15 ADC, 10 mM histidine buffer, pH 6.0, 7% (w/v) sucrose, 0.03% (w/v) polysorbate 80. The composition may be in the form of a lyophilized powder that, upon reconstitution with 5.2 mL sterile water or other solution suitable for injection or infusion (for example, 0.9% saline, Ringer's solution, lactated Ringer's solution, etc.) provides the above aqueous composition. This embodiment, or other embodiments of compositions, may also be in the form of a syringe or other device suitable for injection and/or infusion pre-filled with a quantity of composition suitable for a single administration of anti-huLRRC15 ADC.

7.7. Methods of Use

As discussed previously, for a variety of solid tumors, huLRRC15 is expressed in the tumor stromal microenvironment, but not on the cancer cells per se. Data provided herein demonstrate that anti-huLRRC15 ADCs exert potent anti-tumor activity against these stromal(+)/cancer(−) tumors in vivo. Accordingly, the ADCs and/or pharmaceutical compositions comprising the ADCs may be used therapeutically to treat stromal(+)/cancer(−) tumors.

Generally, the methods involve administering to a human patient having a stromal(+)/cancer(−) tumor an amount of an anti-huLRRC15 ADC effective to provide therapeutic benefit. Stromal(+)/cancer(−) tumors that may be treated with the ADCs include, but are not limited to, adrenal cancers, bladder cancers, breast cancers (e.g., ductal breast cancer, lobular breast cancer, triple negative breast cancer), cervical cancers, endometrial cancers, gastric cancers, lung cancers (for example, mesothelioma and non-small cell lung cancers such as non-small cell lung adenocarcinoma and squamous non-small cell lung cancer), head and neck cancers, liver cancers (e.g., hepatocellular carcinomas), lymphomas (e.g., non-Hodgkin's lymphomas such as mantle cell lymphoma, follicular lymphoma, diffuse large B cell lymphoma), pancreatic cancers, colorectal cancers, ovarian cancers, renal cancers, stomach cancers, testicular cancers, thyroid cancers, and uterine cancers. The cancer may be newly diagnosed and naïve to treatment, or may be relapsed, refractory, or relapsed and refractory, or a metastatic form of a huLRRC15 stromal(+)/cancer(−) tumor.

Indeed, as demonstrated in FIGS. 20A-20E, anti-huLRRC15 ADCs are more effective than both non-targeted and targeted anti-cancer agents against a variety of stromal(+)/cancer(−) tumors. As demonstrated in FIGS. 20A-20E, stromal(+)/cancer(−) tumors that exhibit resistance to other targeted or non-targeted chemotherapies, retain sensitivity to anti-huLRRC15 ADCs.

Moreover, as shown in FIG. 14, stromal(+)/cancer(−) tumors that eventually regrow following treatment with anti-huLRRC15 ADCs remain sensitive to retreatment with anti-huLRRC15 ADCs. Accordingly, the anti-huLRRC15 ADCs described herein provide significant benefits over current targeted and non-targeted approaches toward the treatment of huLRRC15 stromal(+)/cancer(−) tumors.

While not wishing to be bound by theory, the anti-huLRRC15 ADCs may exhibit an anti-tumor effect in part by killing cancer cells that have undergone epithelial-mesenchymal transition (EMT) and have acquired stem cell-like properties such as a mesenchymal phenotype. Data provided herein indicated that cancer cells that acquired mesenchymal-like properties exhibited higher huLRRC15 expression than cells with epithelial characteristics (FIGS. 10 and 11A-11C). Cancer cells that have undergone EMT transition were more sensitive to an anti-huLRRC15 ADC than epithelial cancer cells (FIG. 23D). The higher killing effect may result in part due to the localization of the ADC to LRRC15-expressing cells, followed by release of the cytotoxic agent. Accordingly, an anti-tumor effect exhibited by administration of an anti-huLRRC15 ADC (FIGS. 24A-24G) may be a result in part of the targeting and killing of cancer cells that have undergone EMT and acquired cancer stem cell like properties.

FIGS. 9A-9C demonstrate that bone marrow derived mesenchymal stem cells, hypothesized to localize to the tumor microenvironment and form part of the tumor stroma, exhibited significant levels of huLRRC15 expression (Karnoub, A E et al., Nature (2007), 449, 557-563; Droujinine, I A et al., Oncotarget (2013), 4(5), 651-664). Additionally, significant huLRRC15 expression can be induced by TGFβ in these mesenchymal stem cells (FIGS. 9A-9C). Bone marrow mesenchymal stem cells (BM-MSCs) stimulated with TGFβ to express significant levels of LRRC15 (FIGS. 23B and 23C), were sensitive to killing by an anti-huLRRC15 ADC. The killing effect may be a result in part of the localization to LRRC15-expressing cells by the ADC, followed by release of the cytotoxic agent. Accordingly, an anti-tumor effect exhibited by administration of an anti-huLRRC15 ADC (FIGS. 24A-24G) may be a result in part of the targeting and/or killing of mesenchymal stem cells that make up part of the fibroblast population in the tumor stromal microenvironment. In addition, FIGS. 23B and 23C demonstrate that mesenchymal stem cells are able to take up and process anti-huLRRC15 ADCs, which may directly kill the mesenchymal stem cell as well as kill the cancer cells in proximity to the mesenchymal stem cells via a bystander effect through the release of the cytotoxic and/or cytostatic agent.

Anti-huLRRC15 ADCs may be administered alone (monotherapy) or adjunctive to, or with, other anti-cancer therapies and/or targeted or non-targeted anti-cancer agents. When administered as anti-huLRRC15 ADC monotherapy, one or more anti-huLRRC15 ADCs may be used. Whether administered as monotherapy or adjunctive to, or with, other therapies or agents, an amount of anti-huLRRC15 ADC is administered such that the overall treatment regimen provides therapeutic benefit.

By therapeutic benefit is meant that the use of anti-huLRRC15 ADCs to treat cancer in a patient results in a demonstrated improvement in survival compared with no therapy (when appropriate) or to a known standard of care. In some cases, therapeutic benefit may constitute an improvement in time to disease progression together with an improvement in symptoms or quality of life. In other cases, therapeutic benefit may not translate to an increased period of disease control, but rather a markedly reduced symptom burden resulting in improved quality of life. As will be apparent to those of skill in the art, a therapeutic benefit may be observed using the anti-huLRRC15 ADCs alone (monotherapy) or adjunctive to, or with, other anti-cancer therapies and/or targeted or non-targeted anti-cancer agents.

Typically, therapeutic benefit is assessed using standard clinical tests designed to measure the response to a new treatment for cancer. To assess the therapeutic benefits of the anti-huLRRC15 ADCs described herein one or a combination of the following tests can be used: (1) the Response Evaluation Criteria In Solid Tumors (RECIST) version 1.1, (2) immune-related RECIST (irRECIST), (3) the Eastern Cooperative Oncology Group (ECOG) Performance Status, (4) immune-related response criteria (irRC), (5) disease evaluable by assessment of tumor antigens, (6) validated patient reported outcome scales, and/or (7) Kaplan-Meier estimates for overall survival and progression free survival.

Assessment of the change in tumor burden is an important feature of the clinical evaluation of cancer therapeutics. Both tumor shrinkage (objective response) and time to the development of disease progression are important endpoints in cancer clinical trials. Standardized response criteria, known as RECIST (Response Evaluation Criteria in Solid Tumors), were published in 2000. An update (RECIST 1.1) was released in 2009. RECIST criteria are typically used in clinical trials where objective response is the primary study endpoint, as well as in trials where assessment of stable disease, tumor progression or time to progression analyses are undertaken because these outcome measures are based on an assessment of anatomical tumor burden and its change over the course of the trial. TABLE 3 provides the definitions of the response criteria used to determine objective tumor response to a study drug, such as the anti-huLRRC15 ADCs described herein.

TABLE 3

| Response | Criteria |
| --- | --- |
| Complete Response (CR) | Disappearance of all target lesions. Any pathological lymph nodes (whether target or non-target) must have reduction in short axis to <10 mm. |
| Partial Response (PR) | At least a 30% decrease in the sum of diameters of target lesions, taking as reference the baseline sum diameters. |
| Progressive Disease (PD) | At least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression). |
| Stable Disease (SD) | Neither sufficient shrinkage to qualify for PR nor sufficient increase to qualify for PD, taking as reference the smallest sum diameters while on study. |

Secondary outcome measures that can be used to determine the therapeutic benefit of the anti-huLRRC15 ADCs described herein include, Objective Response Rate (ORR), Progression Free Survival (PFS), Overall Survival (OS), Duration of Overall Response (DOR), and Depth of Response (DpR). ORR is defined as the proportion of the participants who achieve a complete response (CR) or partial response (PR). PFS is defined as the time from the first dose date of an anti-huLRRC15 ADC to either disease progression or death, whichever occurs first. OS is defined as the length of time from either the date of diagnosis or the start of treatment for a disease, that patients diagnosed with the disease are still alive. DOR is defined as the time from the participant's initial CR or PR to the time of disease progression. DpR is defined as the percentage of tumor shrinkage observed at the maximal response point compared to baseline tumor load. Clinical endpoints for both ORR and PFS can be determined based on RECIST 1.1 criteria described above.

Additional criteria that may be used for clinical evaluation specific to cancer patients undergoing immune therapy treatment include the standardized immune-related RECIST (ir-RECIST) criteria. See, e.g., Nishino, M. et al. *Eur. J. Radiol.*, 84(7), pages 1259-1268 (2015 July). These guidelines modified the RECIST 1.1 criteria above with consideration of potential immunomodulatory effects. TABLE 5 provides the definitions of the response criteria used to determine objective tumor response to an immunomodulatory drug, such as the anti-huLRRC15 ADCs described herein.

TABLE 4

| Response | Criteria |
| --- | --- |
| Complete Response (irCR) | Complete disappearance of all measurable and non-measurable lesions. Lymph nodes must decrease to <10 mm in short axis. |
| Partial Response (irPR) | Decrease of ≥30% in total measured tumor burden relative to baseline, non-target lesions are irNN, and no unequivocal progression of new non-measurable lesions |
| Progressive Disease (irPD) | At least a 20% increase and at least 5 mm absolute increase in TMTB compared to nadir, or irPD for non-target or new non-measurable lesions. Confirmation of progression is recommended at least 4 weeks after the first irPD assessment. |
| Non-irCR or non-irPD (irNN) | No target disease was identified at baseline and at follow-up the patient fails to meet criteria for irCR or irPD |
| Stable Disease (irSD) | Neither sufficient shrinkage to qualify for irPR nor sufficient increase to qualify for irPD, taking as reference the smallest sum diameters while on study. |
| irNE | Used in exceptional cases where insufficient data exists. |

The ECOG Scale of Performance Status shown in TABLE 5 is used to describe a patient's level of functioning in terms of their ability to care for themselves, daily activity, and physical ability. The scale was developed by the Eastern Cooperative Oncology Group (ECOG), now part of the ECOG-ACRIN Cancer Research Group, and published in 1982.

TABLE 5

| Grade | ECOG Performance Status |
| --- | --- |
| 0 | Fully active, able to carry on all pre-disease performance without restriction |
| 1 | Restricted in physically strenuous activity but ambulatory and able to carry out work of a light or sedentary nature, e.g., light house work, office work |
| 2 | Ambulatory and capable of all selfcare but unable to carry out any work activities; up and about more than 50% of waking hours |
| 3 | Capable of only limited selfcare; confined to bed or chair more than 50% of waking hours |
| 4 | Completely disabled; cannot carry on any selfcare; totally confined to bed or chair |
| 5 | Dead |

Another set of criteria that can be used to characterize fully and to determine response to immunotherapeutic agents, such as antibody-based cancer therapies, is the immune-related response criteria (irRC), which was developed for measurement of solid tumors in 2009, and updated in 2013 (Wolchok, et al. Clin. Cancer Res. 2009; 15(23): 7412-7420 and Nishino, et al. Clin. Cancer Res. 2013; 19(14): 3936-3943, each of which is incorporated by reference in its entirety). The updated irRC criteria are typically used to assess the effect of an immunotherapeutic agent, such as an anti-huLRRC15 ADC described herein, on tumor burden, and defines response according to TABLE 6.

TABLE 6

| Response | Criteria |
| --- | --- |
| Complete Response (CR) | Disappearance of all target lesions in two consecutive observations not less than 4 weeks apart |
| Partial Response (PR) | At least a 30% decrease in the sum of the longest diameters of target lesions, taking as reference the baseline sum diameters. |
| Progressive Disease (PD) | At least a 20% increase in the sum of diameters of target lesions, taking as reference the smallest sum on study (this includes the baseline sum if that is the smallest on study). (Note: the appearance of one or more new lesions is not considered progression. The measurement of new lesions is included in the sum of the measurements). |
| Stable Disease (SD) | Neither sufficient shrinkage to qualify for PR nor sufficient increase to qualify for PD, taking as reference the smallest sum diameters while on study. |

Tumor antigens that can be used to evaluate the therapeutic benefit of the anti-huLRRC15 ADCs described herein include ApoE, CD11c, CD40, CD45 (PTPRC), CD49D (ITGA4), CD80, CSF1R, CTSD, GZMB, Ly86, MS4A7, PIK3AP1, PIK3CD, CD74, CCL5, CCR5, CXCL10, IFNG, IL10RA1, IL-6, ACTA2, COL7A1, LOX, LRRC15, MCPT8, MMP10, NOG, SERPINE1, STAT1, TGFBR1, CTSS, PGF, VEGFA, C1QA, C1QB, ANGPTL4, EGLN, ANGPTL4, EGLN3, BNIP3, AIF1, CCL5, CXCL10, CXCL11, IFI6, PLOD2, KISS1R, STC2, DDIT4, PFKFB3, PGK1, PDK1, AKR1C1, AKR1C2, CADM1, CDH11, COL6A3, CTGF, HMOX1, KRT33A, LUM, WNT5A, IGFBP3, MMP14, CDCP1, PDGFRA, TCF4, TGF, TGFB1, TGFB2, CD11b, ADGRE1 (EMR1, F4/80), CD86, CD68, MHC-Class II, CD3, HLA-DR, CD4, CD3, CD5, CD19, CD7, CD8, CD16, TCRαβ, TCRγδ, PD-1, PDL-1, CTLA-4, acid phosphatase, ACTH, alkaline phosphatase, alpha-fetoprotein CA-125, CA15-3, CA19-9, CA-195, C-212, CA-549, calcitonin, catecholamines, cathepsin-D, CEA, ERBB2 (HER2/neu), chromagranin-A, c-Myc, EGFR, ERA (estrogen receptor assay), ferritin, gastrin, 5-HIAA, hCG, alpha-HCG, beta-HCG, HVA, LDH1-5, NSE (neuron specific enolase), pancreatic polypeptide, PLAP, PLP, PRA (progesterone receptor A), proinsulin C-peptide, PSA, SMA, SCC, thyroglobulin, TDT, TPA, and alpha-TSH. These antigens can be assessed at the DNA, RNA or protein level using DNA sequencing techniques, RNA sequencing techniques, gene chip microarray, PCR based methods, flow cytometry or immunohistochemistry methods as known to experts in the art.

One exemplary therapeutic benefit resulting from the use of anti-huLRRC15 ADCs described herein to treat stromal (+)/cancer(−) tumors, whether administered as monotherapy or adjunctive to, or with, other therapies or agents, is a complete response. Another exemplary therapeutic benefit resulting from the use of anti-huLRRC15 ADCs described herein to treat stromal(+)/cancer(−) tumors, whether administered as monotherapy or adjunctive to, or with, other therapies or agents, is a partial response.

Validated patient reported outcome scales can also be used to denote response provided by each patient through a specific reporting system. Rather than being disease focused, such outcome scales are concerned with retained function while managing a chronic condition. One non-limiting example of a validated patient reported outcome scale is PROMIS® (Patient Reported Outcomes Measurement Information System) from the United States National Institutes of Health. For example, PROMIS® Physical Function Instrument for adult cancer patients can evaluate self-reported capabilities for the functioning of upper extremities (e.g., dexterity), lower extremities (e.g., walking or mobility), and central regions (e.g., neck, back mobility), and also includes routine daily activities, such as running errands.

Kaplan-Meier curves (Kaplan and Meier, J. Am. Stat. Assoc. 1958; 53(282): 457-481) can also be used to estimate overall survival and progression free survival for cancer patients undergoing anti-huLRRC15 antibody or ADC therapy in comparison to standard of care.

7.7.1. Adjunctive Therapies

Anti-huLRRC15 ADCs may be used adjunctive to, or with, other agents or treatments having anti-cancer properties. When used adjunctively, the anti-huLRRC15 and other agent(s) may be formulated together in a single, combination pharmaceutical formulation, or may be formulated and administered separately, either on a single coordinated dosing regimen or on different dosing regimens. Agents administered adjunctively with anti-huLRRC15 ADCs will typically have complementary activities to the anti-huLRRC15 ADCs such that the ADCs and other agents do not adversely affect each other.

Agents that may be used adjunctively with anti-huLRRC15 ADCs include, but are not limited to, alkylating agents, angiogenesis inhibitors, antibodies, antimetabolites, antimitotics, antiproliferatives, antivirals, aurora kinase inhibitors, apoptosis promoters (for example, Bcl-2 family inhibitors), activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNAs, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteasome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, as well as combinations of one or more of these agents.

BiTE antibodies are bispecific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B.

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH3-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include, but are not limited to, altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, dacarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, and trofosfamide.

Angiogenesis inhibitors include, but are not limited to, endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, and vascular endothelial growth factor receptor tyrosine kinase (VEGFR) inhibitors.

Antimetabolites include, but are not limited to, ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosate, pelitrexol, pentostatin, raltitrexed, Ribavirin, triapine, trimetrexate, S-1, tiazofurin, tegafur, TS-1, vidarabine, and UFT.

Antivirals include, but are not limited to, ritonavir, acyclovir, cidofovir, ganciclovir, foscarnet, zidovudine, ribavirin, and hydroxychloroquine.

Aurora kinase inhibitors include, but are not limited to, ABT-348, AZD-1152, MLN-8054, VX-680, Aurora A-specific kinase inhibitors, Aurora B-specific kinase inhibitors and pan-Aurora kinase inhibitors.

Bcl-2 protein inhibitors include, but are not limited to, AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzene sulfonamide), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, venetoclax and GX-070 (obatoclax).

Bcr-Abl kinase inhibitors include, but are not limited to, DASATINIB® (BMS-354825) and GLEEVEC® (imatinib).

CDK inhibitors include, but are not limited to, AZD-5438, BMI-1040, BMS-032, BMS-387, CVT-2584, flavopyridol, GPC-286199, MCS-5A, PD0332991, PHA-690509, seliciclib (CYC-202, R-roscovitine), and ZK-304709.

COX-2 inhibitors include, but are not limited to, ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, and VIOXX® (rofecoxib).

EGFR inhibitors include, but are not limited to, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, and TYKERB® (lapatinib).

ErbB2 receptor inhibitors include, but are not limited to, CP-724-714, CI-1033 (canertinib), HERCEPTIN® (trastuzumab), TYKERB® (lapatinib), OMNITARG® (2C4, pertuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, and mAB 2B-1.

Histone deacetylase inhibitors include, but are not limited to, depsipeptide, LAQ-824, MS-275, trapoxin, suberoylanilide hydroxamic acid (SAHA), TSA, and valproic acid.

HSP-90 inhibitors include, but are not limited to, 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090, and VER49009.

Inhibitors of apoptosis proteins include, but are not limited to, HGS1029, GDC-0145, GDC-0152, LCL-161, and LBW-242.

Activators of death receptor pathway include, but are not limited to, TRAIL, antibodies or other agents that target TRAIL or death receptors (e.g., DR4 and DR5) such as Apomab, conatumumab, ETR2-ST01, GDC0145 (lexatumumab), HGS-1029, LBY-135, PRO-1762 and trastuzumab.

Kinesin inhibitors include, but are not limited to, Eg5 inhibitors such as AZD4877, ARRY-520; and CENPE inhibitors such as GSK923295A.

JAK-2 inhibitors include, but are not limited to, CEP-701 (lesaurtinib), XL019 and INCB018424.

MEK inhibitors include, but are not limited to, ARRY-142886, ARRY-438162, PD-325901, and PD-98059.

mTOR inhibitors include, but are not limited to, AP-23573, CCI-779, everolimus, RAD-001, rapamycin, temsirolimus, ATP-competitive TORC1/TORC2 inhibitors, including PI-103, PP242, PP30, and Torin 1.

Non-steroidal anti-inflammatory drugs include, but are not limited to, AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), and DAYPRO® (oxaprozin).

PDGFR inhibitors include, but are not limited to, C-451, CP-673 and CP-868596.

Platinum chemotherapeutics include, but are not limited to, cisplatin, ELOXATIN® (oxaliplatin) eptaplatin, lobaplatin, nedaplatin, PARAPLATIN® (carboplatin), satraplatin, and picoplatin.

Polo-like kinase inhibitors include, but are not limited to, BI-2536.

Phosphoinositide-3 kinase (PI3K) inhibitors include, but are not limited to, wortmannin, LY294002, XL-147, CAL-120, ONC-21, AEZS-127, ETP-45658, PX-866, GDC-0941, BGT226, BEZ235, and XL765.

Thrombospondin analogs include, but are not limited to, ABT-510, ABT-567, ABT-898, and TSP-1.

VEGFR inhibitors include, but are not limited to, AVASTIN® (bevacizumab), ABT-869, AEE-788, ANGIOZYME™ (a ribozyme that inhibits angiogenesis (Ribozyme Pharmaceuticals (Boulder, Colo.) and Chiron (Emeryville, Calif.)), axitinib (AG-13736), AZD-2171, CP-547,632, IM-862, MACUGEN® (pegaptamib), NEXAVAR® (sorafenib, BAY43-9006), pazopanib (GW-786034), vatalanib (PTK-787, ZK-222584), SUTENT® (sunitinib, SU-11248), VEGF trap, and ZACTIMA™ (vandetanib, ZD-6474).

Antibiotics include, but are not limited to, intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), and zinostatin.

Topoisomerase inhibitors include, but are not limited to, aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, Onivyde™ (liposomal irinotecan), orathecin, pirarbucin, pixantrone, rubitecan, sobuzoxane, SN-38, tafluposide, and topotecan.

Antibodies include, but are not limited to, AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzumab, pertuzumab, VECTIBIX® (panitumumab) and CD20 antibodies types I and II.

Hormonal therapies include, but are not limited to, ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), and ZOLADEX® (fosrelin, goserelin).

Deltoids and retinoids include, but are not limited to, seocalcitol (EB1089, CB1093), lexacalcitrol (KH1060), fenretinide, PANRETIN® (aliretinoin), ATRAGEN® (liposomal tretinoin), TARGRETIN® (bexarotene), and LGD-1550.

PARP inhibitors include, but are not limited to, ABT-888 (veliparib), olaparib, KU-59436, AZD-2281, AG-014699, BSI-201, BGP-15, INO-1001, and ONO-2231.

Plant alkaloids include, but are not limited to, vincristine, vinblastine, vindesine, and vinorelbine.

Proteasome inhibitors include, but are not limited to, VELCADE® (bortezomib), KYPROLIS® (carfilzomib), MG132, NPI-0052, and PR-171.

Examples of immunologicals include, but are not limited to, interferons, immune checkpoint inhibitors, co-stimulatory agents, and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Immune check point inhibitors include antibodies that target PD-1 (e.g., pembrolizumab, nivolumab), PD-L1 (e.g., durvalumab, atezolizumab, avelumab, MEDI4736, MSB0010718C and MPDL3280A), and CTLA4 (cytotoxic lymphocyte antigen 4; e.g., ipilimumab, tremelimumab). Additional exemplary anti-PD-1 antibodies include those described in U.S. provisional application No. 62/394,314, such as an anti-PD-1 antibody having a heavy chain amino acid sequence according to:

(SEQ ID NO: 91)
EIQLVQSGAEVKKPGSSVKVSCKAS<u>GYTFTHYGMN</u>WVRQAPGQGLEWVG<u>W</u>

<u>VNTYTGEPTYADD</u>FKGRLTFTLDTSTSTAYMELSSLRSEDTAVYYCTR<u>EG</u>

<u>EGLGFGDW</u>GQGTTVTVSS*ASTKGPSVFPLAPSSKSTSGGTAALGCLVKDY*

*FPEPVTVSWNSGALTSGVHTFPAVLQSSGLYSLSSVVTVPSSSLGTQTYI*

```
CNVIVHKPSNTKVDKKVEPKSCDKTHTCPPCPAPEAAGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK
or (SEQ ID NO: 92)
EIQLVQSGAEVKKPGSSVKVSCKASGYTFTHYGMNWVRQAPGQGLEWVGW

VNTYTGEPTYADDFKGRLTFTLDTSTSTAYMELSSLRSEDTAVYYCTREG

EGLGFGDWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPEAAGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSMHEALHNHYTQKSLSLSPG;
``` and
a light chain amino acid sequence according to:

```
                                        (SEQ ID NO: 93)
DVVMTQSPLSLPVTPGEPASISCRSSQSIVHSHGDTYLEWYLQKPGQSPQ

LLIYKVSNRFSGVPDRFSGSGSGTDFTLKISRVEAEDVGVYYCFQGSHIP

VTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC,
``` wherein the underlined amino acids represent the CDRs and the italicized amino acids represent the constant regions.

Co-stimulatory agents include, but are not limited to, antibodies against CD3, CD40, CD40L, CD27, CD28, CSF1R, CD137 (e.g., urelumab), B7H1, GITR, ICOS, CD80, CD86, OX40, OX40L, CD70, HLA-DR, LIGHT, LIGHT-R, TIM3, A2AR, NKG2A, KIR (e.g., lirilumab), TGF-β (e.g., fresolimumab) and combinations thereof.

Other agents include, but are not limited to, ALFAFERONE® (IFN-α), BAM-002 (oxidized glutathione), BEROMUN® (tasonermin), BEXXAR® (tositumomab), CAMPATH® (alemtuzumab), dacarbazine, denileukin, epratuzumab, GRANOCYTE® (lenograstim), lentinan, leukocyte alpha interferon, imiquimod, melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZINBRYTA® (daclizumab high-yield process), and ZEVALIN® ($^{90}$Y-Ibritumomab tiuxetan).

Biological response modifiers are agents that modify defense mechanisms of living organisms or biological responses, such as survival, growth or differentiation of tissue cells to direct them to have anti-tumor activity and include, but are not limited to, krestin, lentinan, sizofiran, picibanil PF-3512676 (CpG-8954), and ubenimex.

Pyrimidine analogs include, but are not limited to, cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), and TROXATYL™ (triacetyluridine troxacitabine).

Purine analogs include, but are not limited to, LANVIS® (thioguanine) and PURI-NETHOL® (mercaptopurine).

Antimitotic agents include, but are not limited to, batabulin, epothilone D (KOS-862), N-(2-((4-hydroxyphenyl)amino)pyridin-3-yl)-4-methoxybenzenesulfonamide, ixabepilone (BMS 247550), TAXOL® (paclitaxel), TAXOTERE® (docetaxel), PNU100940 (109881), patupilone, XRP-9881 (larotaxel), vinflunine, and ZK-EPO (synthetic epothilone).

Ubiquitin ligase inhibitors include, but are not limited to, MDM2 inhibitors, such as nutlins, and NEDD8 inhibitors such as MLN4924.

Anti-huLRRC15 ADCs may also be used to enhance the efficacy of radiation therapy. Examples of radiation therapy include external beam radiation therapy, internal radiation therapy (i.e., brachytherapy) and systemic radiation therapy.

Anti-huLRRC15 ADCs may be administered adjunctive to or with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histrelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), and zorubicin, as well as combinations of any of these agents.

7.8. Dosages and Administration Regimens

The amount of anti-huLRRC15 ADC administered will depend upon a variety of factors, including but not limited to, the particular type of stromal(+)/cancer(−) tumor treated, the stage of the stromal(+)/cancer(−) tumor being treated, the mode of administration, the frequency of administration, the desired therapeutic benefit, and other parameters such as the age, weight and other characteristics of the patient, etc. Determination of dosages effective to provide therapeutic benefit for specific modes and frequency of administration is within the capabilities of those skilled in the art.

Dosages effective to provide therapeutic benefit may be estimated initially from in vivo animal models or clinical. Suitable animal models for a wide variety of diseases are known in the art.

The anti-huLRRC15 ADCs may be administered by any route appropriate to the condition to be treated. An anti-huLRRC15 ADC will typically be administered parenterally, i.e., infusion, subcutaneous, intramuscular, intravenous (IV), intradermal, intrathecal, bolus, intratumor injection or epidural ((Shire et al., 2004, *J. Pharm. Sciences* 93(6):1390-1402)). In one embodiment, an anti-huLRRC15 ADC is provided as a lyophilized powder in a vial. The vials may contain 50 mg, 100 mg, or 200 mg of anti-huLRRC15 ADC. Prior to administration, the lyophilized powder is reconstituted with sterile water for injection (SWFI) or other suitable medium to provide a solution containing 20 mg/mL anti-huLRRC15 ADC. The resulting reconstituted solution is further diluted with saline or other suitable medium and administered via an IV infusion once every 7 days, once every 14 days, once every 21 days, or once every 28 days. In some embodiments, for the first cycle, the infusion occurs over 180 minutes, subsequent infusions are over 90 minutes. In other embodiments, the infusion occurs over 60 minutes.

In one exemplary embodiment, an anti-huLRRC15 ADC is administered once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg, 6.0 mg/kg, 6.3 mg/kg, 6.6 mg/kg, 6.9 mg/kg, or 7.2 mg/kg.

In another exemplary embodiment, an anti-huLRRC15 ADC is administered once every 7 days at 0.15 mg/kg, 0.3 mg/kg, 0.45 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, or 4.2 mg/kg.

In another exemplary embodiment, an anti-huLRRC15 ADC is administered once every 28 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg, 6.0 mg/kg, 6.3 mg/kg, 6.6 mg/kg, 6.9 mg/kg, 7.2 mg/kg, 7.5 mg/kg, 7.8 mg/kg, 8.1 mg/kg, or 8.4 mg/kg.

In another exemplary embodiment, an anti-huLRRC15 ADC is administered once every 21 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg, 6.0 mg/kg, 6.3 mg/kg, 6.6 mg/kg, 6.9 mg/kg, or 7.2 mg/kg.

When administered adjunctive to, or with, other agents, such as other chemotherapeutic agents, the ADCs may be administered on the same schedule as the other agent(s), or on a different schedule. When administered on the same schedule, the ADC may be administered before, after, or concurrently with the other agent. In some embodiments where an ADC is administered adjunctive to, or with, standards of care, the ADC may be initiated prior to commencement of the standard therapy, for example a day, several days, a week, several weeks, a month, or even several months before commencement of standard of care therapy.

In one exemplary embodiment, an anti-huLRRC15 ADC is used adjunctive to gemcitabine (GEMZAR®) to treat pancreatic cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Gemcitabine is administered by intravenous infusion at a dose of 1000 mg/m$^2$ over 30 minutes once weekly for up to 7 weeks, followed by a week of rest from treatment. If myelosuppression is observed, dose modifications as provided in the prescribing information for gemcitabine may be used. Subsequent cycles should consist of infusions once weekly for 3 consecutive weeks out of every 4 weeks. The adjunctive anti-huLRRC15 ADC/gemcitabine therapy is continued until disease progression or no longer tolerated by the patient.

In another exemplary embodiment, an anti-huLRRC15 ADC is used adjunctive to paclitaxel albumin-stabilized nanoparticle formulation (ABRAXANE®) to treat pancreatic cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. The recommended dose and schedule for paclitaxel albumin-stabilized nanoparticle formulation is 125 mg/m$^2$ administered as an intravenous infusion over 30-40 minutes on days 1, 8, and 15 of each 28-day cycle. The adjunctive anti-huLRRC15 ADC/ABRAXANE® therapy is continued until disease progression or no longer tolerated by the patient.

In another exemplary embodiment, an anti-huLRRC15 ADC is used adjunctive to paclitaxel albumin-stabilized nanoparticle formulation (ABRAXANE®) plus gemcitabine (GEMZAR®) to treat pancreatic cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. The recommended dose and schedule for paclitaxel albumin-stabilized nanoparticle formulation is 125 mg/m² administered as an intravenous infusion over 30-40 minutes on days 1, 8, and 15 of each 28-day cycle. Gemcitabine is administered by intravenous infusion at a dose of 1000 mg/m² over 30 minutes once weekly for up to 7 weeks (or until toxicity reducing or holding a dose), followed by a week of rest from treatment. Subsequent cycles should consist of infusions once weekly for 3 consecutive weeks out of every 4 weeks. The adjunctive anti-huLRRC15 ADC/ABRAXANE®/GEMZAR® therapy is continued until disease progression or no longer tolerated by the patient.

In yet another exemplary embodiment, an anti-huLRRC15 ADC is used adjunctive to TARCEVA® (erlotinib) to treat pancreatic cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. The recommended dose and schedule for erlotinib is 100 mg orally, once daily. The adjunctive anti-huLRRC15 ADC/erlotinib therapy is continued until disease progression or no longer tolerated by the patient.

In still another exemplary embodiment, an anti-huLRRC15 ADC is used adjunctive to FOLFIRINOX to treat pancreatic cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. FOLFIRINOX is a combination of four chemotherapy agents: fluorouracil [5-FU], leucovorin, irinotecan and oxaliplatin. In some embodiments, FOLFIRINOX is administered as follows: oxaliplatin, 85 mg/m²; irinotecan, 180 mg/m²; leucovorin, 400 mg/m²; and fluorouracil, 400 mg/m² given as a bolus followed by 2400 mg/m² given as a 46-hour continuous infusion, every 2 weeks. The adjunctive anti-huLRRC15 ADC/FOLFIRINOX therapy is continued until disease progression or no longer tolerated by the patient.

In still another exemplary embodiment, an anti-huLRRC15 ADC is used adjunctive to Onivyde® to treat pancreatic cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Onivyde® is a liposomal irinotecan formulation. In some embodiments, Onivyde® is administered at 70 mg/m² by intravenous infusion over 90 minutes every 2 weeks. The adjunctive anti-huLRRC15 ADC/Onivyde® therapy is continued until disease progression or no longer tolerated by the patient.

In still another exemplary embodiment, an anti-huLRRC15 ADC is used adjunctive to Onivyde®, fluorouracil, and leucovorin to treat pancreatic cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Onivyde® is a liposomal irinotecan formulation. In some embodiments, Onivyde® is administered at 70 mg/m² by intravenous infusion over 90 minutes every 2 weeks, with leucovorin 400 mg/m² and fluorouracil 2400 mg/m² over 46 hours every 2 weeks. The adjunctive anti-huLRRC15 ADC/Onivyde®/leucovorin/fluorouracil therapy is continued until disease progression or no longer tolerated by the patient.

In still another exemplary embodiment, an anti-huLRRC15 ADC is used adjunctive to nivolumab (OPDIV®) to treat pancreatic cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Nivolumab is administered an intravenous infusion at 3 mg/kg over 60 minutes every two weeks. The adjunctive anti-huLRRC15 ADC/nivolumab therapy is continued until disease progression or no longer tolerated by the patient.

In still another exemplary embodiment, an anti-huLRRC15 ADC can be used adjunctive to pembrolizumab (KEYTRUDA®) to treat pancreatic cancer. The anti-huLRRC15 ADC is administered via IV infusion once every 21 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Pembrolizumab is administered as an intravenous infusion at 2 mg/kg over 30 minutes every 3 weeks. The adjunctive anti-huLRRC15 ADC/pembrolizumab therapy is continued until disease progression or no longer tolerated by the patient.

In still another exemplary embodiment, an anti-huLRRC15 ADC is used adjunctive to TARCEVA® (erlotinib) to treat non small cell lung cancer (NSCLC). The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. The recommended dose and schedule for erlotinib is 150 mg orally, once daily. The adjunctive anti-huLRRC15 ADC/erlotinib therapy is continued until disease progression or no longer tolerated by the patient.

In still another exemplary embodiment, an anti-huLRRC15 ADC is used adjunctive to IRESSA® (gefitinib) to treat non small cell lung cancer (NSCLC). The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. The recommended dose and schedule for gefitinib is 250 mg orally, once daily. The adjunctive anti-huLRRC15 ADC/gefitinib therapy is continued until disease progression or no longer tolerated by the patient.

In still another exemplary embodiment, an anti-huLRRC15 ADC is used adjunctive to afatinib to treat non small cell lung cancer (NSCLC). The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. The recommended dose and schedule for afatinib is 40 mg orally, once daily. The adjunctive anti-huLRRC15 ADC/afatinib therapy is continued until disease progression or no longer tolerated by the patient.

In still another exemplary embodiment, an anti-huLRRC15 ADC is used adjunctive to OPDIVO® (nivolumab) to treat non small cell lung cancer (NSCLC). The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Nivolumab is administered an intravenous infusion at 3 mg/kg over 60 minutes every two weeks. The adjunctive anti-huLRRC15 ADC/nivolumab treatment is continued until disease progression or no longer tolerated by the patient.

In still another exemplary embodiment, an anti-huLRRC15 ADC is used adjunctive to OPDIVO® (nivolumab) and YERVOY® (ipilimumab) to treat non small cell lung cancer (NSCLC). The anti-huLRRC15 ADC is administered via IV infusion once every 21 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, for four doses with ipilimumab, then every 14 days at 0.3 mg/kg, 0.6 mg/kg, 0.9 mg/kg, 1.2 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, without ipilimumab. Nivolumab is administered as an intravenous infusion at 3 mg/kg over 60 minutes every two weeks. Ipilimumab is administered intravenously at 3 mg/kg over 90 minutes every three weeks in the first four doses. The adjunctive anti-huLRRC15 ADC/nivolumab/ipilimumab treatment is continued until disease progression or no longer tolerated by the patient.

In still another exemplary embodiment, an anti-huLRRC15 ADC can be used adjunctive to pembrolizumab (KEYTRUDA®) to treat NSCLC. The anti-huLRRC15 ADC is administered via IV infusion once every 21 days at 0.3 mg/kg, 0.6 mg/kg, 0.9 mg/kg, 1.2 mg/kg, 1.5 mg/kg, 1.8 mg/kg, 2.4 mg/kg, 3.0 mg/kg, 3.6 mg/kg, 4.2 mg/kg, 4.8 mg/kg, 5.4 mg/kg, or 6.0 mg/kg. Pembrolizumab is administered as an intravenous infusion at 2 mg/kg over 30 minutes every 3 weeks. The adjunctive anti-huLRRC15 ADC and pembrolizumab therapy is continued until disease progression or no longer tolerated by the patient.

In still another exemplary embodiment, an anti-huLRRC15 ADC is used adjunctive to cisplatin to treat NSCLC. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Cisplatin is administered at 20 mg/m² or more, once every 3 to 4 weeks. The adjunctive anti-huLRRC15 ADC/cisplatin therapy is continued until disease progression or no longer tolerated by the patient.

In still another exemplary embodiment, an anti-huLRRC15 ADC is used adjunctive to carboplatin to treat NSCLC. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Carboplatin is administered at 300 mg/m² or more, once every 4 weeks. The adjunctive anti-huLRRC15 ADC/carboplatin therapy is continued until disease progression or no longer tolerated by the patient.

In still another exemplary embodiment, an anti-huLRRC15 ADC is used adjunctive to veliparib to treat NSCLC. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Veliparib is administered orally, twice a day. The adjunctive anti-huLRRC15 ADC/veliparib therapy is continued until disease progression or no longer tolerated by the patient.

In still another exemplary embodiment, an anti-huLRRC15 ADC is used adjunctive to veliparib and pemetrexed to treat NSCLC. The anti-huLRRC15 ADC is administered via IV infusion once every 21 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Veliparib is administered orally, twice a day. Pemetrexed is administered at 500 mg/m² intravenously every 21 days. The adjunctive anti-huLRRC15 ADC/veliparib/pemetrexed therapy is continued until disease progression or no longer tolerated by the patient.

In still another exemplary embodiment, an anti-huLRRC15 ADC is used adjunctive to cetuximab to treat NSCLC. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Cetuximab is administered at an initial dose of 400 mg/m² over a 120-minute intravenous infusion followed by 250 mg/m² weekly infusion over 60 minutes. The adjunctive anti-huLRRC15 ADC/cetuximab therapy is continued until disease progression or no longer tolerated by the patient.

In still another exemplary embodiment, an anti-huLRRC15 ADC is used adjunctive to ipilimumab (YERVOY®) to treat NSCLC. The anti-huLRRC15 ADC is administered via IV infusion once every 21 days at 0.3 mg/kg, 0.6 mg/kg, 0.9 mg/kg, 1.2 mg/kg, 1.5 mg/kg, 1.8 mg/kg, 2.4 mg/kg, 3.0 mg/kg, 3.6 mg/kg, 4.2 mg/kg, 4.8 mg/kg, 5.4 mg/kg, or 6.0 mg/kg. Ipilimumab is administered at 3 mg/kg intravenously over 90 minutes every 3 weeks for 3 months. The anti-huLRRC15 ADC therapy is continued until disease progression or no longer tolerated by the patient.

In still another exemplary embodiment, an anti-huLRRC15 ADC is used adjunctive to radiation to treat NSCLC. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Typically, external beam radiation therapy is applied for a few minutes up to 5 days a week for 5 to 7 weeks, but this will vary depending on the type of external beam radiation therapy that is used. The adjunctive anti-huLRRC15 ADC/radiation therapy is continued until disease progression or no longer tolerated by the patient.

In still another exemplary embodiment, an anti-huLRRC15 ADC is used adjunctive to doxorubicin to treat breast cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. When used adjunctively with other drugs, the most commonly used dosage of doxorubicin is 40 to 60 mg/m$^2$ given as a single intravenous injection every 21 to 28 days. The adjunctive anti-huLRRC15 ADC/doxorubicin therapy is continued until disease progression or no longer tolerated by the patient.

In still another exemplary embodiment, an anti-huLRRC15 ADC is used adjunctive to gemcitabine to treat breast cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Gemcitabine is administered by intravenous infusion at a dose of 1000 mg/m$^2$ over 30 minutes once weekly for up to 7 weeks (or until toxicity reducing or holding a dose), followed by a week of rest from treatment. Subsequent cycles should consist of infusions once weekly for 3 consecutive weeks out of every 4 weeks. The adjunctive anti-huLRRC15 ADC/gemcitabine therapy is continued until disease progression or no longer tolerated by the patient.

In still another exemplary embodiment, an anti-huLRRC15 ADC is used adjunctive to trastuzumab (HERCEPTIN®) to treat breast cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. The recommended initial loading dose for trastuzumab is 4 mg/kg administered as a 90-minute infusion. The recommended weekly maintenance dose for trastuzumab is 2 mg/kg which can be administered as a 30 minute infusion if the initial loading dose was well tolerated. The adjunctive anti-huLRRC15 ADC/trastuzumab therapy is continued until disease progression or no longer tolerated by the patient.

In still another exemplary embodiment, an anti-huLRRC15 ADC is used adjunctive to capecitabine (XELODA®) to treat breast cancer. The anti-huLRRC15 ADC is administered via IV infusion once every 21 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Capecitabine can be administered at 1250 mg/m$^2$ twice daily for 2 weeks followed by a one week rest period in 3 week cycles. The adjunctive anti-huLRRC15 ADC/capecitabine therapy is continued until disease progression or no longer tolerated by the patient.

In still another exemplary embodiment, an anti-huLRRC15 ADC is used adjunctive to nivolumab (OPDIVO®) to treat breast cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Nivolumab is administered an intravenous infusion at 3 mg/kg over 60 minutes every two weeks. The adjunctive anti-huLRRC15 ADC/nivolumab therapy is continued until disease progression or no longer tolerated by the patient.

In still another exemplary embodiment, an anti-huLRRC15 ADC can be used adjunctive to pembrolizumab (KEYTRUDA®) to treat breast cancer. The anti-huLRRC15 ADC is administered via IV infusion once every 21 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Pembrolizumab is administered as an intravenous infusion at 2 mg/kg over 30 minutes every 3 weeks. The adjunctive anti-huLRRC15 ADC/pembrolizumab therapy is continued until disease progression or no longer tolerated by the patient.

In still another exemplary embodiment, an anti-huLRRC15 ADC is used adjunctively to radiation to treat Head and Neck cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Typically, external beam radiation therapy is applied for a few minutes up to 5 days a week for 5 to 7 weeks, but this will vary depending on the type of external beam radiation therapy that is used. The adjunctive anti-huLRRC15 ADC/radiation therapy is continued until disease progression or no longer tolerated by the patient.

In still another exemplary embodiment, an anti-huLRRC15 ADC is used adjunctive to cetuximab to treat Head and Neck cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Cetuximab is administered at an initial dose of 400 mg/m$^2$ over a 120-minute intravenous infusion followed by 250 mg/m$^2$ weekly infusion over 60 minutes. The adjunctive anti-huLRRC15 ADC/cetuximab therapy is continued until disease progression or no longer tolerated by the patient.

In still another exemplary embodiment, an anti-huLRRC15 ADC is used adjunctive to carboplatin to treat Head and Neck cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Carboplatin is administered at 300 mg/m$^2$ or more, once every 4 weeks. The adjunctive anti-huLRRC15 ADC/carboplatin therapy is continued until disease progression or no longer tolerated by the patient.

In still another exemplary embodiment, an anti-huLRRC15 ADC is used adjunctive to nivolumab (OPDIVO®) to treat Head and Neck cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Nivolumab is administered an intravenous infusion at 3 mg/kg over 60 minutes every two weeks. The adjunctive anti-huLRRC15 ADC/nivolumab therapy is continued until disease progression or no longer tolerated by the patient.

In still another exemplary embodiment, an anti-huLRRC15 ADC can be used adjunctive to pembrolizumab (KEYTRUDA®) to treat Head and Neck cancer. The anti-huLRRC15 ADC is administered via IV infusion once every 21 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Pembrolizumab is administered as an intravenous infusion at 2 mg/kg over 30 minutes every 3 weeks. The adjunctive anti-huLRRC15 ADC/pembrolizumab therapy is continued until disease progression or no longer tolerated by the patient.

In still another exemplary embodiment, an anti-huLRRC15 ADC is used adjunctive to cisplatin to treat Head and Neck cancer. The anti-huLRRC15 ADC is administered via IV infusion once every 14 days at 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Cisplatin is administered as an intravenous infusion at 100 mg/kg every 3 weeks. The adjunctive anti-huLRRC15 ADC/cisplatin therapy is continued until disease progression or no longer tolerated by the patient.

As will be appreciated by those of skill in the art, the recommended dosages for the various agents described above may need to be adjusted to optimize patient response and maximize therapeutic benefit.

8. EXAMPLES

The following Examples, which highlight certain features and properties of exemplary embodiments of anti-huLRRC15 ADCs are provided for purposes of illustration, and not limitation.

Example 1. Preparation of Exemplary Anti-huLRRC15 Antibodies

Antibodies against huLRRC15 were prepared against a cell line expressing huLRRC15 (U118MG glioblastoma cells) using standard techniques. Exemplary antibodies having specified affinities and other desirable characteristics, for example, cross-reactive with cynomolgus LRRC15 ("cynoLRRC15"), were isolated and certain of these antibodies humanized. Exemplary humanized antibodies include huM25, huAD208.4.1, huAD208.12.1, huAD208.14.1, hu139.1 and exemplary murine antibodies include muAD209.9.1 and muAD210.40.9. Sequences of the $V_H$ and $V_L$ chains of these exemplary antibodies are provided in FIGS. 2A and 2B, respectively. Sequences of the heavy and light chains of exemplary antibody huM25 are provided in FIGS. 3A and 3B, respectively. The encoded heavy chain of huM25 is SEQ ID NO:18, and can be C-terminal truncated upon expression in CHO cells to SEQ ID NO:102, with the encoded light chain of huM25 being SEQ ID NO:19.

Binding of these exemplary antibodies to endogenous huLRRC15, as well as their respective $EC_{50}$s, was demonstrated with U118MG glioblastoma cells via a conventional flow cytometry assay using test antibody concentrations of 0.0001 µg/mL, 0.001 µg/mL, 0.01 µg/mL, 0.1 µg/mL, 1 µg/mL, 10 µg/mL and 100 µg/mL. Isotype control antibodies (mouse or human) were used as appropriate. Flow cytometry binding data for various representative anti-huLRRC15 antibodies are shown in FIG. 4. TABLE 7 provides $EC_{50}$ (nM) values for various anti-huLRRC15 antibodies as determined by flow cytometry.

TABLE 7

Binding of Antibodies to Cells Expressing huLRRC15 (Flow Cytometry)

| Antibody | U118MG $EC_{50}$ (nM) | Antibody | U118MG $EC_{50}$ (nM) |
|---|---|---|---|
| muIgG$_{2a}$ Isotype mAb |  | huIgG$_1$ Isotype mAb | NA |
| muM25 | 0.496 | huM25 | 0.498 |
| mu139.10 | 0.207 | hu139.10 | 0.28 |
| muAD208.4.1 | 0.934 | huAD208.4.1 | 0.29 |
| muAD208.14.1 | 2.05 | huAD208.14.1 | 5.25 |
| muAD209.9.1 | 0.787 | | |
| muAD210.40.9 | 0.08 | | |

Example 2. The Anti-huLRRC15 Antibodies Bind the Extracellular Domain of huLRRC15 Shed from the Cell Surface Binding of the exemplary anti-huLRRC15 to the portion of the extracellular domain of huLRRC15 shed from the cell surface was demonstrated in an ELISA assay. huLRRC15-Fc fusion protein was generated using amino acid residues 22 to 526 of SEQ ID NO:3, which corresponds to a portion of the huLRRC15 extracellular protein domain to the cleavage site. 96-well Immulon 4HBX plates (Thermo, cat. #3855) were coated with 100 µL/well of this huLRRC15 fusion ECD protein at 2 µg/mL in carbonate-bicarbonate buffer (Thermo, cat.#28382) pH 9.4 and allowed to bind overnight at 4° C. Plates were washed three times with PBST and then incubated with various concentrations of antibodies in PBST+0.3% BSA at room temperature for one hour. Plates were washed three times with PBST and then incubated with 100 µL of goat anti-human kappa light chain HRP (Bethyl, cat.# A80-115P) at 1:5000 dilution for 30 min at RT. Plates were washed three times in PBST and 100 µL of TMB (Surmodics BioFx cat.# TMBW-1000-01) was added to each well and incubated at RT until color developed (approximately 10 minutes). Reactions were stopped by the addition of 650 nm Stop Reagent for TMB (Surmodics BioFx, cat.# BSTP-0100-01), and optical density (OD) was read at 650 nm (Molecular Devices Versamax PLUS). ELISA binding data for certain exemplary anti-huLRRC15 antibodies are shown in FIG. 5. $EC_{50}$ values for various anti-huLRRC15 antibodies are provided in TABLE 8, below.

All antibodies tested bound the huLRRC15 fusion with $EC_{50}$s in the sub-nanomolar range, indicating that the antibodies bind the portion of the huLRRC15 extracellular domain shed from the cell surface following cleavage.

TABLE 8

Binding of Antibodies to huLRRC15 ECD (ELISA)

| Antibody | huLRRC15-ECD-Fc $EC_{50}$ (nM) | Antibody | huLRRC15-ECD-Fc $EC_{50}$ (nM) |
|---|---|---|---|
| muIgG$_{2a}$ Isotype mAb | NA | huIgG$_1$ Isotype mAb | NA |
| muM25 | 0.22 | huM25 | 0.26 |
| mu139.10 | 0.15 | hu139.10 | 0.11 |
| muAD208.4.1 | 0.15 | huAD208.4.1 | 0.25 |
| muAD208.14.1 | 0.22 | huAD208.14.1 | 0.8 |
| muAD209.9.1 | 0.14 | | |

Example 3. Exemplary Anti-huLRRC15 Antibodies Bind to Different Epitopes

The ability of various exemplary anti-huLRRC15 antibodies to compete with muM25 for binding cells expressing huLRRC15, and hence whether the antibodies bind the same or different epitopes, was assessed in a flow cytometry competition assay using fluorescently labeled muM25 ("muM25-AF488") as a "reference antibody" and unlabeled anti-huLRRC15 antibody as a "test antibody." For the assay, aliquots of U118MG cells (200,000 cells per well) were incubated simultaneously with 1 µg/mL labeled muM25 and either 0.0001, 0.001, 0.01, 0.1, 1, 10 or 100 µg/mL unlabeled test antibody and the amount of bound antibody (normalized to a control aliquot incubated with 1 µg/mL labeled muM25 alone) determined via flow cytometry. Isotype control antibodies (human or mouse) were used as negative controls, and unlabeled muM25 was used as a positive control.

In this assay, competition due to a test antibody binding to the same or a proximal epitope as the labeled reference antibody reduce binding of the reference labeled antibody. A positive result in this assay occurs when a test antibody inhibits ≥20% of the binding of the fluorescently labeled reference antibody at a concentration of test antibody that is 10 times greater than the concentration of the reference antibody.

Unlabeled huM25 competes fully with labeled muM25 as expected (FIG. 6A). Murine antibodies muAD208.4.1 and muAD208.14.1 partially compete with huM25 (FIG. 6B). Both of these antibodies inhibit >20% of the binding of labeled muM25. This indicates that they bind a similar or proximal huLRRC15 epitope as muM25. In contrast, mu139.10, muAD208.12.1 and muAD209.9.1 do not inhibit the binding of labeled muM25, demonstrating that they bind distinct epitopes of huLRRC15 (FIG. 6B).

Example 4. huLRRC15 is Highly Expressed in Stroma of Major Solid Tumor Types Expression of huLRRC15 in the stroma of various solid tumor types was assessed using immunohistochemistry (IHC) staining on formalin fixed paraffin embedded (FFPE) tissues. Biopsies from different tumor types were used to generate tissue microarrays (TMA) which were assessed for huLRRC15 expression. Tissue sections (4 µm) were cut, deparaffinized and antigen retrieval was performed using BORG Decloaker antigen retrieval buffer at 125° C. for 1 min. Leica autostainer was used to block slides and incubate with anti-huLRRC15 antibody (muAD210.40.9 at 1 µg/mL for 60 minutes) and HRP anti-mouse secondary (Dako) together with DAB reagent (Dako) for detection. Results of the experiment are shown in TABLE 9 and FIG. 7.

The TMA samples were scored on a scale of 0 to 4. A score of ≥2 was chosen to identify tumors that express huLRRC15 at high levels. The huLRRC15 staining and expression data in TABLE 9 represents that seen in huLRRC15 stromal positive, cancer negative tumors (FIG. 7).

A number of cancers, such as breast cancer (ductal and lobular as well as triple negative) and head and neck cancer, showed uniformly strong expression of huLRRC15 in tumor stroma, suggesting a broadly applicable treatment regimen could be developed by targeting huLRRC15 in those cancers. Other types of cancers that showed huLRRC15 positive expression in some but not all tumor stromal samples included lung cancers (such as non small cell lung cancers (NSCLC), e.g., adenocarcinoma and squamous NSCLC), pancreatic cancers, bladder cancers, hepatocellular carcinomas, colorectal cancers, ovarian cancers, non-Hodgkin's lymphoma (NHL) (such as mantle cell lymphoma, follicular lymphoma, diffuse large B cell lymphoma, and other lymphomas), testicular cancers, gastric cancers, endometrial cancers, and renal cancers. Prostate cancers did not show huLRRC15 positive expression in stromal samples tested (0/25 samples).

TABLE 9 huLRRC15 Stromal Positive Expression in Cancer (detected by immunohistochemistry)

| Tumor Type | | >2+ | % Positive |
|---|---|---|---|
| Breast | Ductal + Lobular | 72/76 | 95 |
| | Triple Negative | 10/11 | 91 |
| Lung | NSCLC - Adeno | 63/87 | 72 |
| | NSCLC - Squamous | 74/115 | 64 |
| Head & Neck (incl. metastases) | | 47/53 | 89 |
| Pancreatic | | 27/41 | 66 |
| Bladder | | 17/30 | 57 |
| Hepatocellular | | 8/16 | 50 |
| Colorectal | | 19/43 | 44 |
| Ovarian | | 8/18 | 44 |
| Total | | 22/51 | 43 |
| Mantle cell lymphoma | | 4/5 | 80 |
| NHL | Follicular lymphoma | 9/15 | 60 |
| | Diffuse large B cell | 3/6 | 50 |
| | Other NHL | 6/25 | 25 |
| Testicular | | 11/35 | 31 |
| Gastric | | 2/23 | 9 |
| Endometrial | | 2/30 | 7 |
| Renal | | 1/30 | 3 |
| Prostate | | 0/25 | 0 |

Example 5. huLRRC15 Exhibits Limited Expression in Normal Tissues

The expression of huLRRC15 on normal, healthy tissues was assessed using protein immunohistochemical staining of normal tissues. The results are shown in FIG. 8. huLRRC15 has limited expression in most normal tissues, with expression being localized to certain tissues including cardia/pylorus in the stomach, spleen peritrabeculae, osteoblasts, and hair follicles ("ECM" refers to extracellular matrix). Limited expression was also observed in tonsil and placenta (data not shown). No expression of huLRRC15 was observed in major organs (e.g., heart, liver, pancreas, lung).

Example 6. huLRRC15 is Expressed by Mesenchymal Stem Cells

Expression of huLRRC15 was measured by Western blot protein analysis of cancer-associated fibroblast (CAF) cells that originate from a breast cancer patient, or commercial mesenchymal stem cell (MSC) lysates using biotinylated anti-huLRRC15 antibody muAD210.40.9 as shown in FIG. 9A. huLRRC15 was observed to be upregulated in a breast CAF lysate sample upon treatment with TGFβ with low or negligible detectable expression in the absence of TGFβ. By contrast, huLRRC15 expression was higher in the absence of TGFβ in all three MSC lysate samples, and this expression was significantly upregulated upon TGFβ treatment. As previously discussed, MSCs are believed to make up a significant component of the cancer associated fibroblast population in the tumor stroma (Cirri, P and Chiarugi P. American Journal of Cancer Research 2011; 1 (4): 482-497).

Similar upregulation of huLRRC15 expression was observed by flow cytometry of two commercial mesenchymal stem cell populations upon treatment with TGFβ (FIGS. 9B, 9C). In human BM-MSC (Lonza), using CD29, CD44, CD105, CD166 as positive MSC markers and CD14, CD34, and CD45 as negative MSC markers, a significant positive shift in the MSC population expressing huLRRC15 was observed upon treatment with TGFβ as compared with isotype (FIG. 9B). Correspondingly, in murine Balb/c BM-MSC (Cyagen), using CD29, CD44, CD34, and Sca-1 as positive MSC markers and CD117 as a negative MSC marker, a significant increase in the MSC population expressing muLRRC15 was observed upon treatment with TGFβ as compared with isotype (FIG. 9C).

Example 7. huLRRC15 is Associated with Cells Undergoing Epithelial-Mesenchymal Transition The epithelial-mesenchymal transition (EMT) is a cellular mechanism which is believed to confer cellular plasticity on cancer cells. This transition to a more mesenchymal phenotype is thought to increase the motility and invasiveness of a primary cancer cell, potentially leading to cancer metastatis, drug resistance, or evasion of the immune system. See, e.g., Ye, X. and Weinberg, R. A. Trends in Cell Biology, 2015, 25 (11), pages 675-686. Data provided in this Example demonstrate that cancer cells that had undergone EMT had an increased expression of huLRRC15 relative to their parental epithelial cancer cells.

FIG. 10 depicts the effect as determined by Western blot analysis of treating baseline negative A549 (lung cancer) or PANC1 (pancreatic cancer) cells with TGFβ or StemXVivo™ EMT Inducing Media Supplement ("EMT Kit," Catalog #CCM017, R&D Systems) to induce EMT. Proteins recognized as hallmarks of EMT, including N-cadherin, Snail, TCF8/ZEB1, increased expression, and proteins indicative of epithelial cell characteristics such as E-cadherin decreased expression. Expression of the housekeeping protein and protein loading control GAPDH did not change significantly. huLRRC15 expression (measured using anti-LRRC15 antibody muAD210.40.9) was observed to have increased in both A549 and PANC1 cells treated with either TGFβ or EMT Kit, and that have subsequently undergone EMT.

FIGS. 11A-11C show that huLRRC15 expression increased in cells that have undergone EMT, with the reverse mesenchymal-epithelial transition (MET) process occurring with the removal of EMT inducers. FIG. 11A shows A549 or PANC1 cells untreated, or treated with TGFβ or EMT Kit for 5 days. In A549 or PANC1 cells, EpCAM expression, indicating epithelial-like character, was highest in untreated cells. After treatment with TGFβ or EMT Kit, huLRRC15 (as measured with AF647-labeled huM25) in both cell types was induced, while the epithelial marker EpCAM was reduced, suggesting a transition to a more mesenchymal phenotype (huLRRC15 positive). FIG. 11B depicts the morphology of A549 cells treated with TGFβ (10 ng/mL continuously for 9 days) (top left), showing elongated cells with fibrotic-like processes which appear mesenchymal-like, while A549 cells treated with TGFβ (10 ng/mL continuously for 5 days) and then washed to remove the TGFβ no longer exhibited the mesenchymal cell morphology after an additional 4 days (corresponding 9 days total) (bottom left). Hence, the EMT induced by TGFβ was reversible upon its removal. The induction of EMT by TGFβ and reversal of mesenchymal-like properties was also observed by flow cytometry (FIG. 11B). An increase in huLRRC15 expression (indicating more mesenchymal-like characteristics) (upper middle), and a decrease in EpCAM expression (indicating less epithelial-like characteristics) (upper right) was observed after treatment with TGFβ or EMT Kit. Upon discontinuation of TGFβ or EMT Kit treatment, levels of huLRRC15 reverted to that observed at baseline (lower graphs).

FIG. 11C depicts the increase in mesenchymal character, and corresponding decrease in epithelial character, of cells treated with TGFβ, as indicated by huLRRC15 (top graphs) and EpCAM levels (bottom graphs) in A549 (left graphs) or PANC1 (right graphs) cells in vitro. In both A549 and PANC1 cells, huLRRC15 expression increased upon treatment of cells with TGFβ or EMT Kit over 9 days, while EpCAM expression, an indicator of epithelial character, decreased. Consistent with the cell morphology data in FIG. 11B, the protein expression of huLRRC15 and EpCAM indicated the huLRRC15-positive mesenchymal cells reverted to an epithelial-like state after removal of TGFβ or EMT Kit, and additional cell culturing over 4 days.

Example 8. Preparation of Heterogeneous DAR huM25-vcMMAE ADCs

A huM25-val-cit-MMAE ADC composition heterogeneous in DAR was prepared by a two-step chemical process: disulfide reduction of huM25 followed by alkylation (conjugation) with maleimidocaproyl valine-citrulline ("val-cit") para-aminobenzyl alcohol ("PABA") monomethyl auristatin E (referred to herein as "vcMMAE"), illustrated below:

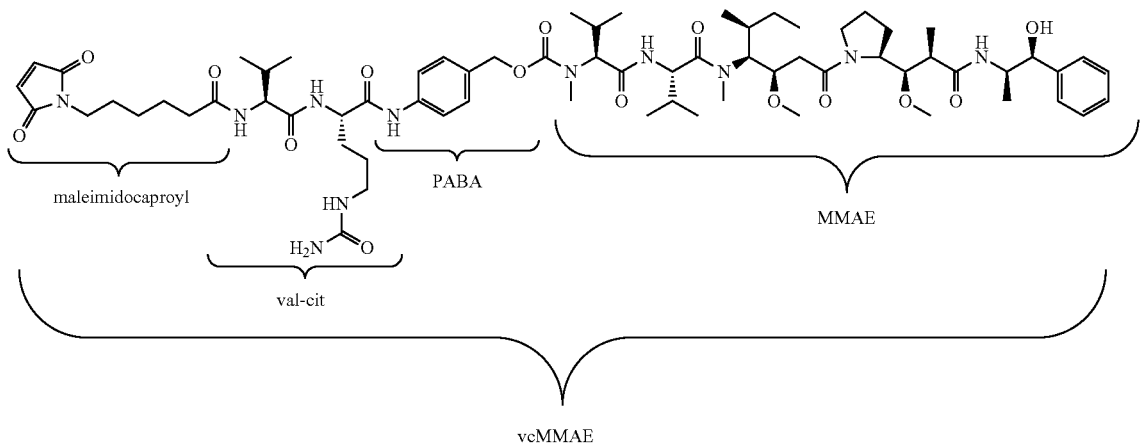 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]

In the first step, a limited number of interchain disulfide bonds of huM25 are reduced with tris(2-carboxyethyl) phosphine ("TCEP") (≥0.8 equiv). Partially-reduced huM25 is then conjugated to vcMMAE (≥1.8 equiv) in DMSO. Residual unreacted vcMMAE is quenched with N-acetyl-L-cysteine.

The top panel of FIG. 12 shows a chromatographic resolution of the resultant ADC preparation. As can be seen, the resultant ADC preparation is a heterogeneous mixture containing antibodies having zero MMAE molecules attached ("DAR0" peak), two MMAE molecules attached ("DAR2" peak), four MMAE molecules attached ("DAR4" peak), six MMAE molecules attached ("DAR6" peak) and eight MMAE molecules attached ("DAR8" peak) and has an average DAR of 4. Using huM25 as an example, specific ADC preparations that comprise heterogeneous mixtures having an average DAR of 4 are designated herein with "DAR4," e.g., huM25-vcMMAE-DAR4.

Example 9. Preparation of huM25-vcMMAE ADCs Enriched in DAR2

Preparations of huM25-vcMMAE ADCs enriched DAR2 (referred to herein as "huM25-vcMMAE-E2") were obtained via hydrophobic interaction chromatographic ("HIC") resolution of the heterogeneous DAR ADC composition of Example 8. General methods for separating heterogeneous ADC mixtures and isolating specific homogeneous species such as the DAR2 and DAR4 peaks via HIC are described by Hamblen et al., 2004, Clin Cancer Res 10:7063-7070.

A chromatogram of the enriched huM25-vcMMAE E2 ADC preparation is shown in the bottom panel of FIG. 12. The preparation is approximately 98% pure in the DAR2 ADC. Using huM25 as an example, specific ADC preparations enriched in DAR2 are designated herein with "E2," e.g., huM25-vcMMAE-E2.

For the preparation of huM25-vcMMAE-E2, the heterogeneous DAR ADC material as described in Example 8 was adjusted to column-binding salt conditions by the addition of ⅓ volume of 4.5M $(NH_4)_2SO_4$ to give 110 mS conductivity. This load material was pumped onto a 2.6×150-cm column packed with 70 mL GE Butyl Sepharose-HP resin and equilibrated with Buffer A [1.5M $(NH_4)_2SO_4$, 20 mM sodium phosphate, pH 7], using a GE ÄKTAprime plus liquid chromatography system. After loading and washing to baseline, unconjugated antibody huM25 ("DAR0") was eluted with a 90 mS step-gradient blend of Buffers A and B (Buffer B=20 mM sodium phosphate, pH 7+25% isopropanol) (retention time=3 min). Next, huM25-vcMMAE-E2 was prepared by elution with a 60 mS step-gradient blend of Buffers A and B (retention time=4 min). The eluted pool of material enriched in huM25-vcMMAE-DAR2 was buffer exchanged and concentrated on a Pellicon® tangential-flow filtration system (membrane XL-30 kD) using 15 mM MES buffer pH 6.0 to afford the E2 preparation. Preparations of "E4" (enriched preparation of huM25-vcMMAE containing 4 MMAE molecules) and "E6" (enriched preparation of huM25-vcMMAE containing 6 MMAE molecules) and "E8" (enriched preparation of huM25-vcMMAE containing 8 MMAE molecules) can also be isolated with this gradient. Final material was quantified via absorbance at 280 nm, assessed for purity via HIC, and assessed for aggregation via size-exclusion chromatography ("SEC").

Example 10. huM25-vcMMAE-E2 ADC has Potent Efficacy Against LRRC15 Stromal(+)/Cancer(−) Tumors The potent anti-tumor activity of an exemplary anti-huLRRC15 ADC, huM25-vcMMAE-E2, against huLRRC15 stromal(+)/cancer(−) tumors was demonstrated in a xenograft model with EBC-1 (human squamous NSCLC) cells. For the experiments, five million cells (EBC-1) that were grown in vitro were inoculated subcutaneously per mouse into the right flank of female SCID-Beige mice. Tumors were size matched at ~200 $mm^3$, and dosed intraperitoneally (IP) Q4D×6 (1 dose given every 4 days for a total of 6 doses) as shown in FIG. 13A. Measurements of the length (L) and width (W) of the tumors were taken via electronic caliper and the volume was calculated according to the following equation: $V=L×W^2/2$. In mice treated at 6 mg/kg, maximum tumor growth inhibition ($TGI_{max}$) of 97% and tumor growth delay (TGD) of 305% was noted for huM25-vcMMAE-E2 treatment, which was significantly improved (p<0.001) compared to treatment with isotype control antibody or corresponding isotype control conjugate administered at the same regimen (FIG. 13A).

Other exemplary anti-huLRRC15 ADCs, huAD208.4.1-vcMMAE-DAR4, huAD208.14.1-vcMMAE-DAR4, and huM25-vcMMAE-DAR4 are also active in this EBC-1 xenograft model. For this experiment, tumors were size matched at ~200 $mm^3$, and dosed intraperitoneally (IP) Q7D×2 (1 dose given every 7 days for a total of 2 doses) as shown in FIG. 13C. In mice treated at 3 mg/kg, huAD208.4.1-vcMMAE-DAR4, huAD208.14.1-vcMMAE-DAR4 and huM25-vcMMAE-DAR4 exhibited $TGI_{max}$ values of 90%, 84% and 88%, respectively. Tumor growth delays of 129%, 114% and 129% was noted for huAD208.4.1-vcMMAE-DAR4, huAD208.14.1-vcMMAE-DAR4 and huM25-vcMMAE-DAR4 respectively, which was significantly improved (p<0.001) compared to treatment with isotype control antibody or corresponding isotype control conjugate administered at the same regimen (FIG. 13C).

The potent anti-tumor activity of huM25-vcMMAE-E2 was also demonstrated in a xenograft model with HPAF-II (human pancreatic) cells. For the experiment, 1 million cells (HPAF-II) that were grown in vitro were inoculated subcutaneously per mouse into the right flank of female SCID-Beige mice. Tumors were size matched at ~200 mm³, and dosed intraperitoneally (IP) Q4Dx6 (1 dose given every 4 days for a total of 6 doses) as shown in FIG. 13B. In mice treated at 6 mg/kg, a $TGI_{max}$ of 76% and a tumor growth delay of 133% was noted, which was significantly improved (p<0.001) compared to treatment with isotype control antibody or corresponding isotype control conjugate administered at the same regimen (FIG. 13B).

The anti-huLRRC15 ADC huM25-vcMMAE-E2 displays potent anti-tumor activity in differing tumor models (FIG. 13A, 13B). Anti tumor efficacy was observed for several anti-huLRRC15 ADCs (FIG. 13C). The efficacies of huAD208.4.1-vcMMAE-DAR4, huAD208.14.1-vcMMAE-DAR4 and huM25-vcMMAE-DAR4 were similar in magnitude ($TGI_{max}$) and duration (TGD) when dosed at 3 mg/kg in EBC1 tumors (FIG. 13C). The efficacies were significantly improved (p<0.001) compared to treatment with an isotype control antibody or a corresponding isotype control conjugate administered at the same regimen.

No anti-tumor activity was observed with huM25-vcMMAE-DAR4 in the xenograft model HCC-827-ER (NSCLC), even though robust huLRRC15 expression was observed by IHC (3+ score). In this experiment, 2 million cells (HCC-827-ER) that were grown in vitro were inoculated subcutaneously per mouse into the right flank of female SCID-Beige mice. Tumors were size matched at ~200 mm³, and dosed intraperitoneally (IP) Q4Dx6 (1 dose given every 4 days for a total of 6 doses), and no significant anti-tumor activity was observed (FIG. 13D).

Example 11. Anti-huLRRC15 ADCs are Active Against Large Tumors that Regrow Following Earlier Rounds of Treatment To demonstrate that tumors that regrow post treatment with anti-huLRRC15 ADCs are sensitive to anti-huLRRC15 ADCs, tumors were treated with an anti-huLRRC15 ADC, permitted to regrow and retreated. For the experiment, SUM190PT human breast cancer cells (developed from a primary human ER negative and PR negative breast cancer tumor) were grown to passage three in vitro. Five million cells per mouse were inoculated subcutaneously into the right flank of female SCID mice. Tumors were size matched at ~250 mm³, antibodies and immunoconjugates were administered IP Q4Dx4 (one dose give every 4 days for a total of 4 doses) at 10 or 3 mg/kg, respectively. At Day 70 post sizematch when tumors had regrown to ~650 mm³, animals were retreated with huM25-vcMMAE-DAR4 IP Q4Dx6 (one dose given every 4 days for a total of 6 doses) at 6 mg/kg. Some large tumors at time of retreatment were harvested for immunohistochemistry assessment of huLRRC15 expression.

Results are shown in FIG. 14. Maximum tumor growth inhibition ($TGI_{max}$) of 77% was observed for initial treatment with huM25-vcMMAE-DAR4, which was significantly (p<0.001) better than the isotype control antibody or corresponding isotype control conjugate administered at the same regimen.

Following retreatment after growth, tumor regression was again observed, indicating tumors remained sensitive to huM25-vcMMAE-DAR4, with an overall TGD of 133% (p<0.01). Expression of huLRRC15 was retained in these previously treated tumors. These findings suggest that because huLRRC15 is expressed on non-cancerous fibroblasts within the tumor, the huLRRC15 antigen is not under the same genetic selective pressure as the cancer cells, allowing the tumors to retain sensitivity to anti-huLRRC15 ADCs.

Example 12. Anti-huLRRC15 ADCs Exert Anti-Cancer Activity Against huLRRC15 Stromal(+)/Cancer(−) Tumors at Least in Part Via Bystander Effect The fact that anti-huLRRC15 ADCs comprising cell permeable cytostatic and/or cytotoxic agents effect anti-tumor activity via a bystander killing effect was demonstrated in EBC-1 squamous lung cancer xenografts with two anti-huLRRC15 ADCs: huM25-vcMMAE-E2 and huM25-mcMMAF-E2. MMAE is capable of traversing cell membranes. Closely related monomethyl auristatin F ("MMAF") is not.

The ADC huM25-mcMMAF-E2 was prepared in a manner analogous to the protocol described for huM25-vcMMAE-E2 in Examples 8 and 9. The structure of the linker-drug moiety mcMMAF is:

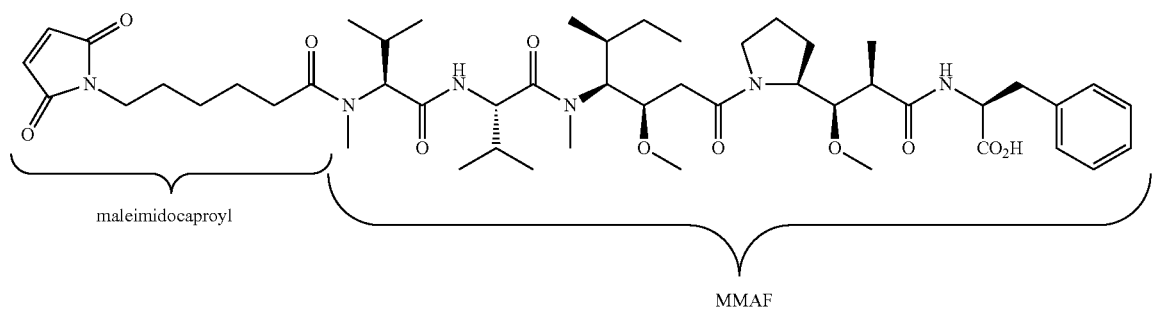

For the experiments, 5 million EBC-1 cells grown in vitro were implanted per mouse into the right flank of SCID-beige mice. Tumors were size-matched at ~300 mm³ and treated on day 0 and day 4 with 6 mg/kg intraperitoneally for each biologic drug shown in FIG. 15A. Tumors were harvested from the mice in each group 11 days post randomization and start of treatment. Tumors were dissociated into single cell suspensions using Miltenyi Biotec gentleMACS Dissociator according to the manufacturer's guidelines for the dissociation of tough tumors. Dissociated tumor cells were passed through a 70 μm filter, counted, and immediately used for flow cytometry. Single-cell suspensions were resuspended in PBS with 10% FBS and 10 μg/mL FcR block (anti-mouse CD16/CD32, clone 93, eBioscience, Cat.#16-0161.) The following directly conjugated antibodies were used for flow cytometry: human $IgG_1$ κ isotype control (AB095) AF647, anti-huLRRC15 (hu208.4.1a. 1a) AF647, anti-FAP (huFAP MAB5) AF647, mouse anti-human CD326 (EPCAM) PE (clone 1B7, eBioscience, Cat.#12-9326), anti-mouse CD11b PE (clone M1/70, eBioscience, Cat.#12-0112), anti mouse CD11c PE (clone N418, eBioscience, Cat.#12-0114), and anti-mouse F4/80 PE (clone BM9, eBioscience, Cat.#12-4801). Ex vivo EBC1 tumor cell suspensions were incubated with fluor-conjugated antibodies for 20 minutes on ice and washed twice using PBS with 1% FBS. Flow cytometry data were collected using a Becton Dickinson FacsCalibur, and data were analyzed using FlowJo™ analysis software (TreeStar). The ex vivo flow cytometry data (FIGS. 15B-15E) are shown as a percentage of cells gated positive for each antigen relative to total live cells gated via FSC/SCC. It should be noted that percentages reported are relative values to the total ex vivo EBC1 tumor and that a reduction in one cell population (e.g., EPCAM positive cancer cells) would result in an inverse increase in remaining cell populations when this analysis method is used.

The data shown in FIGS. 15B-15E demonstrate that huM25-vcMMAE-E2 can result in cancer cell killing of cancer cells (e.g., EBC-1) which do not express the huLRRC15 antigen by targeting the delivery of the ADC to the neighboring huLRRC15 stromal positive cancer associated fibroblasts. When tumors were treated with huLRRC15 targeted ADCs containing the non-cell permeable highly structurally related payload MMAF, there was no in vivo anti-tumor activity. The cancer associated fibroblast population which is known to be huLRRC15 positive (FIG. 7), does not show a decrease in the percentage of fibroblasts found within the tumor (FIG. 15C). Therefore, the fibroblasts are acting as targeting and processing cells for the MMAE payload, which has a more profound growth inhibitory effect on the cancer cells than on the huLRRC15-expressing stromal fibroblasts. An increase in immune infiltrate (CD11c or F4/80 positive cells) was noted post treatment (FIGS. 15D-15E), indicating that this ADC increases the expression of specific immune cell populations within the tumor (e.g., antigen presenting cells). The finding that in vivo anti-huLRRC15 ADCs (e.g., huM25-vcMMAE-E2) increase the expression of specific immune populations within the tumor provide clear rationale for combining anti-huLRRC15 ADCs with immune targeted therapies.

Dissociated single-cell suspensions of the ex vivo EBC1 tumors shown in FIG. 15A were seeded at 120,000 live cells into tissue culture microscopy chamber slides. Cells were allowed to sit and incubate for 48 hours, and then fixed in 2% paraformaldehyde for 15 min at 37° C. The cells were washed with PBS and permeabilized using 0.3% Triton-X in PBS at 37° C. for 30 min. Cells were washed with PBS and blocked in 5% BSA for 30 min at 37° C. Cells were incubated with anti-α-SMA (clone 1A4 DAKO, Cat.#36962) and then detected with AlexaFluor AF594 (Life Technologies, Cat.# A21203) secondary antibody (2 μg/mL) for 30 min at 37° C. Subsequently, cells were stained using anti-human EpCAM-AF488 (Cell Signaling Technology, Cat.#5198) and washed 3× in PBS. Finally the slides were removed from the chambers and mounted with a coverslip using ProLong Diamond Anti-Fade with DAPI (Life Technologies, Cat.#36962). Image acquisition was performed using Zeiss Axiovision Software on a Zeiss Axiovert 200M inverted fluorescent microscope. Statistical differences between groups were determined using unpaired T tests in GraphPad Prism™. Representative images and graphing of cancer cell and fibroblast populations as counted by microscopy are shown in FIG. 15F. Similar to the observations in FIGS. 15B-15E, a significant decrease in cancer cells was noted following the treatment of EBC-1 tumors with huM25-vcMMAE-E2, while a fibroblast population continued to persist. Further, phosphohistone H3 (pHH3) staining indicated that after 72 hours, a higher number of mitotic figures were evident after huM25-vcMMAE-E2 treatment (FIG. 15G), indicating cell cycle arrest in mitosis. The percentage of pHH3 positive cells decreased with additional dosing and longer time (FIG. 15H) correlating with cancer cell death and tumor shrinkage (FIG. 15A). EBC-1 tumors at day 11 post-treatment showed enhanced staining for CD45 and F4/80 after treatment with huM25-vcMMAE-E2 as compared with isotype ADC (FIG. 15I).

The data shown in FIG. 15A-15I suggest that huM25-vcMMAE-E2 works at least in part via huLRRC15 targeted bystander activity from the MMAE payload. MMAE is a cell permeable payload which allows it to pass across cell membranes without active transport. The data shown suggest that MMAE ADCs that bind to huLRRC15 are internalized by the stromal fibroblasts releasing free MMAE which can then be passively taken up by neighboring cancer cells in a bystander fashion resulting in potent cancer cell killing. Localizing anti-huLRRC15 ADCs containing MMAE at a higher concentration within cancer stroma may also result in some non-specific release and cleavage of the valine-citrulline linker extracellularly, which can then cross cancer cell membranes and cause cell death. When the non-cell permeable payload MMAF was conjugated to huM25 and tested in EBC-1 cells, there was no apparent activity, suggesting the cell permeable properties of MMAE is required for huM25-vcMMAE-E2's targeted bystander in vivo activity.

A panel of human tumors shown in FIG. 16 was stained by IHC for the proliferation marker Ki67. The Ki67 positive cancer and stromal cell populations within each tumor were separately counted and graphed. The data show that, in general, cancer cells within several distinct tumor types (e.g., colon, breast, lung, pancreatic, ovarian, melanoma, renal) have a much higher proliferative rate (Ki67 positive) than stromal cells. Since the MMAE payload requires cells to enter mitosis in order to induce mitotic arrest and subsequent cell death, the MMAE payload is going to be more efficacious against rapidly dividing cells (e.g., cancer cells) than slower dividing stromal cells (e.g., fibroblasts).

The data shown in FIG. 17A demonstrate that the non-cell permeable payload MMAF can kill huLRRC15 expressing cancer cells in vitro (e.g., HCT116-huLRRC15) when conjugated to huM25 ($EC_{50}$=0.028 nM), with a potency that is similar to that seen for huM25-vcMMAE-E2 ($EC_{50}$=0.069 nM). These data therefore demonstrate that the huM25-mcMMAF ADC is capable of being efficiently internalized and processed within a cell to release the highly potent anti-mitotic payload MMAF. However, when this same huM25-mcMMAF-E2 ADC was tested in vivo in the PANC1 (3+huLRRC15 stromal positive, cancer negative) tumor model (FIG. 17B), the ADC did not display any in vivo activity, while huM25-vcMMAE-E2 exhibited potent anti-tumor efficacy ($TGI_{max}$ of 94.4%). These findings suggest that huM25-vcMMAE-E2 works at least in part via huLRRC15 targeted bystander activity that relies on MMAE's cell permeable characteristics to kill the cancer cells within the tumor mass.

Example 13. E2 ADCs have Equal or Better Therapeutic Index

The safety profiles of E2, E4 and E2/E4 preparations of huM25-vcMMAE ADCs were assessed in a rat tolerability experiment (FIG. 18A-18B). For the assay, Sprague Dawley wild type rats were dosed with a single IV dose at MMAE equivalent levels of each antibody drug conjugate. Death occurred earlier (day 3/4) and at a higher percentage (50%) with huM25-vcMMAE-E4 than was seen for huM25-vcM-MAE-E2 (day 8, 25%). Double the protein antibody dose was delivered with equal amounts of MMAE, and improved survival for E2 was seen over E4. Fewer deaths occurred in the animals dosed with E2 than E4 ADCs, and the deaths that did occur happened later on Day 8. Broad drug distribution DAR4 has an MTD of 20 mg/kg. Weight loss was not significant for huM25-vcMMAE-E2 when dosed at 60 mg/kg, but there was increased weight loss for rats dosed at the MMAE equivalent dose level of 30 mg/kg with huM25-vcMMAE-E4 (FIG. 18B). This observation demonstrates that higher drug loaded anti-huLRRC15 ADCs are not as well tolerated as when a higher protein dose is delivered with a lower MMAE drug antibody ratio such as 2 cytostatic and/or cytotoxic agents per antibody (E2).

Four preparations of huM25-vcMMAE that differed in their relative DAR profile (E2, E2/E4, E4 or DAR4) were tested for efficacy in EBC1 tumors. 5 million cells were implanted subcutaneously into SCID/Beige mice, and mice were randomized when tumor group mean volumes reached ~200 mm³. HuM25-vcMMAE was administered intraperitoneally at MMAE-equivalent doses every seven days for a total of two doses. Maximum tumor growth inhibition ($TGI_{max}$) of ≥89% and tumor growth delay of 123% was noted in all groups treated with huM25-vcMMAE, which was significantly (p<0.001) better than the isotype control antibody or corresponding isotype control conjugate administered at the same regimen (FIG. 19). All doses were well tolerated and no significant body weight reductions were observed (data not shown). Efficacy in the EBC1 tumor model for huM25-vcMMAE-E2 was comparable to huM25-vcMMAE-E2E4 (i.e., the E2/E4 preparation of huM25-vcMMAE), huM25-vcMMAE-E4 and huM25-vcMMAE-DAR4 indicating that higher order DAR is not required for optimal anti-tumor potency and that higher antibody dosing is possible with huM25-vcMMAE-E2. huM25-vcMMAE-E2 had comparable or slightly better efficacy than huM25-vcMMAE-DAR4 in similar xenograft assays carried out with NCI-H226, PANC1 and HPAF-II tumors (data not shown).

The ability to administer more MMAE by dosing a higher total antibody dose with a lower drug antibody ratio (DAR) of E2 resulted in less toxicity than when dosing with a lower antibody dose with a higher drug antibody ratio (e.g., E4) was shown in rat tolerability studies (FIG. 18A, 18B). Also FIG. 19 shows that using a lower drug-antibody ratio of E2 provides just as much anti-tumor efficacy as ADC preparations containing a higher drug load (e.g., E2/E4, DAR4, E4) when dosed at MMAE equivalent levels. Taken together these data demonstrate that an improved therapeutic index can be achieved by using anti-huLRRC15 ADCs containing 2 drug/linkers per antibody compared to an ADC preparation containing a higher DAR (e.g., DAR4, E4). These data suggest that anti-huLRRC15 ADCs containing a lower DAR will be able to be dosed clinically at higher levels than ADCs containing a higher DAR (e.g., DAR4 or E4) and will have an improved therapeutic index.

Example 14. Anti-huLRRC15 ADCs are Superior to Current Standards of Care

The potency of anti-huLRRC15 ADCs as compared to current standards of care was assessed in xenograft models with NCI-H1650 (squamous NSCLC), HN5 (head and neck), EBC-1 (squamous NSCLC), NW231 (breast) and PANC1 (pancreatic) cancer cells. Anti-huLRRC15 ADC huM25-vcMMAE-E2 was compared to erlotinib, carboplatin, cetuximab, doxorubicin and gemcitabine. Standard of care agents were dosed at maximally efficacious or maximally tolerated dose levels. For FIG. 20A, NCI-H1650 cells (5 million cells) were implanted subcutaneously into SCID/Beige mice and tumors were randomized when they reached ~200 mm³ and dosed with biologics at 6 or 12 mg/kg intraperitoneally on a Q4D×6 (one dose given every 4 days for a total of 6 doses), while erlotinib was dosed orally daily for 10 days at 100 mg/kg, and carboplatin was dosed intraperitoneally Q4D×4 (one dose given every 4 days for a total of 4 doses) at 50 mg/kg. The anti-tumor efficacy for huM25-vcMMAE-E2 ($TGI_{max}$ of 92%, TGD of 450%) was superior to that seen for either erlotinib ($TGI_{max}$ of 90%, TGD of 77%) or carboplatin ($TGI_{max}$ of 56%, TGD of 77%).

Figure 20B:
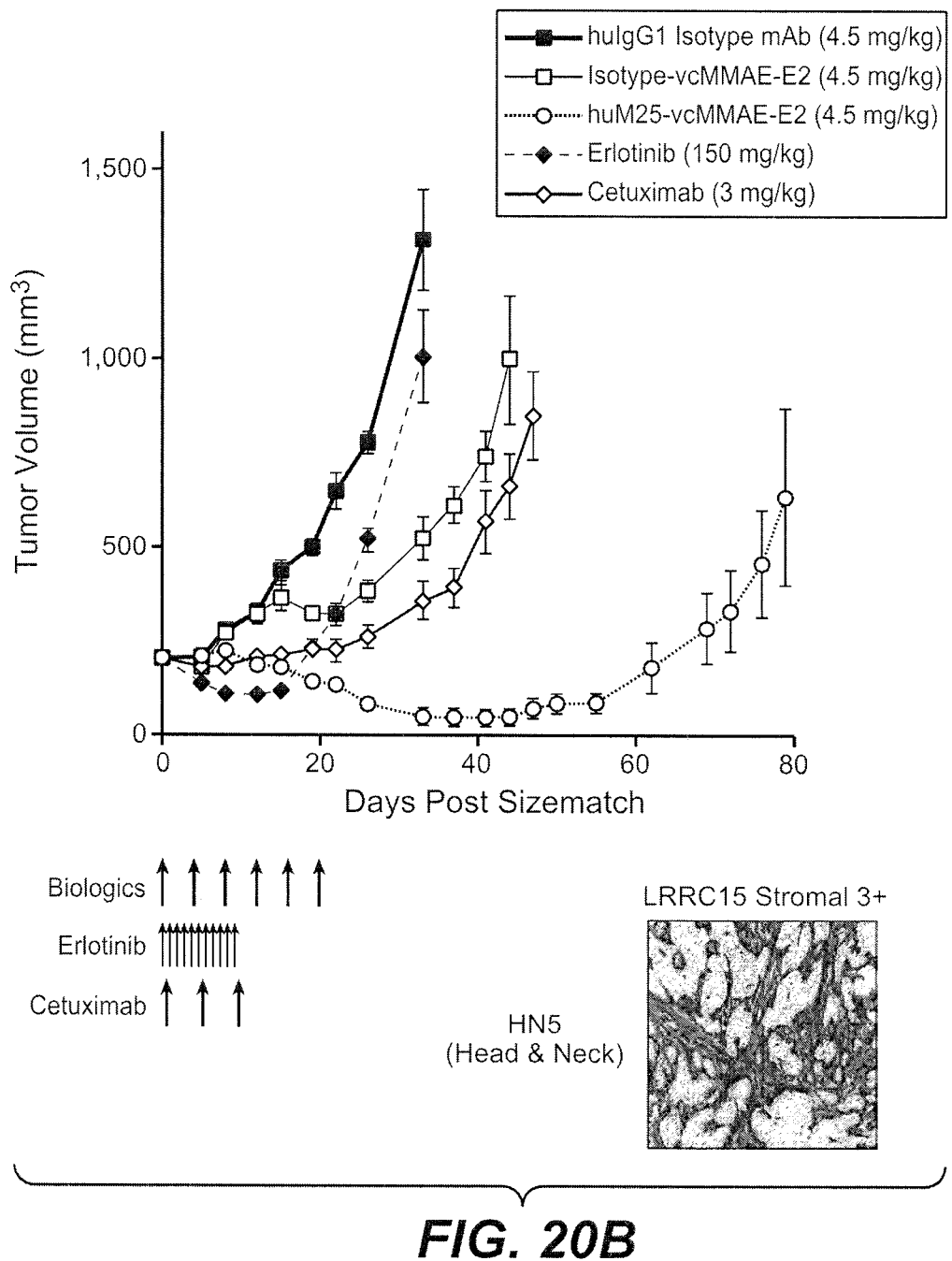

In FIG. 20B, HN5 cells (5 million) were implanted subcutaneously into NSG mice, and mice were randomized when the tumor group mean volumes reached ~200 mm³ and dosed with isotype mAb or ADCs at 4.5 mg/kg intraperitoneally on a Q4D×6 (one dose given every 4 days for a total of 6 doses), while erlotinib was dosed orally daily for 10 days at 150 mg/kg, and cetuximab was dosed intraperitoneally Q7D×3 (one dose given every 7 days for a total of 3 doses) at 3 mg/kg. The anti-tumor efficacy for huM25-vcMMAE-E2 ($TGI_{max}$ of 96%, TGD of 194%) was superior to that seen for either erlotinib ($TGI_{max}$ of 23%, TGD of 12%) or cetuximab ($TGI_{max}$ of 73%, TGD of 59%).

In FIG. 20C, EBC1 cells (5 million) were implanted subcutaneously into SCID/Beige mice and mice were randomized when the tumors reached ~200 mm³ and dosed with biologics at 6 mg/kg intraperitoneally on a Q7D×2 (one dose given every 7 days for a total of 2 doses), while erlotinib was dosed orally daily for 10 days at 50 mg/kg, and carboplatin was dosed intraperitoneally Q4D×3 (one dose given every 4 days for a total of 3 doses) at 50 mg/kg. The anti-tumor efficacy for huM25-vcMMAE-E2 ($TGI_{max}$ of 92%+, TGD of 129%) was superior to that seen for either erlotinib ($TGI_{max}$ of 27%, TGD of 14%) or carboplatin ($TGI_{max}$ of 39%, TGD of 43%).

Figure 20D:
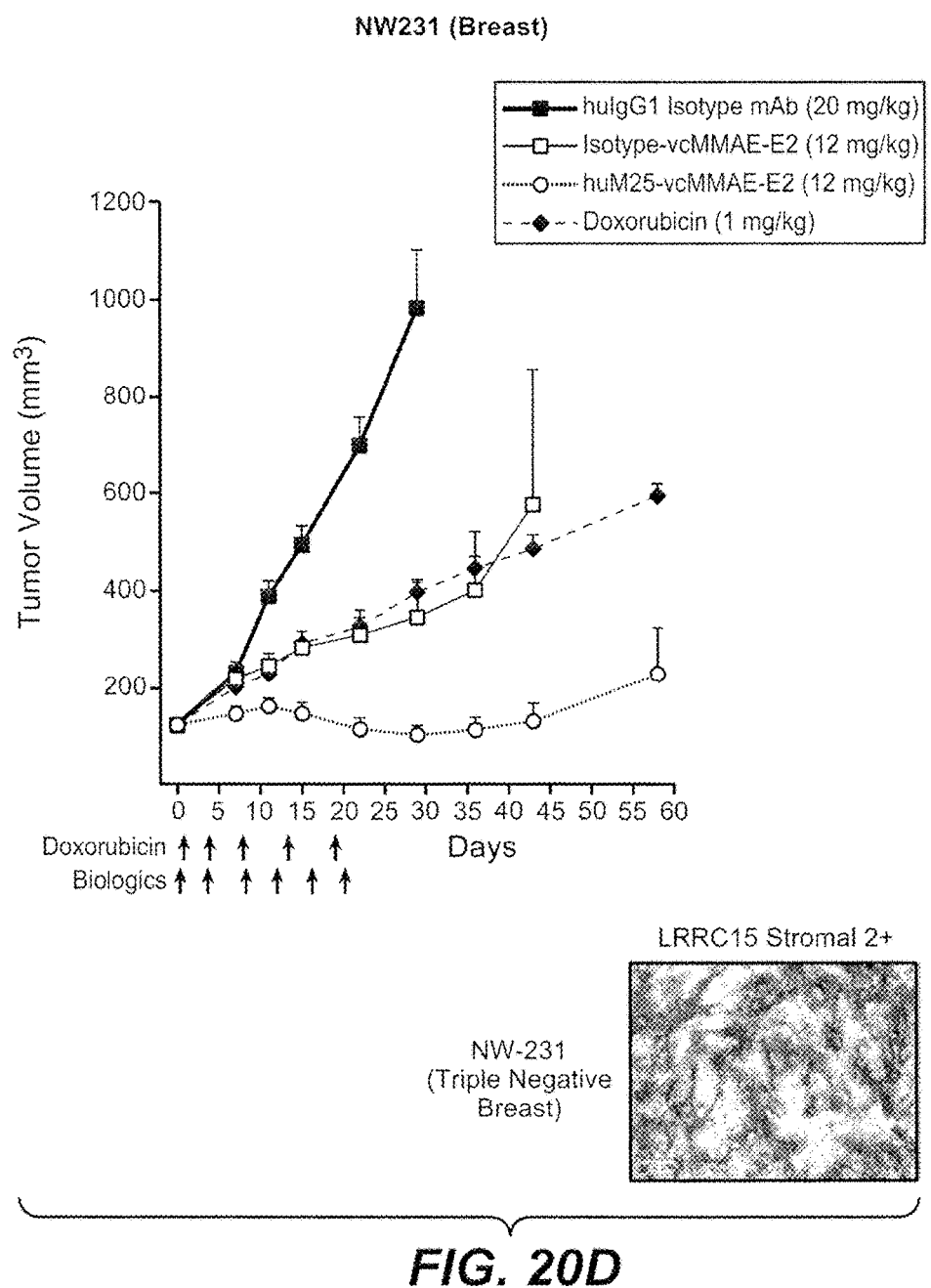

In FIG. 20D, NW231 breast cancer cells (10 million) were implanted subcutaneously into SCID mice, and mice were randomized when the tumors reached ~150 mm³ and dosed with biologics at 12 mg/kg intraperitoneally on a Q4D×6 (one dose given every 4 days for a total of 6 doses), while doxorubicin was dosed intravenously at 1 mg/kg on days 0, 4, 8, 13 and 18. The anti-tumor efficacy for huM25-vcM-MAE-E2 ($TGI_{max}$ of 89%) was superior to that seen for doxorubicin ($TGI_{max}$ of 65%).

In FIG. 20E, PANC1 pancreatic cancer cells (10 million) were implanted subcutaneously into SCID mice, and mice were randomized when the tumors reached ~125 mm³ and dosed with biologics at 12 mg/kg intraperitoneally on a Q4D×6 (one dose given every 4 days for a total of 6 doses), while gemcitabine was dosed intraperitoneally at 100 mg/kg Q3D×4) (one dose given every three days for 4 doses total). The anti-tumor efficacy for huM25-vcMMAE-E2 ($TGI_{max}$ of 94%) was superior to that seen gemcitabine ($TGI_{max}$ of 55%).

The in vivo efficacy data shown in FIG. 20A-20E provides examples of where anti-huLRRC15 ADCs such as huM25-vcMMAE-E2 outperformed standard of care agents (e.g., carboplatin, erlotinib, gemcitabine, cetuximab, doxorubicin) commonly used in cancer therapy. This data suggests that anti-huLRRC15 ADCs (e.g., huM25-vcMMAE-E2) may be more clinically efficacious than certain commonly used anti-cancer therapies.

Example 15. Anti-huLRRC15 ADCs are Active when Administered Adjunctive to Cytotoxic Anti-Cancer Treatments The anti-tumor efficacy of anti-huLRRC15 ADCs administered adjunctive to radiation and other non-targeted chemotherapeutic agents (e.g., gemcitabine, docetaxel, carboplatin) was demonstrated in xenograft models with HPAF-II (pancreatic), EBC-1 (squamous NSCLC) and SCC-15 (head and neck) cells. Improved antitumor activity was seen when anti-huLRRC15 ADCs (e.g., huM25-vcMMAE-E2) were adjunctively administered with these cytotoxic anti-cancer treatments. The efficacy of adjunctive treatment was better than the efficacy seen for either drug alone.

In FIG. 21A, HPAF-II pancreatic cancer cells (1 million) were implanted subcutaneously into SCID mice, and mice were randomized when the tumors reached ~200 mm³ and dosed with biologics at 6 mg/kg intraperitoneally on a Q4D×6 (one dose given every 4 days for a total of 6 doses), while gemcitabine was dosed intraperitoneally at 100 mg/kg (Q3D×4)×2 (one dose given every three days for 4 doses per cycle, 2 cycles with 8 total doses given). In this model at the doses tested, the anti-tumor efficacy seen for huM25-vcMMAE-E2 ($TGI_{max}$ of 57%, TGD of 57%) and gemcitabine ($TGI_{max}$ of 73%, TGD of 117%) increased when used adjunctively ($TGI_{max}$ of 85%, TGD of 183%) to achieve better efficacy than was seen for either single agent alone.

In FIG. 21B, EBC-1 squamous NSCLC cells (5 million) were implanted subcutaneously into SCID/Beige mice, and mice were randomized when the tumors reached ~200 mm³ and dosed with biologics at 6 mg/kg intraperitoneally on a Q7D×2 (one dose given every 7 days for a total of 2 doses), while gemcitabine was dosed intraperitoneally at 100 mg/kg (Q3D×3) (one dose given every three days for 3 doses total). In this model at the doses tested, the anti-tumor efficacy seen for huM25-vcMMAE-E2 at 3 mg/kg ($TGI_{max}$ of 91%, TGD of 144%) and docetaxel ($TGI_{max}$ of 77%, TGD of 48%) increased when used adjunctively ($TGI_{max}$ of 98%, TGD of 348%) to achieve better efficacy than was seen for either single agent alone.

The results shown in FIG. 21C highlight the improved activity when anti-huLRRC15 ADCs (e.g., huM25-vcMMAE-DAR4) are administered adjunctive with docetaxel. EBC-1 squamous NSCLC cells (5 million) were implanted subcutaneously into SCID/Beige mice, and mice were randomized when the tumors reached ~200 mm³ and dosed with biologics at 3 or 6 mg/kg intraperitoneally on a Q4D×6 (one dose given every 4 days for a total of 6 doses), while docetaxel was dosed intravenously once at 7.5 mg/kg Q3D×3 (one dose given every 3 days for a total of 3 doses). In this model at the doses tested, the anti-tumor efficacy seen for huM25-vcMMAE-DAR4 ($TGI_{max}$ of 92%, TGD of 129%) and gemcitabine ($TGI_{max}$ of 95%, TGD of 171%) increased when used adjunctively ($TGI_{max}$ of 98%, TGD of 533%) to achieve better efficacy than was seen for either single agent alone.

Radiation is a commonly used cytotoxic therapy in oncology. Data shown in FIG. 21D highlight the improved activity when anti-huLRRC15 ADCs (e.g., huM25-vcMMAE-E2) are administered adjunctive to radiation therapy. SCC-15 head and neck cancer cells (1 million) were implanted subcutaneously into SCID mice, and mice were randomized when the tumors reached ~200 mm³ and dosed with biologics at 12 mg/kg intraperitoneally on a Q4D×6 (one dose given every 4 days for a total of 6 doses), while the radiation was directed at the tumor with a single radiation dose of 15 Gy on day 0. In this model at the doses tested, the anti-tumor efficacy seen for huM25-vcMMAE-E2 ($TGI_{max}$ of 58%, TGD of 44%) and radiation ($TGI_{max}$ of 66%, TGD of 88%) increased when used adjunctively ($TGI_{max}$ of 90%, TGD of 219%) to achieve better efficacy than was seen for either single agent alone.

The results shown in FIG. 21E highlight the improved activity when anti-huLRRC15 ADCs (e.g., huM25-vcMMAE-E2) are administered adjunctive to carboplatin. SCC-15 head and neck cancer cells (1 million) were implanted subcutaneously into SCID mice, and mice were randomized when the tumors reached ~200 mm³ and dosed with biologics at 12 mg/kg intraperitoneally on a Q7D×6 (one dose given every 7 days for a total of 6 doses), while carboplatin was dosed intraperitoneally once at 50 mg/kg Q4D×4 (one dose given every 4 days for a total of 4 doses). In this model at the doses tested, the anti-tumor efficacy seen for huM25-vcMMAE-E2 ($TGI_{max}$ of 58%, TGD of 44%) and carboplatin ($TGI_{max}$ of 56%, TGD of 33%) increased when used adjunctively ($TGI_{max}$ of 86%, TGD of 83%) to achieve better efficacy than was seen for either single agent alone.

The data outlined in FIG. 21A-21E demonstrate that anti-huLRRC15 ADCs used adjunctive to cytotoxic anti-cancer agents (e.g., gemcitabine, docetaxel, carboplatin, radiation) have improved efficacy as compared to each agent alone. This suggests that anti-huLRRC15 ADCs such as huM25-vcMMAE-E2 when administered adjunctive to cytotoxic anti-cancer agents may be more effective in cancer patients than either agent alone.

Example 16. Anti-huLRRC15 ADCs are Active when Administered Adjunctive to Other Targeted Anti-Cancer Agents The anti-tumor efficacy of anti-huLRRC15 ADCs administered adjunctive to other targeted chemotherapeutic agents (e.g., erlotinib, cetuximab, anti-PD-1 antibody) was demonstrated in xenograft models with NCI-H1650 (adeno NSCLC), HN5 (head & neck), SCC-15 (head & neck) and MC38 (mouse syngeneic colorectal) cancer cells. Improved antitumor activity was seen when anti-huLRRC15 ADCs (e.g., huM25-vcMMAE-E2) were administered adjunctive to these targeted anti-cancer treatments. The adjunctive efficacy was better than the efficacy of either drug alone.

The results shown in FIG. 22A highlight the improved activity when anti-huLRRC15 ADCs (e.g., huM25-vcMMAE-E2) are administered adjunctive to erlotinib. NCI-H1650 NSCLC cancer cells (5 million) were implanted subcutaneously into SCID/Beige mice, and mice were randomized when the tumors reached ~200 mm³ and dosed with biologics at 6 or 12 mg/kg intraperitoneally on a Q4D×6 (one dose given every 4 days for a total of 6 doses), while erlotinib was dosed orally daily at 100 mg/kg for 10 doses. In this model at the doses tested, the anti-tumor efficacy seen for huM25-vcMMAE-E2 ($TGI_{max}$ of 92%, TGD of 450%) and erlotinib ($TGI_{max}$ of 90%, TGD of 77%) increased when used adjunctively ($TGI_{max}$ of 92%, TGD of >538%) to achieve better efficacy than was seen for either single agent alone.

The results shown in FIG. 22B highlight the improved activity when anti-huLRRC15 ADCs (e.g., huM25-vcM-MAE-E2) are administered adjunctive to cetuximab. SCC-15 head and neck cancer cells (1 million) were implanted subcutaneously into SCID mice, and mice were randomized when the tumors reached ~200 mm³ and dosed with isotype antibodies or ADCs at 12 mg/kg intraperitoneally on a Q7D×6 (one dose given every 7 days for a total of 6 doses), while cetuximab was dosed intraperitoneally at 3 mg/kg Q7D×3 (one dose given every 7 days for a total of 3 doses). In this model at the doses tested, the anti-tumor efficacy seen for huM25-vcMMAE-E2 ($TGI_{max}$ of 58%, TGD of 44%) and cetuximab ($TGI_{max}$ of 66%, TGD of 58%) increased when used adjunctively ($TGI_{max}$ of 87%, TGD of 125%) to achieve better efficacy than was seen for either single agent alone.

The results shown in FIG. 22C highlight the improved activity when anti-huLRRC15 ADCs (e.g., huM25-vcM-MAE-E2) are administered adjunctive to anti-PD-1 targeted agents, such as an anti-PD-1 antibody. Exemplary anti-PD-1 antibodies include those described in U.S. provisional application No. 62/394,314, such as the anti-PD-1 antibody having a heavy chain amino acid sequence of SEQ ID NO:91 or 92, and a light chain amino acid sequence of SEQ ID NO:93, used in this Example.

($TGI_{max}$ of 87%) than either agent alone. Given that huM25-vcMMAE-E2 did not have single agent activity in this model the improved activity when used adjunctively with anti-PD-1 antibody was unexpected. This novel finding suggests that anti-huLRRC15 ADCs, when used adjunctively with immune modulating agents such as anti-PD-1 antibody may have improved anti-cancer activity over either agent alone.

The data outlined in FIG. 22A-22C demonstrate that anti-huLRRC15 ADCs administered adjunctive to targeted anti-cancer agents (e.g., anti-PD-1 antibody, erlotinib, cetuximab) have improved efficacy as compared to each agent alone. This suggests that anti-huLRRC15 ADCs such as huM25-vcMMAE-E2 may be more effective clinically when used adjunctively to targeted anti-cancer agents in cancer patients than either agent alone.

Example 17. Anti-huLRRC15 ADCs Comprising DNA-Damaging Payloads are Active

The potent anti-tumor activity of anti-huLRRC15 ADCs comprising DNA-damaging cytostatic and/or cytotoxic agents against several types of huLRRC15 stromal(+)/cancer(−) tumors was demonstrated with different exemplary ADCs in xenograft models with EBC-1 (squamous NSCLC), NCI-H1650 (adeno NSCLC), HN-5 (head and neck), HPAF-II (pancreatic) and PANC-1 (pancreatic) cancer cells.

For the experiments, anti-huLRRC15 ADCs comprising a pyrrolobenzodiazepine dimer ("PBD") cytostatic and/or cytotoxic agent were prepared by conjugating the PBD synthon illustrated below ("vaPBD") with anti-huLRRC15 antibody huAD208.4.1 or an isotype control antibody to yield a DAR of 2. Preparation of the huAD208.4.1-PBD-DAR2 ADC was accomplished according to the procedure described in Example 8.

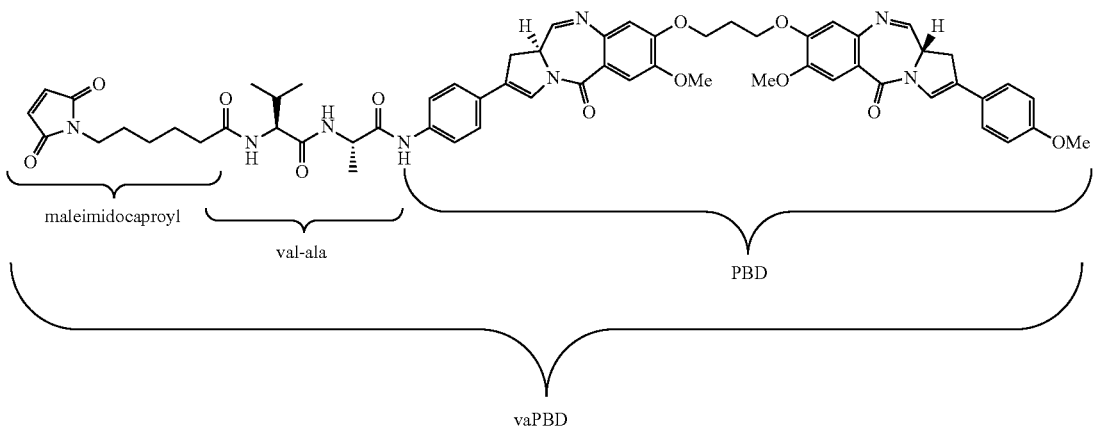 [SMILES: COc1ccc(C2=CN3C(=O)c4cc(OC)c(OCCCOc5cc6c(cc5OC)C(=O)N5C=C(c7ccc(NC(=O)[C@H](C)NC(=O)[C@@H](NC(=O)CCCCCN8C(=O)C=CC8=O)C(C)C)cc7)C[C@H]5C=N6)cc4N=C[C@@H]3C2)cc1 ; "PBD" ; "vaPBD"]

MC-38 mouse colorectal cancer cells (250,000) were implanted subcutaneously into C57BL/6 mice, and mice were randomized when the tumors reached ~100 mm³ and dosed with isotype antibodies or ADCs at 12 mg/kg intraperitoneally on a Q4D×6 (one dose given every 4 days for a total of 6 doses), while the anti-PD-1 antibody ("Anti-PD1 mAb") was dosed intraperitoneally at 2 mg/kg Q4D×6 (one dose given every 4 days for a total of 6 doses). In this model huM25-vcMMAE-E2 did not show single agent activity, while the anti-PD-1 antibody alone did display efficacy ($TGI_{max}$ of 67%). huM25-vcMMAE-E2 administered adjunctively with anti-PD-1 antibody was more efficacious In an analogous manner, PBD-containing ADCs were prepared with huM25 comprising an engineered S239C mutation in the constant region ("huM25-S239C") to allow for preferential generation of a DAR2 ADC with vaPBD shown above. As used herein, huM25-S239C refers to an anti-huLRRC15 antibody or ADC having a heavy chain amino acid sequence according to SEQ ID NO:100 or 103, and a light chain amino acid sequence according to SEQ ID NO:19. Accordingly, ADCs comprising the S239C mutation did not require chromatographic separation in order to exhibit enrichment in ADCs having DAR2. Hence, the ADCs prepared comprising a huLRRC15 antibody and S239C mutation, including those comprising huM25-S239C, are referred to herein as "E2."

FIG. 23A shows that in vitro cell killing of 3T12-huL-RRC15 transfected cells by huLRRC15-targeting ADC huM25-S239C-PBD-E2 (i.e., the ADC formed with huM25 variable domains with S239C variant in the Fc region to allow for selective formation of DAR2 preparation of the vaPBD adduct) is significantly higher than that of isotype ADC isotype-S239C-PBD-E2 having the same Fc region and PBD drug displayed in the same manner. Such a result is presumably owing to the localization of the ADC huM25-S239C-PBD-E2 to the huLRRC15-expressing cell surface before being internalized and enzymatically processed to release the cytotoxic PBD agent.

Example 18. Anti-huLRRC15 PBD ADCs Kill Cells with Mesenchymal Properties

As described above in Example 7, cancer cells that have undergone EMT had an increased expression of huLRRC15 as compared to cells that had not undergone EMT. Data provided in the present Example show that this increased level of huLRRC15 expression correlated with an increased sensitivity to ADCs that targeted huLRRC15. As shown in FIGS. 23B and 23C, anti-LRRC15 ADC huAD208.4.1-PBD-DAR2, which was cross-reactive to human and mouse LRRC15, demonstrated cell killing effects in vitro against mesenchymal stem cells expressing LRRC15. In human BM-MSC (Lonza) treated with 10 ng/mL TGFβ, huAD208.4.1-PBD-DAR2 exhibited a higher cell killing effect than isotype-PBD-DAR2 at the same doses (FIG. 23B). A similar in vitro cell killing effect profile was also observed in murine Balb/c BM-MSC (Cyagen) treated with TGFβ (10 ng/mL) and each of the ADCs (FIG. 23C).

Additionally, FIG. 23D depicts experiments in which anti-huLRRC ADCs killed A549 lung cancer cells that have undergone epithelial-mesenchymal transition (EMT). Standard A549 cells did not show a viability difference after treatment with isotype-S239C-PBD-E2 or huM25-S239C-PBD-E2 (top graph). However, in A549-EMT transformed cells treated with TGFβ, the huLRRC15-specific ADC huM25-S239C-PBD-E2 exhibited a significantly higher cell killing effect than isotype ADC ($EC_{50}$=0.01 nM vs. 2.3 nM for isotype ADC) (bottom graph).

Example 19. Anti-huLRRC15 PBD ADCs Exhibit In Vivo Anti-Tumor Effects

The above Examples show that huLRRC15 expression was increased in certain cancer cells that have undergone EMT, and those cells were more sensitive to huLRRC15 ADCs in vitro. The data provided in the present Example demonstrate that the same huLRRC15 ADCs exhibit significant in vivo efficacy. FIG. 24A depicts the effect of treating SCID mice with EBC-1 squamous NSCLC tumors. EBC-1 squamous NSCLC cells (5 million) were implanted subcutaneously into SCID mice, and mice were randomized when the tumors reached ~175 mm³ and dosed with ADC or isotype antibody at 0.6 mg/kg intraperitoneally on day 0. With a single dose of ADC, huM25-S239C-PBD-E2 demonstrated significant anti-tumor effect after 13 days as compared to the same dose of isotype-S239C-PBD-E2 (p<0.01).

FIGS. 24B-24D depicts immunohistochemistry results from the in vivo experiment depicted in FIG. 24A, consistent with an immunological anti-tumor response. FIG. 24B shows images of exemplary tumor slices stained for α-SMA, a cancer-associated fibroblast marker, at 1× (top pictures) and 20× (bottom pictures) magnification. The samples were taken from mice dosed with isotype antibody (left), isotype-S239C-PBD-E2 ADC (middle) and huM25-S239C-PBD-E2 (right), showing 80%, 90%, and 60% α-SMA tumor positivity, respectively. The α-SMA quantification across samples is depicted in FIG. 24C, indicating a trend to lowering α-SMA upon treatment with huLRRC15-specific ADC. Additionally, FIG. 24D shows an increase in both F4/80 and CD11c expression with treatment of huLRRC15 ADC, suggesting an initiation of an immunological response within the tumor.

FIG. 24E depicts another exemplary embodiment of an ADC—huM25-S239C-PBD-E2—that comprised a DNA-damaging payload and led to anti-tumor activity in vivo in a NCI-H1650 xenograft model. NCI-H1650 NSCLC cancer cells (5 million) were implanted subcutaneously into SCID/Beige mice, and mice were randomized when the tumors reached ~200 mm³ and dosed on day 0 with isotype or ADC at 0.1, 0.3, or 0.6 mg/kg intraperitoneally. The ADC huM25-S239C-PBD-E2 showed a dose-dependent anti-tumor effect at 0.1, 0.3, and 0.6 mg/kg as compared with isotype antibody, when measured by tumor volume in number of days post sizematch and a single dose of the ADC.

FIG. 24F shows that the LRRC15-targeting ADC huM25-S239C-PBD-E2 induced a statistically significant anti-tumor effect on tumor volume in a NCI-H1650 xenograft model (p<0.05), when compared to the isotype ADC with the same DNA-damaging payload at the same concentration, consistent with targeted delivery of the huLRRC15 antibody component causing localization of the ADC, thereby allowing the DNA-damaging payload to enhance cancer cell killing.

FIG. 24G depicts another exemplary embodiment of an ADC—huAD208.4.1-PBD-DAR2—that comprised a DNA-damaging payload and led to anti-tumor activity in vivo. NCI-H1650 adeno NSCLC cells (5 million) were implanted subcutaneously into SCID/Beige mice, and mice were randomized when the tumors reached ~225 mm³ and dosed with ADC at 0.6 mg/kg or isotype antibody at 12 mg/kg intraperitoneally once on day 0. The anti-tumor efficacy for this anti-huLRRC15 PBD ADC ("huAD208.4.1-PBD-DAR2") was $TGI_{max}$ of 95%, and TGD of >388%.

In FIG. 24H, EBC-1 squamous NSCLC cells (5 million) were implanted subcutaneously into SCID mice, and mice were randomized when the tumors reached ~225 mm³ and dosed with ADC at 0.6 mg/kg Q7D×2 (one dose given every 7 days for a total of 2 doses) or isotype antibody at 6 mg/kg intraperitoneally starting on day 0. The anti-tumor efficacy of huAD208.4.1-PBD-DAR2 was $TGI_{max}$ of 91%, and TGD of >600%.

The potent anti-tumor activity shown in FIGS. 24A-24H with anti-huLRRC15 ADCs comprising the DNA-damaging cytostatic and/or cytotoxic agent PBD demonstrates that the huLRRC15 target may be used to deliver anti-huLRRC15 ADCs containing cytostatic and/or cytotoxic agents with differing mechanisms of action (e.g., DNA damage via pyrrolobenzodiazepine delivery) to the tumor site to elicit an anti-tumor response. These findings suggest different anti-huLRRC15 antibodies (e.g., huAD208.4.1, huM25, huAD208.14.1, hu139.10, muAD210.40.9, or muAD208.9.1) can be conjugated with differing cytostatic and/or cytotoxic agents to successfully deliver the agent(s) to a tumor and induce cancer growth inhibition.

9. EMBODIMENTS

1. An antibody or binding fragment thereof that specifically binds huLRRC15 extracellular domain, wherein said extracellular domain comprises the proteolytic cleavage site defined by Arg$^{527}$ and Ser$^{528}$ of SEQ ID NO:3.

2. The antibody or binding fragment of Embodiment 1 that competes for binding cells expressing human LRRC15 with a control antibody selected from huM25, huAD208.4.1, huAD208.12.1, huAD208.14.1, hu139.10, muAD210.40.9, and muAD209.9.1.

3. The antibody or binding fragment of Embodiment 1 in which the control antibody is huM25.

4. The antibody or binding fragment of Embodiment 1 in which the control antibody is huAD208.4.1.

5. The antibody or binding fragment of Embodiment 1, which comprises a $V_H$ chain having three CDRs in which:
$V_H$ CDR#1 corresponds in sequence to SEQ ID NO:10, $V_H$ CDR#2 corresponds in sequence to SEQ ID NO:11 and $V_H$ CDR#3 corresponds in sequence to SEQ ID NO:12;
$V_H$ CDR#1 corresponds in sequence to SEQ ID NO:20, $V_H$ CDR#2 corresponds in sequence to SEQ ID NO:21 and $V_H$ CDR#3 corresponds in sequence to SEQ ID NO:22;
$V_H$ CDR#1 corresponds in sequence to SEQ ID NO:30, $V_H$ CDR#2 corresponds in sequence to SEQ ID NO:31 and $V_H$ CDR#3 corresponds in sequence to SEQ ID NO:32;
$V_H$ CDR#1 corresponds in sequence to SEQ ID NO:40, $V_H$ CDR#2 corresponds in sequence to SEQ ID NO:41 and $V_H$ CDR#3 corresponds in sequence to SEQ ID NO:42;
$V_H$ CDR#1 corresponds in sequence to SEQ ID NO:50, $V_H$ CDR#2 corresponds in sequence to SEQ ID NO:51 and $V_H$ CDR#3 corresponds in sequence to SEQ ID NO:52;
$V_H$ CDR#1 corresponds in sequence to SEQ ID NO:60, $V_H$ CDR#2 corresponds in sequence to SEQ ID NO:61 and $V_H$ CDR#3 corresponds in sequence to SEQ ID NO:62; or
$V_H$ CDR#1 corresponds in sequence to SEQ ID NO:70, $V_H$ CDR#2 corresponds in sequence to SEQ ID NO:71 and $V_H$ CDR#3 corresponds in sequence to SEQ ID NO:72.

6. The antibody or binding fragment of Embodiment 1, which comprises a $V_L$ chain having three CDRs in which:
$V_L$ CDR#1 corresponds in sequence to SEQ ID NO:13, $V_L$ CDR#2 corresponds in sequence to SEQ ID NO:14 and $V_L$ CDR#3 corresponds in sequence to SEQ ID NO:15;
$V_L$ CDR#1 corresponds in sequence to SEQ ID NO:23, $V_L$ CDR#2 corresponds in sequence to SEQ ID NO:24 and $V_L$ CDR#3 corresponds in sequence to SEQ ID NO:25;
$V_L$ CDR#1 corresponds in sequence to SEQ ID NO:33, $V_L$ CDR#2 corresponds in sequence to SEQ ID NO:34 and $V_L$ CDR#3 corresponds in sequence to SEQ ID NO:35;
$V_L$ CDR#1 corresponds in sequence to SEQ ID NO:43, $V_L$ CDR#2 corresponds in sequence to SEQ ID NO:44 and $V_L$ CDR#3 corresponds in sequence to SEQ ID NO:45;
$V_L$ CDR#1 corresponds in sequence to SEQ ID NO:53, $V_L$ CDR#2 corresponds in sequence to SEQ ID NO:54 and $V_L$ CDR#3 corresponds in sequence to SEQ ID NO:55;
$V_L$ CDR#1 corresponds in sequence to SEQ ID NO:63, $V_L$ CDR#2 corresponds in sequence to SEQ ID NO:64 and $V_L$ CDR#3 corresponds in sequence to SEQ ID NO:65; or
$V_L$ CDR#1 corresponds in sequence to SEQ ID NO:73, $V_L$ CDR#2 corresponds in sequence to SEQ ID NO:74 and $V_L$ CDR#3 corresponds in sequence to SEQ ID NO:75.

7. The antibody or binding fragment of Embodiment 1 which comprises a $V_H$ chain corresponding in sequence to SEQ ID NO:16 and a $V_L$ chain corresponding in sequence to SEQ ID NO:17.

8. The antibody or binding fragment of Embodiment 1 which comprises a $V_H$ chain corresponding in sequence to SEQ ID NO:26 and a $V_L$ chain corresponding in sequence to SEQ ID NO:27.

9. The antibody or binding fragment of any one of Embodiments 1-7 which comprises a heavy chain corresponding in sequence to SEQ ID NO:18 and a light chain corresponding in sequence to SEQ ID NO:19.

10. The antibody of Embodiment 1 which is an IgG$_1$.

11. The antibody of Embodiment 1 having one or more reduced cysteine residues bearing a free sulfhydryl group.

12. An antibody drug conjugate ("ADC") comprising a cytotoxic and/or cytostatic agent linked to an antibody by way of a linker, wherein the antibody is an antibody according to any one of Embodiments 1-11, the cytotoxic and/or cytostatic agent is capable of traversing a cell membrane, and the linker is cleavable by a lysosomal enzyme.

13. The ADC of Embodiment 12 which has an average drug-to-antibody ratio in the range of 1-10.

14. The ADC of Embodiment 12 which has an average drug-to-antibody ratio in the range of 2-4.

15. The ADC of Embodiment 12 in which the lysosomal enzyme is Cathepsin B.

16. The ADC of Embodiment 15 in which the linker comprises a segment according to structural formula (IVa), (IVb), (IVc), or (IVd):

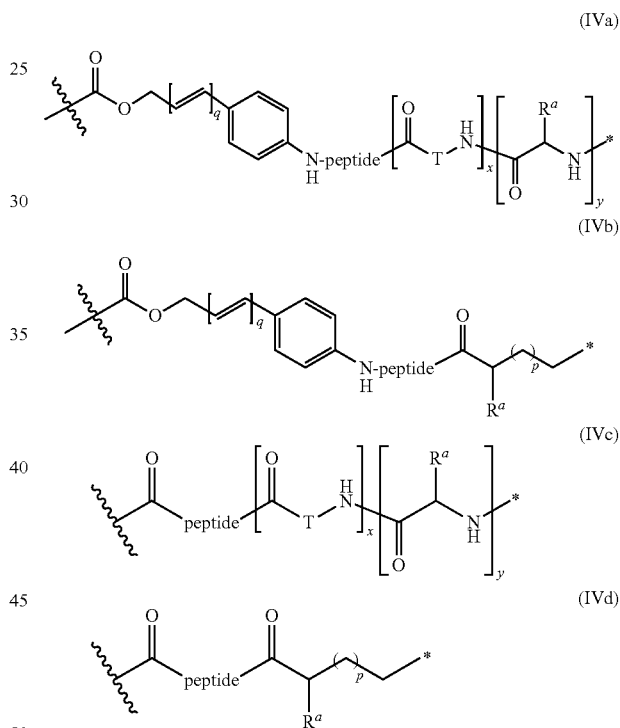

or a salt thereof, wherein:
peptide represents a peptide (illustrated C→N and not showing the carboxy and amino "termini") cleavable by a lysosomal enzyme;
T represents a polymer comprising one or more ethylene glycol units or an alkylene chain, or combinations thereof;
$R^a$ is selected from hydrogen, alkyl, sulfonate and methyl sulfonate;
p is an integer ranging from 0 to 5;
q is 0 or 1;
x is 0 or 1;
y is 0 or 1;
† represents the point of attachment of the linker to a cytotoxic and/or cytostatic agent; and
* represents the point of attachment to the remainder of the linker.

17. The ADC of Embodiment 16 in which peptide is selected from the group consisting of Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; and Val-Ala and salts thereof.

18. The ADC of Embodiment 12 in which the lysosomal enzyme is β-glucuronidase.

19. The ADC of Embodiment 12 in which the cytotoxic and/or cytostatic agent is MMAE.

20. The ADC of Embodiment 12 in which the cytotoxic and/or cytostatic agent is a PBD dimer.

21. The ADC of Embodiment 12 in which the antibody comprises three $V_H$ CDRs corresponding in sequence, respectively, to SEQ ID NO:10, SEQ ID NO:11 and SEQ ID NO:12 and three $V_L$ CDRs corresponding in sequence, respectively, to SEQ ID NO:13, SEQ ID NO:14 and SEQ ID NO:15.

22. The ADC of Embodiment 21 in which the antibody comprises a $V_H$ corresponding in sequence to SEQ ID NO:16.

23. The ADC of Embodiment 21 in which the antibody comprises a $V_L$ corresponding in sequence to SEQ ID NO:17.

24. The ADC of Embodiment 21 in which the antibody comprises a $V_H$ corresponding in sequence to SEQ ID NO:16 and a $V_L$ corresponding to SEQ ID NO:17.

25. The ADC of Embodiment 24 which is an $IgG_1$.

26. The ADC of Embodiment 21 in which the antibody comprises three $V_H$ CDRs corresponding in sequence, respectively, to SEQ ID NO:20, SEQ ID NO:21 and SEQ ID NO:22 and three $V_L$ CDRs corresponding in sequence, respectively, to SEQ ID NO:23, SEQ ID NO:24 and SEQ ID NO:25.

27. The ADC of Embodiment 26 in which the antibody comprises a $V_H$ chain corresponding in sequence to SEQ ID NO:26.

28. The ADC of Embodiment 26 in which the antibody comprises a $V_L$ chain corresponding in sequence to SEQ ID NO:27.

29. The ADC of Embodiment 26 in which the antibody comprises a $V_H$ chain corresponding in sequence to SEQ ID NO:26 and a $V_L$ chain corresponding in sequence to SEQ ID NO:27.

30. The ADC of Embodiment 29 which is an $IgG_1$.

31. The ADC of Embodiment 12 in which the antibody is huM25.

32. The ADC of Embodiment 12 in which the antibody is huAD208.4.1.

33. The ADC of Embodiment 12 in which the antibody competes for binding huLRRC15 with huM25 in an in vitro assay.

34. The ADC of Embodiment 12 in which the antibody competes for binding huLRRC15 with huAD208.4.1 in an in vitro assay.

35. The ADC of Embodiment 12 which is a compound according to structural formula (I):

$$[\text{D-L-XY-}]_n\text{-Ab} \quad\quad (I)$$

or a salt thereof, wherein:
D is the cytotoxic and/or cytostatic agent;
L is the linker;
Ab is the antibody;
XY represents a covalent linkage linking linker L to antibody Ab; and
n is an integer ranging from 2 to 8.

36. The ADC of Embodiment 35 in which n is 2, 3 or 4.

37. The ADC of Embodiment 35 in which XY is a linkage formed with an amino group on antibody Ab.

38. The ADC of Embodiment 37 in which XY is an amide or a thiourea.

39. The ADC of Embodiment 35 in which XY is a linkage formed with a sulfydryl group on antibody Ab.

40. The ADC of Embodiment 39 in which XY is a thioether.

41. The ADC of Embodiment 35 in which the compound according to structural formula (I) has the structure of formula (IIa):

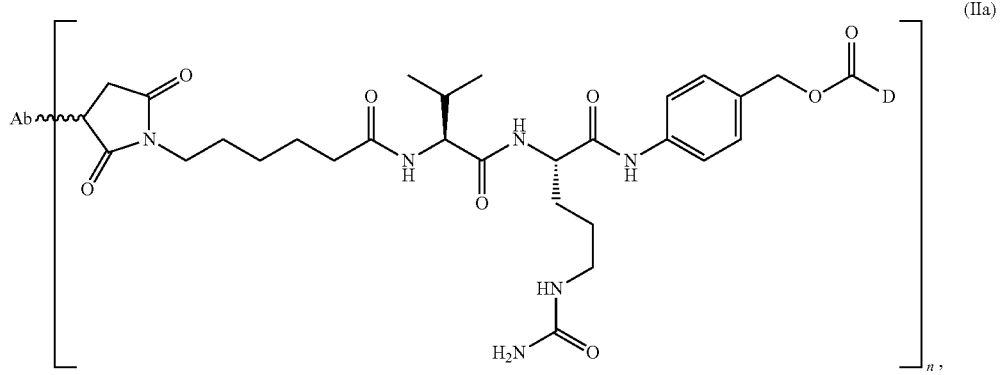

where Ab is antibody huM25.

42. The ADC of Embodiment 35 which has the structure:

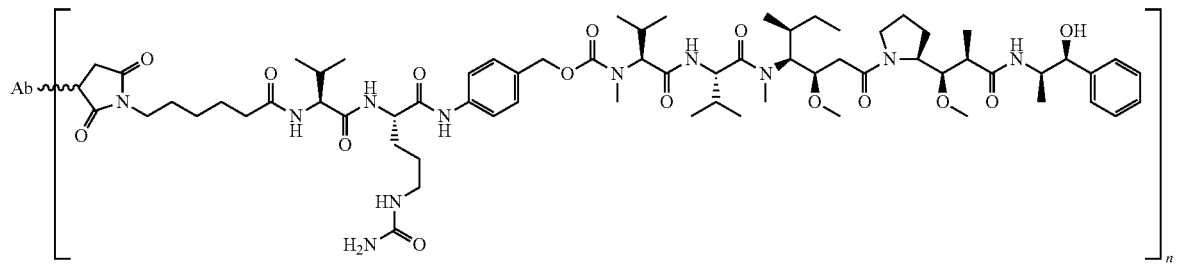

where Ab is antibody huM25 and n is 2 or 4.

43. The ADC of Embodiment 35 in which the compound according to structural formula (I) has the structure of formula (IIb):

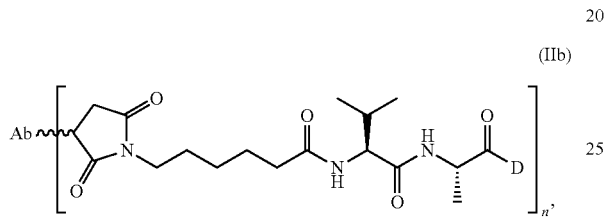

where Ab is antibody huAD208.4.1.

44. The ADC of Embodiment 35 which has the structure:

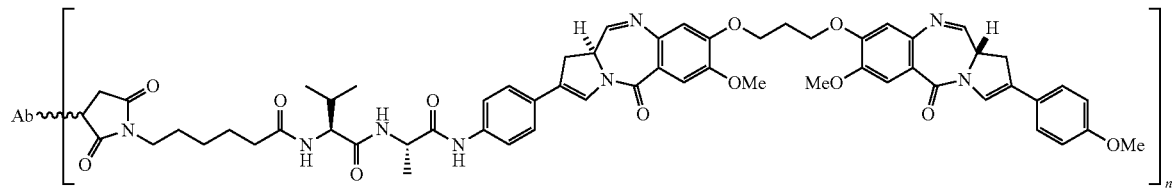

where Ab is huAD208.4.1 and n is 2 or 4.

45. A composition comprising an ADC according to any one of Embodiments 12-44 and a carrier, excipient and/or diluent.

46. The composition of Embodiment 45 which is formulated for pharmaceutical use in humans.

47. The composition of Embodiment 45 which is in unit dosage form.

48. An ADC formed by contacting an antibody that specifically binds huLRRC15 extracellular domain, wherein said extracellular domain comprises the proteolytic cleavage site defined by $Arg^{527}$ and $Ser^{528}$ of SEQ ID NO:3, with a synthon according to structural formula (III) D-L-W, where D is a cytotoxic and/or cytostatic agent capable of crossing a cell membrane, L is a linker cleavable by a lysosomal enzyme and $R^x$ comprises a functional group capable of covalently linking the synthon to the antibody, under conditions in which the synthon covalently links the synthon to the antibody.

49. The ADC of Embodiment 48 in which the antibody is huM25 and the cytotoxic and/or cytostatic agent is MMAE.

50. The ADC of Embodiment 49 which has the structure

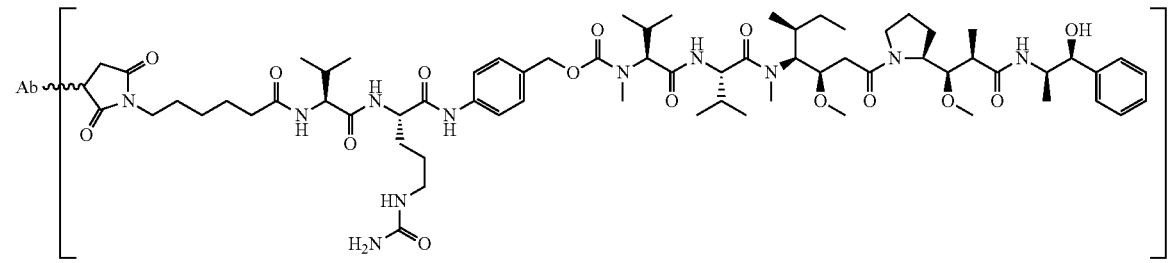

where Ab is the antibody, and n is 2 or 4.

51. The ADC of Embodiment 48 in which the antibody is huAD208.4.1 and the cytotoxic and/or cytostatic agent is a PBD dimer.

52. The ADC of Embodiment 51 which has the structure

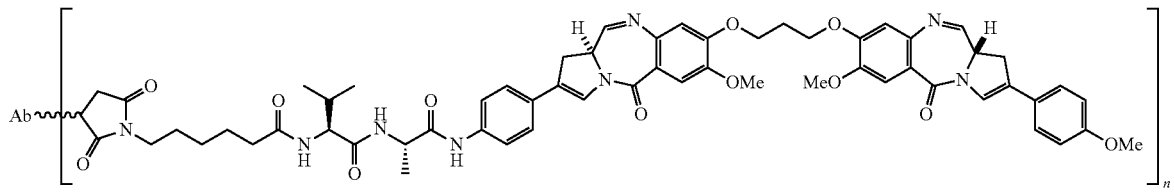

where Ab is the antibody, and n is 2 or 4.

53. The ADC according to any one of Embodiments 48-52 in which the contacting step is carried out under conditions such that the ADC has a DAR of 2, 3 or 4.

54. A composition comprising an ADC according to Embodiment 48 and an excipient, carrier and/or diluent.

55. The composition of Embodiment 54 which is formulated for pharmaceutical use in humans.

56. The composition of Embodiment 55 which is in unit dosage form.

57. A method of making an ADC, comprising contacting an antibody that specifically binds huLRRC15 extracellular domain, wherein said extracellular domain comprises the proteolytic cleavage site defined by $Arg^{527}$ and $Ser^{528}$ of SEQ ID NO:3, with a synthon according to structural formula (III) D-L-W, where D is cytotoxic and/or cytostatic agent capable of crossing a cell membrane, L is a linker capable of being cleaved by a lysosomal enzyme, and $R^x$ comprises a functional group capable of covalently linking the synthon to the antibody, under conditions in which the synthon covalently links the synthon to the antibody.

58. The method of Embodiment 57 in which the antibody is huM25 and the cytotoxic and/or cytostatic agent is MMAE.

59. The method of Embodiment 57 in which the antibody is huAD208.4.1 and the cytotoxic and/or cytostatic agent is a PBD dimer.

60. A method of treating a huLRRC15 stromal(+)/cancer(−) tumor, comprising administering to a human having a huLRRC15 stromal(+)/cancer(−) tumor an amount of an ADC according to any one of Embodiments 12-44 sufficient to provide therapeutic benefit.

61. The method of Embodiment 60 in which the huLRRC15 stromal(+)/cancer(−) tumor is relapsed, refractory, or relapsed and refractory.

62. The method of Embodiment 60 in which the huLRRC15 stromal(+)/cancer(−) tumor is breast cancer, lung cancer, head and neck cancer, pancreatic cancer, colorectal cancer, ovarian cancer, testicular cancer, bladder cancer, or renal cancer.

63. The method of Embodiment 60 in which the huLRRC15 stromal(+)/cancer(−) tumor is a metastatic cancer.

64. The method of Embodiment 60 in which the ADC is administered as monotherapy.

65. The method of Embodiment 64 in which the ADC is administered intravenously at a dose ranging from about 0.3 mg/kg to about 6.0 mg/kg.

66. The method of Embodiment 60 in which the ADC is administered adjunctive to or with another anti-cancer therapy or agent.

67. The method of Embodiment 66 in which the anti-cancer therapy or agent is a non-targeted anti-cancer therapy.

68. The method of Embodiment 67 in which the non-targeted anti-cancer therapy is cisplatin, gemcitabine, docetaxel, carboplatin, or radiation.

69. The method of Embodiment 66 in which anti-cancer therapy or agent is a targeted anti-cancer agent.

70. The method of Embodiment 69 in which the huLRRC15 stromal(+)/cancer(−) tumor is breast cancer and the targeted anti-cancer agent is trastuzumab, pertuzumab, ado-trastuzumab emtansine, pembrolizumab, nivolumab, lapatinib, palbociclib, or everolimus.

71. The method of Embodiment 69 in which the huLRRC15 stromal(+)/cancer(−) tumor is NSC lung cancer and the targeted anti-cancer agent is bevacizumab, ramucirumab, pembrolizumab, nivolumab, atezolizumab, erlotinib, afatinib, gefitinib, crizotinib, or ceritinib.

72. The method of Embodiment 69 in which the huLRRC15 stromal(+)/cancer(−) tumor is head and neck cancer and the targeted anti-cancer agent is cetuximab, panitumumab, zalutumumab, nimotuzumab, pembrolizumab, nivolumab, gefinitib, erlotinib, lapatinib, afatinib, dacomitinib, bevacizumab, sorafenib, sunitinib, or vandetanib.

73. The method of Embodiment 69 in which the huLRRC15 stromal(+)/cancer(−) tumor is pancreatic cancer and the targeted anti-cancer agent is pembrolizumab, nivolumab, sunitinib, everolimus, or erlotinib.

74. The method of Embodiment 69 in which the huLRRC15 stromal(+)/cancer(−) tumor is colorectal cancer and the targeted anti-cancer agent is bevacizumab, ramucirumab, ziv-aflibercept, cetuximab, pembrolizumab, nivolumab, durvalumab, atezolizumab, or regorafenib.

75. The method of Embodiment 69 in which the huLRRC15 stromal(+)/cancer(−) tumor is ovarian cancer and the targeted anti-cancer agent is bevacizumab, pembrolizumab, nivolumab, aflibercept, nintedanib, trebananib, pazopanib, sunitinib, sorafenib, cediranib, olaparib, or niraparib.

76. The method of Embodiment 60 in which the ADC is administered adjunctively with or to a non-targeted anti-cancer therapy and a targeted anti-cancer agent.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An anti-huLRRC15 antibody drug conjugate (ADC) comprising an antimitotic agent linked to an anti-huLRRC15 antibody by way of a linker, wherein the ADC has a structure of formula (I):

[D-L-XY]$_n$-Ab     (I)

or a salt thereof, wherein:

D is the antimitotic agent;
L is the linker;
Ab is the anti-huLRRC15 antibody;
XY represents a covalent linkage linking linker L to antibody Ab; and
n is an integer ranging from 2 to 8;
wherein
Ab comprises
a $V_H$ chain comprising the sequence of SEQ ID NO:16 and a $V_L$ chain comprising the sequence of SEQ ID NO:17,
a $V_H$ chain comprising the sequence of SEQ ID NO:26 and a $V_L$ chain comprising the sequence of SEQ ID NO:27,
a $V_H$ chain comprising the sequence of SEQ ID NO:36 and a $V_L$ chain comprising the sequence of SEQ ID NO:37,
a $V_H$ chain comprising the sequence of SEQ ID NO:46 and a $V_L$ chain comprising the sequence of SEQ ID NO:47,
a $V_H$ chain comprising the sequence of SEQ ID NO:56 and a $V_L$ chain comprising the sequence of SEQ ID NO:57,
a $V_H$ chain comprising the sequence of SEQ ID NO:66 and a $V_L$ chain comprising the sequence of SEQ ID NO:67, or
a $V_H$ chain comprising the sequence of SEQ ID NO:76 and a $V_L$ chain comprising the sequence of SEQ ID NO:77.

2. The ADC of claim 1 in which n is 2, 3 or 4.

3. The ADC of claim 1 in which XY is a thioether linkage formed with a sulfydryl group on antibody Ab.

4. The ADC of claim 1 in which L comprises Val-Cit or Val-Ala.

5. The ADC of claim 1 in which D is an auristatin.

6. The ADC of claim 1 in which Ab is an IgG$_1$.

7. The ADC of claim 1 which has a structure of formula (IIa):

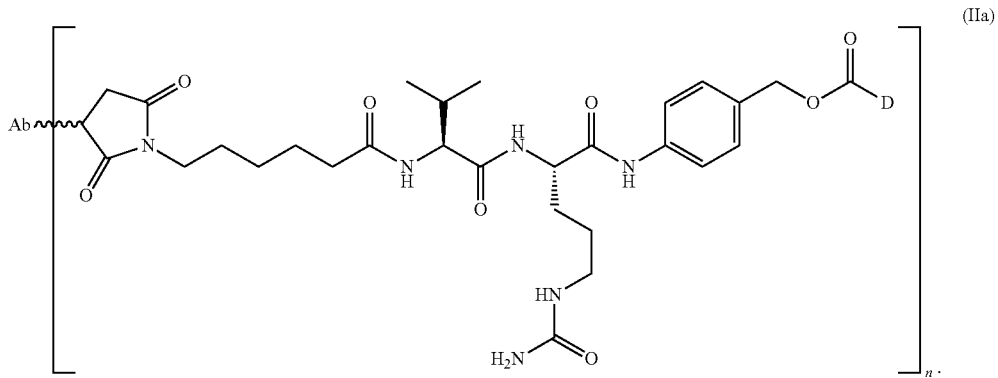

8. The ADC of claim 7 in which n is 2, 3 or 4.
9. The ADC of claim 7 in which Ab comprises:
   (a) a heavy chain having the amino acid sequence of SEQ ID NOS: 18, 100, 102, or 103; and a light chain of SEQ ID NO:19; or
   (b) a heavy chain having the amino acid sequence of SEQ ID NOS: 28, 101, 104, or 105; and a light chain of SEQ ID NO:29.
10. The ADC of claim 7 which has a structure of formula (IIIa):

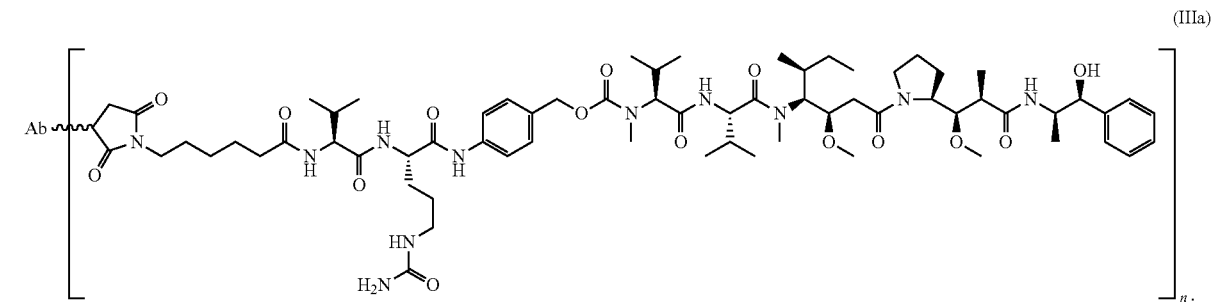

11. The ADC of claim 10 in which n is 2 or 4.
12. The ADC of claim 10 in which Ab comprises:
   (a) a heavy chain having the amino acid sequence of SEQ ID NOS: 18, 100, 102, or 103; and a light chain of SEQ ID NO:19; or
   (b) a heavy chain having the amino acid sequence of SEQ ID NOS: 28, 101, 104, or 105; and a light chain of SEQ ID NO:29.
13. An anti-huLRRC15 antibody drug conjugate (ADC) comprising a DNA intercalating agent linked to an anti-huLRRC15 antibody by way of a linker, wherein the ADC has a structure of formula (I):

[D-L-XY]$_n$-Ab     (I)

or a salt thereof, wherein:
D is the DNA intercalating agent;
L is the linker;
Ab is the anti-huLRRC15 antibody;
XY represents a covalent linkage linking linker L to antibody Ab; and
n is an integer ranging from 2 to 8;

wherein
Ab comprises
a $V_H$ chain comprising the sequence of SEQ ID NO:16 and a $V_L$ chain comprising the sequence of SEQ ID NO: 17,
a $V_H$ chain comprising the sequence of SEQ ID NO:26 and a $V_L$ chain comprising the sequence of SEQ ID NO:27,
a $V_H$ chain comprising the sequence of SEQ ID NO:36 and a $V_L$ chain comprising the sequence of SEQ ID NO:37,
a $V_H$ chain comprising the sequence of SEQ ID NO:46 and a $V_L$ chain comprising the sequence of SEQ ID NO:47,
a $V_H$ chain comprising the sequence of SEQ ID NO:56 and a $V_L$ chain comprising the sequence of SEQ ID NO:57,
a $V_H$ chain comprising the sequence of SEQ ID NO:66 and a $V_L$ chain comprising the sequence a SEQ ID NO:67, or
a $V_H$ chain comprising the sequence of SEQ ID NO:76 and a $V_L$ chain comprising the sequence of SEQ ID NO:77.

14. The ADC of claim 13 in which n is 2, 3 or 4.
15. The ADC of claim 13 in which XY is a thioether linkage formed with a sulfydryl group on antibody Ab.
16. The ADC of claim 13 in which L comprises Val-Cit or Val-Ala.
17. The ADC of claim 13 in which D is a pyrrolobenzodiazepine.
18. The ADC of claim 13 in which Ab is an IgG$_1$.
19. The ADC of claim 13 which has a structure of formula (IIb):

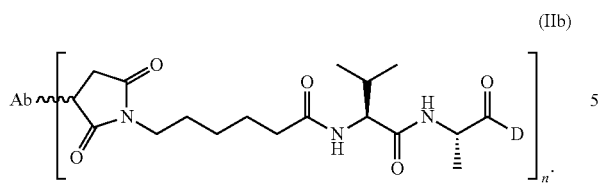

(IIb)

20. The ADC of claim 19 in which n is 2, 3 or 4.
21. The ADC of claim 19 in which Ab comprises:
   (a) a heavy chain having the amino acid sequence of SEQ ID NO: 18, 100, 102, or 103; and a light chain of SEQ ID NO:19; or
   (b) a heavy chain having the amino acid sequence of SEQ ID NO: 28, 101, 104, or 105; and
   a light chain of SEQ ID NO:29.
22. The ADC of claim 19 which has a structure of formula (IIIb)

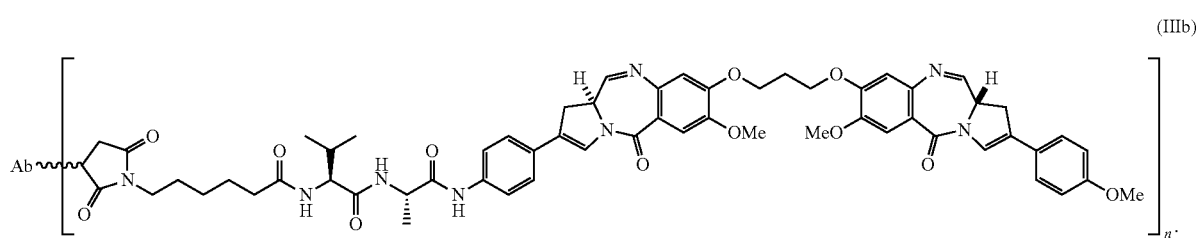

23. The ADC of claim 22 in which n is 2 or 4.
24. The ADC of claim 22 in which Ab comprises:
   (a) a heavy chain having the amino acid sequence of SEQ ID NOS: 18, 100, 102, or 103; and a light chain of SEQ ID NO:19; or
   (b) a heavy chain having the amino acid sequence of SEQ ID NOS: 28, 101, 104, or 105; and a light chain of SEQ ID NO:29.
25. A pharmaceutical composition comprising an ADC of claim 1 and a pharmaceutically acceptable carrier.
26. A pharmaceutical composition comprising an ADC of claim 13 and a pharmaceutically acceptable carrier.
27. An anti-huLRRC15 antibody or an anti-huLRRC15 binding fragment thereof which comprises:
   a $V_H$ chain comprising the sequence of SEQ ID NO:16 and a $V_L$ chain comprising the sequence of SEQ ID NO:17;
   a $V_H$ chain comprising the sequence of SEQ ID NO:26 and a $V_L$ chain comprising the sequence of SEQ ID NO:27;
   a $V_H$ chain comprising the sequence of SEQ ID NO:36 and a $V_L$ chain comprising the sequence of SEQ ID NO:37;
   a $V_H$ chain comprising the sequence of SEQ ID NO:46 and a $V_L$ chain comprising the sequence of SEQ ID NO:47;
   a $V_H$ chain comprising the sequence of SEQ ID NO:56 and a $V_L$ chain comprising the sequence of SEQ ID NO:57;
   a $V_H$ chain comprising the sequence of SEQ ID NO:66 and a $V_L$ chain comprising the sequence of SEQ ID NO:67; or
   a $V_H$ chain comprising the sequence of SEQ ID NO:76 and a $V_L$ chain comprising the sequence of SEQ ID NO:77.

* * * * *

SEQUENCE LISTING

<160> NUMBER OF SEQ ID NOS: 111

<210> SEQ ID NO 1
<211> LENGTH: 587
<212> TYPE: PRT
<213> ORGANISM: Homo sapiens

<400> SEQUENCE: 1

Met Pro Leu Asp Lys Ala Met Pro Leu Lys His Tyr Leu Leu Leu Leu
1               5                   10                  15

Val Gly Cys Gln Ala Trp Gly Ala Gly Leu Ala Tyr His Gly Cys Pro
            20                  25                  30

Ser Glu Cys Thr Cys Ser Arg Ala Ser Gln Val Glu Cys Thr Gly Ala
        35                  40                  45

Arg Ile Val Ala Val Pro Thr Pro Leu Pro Trp Asn Ala Met Ser Leu
    50                  55                  60

Gln Ile Leu Asn Thr His Ile Thr Glu Leu Asn Glu Ser Pro Phe Leu
65                  70                  75                  80

Asn Ile Ser Ala Leu Ile Ala Leu Arg Ile Glu Lys Asn Glu Leu Ser
                85                  90                  95

Arg Ile Thr Pro Gly Ala Phe Arg Asn Leu Gly Ser Leu Arg Tyr Leu
            100                 105                 110

Ser Leu Ala Asn Asn Lys Leu Gln Val Leu Pro Ile Gly Leu Phe Gln
        115                 120                 125

Gly Leu Asp Ser Leu Glu Ser Leu Leu Leu Ser Ser Asn Gln Leu Leu
130                 135                 140

Gln Ile Gln Pro Ala His Phe Ser Gln Cys Ser Asn Leu Lys Glu Leu
145                 150                 155                 160

Gln Leu His Gly Asn His Leu Glu Tyr Ile Pro Asp Gly Ala Phe Asp
                165                 170                 175

His Leu Val Gly Leu Thr Lys Leu Asn Leu Gly Lys Asn Ser Leu Thr
            180                 185                 190

His Ile Ser Pro Arg Val Phe Gln His Leu Gly Asn Leu Gln Val Leu
        195                 200                 205

Arg Leu Tyr Glu Asn Arg Leu Thr Asp Ile Pro Met Gly Thr Phe Asp
210                 215                 220

Gly Leu Val Asn Leu Gln Glu Leu Ala Leu Gln Gln Asn Gln Ile Gly
225                 230                 235                 240

Leu Leu Ser Pro Gly Leu Phe His Asn Asn His Asn Leu Gln Arg Leu
                245                 250                 255

Tyr Leu Ser Asn Asn His Ile Ser Gln Leu Pro Pro Ser Val Phe Met
            260                 265                 270

Gln Leu Pro Gln Leu Asn Arg Leu Thr Leu Phe Gly Asn Ser Leu Lys
        275                 280                 285

Glu Leu Ser Pro Gly Ile Phe Gly Pro Met Pro Asn Leu Arg Glu Leu
290                 295                 300

Trp Leu Tyr Asp Asn His Ile Ser Ser Leu Pro Asp Asn Val Phe Ser
305                 310                 315                 320

Asn Leu Arg Gln Leu Gln Val Leu Ile Leu Ser Arg Asn Gln Ile Ser
                325                 330                 335

Phe Ile Ser Pro Gly Ala Phe Asn Gly Leu Thr Glu Leu Arg Glu Leu
            340                 345                 350

Ser Leu His Thr Asn Ala Leu Gln Asp Leu Asp Gly Asn Val Phe Arg
        355                 360                 365

-continued

```
Met Leu Ala Asn Leu Gln Asn Ile Ser Leu Gln Asn Asn Arg Leu Arg
    370                 375                 380

Gln Leu Pro Gly Asn Ile Phe Ala Asn Val Asn Gly Leu Met Ala Ile
385                 390                 395                 400

Gln Leu Gln Asn Gln Leu Glu Asn Leu Pro Leu Gly Ile Phe Asp
                405                 410                 415

His Leu Gly Lys Leu Cys Glu Leu Arg Leu Tyr Asp Asn Pro Trp Arg
                420                 425                 430

Cys Asp Ser Asp Ile Leu Pro Leu Arg Asn Trp Leu Leu Asn Gln
                435                 440                 445

Pro Arg Leu Gly Thr Asp Thr Val Pro Val Cys Phe Ser Pro Ala Asn
450                 455                 460

Val Arg Gly Gln Ser Leu Ile Ile Ile Asn Val Asn Val Ala Val Pro
465                 470                 475                 480

Ser Val His Val Pro Glu Val Pro Ser Tyr Pro Glu Thr Pro Trp Tyr
                485                 490                 495

Pro Asp Thr Pro Ser Tyr Pro Asp Thr Thr Ser Val Ser Thr Thr
                500                 505                 510

Glu Leu Thr Ser Pro Val Glu Asp Tyr Thr Asp Leu Thr Thr Ile Gln
                515                 520                 525

Val Thr Asp Asp Arg Ser Val Trp Gly Met Thr Gln Ala Gln Ser Gly
530                 535                 540

Leu Ala Ile Ala Ala Ile Val Ile Gly Ile Val Ala Leu Ala Cys Ser
545                 550                 555                 560

Leu Ala Ala Cys Val Gly Cys Cys Cys Lys Lys Arg Ser Gln Ala
                565                 570                 575

Val Leu Met Gln Met Lys Ala Pro Asn Glu Cys
                580                 585

<210> SEQ ID NO 2
<211> LENGTH: 1761
<212> TYPE: DNA
<213> ORGANISM: Homo sapiens
<220> FEATURE:
<221> NAME/KEY: CDS
<222> LOCATION: (1)..(1761)

<400> SEQUENCE: 2 atg cct ttg gac aag gct atg cca ctg aag cat tat ctc ctt ttg ctg      48
Met Pro Leu Asp Lys Ala Met Pro Leu Lys His Tyr Leu Leu Leu Leu
1               5                   10                  15 gtg ggc tgc caa gcc tgg ggt gca ggg ttg gcc tac cat ggc tgc cct      96
Val Gly Cys Gln Ala Trp Gly Ala Gly Leu Ala Tyr His Gly Cys Pro
                20                  25                  30 agc gag tgt acc tgc tcc agg gcc tcc cag gtg gag tgc acc ggg gca     144
Ser Glu Cys Thr Cys Ser Arg Ala Ser Gln Val Glu Cys Thr Gly Ala
            35                  40                  45 cgc att gtg gca gtg ccc acc cct ctg ccc tgg aac gcc atg agc ctg     192
Arg Ile Val Ala Val Pro Thr Pro Leu Pro Trp Asn Ala Met Ser Leu
        50                  55                  60 cag atc ctc aac acg cac atc act gaa ctc aat gag tcc ccg ttc ctc     240
Gln Ile Leu Asn Thr His Ile Thr Glu Leu Asn Glu Ser Pro Phe Leu
65                  70                  75                  80 aat atc tca gcc ctc atc gcc ctg agg att gag aag aat gag ctg tcg     288
Asn Ile Ser Ala Leu Ile Ala Leu Arg Ile Glu Lys Asn Glu Leu Ser
                85                  90                  95 cgc atc acg cct ggg gcc ttc cga aac ctg ggc tcg ctg cgc tat ctc     336
Arg Ile Thr Pro Gly Ala Phe Arg Asn Leu Gly Ser Leu Arg Tyr Leu
```

```
            100                 105                 110
agc ctc gcc aac aac aag ctg cag gtt ctg ccc atc ggc ctc ttc cag         384
Ser Leu Ala Asn Asn Lys Leu Gln Val Leu Pro Ile Gly Leu Phe Gln
            115                 120                 125 ggc ctg gac agc ctc gag tct ctc ctt ctg tcc agt aac cag ctg ttg         432
Gly Leu Asp Ser Leu Glu Ser Leu Leu Leu Ser Ser Asn Gln Leu Leu
        130                 135                 140 cag atc cag ccg gcc cac ttc tcc cag tgc agc aac ctc aag gag ctg         480
Gln Ile Gln Pro Ala His Phe Ser Gln Cys Ser Asn Leu Lys Glu Leu
145                 150                 155                 160 cag ttg cac ggc aac cac ctg gaa tac atc cct gac gga gcc ttc gac         528
Gln Leu His Gly Asn His Leu Glu Tyr Ile Pro Asp Gly Ala Phe Asp
                165                 170                 175 cac ctg gta gga ctc acg aag ctc aat ctg ggc aag aat agc ctc acc         576
His Leu Val Gly Leu Thr Lys Leu Asn Leu Gly Lys Asn Ser Leu Thr
            180                 185                 190 cac atc tca ccc agg gtc ttc cag cac ctg ggc aac ctc cag gtc ctc         624
His Ile Ser Pro Arg Val Phe Gln His Leu Gly Asn Leu Gln Val Leu
        195                 200                 205 cgg ctg tat gag aac agg ctc acg gat atc ccc atg ggc act ttt gat         672
Arg Leu Tyr Glu Asn Arg Leu Thr Asp Ile Pro Met Gly Thr Phe Asp
210                 215                 220 ggg ctt gtt aac ctg cag gaa ctg gct ctg cag cag aac cag att gga         720
Gly Leu Val Asn Leu Gln Glu Leu Ala Leu Gln Gln Asn Gln Ile Gly
225                 230                 235                 240 ctg ctc tcc cct ggt ctc ttc cac aac aac cac aac ctc cag aga ctc         768
Leu Leu Ser Pro Gly Leu Phe His Asn Asn His Asn Leu Gln Arg Leu
                245                 250                 255 tac ctg tcc aac aac cac atc tcc cag ctg cca ccc agc gtc ttc atg         816
Tyr Leu Ser Asn Asn His Ile Ser Gln Leu Pro Pro Ser Val Phe Met
            260                 265                 270 cag ctg ccc cag ctc aac cgt ctt act ctc ttt ggg aat tcc ctg aag         864
Gln Leu Pro Gln Leu Asn Arg Leu Thr Leu Phe Gly Asn Ser Leu Lys
        275                 280                 285 gag ctc tct ccg ggg atc ttc ggg ccc atg ccc aac ctg cgg gag ctt         912
Glu Leu Ser Pro Gly Ile Phe Gly Pro Met Pro Asn Leu Arg Glu Leu
        290                 295                 300 tgg ctc tat gac aac cac atc tct tct cta ccc gac aat gtc ttc agc         960
Trp Leu Tyr Asp Asn His Ile Ser Ser Leu Pro Asp Asn Val Phe Ser
305                 310                 315                 320 aac ctc cgc cag ttg cag gtc ctg att ctt agc cgc aat cag atc agc        1008
Asn Leu Arg Gln Leu Gln Val Leu Ile Leu Ser Arg Asn Gln Ile Ser
                325                 330                 335 ttc atc tcc ccg ggt gcc ttc aac ggg cta acg gag ctt cgg gag ctg        1056
Phe Ile Ser Pro Gly Ala Phe Asn Gly Leu Thr Glu Leu Arg Glu Leu
            340                 345                 350 tcc ctc cac acc aac gca ctg cag gac ctg gac ggg aac gtc ttc cgc        1104
Ser Leu His Thr Asn Ala Leu Gln Asp Leu Asp Gly Asn Val Phe Arg
        355                 360                 365 atg ttg gcc aac ctg cag aac atc tcc ctg cag aac aac cgc ctc aga        1152
Met Leu Ala Asn Leu Gln Asn Ile Ser Leu Gln Asn Asn Arg Leu Arg
    370                 375                 380 cag ctc cca ggg aat atc ttc gcc aac gtc aat ggc ctc atg gcc atc        1200
Gln Leu Pro Gly Asn Ile Phe Ala Asn Val Asn Gly Leu Met Ala Ile
385                 390                 395                 400 cag ctg cag aac aac cag ctg gag aac ttg ccc ctc ggc atc ttc gat        1248
Gln Leu Gln Asn Asn Gln Leu Glu Asn Leu Pro Leu Gly Ile Phe Asp
                405                 410                 415 cac ctg ggg aaa ctg tgt gag ctg cgg ctg tat gac aat ccc tgg agg        1296
```

-continued

```
                His Leu Gly Lys Leu Cys Glu Leu Arg Leu Tyr Asp Asn Pro Trp Arg
                            420                 425                 430 tgt gac tca gac atc ctt ccg ctc cgc aac tgg ctc ctg ctc aac cag           1344
Cys Asp Ser Asp Ile Leu Pro Leu Arg Asn Trp Leu Leu Leu Asn Gln
            435                 440                 445 cct agg tta ggg acg gac act gta cct gtg tgt ttc agc cca gcc aat           1392
Pro Arg Leu Gly Thr Asp Thr Val Pro Val Cys Phe Ser Pro Ala Asn
450                 455                 460 gtc cga ggc cag tcc ctc att atc atc aat gtc aac gtt gct gtt cca           1440
Val Arg Gly Gln Ser Leu Ile Ile Ile Asn Val Asn Val Ala Val Pro
465                 470                 475                 480 agc gtc cat gtc ccc gag gtg cct agt tac cca gaa aca cca tgg tac           1488
Ser Val His Val Pro Glu Val Pro Ser Tyr Pro Glu Thr Pro Trp Tyr
            485                 490                 495 cca gac aca ccc agt tac cct gac acc aca tcc gtc tct tct acc act           1536
Pro Asp Thr Pro Ser Tyr Pro Asp Thr Thr Ser Val Ser Ser Thr Thr
            500                 505                 510 gag cta acc agc cct gtg gaa gac tac act gat ctg act acc att cag           1584
Glu Leu Thr Ser Pro Val Glu Asp Tyr Thr Asp Leu Thr Thr Ile Gln
            515                 520                 525 gtc act gat gac cgc agc gtt tgg ggc atg acc cag gcc cag agc ggg           1632
Val Thr Asp Asp Arg Ser Val Trp Gly Met Thr Gln Ala Gln Ser Gly
530                 535                 540 ctg gcc att gcc gcc att gta att ggc att gtc gcc ctg gcc tgc tcc           1680
Leu Ala Ile Ala Ala Ile Val Ile Gly Ile Val Ala Leu Ala Cys Ser
545                 550                 555                 560 ctg gct gcc tgc gtc ggc tgt tgc tgc aag aag agg agc caa gct           1728
Leu Ala Ala Cys Val Gly Cys Cys Cys Lys Lys Arg Ser Gln Ala
            565                 570                 575 gtc ctg atg cag atg aag gca ccc aat gag tgt                               1761
Val Leu Met Gln Met Lys Ala Pro Asn Glu Cys
            580                 585

<210> SEQ ID NO 3
<211> LENGTH: 581
<212> TYPE: PRT
<213> ORGANISM: Homo sapiens

<400> SEQUENCE: 3

Met Pro Leu Lys His Tyr Leu Leu Leu Val Gly Cys Gln Ala Trp
1               5                   10                  15

Gly Ala Gly Leu Ala Tyr His Gly Cys Pro Ser Glu Cys Thr Cys Ser
            20                  25                  30

Arg Ala Ser Gln Val Glu Cys Thr Gly Ala Arg Ile Val Ala Val Pro
        35                  40                  45

Thr Pro Leu Pro Trp Asn Ala Met Ser Leu Gln Ile Leu Asn Thr His
    50                  55                  60

Ile Thr Glu Leu Asn Glu Ser Pro Phe Leu Asn Ile Ser Ala Leu Ile
65                  70                  75                  80

Ala Leu Arg Ile Glu Lys Asn Glu Leu Ser Arg Ile Thr Pro Gly Ala
                85                  90                  95

Phe Arg Asn Leu Gly Ser Leu Arg Tyr Leu Ser Leu Ala Asn Asn Lys
            100                 105                 110

Leu Gln Val Leu Pro Ile Gly Leu Phe Gln Gly Leu Asp Ser Leu Glu
        115                 120                 125

Ser Leu Leu Leu Ser Ser Asn Gln Leu Leu Gln Ile Gln Pro Ala His
    130                 135                 140

Phe Ser Gln Cys Ser Asn Leu Lys Glu Leu Gln Leu His Gly Asn His
```

```
                145                 150                 155                 160
Leu Glu Tyr Ile Pro Asp Gly Ala Phe Asp His Leu Val Gly Leu Thr
                    165                 170                 175
Lys Leu Asn Leu Gly Lys Asn Ser Leu Thr His Ile Ser Pro Arg Val
                    180                 185                 190
Phe Gln His Leu Gly Asn Leu Gln Val Leu Arg Leu Tyr Glu Asn Arg
                    195                 200                 205
Leu Thr Asp Ile Pro Met Gly Thr Phe Asp Gly Leu Val Asn Leu Gln
                    210                 215                 220
Glu Leu Ala Leu Gln Gln Asn Gln Ile Gly Leu Leu Ser Pro Gly Leu
225                 230                 235                 240
Phe His Asn Asn His Asn Leu Gln Arg Leu Tyr Leu Ser Asn Asn His
                    245                 250                 255
Ile Ser Gln Leu Pro Pro Ser Val Phe Met Gln Leu Pro Gln Leu Asn
                    260                 265                 270
Arg Leu Thr Leu Phe Gly Asn Ser Leu Lys Glu Leu Ser Pro Gly Ile
                    275                 280                 285
Phe Gly Pro Met Pro Asn Leu Arg Glu Leu Trp Leu Tyr Asp Asn His
                    290                 295                 300
Ile Ser Ser Leu Pro Asp Asn Val Phe Ser Asn Leu Arg Gln Leu Gln
305                 310                 315                 320
Val Leu Ile Leu Ser Arg Asn Gln Ile Ser Phe Ile Ser Pro Gly Ala
                    325                 330                 335
Phe Asn Gly Leu Thr Glu Leu Arg Glu Leu Ser Leu His Thr Asn Ala
                    340                 345                 350
Leu Gln Asp Leu Asp Gly Asn Val Phe Arg Met Leu Ala Asn Leu Gln
                    355                 360                 365
Asn Ile Ser Leu Gln Asn Asn Arg Leu Arg Gln Leu Pro Gly Asn Ile
                    370                 375                 380
Phe Ala Asn Val Asn Gly Leu Met Ala Ile Gln Leu Gln Asn Asn Gln
385                 390                 395                 400
Leu Glu Asn Leu Pro Leu Gly Ile Phe Asp His Leu Gly Lys Leu Cys
                    405                 410                 415
Glu Leu Arg Leu Tyr Asp Asn Pro Trp Arg Cys Asp Ser Asp Ile Leu
                    420                 425                 430
Pro Leu Arg Asn Trp Leu Leu Leu Asn Gln Pro Arg Leu Gly Thr Asp
                    435                 440                 445
Thr Val Pro Val Cys Phe Ser Pro Ala Asn Val Arg Gly Gln Ser Leu
                    450                 455                 460
Ile Ile Ile Asn Val Asn Val Ala Val Pro Ser Val His Val Pro Glu
465                 470                 475                 480
Val Pro Ser Tyr Pro Glu Thr Pro Trp Tyr Pro Asp Thr Pro Ser Tyr
                    485                 490                 495
Pro Asp Thr Thr Ser Val Ser Ser Thr Thr Glu Leu Thr Ser Pro Val
                    500                 505                 510
Glu Asp Tyr Thr Asp Leu Thr Thr Ile Gln Val Thr Asp Asp Arg Ser
                    515                 520                 525
Val Trp Gly Met Thr Gln Ala Gln Ser Gly Leu Ala Ile Ala Ala Ile
                    530                 535                 540
Val Ile Gly Ile Val Ala Leu Ala Cys Ser Leu Ala Ala Cys Val Gly
545                 550                 555                 560
Cys Cys Cys Cys Lys Lys Arg Ser Gln Ala Val Leu Met Gln Met Lys
                    565                 570                 575
```

Ala Pro Asn Glu Cys
            580

<210> SEQ ID NO 4
<211> LENGTH: 1743
<212> TYPE: DNA
<213> ORGANISM: Homo sapiens
<220> FEATURE:
<221> NAME/KEY: CDS
<222> LOCATION: (1)..(1743)

<400> SEQUENCE: 4

| | | | | | | | | | | | | | | | | |
|---|---|---|---|---|---|---|---|---|---|---|---|---|---|---|---|---|
| atg | cca | ctg | aag | cat | tat | ctc | ctt | ttg | ctg | gtg | ggc | tgc | caa | gcc | tgg | 48 |
| Met | Pro | Leu | Lys | His | Tyr | Leu | Leu | Leu | Leu | Val | Gly | Cys | Gln | Ala | Trp | |
| 1 | | | | 5 | | | | | 10 | | | | | 15 | | |

| ggt | gca | ggg | ttg | gcc | tac | cat | ggc | tgc | cct | agc | gag | tgt | acc | tgc | tcc | 96 |
|---|---|---|---|---|---|---|---|---|---|---|---|---|---|---|---|---|
| Gly | Ala | Gly | Leu | Ala | Tyr | His | Gly | Cys | Pro | Ser | Glu | Cys | Thr | Cys | Ser | |
| | | | 20 | | | | | 25 | | | | | 30 | | | |

| agg | gcc | tcc | cag | gtg | gag | tgc | acc | ggg | gca | cgc | att | gtg | gca | gtg | ccc | 144 |
|---|---|---|---|---|---|---|---|---|---|---|---|---|---|---|---|---|
| Arg | Ala | Ser | Gln | Val | Glu | Cys | Thr | Gly | Ala | Arg | Ile | Val | Ala | Val | Pro | |
| | | 35 | | | | | 40 | | | | | 45 | | | | |

| acc | cct | ctg | ccc | tgg | aac | gcc | atg | agc | ctg | cag | atc | ctc | aac | acg | cac | 192 |
|---|---|---|---|---|---|---|---|---|---|---|---|---|---|---|---|---|
| Thr | Pro | Leu | Pro | Trp | Asn | Ala | Met | Ser | Leu | Gln | Ile | Leu | Asn | Thr | His | |
| 50 | | | | | 55 | | | | | 60 | | | | | | |

| atc | act | gaa | ctc | aat | gag | tcc | ccg | ttc | ctc | aat | atc | tca | gcc | ctc | atc | 240 |
|---|---|---|---|---|---|---|---|---|---|---|---|---|---|---|---|---|
| Ile | Thr | Glu | Leu | Asn | Glu | Ser | Pro | Phe | Leu | Asn | Ile | Ser | Ala | Leu | Ile | |
| 65 | | | | | 70 | | | | | 75 | | | | | 80 | |

| gcc | ctg | agg | att | gag | aag | aat | gag | ctg | tcg | cgc | atc | acg | cct | ggg | gcc | 288 |
|---|---|---|---|---|---|---|---|---|---|---|---|---|---|---|---|---|
| Ala | Leu | Arg | Ile | Glu | Lys | Asn | Glu | Leu | Ser | Arg | Ile | Thr | Pro | Gly | Ala | |
| | | | | 85 | | | | | 90 | | | | | 95 | | |

| ttc | cga | aac | ctg | ggc | tcg | ctg | cgc | tat | ctc | agc | ctc | gcc | aac | aac | aag | 336 |
|---|---|---|---|---|---|---|---|---|---|---|---|---|---|---|---|---|
| Phe | Arg | Asn | Leu | Gly | Ser | Leu | Arg | Tyr | Leu | Ser | Leu | Ala | Asn | Asn | Lys | |
| | | | 100 | | | | | 105 | | | | | 110 | | | |

| ctg | cag | gtt | ctg | ccc | atc | ggc | ctc | ttc | cag | ggc | ctg | gac | agc | ctc | gag | 384 |
|---|---|---|---|---|---|---|---|---|---|---|---|---|---|---|---|---|
| Leu | Gln | Val | Leu | Pro | Ile | Gly | Leu | Phe | Gln | Gly | Leu | Asp | Ser | Leu | Glu | |
| | | 115 | | | | | 120 | | | | | 125 | | | | |

| tct | ctc | ctt | ctg | tcc | agt | aac | cag | ctg | ttg | cag | atc | cag | ccg | gcc | cac | 432 |
|---|---|---|---|---|---|---|---|---|---|---|---|---|---|---|---|---|
| Ser | Leu | Leu | Leu | Ser | Ser | Asn | Gln | Leu | Leu | Gln | Ile | Gln | Pro | Ala | His | |
| | 130 | | | | | 135 | | | | | 140 | | | | | |

| ttc | tcc | cag | tgc | agc | aac | ctc | aag | gag | ctg | cag | ttg | cac | ggc | aac | cac | 480 |
|---|---|---|---|---|---|---|---|---|---|---|---|---|---|---|---|---|
| Phe | Ser | Gln | Cys | Ser | Asn | Leu | Lys | Glu | Leu | Gln | Leu | His | Gly | Asn | His | |
| 145 | | | | | 150 | | | | | 155 | | | | | 160 | |

| ctg | gaa | tac | atc | cct | gac | gga | gcc | ttc | gac | cac | ctg | gta | gga | ctc | acg | 528 |
|---|---|---|---|---|---|---|---|---|---|---|---|---|---|---|---|---|
| Leu | Glu | Tyr | Ile | Pro | Asp | Gly | Ala | Phe | Asp | His | Leu | Val | Gly | Leu | Thr | |
| | | | | 165 | | | | | 170 | | | | | 175 | | |

| aag | ctc | aat | ctg | ggc | aag | aat | agc | ctc | acc | cac | atc | tca | ccc | agg | gtc | 576 |
|---|---|---|---|---|---|---|---|---|---|---|---|---|---|---|---|---|
| Lys | Leu | Asn | Leu | Gly | Lys | Asn | Ser | Leu | Thr | His | Ile | Ser | Pro | Arg | Val | |
| | | | 180 | | | | | 185 | | | | | 190 | | | |

| ttc | cag | cac | ctg | ggc | aac | ctc | cag | gtc | ctc | cgg | ctg | tat | gag | aac | agg | 624 |
|---|---|---|---|---|---|---|---|---|---|---|---|---|---|---|---|---|
| Phe | Gln | His | Leu | Gly | Asn | Leu | Gln | Val | Leu | Arg | Leu | Tyr | Glu | Asn | Arg | |
| | | 195 | | | | | 200 | | | | | 205 | | | | |

| ctc | acg | gat | atc | ccc | atg | ggc | act | ttt | gat | ggg | ctt | gtt | aac | ctg | cag | 672 |
|---|---|---|---|---|---|---|---|---|---|---|---|---|---|---|---|---|
| Leu | Thr | Asp | Ile | Pro | Met | Gly | Thr | Phe | Asp | Gly | Leu | Val | Asn | Leu | Gln | |
| | 210 | | | | | 215 | | | | | 220 | | | | | |

| gaa | ctg | gct | ctg | cag | cag | aac | cag | att | gga | ctg | ctc | tcc | cct | ggt | ctc | 720 |
|---|---|---|---|---|---|---|---|---|---|---|---|---|---|---|---|---|
| Glu | Leu | Ala | Leu | Gln | Gln | Asn | Gln | Ile | Gly | Leu | Leu | Ser | Pro | Gly | Leu | |
| 225 | | | | | 230 | | | | | 235 | | | | | 240 | |

| ttc | cac | aac | aac | cac | aac | ctc | cag | aga | ctc | tac | ctg | tcc | aac | aac | cac | 768 |
|---|---|---|---|---|---|---|---|---|---|---|---|---|---|---|---|---|
| Phe | His | Asn | Asn | His | Asn | Leu | Gln | Arg | Leu | Tyr | Leu | Ser | Asn | Asn | His | |
| | | | | 245 | | | | | 250 | | | | | 255 | | |

-continued

| | |
|---|---|
| atc tcc cag ctg cca ccc agc gtc ttc atg cag ctg ccc cag ctc aac<br>Ile Ser Gln Leu Pro Pro Ser Val Phe Met Gln Leu Pro Gln Leu Asn<br>260                         265                     270 | 816 |
| cgt ctt act ctc ttt ggg aat tcc ctg aag gag ctc tct ccg ggg atc<br>Arg Leu Thr Leu Phe Gly Asn Ser Leu Lys Glu Leu Ser Pro Gly Ile<br>        275                     280                     285 | 864 |
| ttc ggg ccc atg ccc aac ctg cgg gag ctt tgg ctc tat gac aac cac<br>Phe Gly Pro Met Pro Asn Leu Arg Glu Leu Trp Leu Tyr Asp Asn His<br>290                         295                     300 | 912 |
| atc tct tct cta ccc gac aat gtc ttc agc aac ctc cgc cag ttg cag<br>Ile Ser Ser Leu Pro Asp Asn Val Phe Ser Asn Leu Arg Gln Leu Gln<br>305                       310                     315                     320 | 960 |
| gtc ctg att ctt agc cgc aat cag atc agc ttc atc tcc ccg ggt gcc<br>Val Leu Ile Leu Ser Arg Asn Gln Ile Ser Phe Ile Ser Pro Gly Ala<br>                325                     330                     335 | 1008 |
| ttc aac ggg cta acg gag ctt cgg gag ctg tcc ctc cac acc aac gca<br>Phe Asn Gly Leu Thr Glu Leu Arg Glu Leu Ser Leu His Thr Asn Ala<br>340                         345                     350 | 1056 |
| ctg cag gac ctg gac ggg aac gtc ttc cgc atg ttg gcc aac ctg cag<br>Leu Gln Asp Leu Asp Gly Asn Val Phe Arg Met Leu Ala Asn Leu Gln<br>        355                     360                     365 | 1104 |
| aac atc tcc ctg cag aac aac cgc ctc aga cag ctc cca ggg aat atc<br>Asn Ile Ser Leu Gln Asn Asn Arg Leu Arg Gln Leu Pro Gly Asn Ile<br>370                       375                     380 | 1152 |
| ttc gcc aac gtc aat ggc ctc atg gcc atc cag ctg cag aac aac cag<br>Phe Ala Asn Val Asn Gly Leu Met Ala Ile Gln Leu Gln Asn Asn Gln<br>385                       390                     395                     400 | 1200 |
| ctg gag aac ttg ccc ctc ggc atc ttc gat cac ctg ggg aaa ctg tgt<br>Leu Glu Asn Leu Pro Leu Gly Ile Phe Asp His Leu Gly Lys Leu Cys<br>                     405                     410                     415 | 1248 |
| gag ctg cgg ctg tat gac aat ccc tgg agg tgt gac tca gac atc ctt<br>Glu Leu Arg Leu Tyr Asp Asn Pro Trp Arg Cys Asp Ser Asp Ile Leu<br>420                         425                     430 | 1296 |
| ccg ctc cgc aac tgg ctc ctg ctc aac cag cct agg tta ggg acg gac<br>Pro Leu Arg Asn Trp Leu Leu Leu Asn Gln Pro Arg Leu Gly Thr Asp<br>                435                     440                     445 | 1344 |
| act gta cct gtg tgt ttc agc cca gcc aat gtc cga ggc cag tcc ctc<br>Thr Val Pro Val Cys Phe Ser Pro Ala Asn Val Arg Gly Gln Ser Leu<br>450                         455                     460 | 1392 |
| att atc atc aat gtc aac gtt gct gtt cca agc gtc cat gtc ccc gag<br>Ile Ile Ile Asn Val Asn Val Ala Val Pro Ser Val His Val Pro Glu<br>465                       470                     475                     480 | 1440 |
| gtg cct agt tac cca gaa aca cca tgg tac cca gac aca ccc agt tac<br>Val Pro Ser Tyr Pro Glu Thr Pro Trp Tyr Pro Asp Thr Pro Ser Tyr<br>                     485                     490                     495 | 1488 |
| cct gac acc aca tcc gtc tct tct acc act gag cta acc agc cct gtg<br>Pro Asp Thr Thr Ser Val Ser Ser Thr Thr Glu Leu Thr Ser Pro Val<br>        500                     505                     510 | 1536 |
| gaa gac tac act gat ctg act acc att cag gtc act gat gac cgc agc<br>Glu Asp Tyr Thr Asp Leu Thr Thr Ile Gln Val Thr Asp Asp Arg Ser<br>515                       520                     525 | 1584 |
| gtt tgg ggc atg acc cag gcc cag agc ggg ctg gcc att gcc gcc att<br>Val Trp Gly Met Thr Gln Ala Gln Ser Gly Leu Ala Ile Ala Ala Ile<br>530                       535                     540 | 1632 |
| gta att ggc att gtc gcc ctg gcc tgc tcc ctg gct gcc tgc gtc ggc<br>Val Ile Gly Ile Val Ala Leu Ala Cys Ser Leu Ala Ala Cys Val Gly<br>545                       550                     555                     560 | 1680 |
| tgt tgc tgc tgc aag aag agg agc caa gct gtc ctg atg cag atg aag<br>Cys Cys Cys Cys Lys Lys Arg Ser Gln Ala Val Leu Met Gln Met Lys<br>                565                     570                     575 | 1728 |

-continued

```
gca ccc aat gag tgt                                              1743
Ala Pro Asn Glu Cys
        580
```

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Tyr Trp Ile Glu
1               5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Ile Leu Pro Gly Ser Asp Thr Thr Asn Tyr Asn Glu Lys Phe Lys
1               5                   10                  15

Asp

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 12

Asp Arg Gly Asn Tyr Arg Ala Trp Phe Gly Tyr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ala Ser Gln Asp Ile Ser Asn Tyr Leu Asn
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Thr Ser Arg Leu His Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Gln Gly Glu Ala Leu Pro Trp Thr
1               5

<210> SEQ ID NO 16
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Ser Ser Tyr
            20                  25                  30

Trp Ile Glu Trp Val Lys Gln Ala Pro Gly Gln Gly Leu Glu Trp Ile
        35                  40                  45

Gly Glu Ile Leu Pro Gly Ser Asp Thr Thr Asn Tyr Asn Glu Lys Phe
    50                  55                  60

Lys Asp Arg Ala Thr Phe Thr Ser Asp Thr Ser Ile Asn Thr Ala Tyr
65                  70                  75                  80

Met Glu Leu Ser Arg Leu Arg Ser Asp Thr Ala Val Tyr Tyr Cys
                85                  90                  95

Ala Arg Asp Arg Gly Asn Tyr Arg Ala Trp Phe Gly Tyr Trp Gly Gln
            100                 105                 110
```

```
Gly Thr Leu Val Thr Val Ser Ser
        115             120

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Gly Ala Val Lys Phe Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Glu Ala Leu Pro Trp
                85                  90                  95

Thr Phe Gly Gly Gly Thr Lys Val Glu Ile Lys
            100                 105

<210> SEQ ID NO 18
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Ser Ser Tyr
            20                  25                  30

Trp Ile Glu Trp Val Lys Gln Ala Pro Gly Gln Gly Leu Glu Trp Ile
        35                  40                  45

Gly Glu Ile Leu Pro Gly Ser Asp Thr Thr Asn Tyr Asn Glu Lys Phe
    50                  55                  60

Lys Asp Arg Ala Thr Phe Thr Ser Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Arg Gly Asn Tyr Arg Ala Trp Phe Gly Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
        210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 19
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Ser Asn Tyr
            20                  25                  30
Leu Asn Trp Tyr Gln Gln Lys Pro Gly Gly Ala Val Lys Phe Leu Ile
        35                  40                  45
Tyr Tyr Thr Ser Arg Leu His Ser Gly Val Pro Ser Arg Phe Ser Gly
    50                  55                  60
Ser Gly Ser Gly Thr Asp Tyr Thr Leu Thr Ile Ser Ser Leu Gln Pro
65                  70                  75                  80
```

Glu Asp Phe Ala Thr Tyr Phe Cys Gln Gln Gly Ala Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Tyr Tyr Ile His
1               5

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Val Tyr Pro Tyr Ile Gly Gly Thr Asn Tyr Asn Gln Lys Phe Lys
1               5                   10                  15

Gly

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Asp Asn Lys Tyr Asp Ala Met Asp Tyr
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Arg Ala Ser Gln Ser Val Ser Thr Ser Ser Tyr Ser Tyr Met His
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Ala Ser Ser Leu Glu Ser
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Gln Ser Trp Glu Ile Arg Thr
1               5

<210> SEQ ID NO 26
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Tyr Ile His Trp Val Lys Gln Ala Pro Gly Gln Gly Leu Glu Trp Ile
        35                  40                  45

Gly Leu Val Tyr Pro Tyr Ile Gly Gly Thr Asn Tyr Asn Gln Lys Phe
    50                  55                  60

Lys Gly Lys Ala Thr Leu Thr Val Asp Thr Ser Thr Thr Thr Ala Tyr
65                  70                  75                  80

Met Glu Met Ser Ser Leu Arg Ser Glu Asp Thr Ala Val Tyr Tyr Cys
                85                  90                  95

Ala Arg Gly Asp Asn Lys Tyr Asp Ala Met Asp Tyr Trp Gly Gln Gly
            100                 105                 110

Thr Thr Val Thr Val Ser Ser
        115

<210> SEQ ID NO 27
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Ser Leu Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Glu Gln Ser Trp
                85                  90                  95

Glu Ile Arg Thr Phe Gly Gly Gly Thr Lys Val Glu Ile Lys
            100                 105                 110

<210> SEQ ID NO 28
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Tyr Ile His Trp Val Lys Gln Ala Pro Gly Gln Gly Leu Glu Trp Ile
        35                  40                  45

Gly Leu Val Tyr Pro Tyr Ile Gly Gly Thr Asn Tyr Asn Gln Lys Phe
50                  55                  60

Lys Gly Lys Ala Thr Leu Thr Val Asp Thr Ser Thr Thr Thr Ala Tyr
65                  70                  75                  80

Met Glu Met Ser Ser Leu Arg Ser Glu Asp Thr Ala Val Tyr Tyr Cys
                85                  90                  95

Ala Arg Gly Asp Asn Lys Tyr Asp Ala Met Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

```
Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
            275             280             285

Ala Lys Thr Lys Pro Arg Glu Glu Gln Tyr Asn Ser Thr Tyr Arg Val
            290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
            340             345             350

Leu Pro Pro Ser Arg Glu Glu Met Thr Lys Asn Gln Val Ser Leu Thr
            355             360             365

Cys Leu Val Lys Gly Phe Tyr Pro Ser Asp Ile Ala Val Glu Trp Glu
            370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445

Lys

<210> SEQ ID NO 29
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Ser Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Glu Gln Ser Trp
                85                  90                  95

Glu Ile Arg Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140
```

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
            165                 170                 175

Ser Leu Ser Ser Thr Leu Thr Leu Ser Lys Ala Asp Tyr Glu Lys His
        180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asn Tyr Trp Met His
1               5

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Met Ile His Pro Asn Ser Gly Ser Thr Lys His Asn Glu Lys Phe Arg
1               5                   10                  15

Gly

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Asp Phe Gly Asn Tyr Arg Trp Tyr Phe Asp Val
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ala Ser Gln Ser Ser Ser Asn Asn Leu His
1               5                   10

<210> SEQ ID NO 34
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 34

Tyr Val Ser Gln Ser Ile Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Gln Ser Asn Ser Trp Pro Phe Thr
1               5

<210> SEQ ID NO 36
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
                20                  25                  30

Trp Met His Trp Val Lys Gln Ala Pro Gly Gln Gly Leu Glu Trp Ile
            35                  40                  45

Gly Met Ile His Pro Asn Ser Gly Ser Thr Lys His Asn Glu Lys Phe
        50                  55                  60

Arg Gly Lys Ala Thr Leu Thr Val Asp Glu Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Phe Gly Asn Tyr Arg Trp Tyr Phe Asp Val Trp Gly
            100                 105                 110

Gln Gly Thr Thr Val Thr Val Ser Ser
        115                 120

<210> SEQ ID NO 37
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ser Ser Asn Asn
                20                  25                  30

Leu His Trp Tyr Gln Gln Lys Pro Gly Gln Ala Pro Arg Val Leu Ile
            35                  40                  45

Lys Tyr Val Ser Gln Ser Ile Ser Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asn Ser Trp Pro Phe
                85                  90                  95

Thr Phe Gly Gln Gly Thr Lys Leu Glu Ile Lys
            100                 105

<210> SEQ ID NO 38

<400> SEQUENCE: 38

000

<210> SEQ ID NO 39

<400> SEQUENCE: 39

000

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Tyr Tyr Ile His
1               5

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Val Tyr Pro Tyr Ile Gly Gly Ser Ser Tyr Asn Gln Gln Phe Lys
1               5                   10                  15

Gly

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Asp Asn Asn Tyr Asp Ala Met Asp Tyr
1               5                   10

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Ala Ser Gln Ser Val Ser Thr Ser Thr Tyr Asn Tyr Met His
1               5                   10                  15

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Tyr Ala Ser Asn Leu Glu Ser
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

His His Thr Trp Glu Ile Arg Thr
1               5

<210> SEQ ID NO 46
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
                20                  25                  30

Tyr Ile His Trp Val Lys Gln Ala Pro Gly Gln Gly Leu Glu Trp Ile
            35                  40                  45

Gly Leu Val Tyr Pro Tyr Ile Gly Gly Ser Tyr Asn Gln Gln Phe
        50                  55                  60

Lys Gly Lys Ala Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Asn Asn Tyr Asp Ala Met Asp Tyr Trp Gly Gln Gly
                100                 105                 110

Thr Thr Val Thr Val Ser Ser
        115

<210> SEQ ID NO 47
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Val Leu Thr Gln Ser Pro Asp Ser Leu Ala Val Ser Leu Gly
1               5                   10                  15

Glu Arg Ala Thr Ile Ser Cys Arg Ala Ser Gln Ser Val Ser Thr Ser
            20                  25                  30

Thr Tyr Asn Tyr Met His Trp Tyr Gln Gln Lys Pro Gly Gln Pro Pro
                35                  40                  45

Lys Leu Leu Val Lys Tyr Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys His His Thr Trp
                 85                  90                  95

Glu Ile Arg Thr Phe Gly Gly Gly Thr Lys Val Glu Ile Lys
            100                 105                 110

<210> SEQ ID NO 48

<400> SEQUENCE: 48

000

<210> SEQ ID NO 49

<400> SEQUENCE: 49

000

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Tyr Gly Val His
1               5

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Val Ile Trp Ala Gly Gly Ser Thr Asn Tyr Asn Ser Ala Leu Met Ser
1               5                   10                  15

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

His Met Ile Thr Glu Asp Tyr Tyr Gly Met Asp Tyr
1               5                   10

<210> SEQ ID NO 53
<211> LENGTH: 17
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 53

Lys Ser Ser Gln Ser Leu Leu Asn Ser Arg Thr Arg Lys Asn Tyr Leu
1               5                   10                  15
Ala

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Trp Ala Ser Thr Arg Glu Ser
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Gln Ser Tyr Asn Leu Pro Thr
1               5

<210> SEQ ID NO 56
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ser Tyr
            20                  25                  30

Gly Val His Trp Val Arg Gln Ala Thr Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Thr Ile Ser Lys Glu Asn Ala Lys Ser Ser Val Tyr Leu
65                  70                  75                  80

Gln Met Asn Ser Leu Arg Ala Gly Asp Thr Ala Met Tyr Tyr Cys Ala
                85                  90                  95

Thr His Met Ile Thr Glu Asp Tyr Tyr Gly Met Asp Tyr Trp Gly Gln
            100                 105                 110

Gly Thr Thr Val Thr Val Ser Ser
        115                 120

<210> SEQ ID NO 57
<211> LENGTH: 112
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 57

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Pro Thr Phe Gly Gly Gly Thr Lys Val Glu Ile Lys
            100                 105                 110

<210> SEQ ID NO 58

<400> SEQUENCE: 58

000

<210> SEQ ID NO 59

<400> SEQUENCE: 59

000

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Asn Tyr Trp Leu Gly
1               5

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Asp Ile Tyr Pro Gly Gly Gly Asn Thr Tyr Tyr Asn Glu Lys Leu Lys
1               5                   10                  15

Gly

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Trp Gly Asp Lys Lys Gly Asn Tyr Phe Ala Tyr
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Ala Ser Ser Ser Val Tyr Ser Ser Tyr Leu His
1               5                   10

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Thr Ser Asn Leu Ala Ser
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

His Gln Tyr His Arg Ser Pro Thr
1               5

<210> SEQ ID NO 66
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Gln Gln Ser Gly Ala Glu Leu Val Arg Pro Gly Thr
1               5                   10                  15

Ser Val Lys Ile Ser Cys Lys Ala Ser Gly Tyr Asp Phe Thr Asn Tyr
                20                  25                  30

Trp Leu Gly Trp Val Lys Gln Arg Pro Gly His Gly Leu Glu Trp Ile
            35                  40                  45

Gly Asp Ile Tyr Pro Gly Gly Gly Asn Thr Tyr Tyr Asn Glu Lys Leu
        50                  55                  60

Lys Gly Lys Ala Thr Leu Thr Ala Asp Lys Ser Ser Thr Ala Tyr
65                  70                  75                  80

Ile His Leu Ile Ser Leu Thr Ser Glu Asp Ser Ser Val Tyr Phe Cys
                85                  90                  95

Ala Arg Trp Gly Asp Lys Lys Gly Asn Tyr Phe Ala Tyr Trp Gly Gln

```
                100                 105                 110
Gly Thr Leu Val Thr Val Ser Ala
        115                 120

<210> SEQ ID NO 67
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Tyr Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Thr Phe Gly Gly Gly Thr Lys Leu Glu Ile Lys
            100                 105

<210> SEQ ID NO 68

<400> SEQUENCE: 68

000

<210> SEQ ID NO 69

<400> SEQUENCE: 69

000

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asn Phe Gly Met Asn
1               5

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Trp Ile Asn Leu Tyr Thr Gly Glu Pro Thr Phe Ala Asp Asp Phe Lys
1               5                   10                  15
```

Gly

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Gly Glu Thr Tyr Tyr Arg Tyr Asp Gly Phe Ala Tyr
1               5                   10

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Ser Ser Lys Ser Leu Leu His Ser Asn Gly Asn Thr His Leu Tyr
1               5                   10                  15

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Met Ser Asn Leu Ala Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Met Gln Leu Leu Glu Tyr Pro Tyr Thr
1               5

<210> SEQ ID NO 76
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Ala Ile Thr Asn Phe
            20                  25                  30

Gly Met Asn Trp Val Lys Gln Ala Pro Gly Lys Gly Leu Lys Trp Met
        35                  40                  45

Gly Trp Ile Asn Leu Tyr Thr Gly Glu Pro Thr Phe Ala Asp Asp Phe

```
                    50                   55                  60
Lys Gly Arg Phe Ala Phe Ser Leu Glu Thr Ser Ala Ser Thr Ala Tyr
 65                   70                  75                  80

Leu Gln Ile Asn Asn Leu Lys Asn Glu Asp Thr Val Ile Tyr Phe Cys
                     85                  90                  95

Ala Arg Lys Gly Glu Thr Tyr Tyr Arg Tyr Asp Gly Phe Ala Tyr Trp
                    100                 105                 110

Gly Gln Gly Thr Leu Val Thr Val Ser Ala
            115                 120
```

<210> SEQ ID NO 77
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

```
Asp Ile Val Met Thr Gln Ala Ala Pro Ser Val Pro Val Thr Pro Gly
 1               5                  10                  15

Glu Ser Val Ser Ile Ser Cys Arg Ser Ser Lys Ser Leu Leu His Ser
                20                  25                  30

Asn Gly Asn Thr His Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln Leu
                 85                  90                  95

Leu Glu Tyr Pro Tyr Thr Phe Gly Gly Gly Thr Lys Leu Glu Ile Glu
                100                 105                 110
```

<210> SEQ ID NO 78

<400> SEQUENCE: 78

000

<210> SEQ ID NO 79

<400> SEQUENCE: 79

000

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Gly Phe Leu Gly
 1
```

<210> SEQ ID NO 81
<211> LENGTH: 4
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 81

Ala Leu Ala Leu
1

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Gly Gly Gly Ser Gly Gly Gly Gly Ser Gly Gly Gly Gly Ser
1               5                   10                  15

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000
```

<210> SEQ ID NO 91
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Ile Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Val
        35                  40                  45

Gly Trp Val Asn Thr Tyr Thr Gly Glu Pro Thr Tyr Ala Asp Asp Phe
    50                  55                  60

Lys Gly Arg Leu Thr Phe Thr Leu Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Glu Gly Leu Gly Phe Gly Asp Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 92
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Ile Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Val
        35                  40                  45

Gly Trp Val Asn Thr Tyr Thr Gly Glu Pro Thr Tyr Ala Asp Asp Phe
50                  55                  60

Lys Gly Arg Leu Thr Phe Thr Leu Asp Thr Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Thr Arg Glu Gly Glu Gly Leu Gly Phe Gly Asp Trp Gly Gln Gly Thr
        100                 105                 110

Thr Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala

```
                275                 280                 285
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 93
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

His Gly Asp Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Val Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215
```

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Ser Ser Tyr
            20                  25                  30

Trp Ile Glu Trp Val Lys Gln Ala Pro Gly Gln Gly Leu Glu Trp Ile
        35                  40                  45

Gly Glu Ile Leu Pro Gly Ser Asp Thr Thr Asn Tyr Asn Glu Lys Phe
    50                  55                  60

Lys Asp Arg Ala Thr Phe Thr Ser Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Arg Gly Asn Tyr Arg Ala Trp Phe Gly Tyr Trp Gly Gln
            100                 105                 110
```

```
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Cys Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 101
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Val Gln Ser Gly Ala Glu Val Lys Lys Pro Gly Ser
```

-continued

```
1               5                   10                  15
Ser Val Lys Val Ser Cys Lys Ala Ser Gly Phe Thr Phe Thr Asp Tyr
            20                  25                  30

Tyr Ile His Trp Val Lys Gln Ala Pro Gly Gln Gly Leu Glu Trp Ile
            35                  40                  45

Gly Leu Val Tyr Pro Tyr Ile Gly Gly Thr Asn Tyr Asn Gln Lys Phe
            50                  55                  60

Lys Gly Lys Ala Thr Leu Thr Val Asp Thr Ser Thr Thr Thr Ala Tyr
65                  70                  75                  80

Met Glu Met Ser Ser Leu Arg Ser Glu Asp Thr Ala Val Tyr Tyr Cys
                85                  90                  95

Ala Arg Gly Asp Asn Lys Tyr Asp Ala Met Asp Tyr Trp Gly Gln Gly
                100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Cys Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

Ala Leu His Asn His Tyr Thr Gln Lys Ser Leu Ser Leu Ser Pro Gly
        435                 440                 445

Lys

<210> SEQ ID NO 102
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Ser Ser Tyr
            20                  25                  30

Trp Ile Glu Trp Val Lys Gln Ala Pro Gly Gln Gly Leu Glu Trp Ile
        35                  40                  45

Gly Glu Ile Leu Pro Gly Ser Asp Thr Thr Asn Tyr Asn Glu Lys Phe
    50                  55                  60

Lys Asp Arg Ala Thr Phe Thr Ser Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Arg Gly Asn Tyr Arg Ala Trp Phe Gly Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

-continued

```
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 103
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Val Gln Ser Gly Ala Glu Val Lys Lys Pro Gly Ala
1               5                   10                  15
Ser Val Lys Val Ser Cys Lys Ala Ser Gly Tyr Lys Phe Ser Ser Tyr
                20                  25                  30
Trp Ile Glu Trp Val Lys Gln Ala Pro Gly Gln Gly Leu Glu Trp Ile
            35                  40                  45
Gly Glu Ile Leu Pro Gly Ser Asp Thr Thr Asn Tyr Asn Glu Lys Phe
        50                  55                  60
Lys Asp Arg Ala Thr Phe Thr Ser Asp Thr Ser Ile Asn Thr Ala Tyr
65                  70                  75                  80
Met Glu Leu Ser Arg Leu Arg Ser Asp Thr Ala Val Tyr Tyr Cys
                85                  90                  95
Ala Arg Asp Arg Gly Asn Tyr Arg Ala Trp Phe Gly Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
```

Pro Cys Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 104
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Tyr Ile His Trp Val Lys Gln Ala Pro Gly Gln Gly Leu Glu Trp Ile
        35                  40                  45

Gly Leu Val Tyr Pro Tyr Ile Gly Gly Thr Asn Tyr Asn Gln Lys Phe
    50                  55                  60

Lys Gly Lys Ala Thr Leu Thr Val Asp Thr Ser Thr Thr Thr Ala Tyr
65                  70                  75                  80

Met Glu Met Ser Ser Leu Arg Ser Glu Asp Thr Ala Val Tyr Tyr Cys
                85                  90                  95

Ala Arg Gly Asp Asn Lys Tyr Asp Ala Met Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 105
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
                20                  25                  30

Tyr Ile His Trp Val Lys Gln Ala Pro Gly Gln Gly Leu Glu Trp Ile
            35                  40                  45

Gly Leu Val Tyr Pro Tyr Ile Gly Gly Thr Asn Tyr Asn Gln Lys Phe
```

```
            50                  55                  60
Lys Gly Lys Ala Thr Leu Thr Val Asp Thr Ser Thr Thr Thr Ala Tyr
 65                  70                  75                  80

Met Glu Met Ser Ser Leu Arg Ser Glu Asp Thr Ala Val Tyr Tyr Cys
                 85                  90                  95

Ala Arg Gly Asp Asn Lys Tyr Asp Ala Met Asp Tyr Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Cys Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 106

<400> SEQUENCE: 106
```

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Gly Ala Val Lys Phe Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Glu Ala Leu Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ala
    210
```

<210> SEQ ID NO 111
<211> LENGTH: 217

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Ser Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Glu Gln Ser Trp
                85                  90                  95

Glu Ile Arg Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Ala
    210                 215
```